(12) United States Patent
Ashley et al.

(10) Patent No.: US 6,509,455 B1
(45) Date of Patent: Jan. 21, 2003

(54) RECOMBINANT NARBONOLIDE POLYKETIDE SYNTHASE

(75) Inventors: Gary Ashley, Alameda, CA (US); Melanie C. Betlach, Burlingame, CA (US); Mary Betlach, San Francisco, CA (US); Robert McDaniel, Palo Alto, CA (US); Li Tang, Foster City, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 9 days.

(21) Appl. No.: 09/657,440

(22) Filed: Sep. 7, 2000

Related U.S. Application Data

(60) Division of application No. 09/320,878, filed on May 27, 1999, now Pat. No. 6,117,659, which is a continuation-in-part of application No. 09/141,908, filed on Aug. 28, 1998, which is a continuation-in-part of application No. 09/073,538, filed on May 6, 1998, which is a continuation-in-part of application No. 08/846,247, filed on Apr. 30, 1997, now Pat. No. 6,391,594.
(60) Provisional application No. 60/134,990, filed on May 20, 1999, provisional application No. 60/119,139, filed on Feb. 8, 1999, provisional application No. 60/100,880, filed on Sep. 22, 1998, and provisional application No. 60/087,080, filed on May 28, 1998.

(51) Int. Cl.$^7$ .............................................. C07H 21/04
(52) U.S. Cl. ................... 536/23.2; 435/193; 435/320.1; 536/23.7
(58) Field of Search ............................. 435/193, 252.3, 435/252.33, 320.1; 536/23.2, 23.7

(56) References Cited

U.S. PATENT DOCUMENTS

| | | | |
|---|---|---|---|
| 4,551,433 A | 11/1985 | DeBoer | 435/253 |
| 4,874,748 A | 10/1989 | Katz et al. | 514/29 |
| 5,063,155 A | 11/1991 | Cox et al. | 435/76 |
| 5,098,837 A | 3/1992 | Beckmann et al. | 435/172.3 |
| 5,149,639 A | 9/1992 | Katz et al. | 435/76 |
| 5,168,052 A | 12/1992 | Cox et al. | 435/72 |
| 5,252,474 A | 10/1993 | Gewain et al. | 435/172.3 |
| 5,514,544 A | 5/1996 | Rao et al. | 435/6 |
| 5,672,491 A | 9/1997 | Khosla et al. | 435/148 |
| 5,712,146 A | 1/1998 | Khosla et al. | 435/252.35 |
| 5,712,496 A | 1/1998 | Takahashi et al. | 257/64 |
| 5,824,513 A | 10/1998 | Katz et al. | 435/76 |
| 5,998,194 A | 12/1999 | Summers, Jr. et al. | 435/252.33 |
| 6,200,813 B1 | 3/2001 | Katz et al. | |
| 6,265,202 B1 | 7/2001 | Sherman et al. | 435/252.31 |

FOREIGN PATENT DOCUMENTS

| | | |
|---|---|---|
| EP | 0 238 323 A2 | 9/1987 |
| EP | 0 238 323 B1 | 12/1994 |
| EP | 0 791 655 A2 | 8/1997 |
| EP | 0 791 656 A2 | 8/1997 |
| WO | WO 93/13663 | 7/1993 |
| WO | WO 95/08548 | 3/1995 |
| WO | WO 96/40968 | 12/1996 |
| WO | WO 97/02358 | 1/1997 |
| WO | WO 97/23630 | 3/1997 |
| WO | WO 97/13845 | 4/1997 |
| WO | WO 97/22711 | 6/1997 |
| WO | WO 98/01456 | 1/1998 |
| WO | WO 98/01546 | 1/1998 |
| WO | WO 98/01571 | 1/1998 |
| WO | WO 98/27203 | 6/1998 |
| WO | WO 00/00620 | 1/2000 |

OTHER PUBLICATIONS

Bartel, et al., "Biosynthesis of anthraquinones by interspecies cloning of actinorhodin biosynthesis genes in streptomycetes: Clarification of actinorhodin gene functions," *J Bacteriol* (1990) 172(9):4816–4826.

Beck, J., et al., "the multifunctional 6–methylsalicylic acid synthase gene of *Penicillin patulum* its gene structure relative of that of other polyketide synthases," *Eur J Biochem* (1990) 192:487–498.

Bibb, et al., "Analysis of the nucleotide sequence of the *Streptomyces glaucescens* tcml genes provides key information about the enzymology of polyketide antibiotic biosynthesis," *EMBO J* (1989) 8(9):2727–2735.

Brown, M. J. B. et al., "A Mutant Generated by Expression of an Engineered DEBS1 Protein from the Erythromycin–Producing Polyketide Synthase (PKS) in *Streptomyces Coelicolor* Produces the Triketide as a Lactone, but the Major Product is the Nor–Analogue Derived from Acetate as Starter Acid," *Journal of the Chemical Society*, Chemical Communications, GB, Chemical Society. No. 15, 1995, pp. 1517–1518, XP0020447929 ISSN: 0022–4936.

Caballero et al., "Organisation and functions of the actVA region of the actinorhodin biosynthetic gene cluster of *Streptomyces coelicolor*," *Mol Gen Genet* (1991) 230:401–412.

Caffrey et al., FEBS Lett. (1992), 304:225–228.

Cane, D.E. et al., J. Am. Chem. Soc. (1993), 115:522–526.

Cane, D.E. et al., J. Antibiotics (1995), 48:647–651.

Cortes, J., et al., "An unusually large multifunctional polypeptide in the erythromycin–producing polyketide synthase of *Saccharopolyspora erythraea*," *Nature* (Nov. 8, 1990) 348:176–178.

Dalbie–Mcfarland et al., Proc Natl Acad Sci USA (1982), 79:6409.

Donadio et al., "Biosynthesis of the erythromycin macrolactone and a rational approach for producing hybrid macrolides," *Gene* (1992) 115:97–103.

(List continued on next page.)

Primary Examiner—Nashaat T. Nashed
(74) Attorney, Agent, or Firm—Kate M. Murashige; Kevin Kaster

(57) ABSTRACT

Recombinant DNA compounds that encode all or a portion of the narbonolide polyketide synthase are used to express recombinant polyketide synthase genes in host cells for the production of narbonolide, narbonolide derivatives, and polyketides that are useful as antibiotics and as intermediates in the synthesis of compounds with pharmaceutical value.

2 Claims, 6 Drawing Sheets

OTHER PUBLICATIONS

Donadio et al., Industrial Microorganism, Basic and Applied Molecular Genetics 1993, R.H. Baltz, G.D. Hegeman and P1L. Skatrud (eds) (Amer. Soc. Microbial), Washington, D.C. p. 257–265.

Donadio, S. et al., Proc Natl Acad Sci USA (1993), 90:7119–7123.

Donadio, S., et al., "Modular Organization of Genes Required for Complex Polyketide Biosynthesis," Science (May 3, 1991) 252:675–679.

Evans, D.A. et al., J. Am. Chem. Soc. (1992), 114: 9434–9453.

Fernandez–Moreno et al., "Nucleotide sequence and deduced functions of a set of cotranscribed genes of Streptomyces coelicolor A3(2) including the polyketide synthase for the antibiotic actinorhodin," J Biol Chem (1992) 267:19278–19290.

Fernandez–Moreno et al., "the act cluster contains regulatory and antibiotic export genes, direct targets for translational control by the bldA tRNA gene of Streptomyces," Cell (1991) 66:769–780.

Floss, "Genetic engineering of hybrid antibiotics—a progress report," Tetrahydron (1991) 47(31):6045–6058.

Fraley, R.T., et al., "Expression of bacterial genes in plant cells," Proc Natl Acad Sci USA (1983), 80:4803–4807.

Fu, "Engineered biosynthesis of novel polyketides: Stereochemical course of two reactions catalyzed by a polyketide synthase," Biochemistry (1994) 33(31):9321–9326.

Geisselsoder, J., et al., "Efficient site–directed in vitro mutagenesis," BioTechniques (1987), 5:786–791.

Hallam, "Nucleotide sequence, transcription and deduced function of a gene involved in polyketide antibiotic synthesis in Streptomyces coelicolor," Gene (1988) 74:305–320.

Hamilton et al., J. Bacteriol (1989), 171:4617.

Hopwood et al., "Product of 'hybrid' antibiotics by genetic engineering," Nature (1985) 314(6012):642–644.

Ireland, R.E., et al., J. Org. Chem, (1980), 45:1868–1880.

Jay, E., et al., J. Biol. Chem. (1984), 259:6311–6317.

Kao, C.M. et al., J. Am. Chem. Soc. (1994), 116:11612–11613.

Kao, C.M. et al., Science (1994), 265:509–512.

Katz et al., "Polyketide synthesis: Prospects for hybrid antibiotics," Ann. Review Microbiol (1993) 47:875–912.

Khosla, Chaitan et al., "Generation of polyketide libraries via combinatorial biosynthesis," Tibtech Sep. 1996 (vol. 14) pp. 335–341.

Khosla, C., et al., "Genetic construction and functional analysis of hybrid polyketide synthases containing heterologous acyl carrier proteins," J Bacteriol (1993), 175:2197–2204.

Khosla, et al., "Targeted gene replacements in a Streptomyces polyketide synthase gene cluster: role for the acyl carrier protein," Mole Microbiol (1992) 6(21):3237–3249.

Kuhstoss, S. et al., Gene (1996) 183:231–236.

Kunkel, T.A., Proc Natl Acad Sci USA (1985), 82:488.

Lambalot, R.H. et al., J. Antibiotics (1992), 45:1981–1982.

Lehrer, R. et al., J. Immunol Meth (1991), 137:167–173.

MacNeil, D.J., J. Bacteriol (1988), 170:5607.

MacNeil, D.J., et al., "Complex organization of the Streptomyces avermitilis genes encoding the avermectin polyketide synthase," Gene (1992) 115:119–125.

Malpartida et al., "Homology between Streptomyces genes coding for synthesis of different polyketides used to clone antibiotic biosynthetic genes," Nature (1987) 325(6107):818–821.

Malpartida et al., "Physical and genetic characteristics of the gene cluster for the antibiotic actinorhodin in Streptomyces coelicolor A3(2)," Mol Gen Genet (1986) 205:66–73.

Malpartida, F., et al., "Molecular cloning of the whole biosynthetic pathway of a streptomyces antibiotic and its expression in a heterologous host," Nature (1984), 309:462–464.

Marsden, A.F.A., et al., "Engineering Broader Specificity into an Antibiotic–Producing Polyketide Synthase," Science (Jan. 9, 1998) 279:199–202.

McDaniel et al., 1993 "Engineered biosynthesis of novel polyketides", Science 262:1546–1550 (1993).

Martin, S.F. et al., J. Am. Chem. Soc. (1997), 119:3193.

Masamune et al., J. Am. Chem. Soc. (1975), 97:3512–3513.

Netlach, M.C., et al., "Characterization of the Macrolide P–450 Hydroxylase from Streptomyces venezuelae which Converts Narbomycin t Picromycin," Bichemistry (1998) 37:14937–14942.

Oliynyk, M., et al., "A hybrid modular polyketide synthase obtained by domain swapping," Chemistry & Biology (Oct. 1996) 3:833–839.

Perun, T.J., Drug Action and Drug Resistance in Bacteria, vol. 1, S. Mitsuhashi (ed) Univ. Park Press, Baltimore, 1977.

Sherman et al., "Functional replacement of genes for individual polyketide synthase components in Streptomyces coelicolor A3(2) by heterogenous genes from a different polyketide pathway," J Bacteriol (1992) 174:6184–6190.

Sherman et al., "Structure and deduced function of the granaticin–producing polyketide synthase gene cluster of Streptomyces violaceoruber Tü22," EMBO J (1989) 8:2717–2725.

Toshima, K. et al., J. Am. Chem. Soc. (1995), 117:3717.

Tuan et al., Gene (1990), 90:21–29.

Vedejs, E. et al., J Am Chem Soc (1987), 109:5437–5446.

Vedejs, E. et al., J Am Chem Soc (1989), 111:8430–8438.

Weber, J.M. et al, "Genetic Analysis of Erythromycin Production in Streptomyces erythreus," J. of Bacteriology, vol. 164, No. 1, issued Oct. 1985, pp. 425–433, See the entire document.

Weber, J.M. et al, "Organization of a Cluster of Erythromycin Genes in Saccharomyces erythraea," J. of Bacteriology, vol. 172, No. 5, issued May 1990, pp. 2372–2383. See the entire document.

Woodward, R.B. et al., J. Am. Chem. Soc. (1981), 103:3215.

Xue, Y. et al., "Hydroxylation of macrolactones YC–17 and narbomycin is mediated by the pike–encoded cytochrome P450 in Streptomyces venezuelae," Chemistry & Biology (1998), 5:661–667.

Xue, Y. et al., "A gene cluster for macrolide antibiotic biosynthesis in Streptomyces venezuelae: Architecture of metabolic diversity," Proc. Natl. Acad. Sci. USA (1988), 95:12111–12116.

Zoller, et al., Methods in Enzymology (1983), 100:468.

Matsumoto, T. et al, Tetrahedron Lett. (1988) 29, 3575.

Chuck, J. "The amino acid sequencing of the putative methymycin synthase from Streptomyces Venezuelae", unpublished.

SEQUENCE LISTING

<160> NUMBER OF SEQ ID NOS: 34

<210> SEQ ID NO 1
<211> LENGTH: 4551
<212> TYPE: PRT
<213> ORGANISM: Streptomyces venezuelae

<400> SEQUENCE: 1

Met Ser Thr Val Ser Lys Ser Glu Ser Glu Glu Phe Val Ser Val Ser

-continued

```
  1               5                  10                 15
Asn Asp Ala Gly Ser Ala His Gly Thr Ala Glu Pro Val Ala Val Val
             20                 25                 30
Gly Ile Ser Cys Arg Val Pro Gly Ala Arg Asp Pro Arg Glu Phe Trp
             35                 40                 45
Glu Leu Leu Ala Ala Gly Gly Gln Ala Val Thr Asp Val Pro Ala Asp
     50                 55                 60
Arg Trp Asn Ala Gly Asp Phe Tyr Asp Pro Asp Arg Ser Ala Pro Gly
 65                 70                 75                 80
Arg Ser Asn Ser Arg Trp Gly Gly Phe Ile Glu Asp Val Asp Arg Phe
                 85                 90                 95
Asp Ala Ala Phe Phe Gly Ile Ser Pro Arg Glu Ala Ala Glu Met Asp
             100                105                110
Pro Gln Gln Arg Leu Ala Leu Glu Leu Gly Trp Glu Ala Leu Glu Arg
             115                120                125
Ala Gly Ile Asp Pro Ser Ser Leu Thr Gly Thr Arg Thr Gly Val Phe
             130                135                140
Ala Gly Ala Ile Trp Asp Asp Tyr Ala Thr Leu Lys His Arg Gln Gly
145                150                155                160
Gly Ala Ala Ile Thr Pro His Thr Val Thr Gly Leu His Arg Gly Ile
                 165                170                175
Ile Ala Asn Arg Leu Ser Tyr Thr Leu Gly Leu Arg Gly Pro Ser Met
                 180                185                190
Val Val Asp Ser Gly Gln Ser Ser Leu Val Ala Val His Leu Ala
             195                200                205
Cys Glu Ser Leu Arg Arg Gly Glu Ser Glu Leu Ala Leu Ala Gly Gly
             210                215                220
Val Ser Leu Asn Leu Val Pro Asp Ser Ile Ile Gly Ala Ser Lys Phe
225                230                235                240
Gly Gly Leu Ser Pro Asp Gly Arg Ala Tyr Thr Phe Asp Ala Arg Ala
                 245                250                255
Asn Gly Tyr Val Arg Gly Glu Gly Gly Gly Phe Val Val Leu Lys Arg
                 260                265                270
Leu Ser Arg Ala Val Ala Asp Gly Asp Pro Val Leu Ala Val Ile Arg
             275                280                285
Gly Ser Ala Val Asn Asn Gly Gly Ala Ala Gln Gly Met Thr Thr Pro
290                295                300
Asp Ala Gln Ala Gln Glu Ala Val Leu Arg Glu Ala His Glu Arg Ala
305                310                315                320
Gly Thr Ala Pro Ala Asp Val Arg Tyr Val Glu Leu His Gly Thr Gly
             325                330                335
Thr Pro Val Gly Asp Pro Ile Glu Ala Ala Leu Gly Ala Ala Leu
             340                345                350
Gly Thr Gly Arg Pro Ala Gly Gln Pro Leu Leu Val Gly Ser Val Lys
             355                360                365
Thr Asn Ile Gly His Leu Glu Gly Ala Ala Gly Ile Ala Gly Leu Ile
     370                375                380
Lys Ala Val Leu Ala Val Arg Gly Arg Ala Leu Pro Ala Ser Leu Asn
385                390                395                400
Tyr Glu Thr Pro Asn Pro Ala Ile Pro Phe Glu Glu Leu Asn Leu Arg
                 405                410                415
Val Asn Thr Glu Tyr Leu Pro Trp Glu Pro Glu His Asp Gly Gln Arg
             420                425                430
```

-continued

```
Met Val Val Gly Val Ser Ser Phe Gly Met Gly Thr Asn Ala His
            435                 440                 445
Val Val Leu Glu Glu Ala Pro Gly Val Val Glu Gly Ala Ser Val Val
    450                 455                 460
Glu Ser Thr Val Gly Ser Ala Val Gly Gly Val Val Pro Trp
465                 470                 475                 480
Val Val Ser Ala Lys Ser Ala Ala Leu Asp Ala Gln Ile Glu Arg
                485                 490                 495
Leu Ala Ala Phe Ala Ser Arg Asp Arg Thr Asp Gly Val Asp Ala Gly
            500                 505                 510
Ala Val Asp Ala Gly Ala Val Asp Ala Gly Val Ala Arg Val Leu
            515                 520                 525
Ala Gly Gly Arg Ala Gln Phe Glu His Arg Ala Val Val Gly Ser
    530                 535                 540
Gly Pro Asp Asp Leu Ala Ala Leu Ala Ala Pro Glu Gly Leu Val
545                 550                 555                 560
Arg Gly Val Ala Ser Gly Val Gly Arg Val Ala Phe Val Phe Pro Gly
                565                 570                 575
Gln Gly Thr Gln Trp Ala Gly Met Gly Ala Glu Leu Leu Asp Ser Ser
            580                 585                 590
Ala Val Phe Ala Ala Met Ala Glu Cys Glu Ala Ala Leu Ser Pro
    595                 600                 605
Tyr Val Asp Trp Ser Leu Glu Ala Val Arg Gln Ala Pro Gly Ala
    610                 615                 620
Pro Thr Leu Glu Arg Val Asp Val Val Gln Pro Val Thr Phe Ala Val
625                 630                 635                 640
Met Val Ser Leu Ala Arg Val Trp Gln His His Gly Val Thr Pro Gln
                645                 650                 655
Ala Val Val Gly His Ser Gln Gly Glu Ile Ala Ala Ala Tyr Val Ala
                660                 665                 670
Gly Ala Leu Ser Leu Asp Asp Ala Ala Arg Val Val Thr Leu Arg Ser
            675                 680                 685
Lys Ser Ile Ala Ala His Leu Ala Gly Lys Gly Gly Met Leu Ser Leu
    690                 695                 700
Ala Leu Ser Glu Asp Ala Val Leu Glu Arg Leu Ala Gly Phe Asp Gly
705                 710                 715                 720
Leu Ser Val Ala Ala Val Asn Gly Pro Thr Ala Thr Val Val Ser Gly
                725                 730                 735
Asp Pro Val Gln Ile Glu Glu Leu Ala Arg Ala Cys Glu Ala Asp Gly
            740                 745                 750
Val Arg Ala Arg Val Ile Pro Val Asp Tyr Ala Ser His Ser Arg Gln
            755                 760                 765
Val Glu Ile Ile Glu Ser Glu Leu Ala Glu Val Leu Ala Gly Leu Ser
    770                 775                 780
Pro Gln Ala Pro Arg Val Pro Phe Phe Ser Thr Leu Glu Gly Ala Trp
785                 790                 795                 800
Ile Thr Glu Pro Val Leu Asp Gly Gly Tyr Trp Tyr Arg Asn Leu Arg
                805                 810                 815
His Arg Val Gly Phe Ala Pro Ala Val Glu Thr Leu Ala Thr Asp Glu
            820                 825                 830
Gly Phe Thr His Phe Val Glu Val Ser Ala His Pro Val Leu Thr Met
    835                 840                 845
```

-continued

```
Ala Leu Pro Gly Thr Val Thr Gly Leu Ala Thr Leu Arg Arg Asp Asn
    850                 855                 860

Gly Gly Gln Asp Arg Leu Val Ala Ser Leu Ala Glu Ala Trp Ala Asn
865                 870                 875                 880

Gly Leu Ala Val Asp Trp Ser Pro Leu Leu Pro Ser Ala Thr Gly His
                885                 890                 895

His Ser Asp Leu Pro Thr Tyr Ala Phe Gln Thr Glu Arg His Trp Leu
            900                 905                 910

Gly Glu Ile Glu Ala Leu Ala Pro Ala Gly Glu Pro Ala Val Gln Pro
        915                 920                 925

Ala Val Leu Arg Thr Glu Ala Ala Glu Pro Ala Glu Leu Asp Arg Asp
    930                 935                 940

Glu Gln Leu Arg Val Ile Leu Asp Lys Val Arg Ala Gln Thr Ala Gln
945                 950                 955                 960

Val Leu Gly Tyr Ala Thr Gly Gly Gln Ile Glu Val Asp Arg Thr Phe
                965                 970                 975

Arg Glu Ala Gly Cys Thr Ser Leu Thr Gly Val Asp Leu Arg Asn Arg
            980                 985                 990

Ile Asn Ala Ala Phe Gly Val Arg Met Ala Pro Ser Met Ile Phe Asp
        995                 1000                1005

Phe Pro Thr Pro Glu Ala Leu Ala Glu Gln Leu Leu Leu Val Val His
    1010                1015                1020

Gly Glu Ala Ala Ala Asn Pro Ala Gly Ala Glu Pro Ala Pro Val Ala
1025                1030                1035                1040

Ala Ala Gly Ala Val Asp Glu Pro Val Ala Ile Val Gly Met Ala Cys
                1045                1050                1055

Arg Leu Pro Gly Gly Val Ala Ser Pro Glu Asp Leu Trp Arg Leu Val
            1060                1065                1070

Ala Gly Gly Gly Asp Ala Ile Ser Glu Phe Pro Gln Asp Arg Gly Trp
        1075                1080                1085

Asp Val Glu Gly Leu Tyr His Pro Asp Pro Glu His Pro Gly Thr Ser
    1090                1095                1100

Tyr Val Arg Gln Gly Gly Phe Ile Glu Asn Val Ala Gly Phe Asp Ala
1105                1110                1115                1120

Ala Phe Phe Gly Ile Ser Pro Arg Glu Ala Leu Ala Met Asp Pro Gln
                1125                1130                1135

Gln Arg Leu Leu Leu Glu Thr Ser Trp Glu Ala Val Glu Asp Ala Gly
            1140                1145                1150

Ile Asp Pro Thr Ser Leu Arg Gly Arg Gln Val Gly Val Phe Thr Gly
        1155                1160                1165

Ala Met Thr His Glu Tyr Gly Pro Ser Leu Arg Asp Gly Gly Glu Gly
    1170                1175                1180

Leu Asp Gly Tyr Leu Leu Thr Gly Asn Thr Ala Ser Val Met Ser Gly
1185                1190                1195                1200

Arg Val Ser Tyr Thr Leu Gly Leu Glu Gly Pro Ala Leu Thr Val Asp
                1205                1210                1215

Thr Ala Cys Ser Ser Ser Leu Val Ala Leu His Leu Ala Val Gln Ala
            1220                1225                1230

Leu Arg Lys Gly Glu Val Asp Met Ala Leu Ala Gly Gly Val Ala Val
        1235                1240                1245

Met Pro Thr Pro Gly Met Phe Val Glu Phe Ser Arg Gln Arg Gly Leu
    1250                1255                1260

Ala Gly Asp Gly Arg Ser Lys Ala Phe Ala Ala Ser Ala Asp Gly Thr
```

-continued

```
1265            1270            1275            1280

Ser Trp Ser Glu Gly Val Gly Val Leu Leu Val Glu Arg Leu Ser Asp
            1285            1290            1295

Ala Arg Arg Asn Gly His Gln Val Leu Ala Val Val Arg Gly Ser Ala
        1300            1305            1310

Val Asn Gln Asp Gly Ala Ser Asn Gly Leu Thr Ala Pro Asn Gly Pro
    1315            1320            1325

Ser Gln Gln Arg Val Ile Arg Arg Ala Leu Ala Asp Ala Arg Leu Thr
1330            1335            1340

Thr Ser Asp Val Asp Val Val Glu Ala His Gly Thr Gly Thr Arg Leu
1345            1350            1355            1360

Gly Asp Pro Ile Glu Ala Gln Ala Leu Ile Ala Thr Tyr Gly Gln Gly
            1365            1370            1375

Arg Asp Asp Glu Gln Pro Leu Arg Leu Gly Ser Leu Lys Ser Asn Ile
        1380            1385            1390

Gly His Thr Gln Ala Ala Ala Gly Val Ser Gly Val Ile Lys Met Val
    1395            1400            1405

Gln Ala Met Arg His Gly Leu Leu Pro Lys Thr Leu His Val Asp Glu
1410            1415            1420

Pro Ser Asp Gln Ile Asp Trp Ser Ala Gly Ala Val Glu Leu Leu Thr
1425            1430            1435            1440

Glu Ala Val Asp Trp Pro Glu Lys Gln Asp Gly Gly Leu Arg Arg Ala
            1445            1450            1455

Ala Val Ser Ser Phe Gly Ile Ser Gly Thr Asn Ala His Val Val Leu
        1460            1465            1470

Glu Glu Ala Pro Val Val Glu Gly Ala Ser Val Val Glu Pro Ser
    1475            1480            1485

Val Gly Gly Ser Ala Val Gly Gly Val Thr Pro Trp Val Val Ser
    1490            1495            1500

Ala Lys Ser Ala Ala Ala Leu Asp Ala Gln Ile Glu Arg Leu Ala Ala
1505            1510            1515            1520

Phe Ala Ser Arg Asp Arg Thr Asp Asp Ala Asp Ala Gly Ala Val Asp
            1525            1530            1535

Ala Gly Ala Val Ala His Val Leu Ala Asp Gly Arg Ala Gln Phe Glu
        1540            1545            1550

His Arg Ala Val Ala Leu Gly Ala Gly Ala Asp Asp Leu Val Gln Ala
    1555            1560            1565

Leu Ala Asp Pro Asp Gly Leu Ile Arg Gly Thr Ala Ser Gly Val Gly
1570            1575            1580

Arg Val Ala Phe Val Phe Pro Gly Gln Gly Thr Gln Trp Ala Gly Met
1585            1590            1595            1600

Gly Ala Glu Leu Leu Asp Ser Ser Ala Val Phe Ala Ala Ala Met Ala
            1605            1610            1615

Glu Cys Glu Ala Ala Leu Ser Pro Tyr Val Asp Trp Ser Leu Glu Ala
        1620            1625            1630

Val Val Arg Gln Ala Pro Gly Ala Pro Thr Leu Glu Arg Val Asp Val
    1635            1640            1645

Val Gln Pro Val Thr Phe Ala Val Met Val Ser Leu Ala Arg Val Trp
    1650            1655            1660

Gln His His Gly Val Thr Pro Gln Ala Val Val Gly His Ser Gln Gly
1665            1670            1675            1680

Glu Ile Ala Ala Ala Tyr Val Ala Gly Ala Leu Pro Leu Asp Asp Ala
            1685            1690            1695
```

-continued

```
Ala Arg Val Val Thr Leu Arg Ser Lys Ser Ile Ala Ala His Leu Ala
        1700                1705                1710
Gly Lys Gly Gly Met Leu Ser Leu Ala Leu Asn Glu Asp Ala Val Leu
        1715                1720                1725
Glu Arg Leu Ser Asp Phe Asp Gly Leu Ser Val Ala Ala Val Asn Gly
        1730                1735                1740
Pro Thr Ala Thr Val Val Ser Gly Asp Pro Val Gln Ile Glu Glu Leu
1745                1750                1755                1760
Ala Gln Ala Cys Lys Ala Asp Gly Phe Arg Ala Arg Ile Ile Pro Val
            1765                1770                1775
Asp Tyr Ala Ser His Ser Arg Gln Val Glu Ile Ile Glu Ser Glu Leu
        1780                1785                1790
Ala Gln Val Leu Ala Gly Leu Ser Pro Gln Ala Pro Arg Val Pro Phe
        1795                1800                1805
Phe Ser Thr Leu Glu Gly Thr Trp Ile Thr Glu Pro Val Leu Asp Gly
        1810                1815                1820
Thr Tyr Trp Tyr Arg Asn Leu Arg His Arg Val Gly Phe Ala Pro Ala
1825                1830                1835                1840
Ile Glu Thr Leu Ala Val Asp Glu Gly Phe Thr His Phe Val Glu Val
            1845                1850                1855
Ser Ala His Pro Val Leu Thr Met Thr Leu Pro Glu Thr Val Thr Gly
        1860                1865                1870
Leu Gly Thr Leu Arg Arg Glu Gln Gly Gly Gln Glu Arg Leu Val Thr
        1875                1880                1885
Ser Leu Ala Glu Ala Trp Val Asn Gly Leu Pro Val Ala Trp Thr Ser
        1890                1895                1900
Leu Leu Pro Ala Thr Ala Ser Arg Pro Gly Leu Pro Thr Tyr Ala Phe
1905                1910                1915                1920
Gln Ala Glu Arg Tyr Trp Leu Glu Asn Thr Pro Ala Ala Leu Ala Thr
            1925                1930                1935
Gly Asp Asp Trp Arg Tyr Arg Ile Asp Trp Lys Arg Leu Pro Ala Ala
        1940                1945                1950
Glu Gly Ser Glu Arg Thr Gly Leu Ser Gly Arg Trp Leu Ala Val Thr
        1955                1960                1965
Pro Glu Asp His Ser Ala Gln Ala Ala Ala Val Leu Thr Ala Leu Val
        1970                1975                1980
Asp Ala Gly Ala Lys Val Glu Val Leu Thr Ala Gly Ala Asp Asp Asp
1985                1990                1995                2000
Arg Glu Ala Leu Ala Ala Arg Leu Thr Ala Leu Thr Thr Gly Asp Gly
            2005                2010                2015
Phe Thr Gly Val Val Ser Leu Leu Asp Gly Leu Val Pro Gln Val Ala
        2020                2025                2030
Trp Val Gln Ala Leu Gly Asp Ala Gly Ile Lys Ala Pro Leu Trp Ser
        2035                2040                2045
Val Thr Gln Gly Ala Val Ser Val Gly Arg Leu Asp Thr Pro Ala Asp
        2050                2055                2060
Pro Asp Arg Ala Met Leu Trp Gly Leu Gly Arg Val Val Ala Leu Glu
2065                2070                2075                2080
His Pro Glu Arg Trp Ala Gly Leu Val Asp Leu Pro Ala Gln Pro Asp
            2085                2090                2095
Ala Ala Ala Leu Ala His Leu Val Thr Ala Leu Ser Gly Ala Thr Gly
        2100                2105                2110
```

```
Glu Asp Gln Ile Ala Ile Arg Thr Thr Gly Leu His Ala Arg Arg Leu
    2115                2120                2125

Ala Arg Ala Pro Leu His Gly Arg Arg Pro Thr Arg Asp Trp Gln Pro
2130                2135                2140

His Gly Thr Val Leu Ile Thr Gly Gly Thr Gly Ala Leu Gly Ser His
2145                2150                2155                2160

Ala Ala Arg Trp Met Ala His His Gly Ala Glu His Leu Leu Leu Val
            2165                2170                2175

Ser Arg Ser Gly Glu Gln Ala Pro Gly Ala Thr Gln Leu Thr Ala Glu
        2180                2185                2190

Leu Thr Ala Ser Gly Ala Arg Val Thr Ile Ala Ala Cys Asp Val Ala
    2195                2200                2205

Asp Pro His Ala Met Arg Thr Leu Leu Asp Ala Ile Pro Ala Glu Thr
2210                2215                2220

Pro Leu Thr Ala Val Val His Thr Ala Gly Ala Leu Asp Asp Gly Ile
2225                2230                2235                2240

Val Asp Thr Leu Thr Ala Glu Gln Val Arg Arg Ala His Arg Ala Lys
            2245                2250                2255

Ala Val Gly Ala Ser Val Leu Asp Glu Leu Thr Arg Asp Leu Asp Leu
        2260                2265                2270

Asp Ala Phe Val Leu Phe Ser Ser Val Ser Ser Thr Leu Gly Ile Pro
    2275                2280                2285

Gly Gln Gly Asn Tyr Ala Pro His Asn Ala Tyr Leu Asp Ala Leu Ala
2290                2295                2300

Ala Arg Arg Arg Ala Thr Gly Arg Ser Ala Val Ser Val Ala Trp Gly
2305                2310                2315                2320

Pro Trp Asp Gly Gly Met Ala Ala Gly Asp Val Ala Glu Arg
            2325                2330                2335

Leu Arg Asn His Gly Val Pro Gly Met Asp Pro Glu Leu Ala Leu Ala
        2340                2345                2350

Ala Leu Glu Ser Ala Leu Gly Arg Asp Glu Thr Ala Ile Thr Val Ala
    2355                2360                2365

Asp Ile Asp Trp Asp Arg Phe Tyr Leu Ala Tyr Ser Ser Gly Arg Pro
2370                2375                2380

Gln Pro Leu Val Glu Glu Leu Pro Glu Val Arg Arg Ile Ile Asp Ala
2385                2390                2395                2400

Arg Asp Ser Ala Thr Ser Gly Gln Gly Gly Ser Ser Ala Gln Gly Ala
            2405                2410                2415

Asn Pro Leu Ala Glu Arg Leu Ala Ala Ala Pro Gly Glu Arg Thr
        2420                2425                2430

Glu Ile Leu Leu Gly Leu Val Arg Ala Gln Ala Ala Val Leu Arg
    2435                2440                2445

Met Arg Ser Pro Glu Asp Val Ala Ala Asp Arg Ala Phe Lys Asp Ile
    2450                2455                2460

Gly Phe Asp Ser Leu Ala Gly Val Glu Leu Arg Asn Arg Leu Thr Arg
2465                2470                2475                2480

Ala Thr Gly Leu Gln Leu Pro Ala Thr Leu Val Phe Asp His Pro Thr
            2485                2490                2495

Pro Leu Ala Leu Val Ser Leu Leu Arg Ser Glu Phe Leu Gly Asp Glu
        2500                2505                2510

Glu Thr Ala Asp Ala Arg Arg Ser Ala Ala Leu Pro Ala Thr Val Gly
    2515                2520                2525

Ala Gly Ala Gly Ala Gly Ala Gly Thr Asp Ala Asp Asp Pro Ile
```

-continued

```
                2530                2535                2540
Ala Ile Val Ala Met Ser Cys Arg Tyr Pro Gly Asp Ile Arg Ser Pro
2545                2550                2555                2560
Glu Asp Leu Trp Arg Met Leu Ser Glu Gly Gly Glu Gly Ile Thr Pro
                2565                2570                2575
Phe Pro Thr Asp Arg Gly Trp Asp Leu Asp Gly Leu Tyr Asp Ala Asp
                2580                2585                2590
Pro Asp Ala Leu Gly Arg Ala Tyr Val Arg Glu Gly Gly Phe Leu His
                2595                2600                2605
Asp Ala Ala Glu Phe Asp Ala Glu Phe Phe Gly Val Ser Pro Arg Glu
    2610                2615                2620
Ala Leu Ala Met Asp Pro Gln Gln Arg Met Leu Leu Thr Thr Ser Trp
2625                2630                2635                2640
Glu Ala Phe Glu Arg Ala Gly Ile Glu Pro Ala Ser Leu Arg Gly Ser
                2645                2650                2655
Ser Thr Gly Val Phe Ile Gly Leu Ser Tyr Gln Asp Tyr Ala Ala Arg
                2660                2665                2670
Val Pro Asn Ala Pro Arg Gly Val Glu Gly Tyr Leu Leu Thr Gly Ser
        2675                2680                2685
Thr Pro Ser Val Ala Ser Gly Arg Ile Ala Tyr Thr Phe Gly Leu Glu
        2690                2695                2700
Gly Pro Ala Thr Thr Val Asp Thr Ala Cys Ser Ser Ser Leu Thr Ala
2705                2710                2715                2720
Leu His Leu Ala Val Arg Ala Leu Arg Ser Gly Glu Cys Thr Met Ala
                2725                2730                2735
Leu Ala Gly Gly Val Ala Met Met Ala Thr Pro His Met Phe Val Glu
                2740                2745                2750
Phe Ser Arg Gln Arg Ala Leu Ala Pro Asp Gly Arg Ser Lys Ala Phe
                2755                2760                2765
Ser Ala Asp Ala Asp Gly Phe Gly Ala Ala Glu Gly Val Gly Leu Leu
        2770                2775                2780
Leu Val Glu Arg Leu Ser Asp Ala Arg Arg Asn Gly His Pro Val Leu
2785                2790                2795                2800
Ala Val Val Arg Gly Thr Ala Val Asn Gln Asp Gly Ala Ser Asn Gly
                2805                2810                2815
Leu Thr Ala Pro Asn Gly Pro Ser Gln Gln Arg Val Ile Arg Gln Ala
            2820                2825                2830
Leu Ala Asp Ala Arg Leu Ala Pro Gly Asp Ile Asp Ala Val Glu Thr
        2835                2840                2845
His Gly Thr Gly Thr Ser Leu Gly Asp Pro Ile Glu Ala Gln Gly Leu
    2850                2855                2860
Gln Ala Thr Tyr Gly Lys Glu Arg Pro Ala Glu Arg Pro Leu Ala Ile
2865                2870                2875                2880
Gly Ser Val Lys Ser Asn Ile Gly His Thr Gln Ala Ala Ala Gly Ala
                2885                2890                2895
Ala Gly Ile Ile Lys Met Val Leu Ala Met Arg His Gly Thr Leu Pro
                2900                2905                2910
Lys Thr Leu His Ala Asp Glu Pro Ser Pro His Val Asp Trp Ala Asn
        2915                2920                2925
Ser Gly Leu Ala Leu Val Thr Glu Pro Ile Asp Trp Pro Ala Gly Thr
    2930                2935                2940
Gly Pro Arg Arg Ala Ala Val Ser Ser Phe Gly Ile Ser Gly Thr Asn
2945                2950                2955                2960
```

-continued

Ala His Val Val Leu Glu Gln Ala Pro Asp Ala Ala Gly Glu Val Leu
                2965                2970                2975

Gly Ala Asp Glu Val Pro Glu Val Ser Glu Thr Val Ala Met Ala Gly
            2980                2985                2990

Thr Ala Gly Thr Ser Glu Val Ala Glu Gly Ser Glu Ala Ser Glu Ala
            2995                3000                3005

Pro Ala Ala Pro Gly Ser Arg Glu Ala Ser Leu Pro Gly His Leu Pro
        3010                3015                3020

Trp Val Leu Ser Ala Lys Asp Glu Gln Ser Leu Arg Gly Gln Ala Ala
3025                3030                3035                3040

Ala Leu His Ala Trp Leu Ser Glu Pro Ala Ala Asp Leu Ser Asp Ala
            3045                3050                3055

Asp Gly Pro Ala Arg Leu Arg Asp Val Gly Tyr Thr Leu Ala Thr Ser
            3060                3065                3070

Arg Thr Ala Phe Ala His Arg Ala Ala Val Thr Ala Ala Asp Arg Asp
        3075                3080                3085

Gly Phe Leu Asp Gly Leu Ala Thr Leu Ala Gln Gly Gly Thr Ser Ala
        3090                3095                3100

His Val His Leu Asp Thr Ala Arg Asp Gly Thr Thr Ala Phe Leu Phe
3105                3110                3115                3120

Thr Gly Gln Gly Ser Gln Arg Pro Gly Ala Gly Arg Glu Leu Tyr Asp
            3125                3130                3135

Arg His Pro Val Phe Ala Arg Ala Leu Asp Glu Ile Cys Ala His Leu
            3140                3145                3150

Asp Gly His Leu Glu Leu Pro Leu Leu Asp Val Met Phe Ala Ala Glu
            3155                3160                3165

Gly Ser Ala Glu Ala Ala Leu Leu Asp Glu Thr Arg Tyr Thr Gln Cys
        3170                3175                3180

Ala Leu Phe Ala Leu Glu Val Ala Leu Phe Arg Leu Val Glu Ser Trp
3185                3190                3195                3200

Gly Met Arg Pro Ala Ala Leu Leu Gly His Ser Val Gly Glu Ile Ala
            3205                3210                3215

Ala Ala His Val Ala Gly Val Phe Ser Leu Ala Asp Ala Ala Arg Leu
            3220                3225                3230

Val Ala Ala Arg Gly Arg Leu Met Gln Glu Leu Pro Ala Gly Gly Ala
        3235                3240                3245

Met Leu Ala Val Gln Ala Ala Glu Asp Glu Ile Arg Val Trp Leu Glu
        3250                3255                3260

Thr Glu Glu Arg Tyr Ala Gly Arg Leu Asp Val Ala Ala Val Asn Gly
3265                3270                3275                3280

Pro Glu Ala Ala Val Leu Ser Gly Asp Ala Asp Ala Ala Arg Glu Ala
            3285                3290                3295

Glu Ala Tyr Trp Ser Gly Leu Gly Arg Arg Thr Arg Ala Leu Arg Val
            3300                3305                3310

Ser His Ala Phe His Ser Ala His Met Asp Gly Met Leu Asp Gly Phe
        3315                3320                3325

Arg Ala Val Leu Glu Thr Val Glu Phe Arg Arg Pro Ser Leu Thr Val
        3330                3335                3340

Val Ser Asn Val Thr Gly Leu Ala Ala Gly Pro Asp Asp Leu Cys Asp
3345                3350                3355                3360

Pro Glu Tyr Trp Val Arg His Val Arg Gly Thr Val Arg Phe Leu Asp
            3365                3370                3375

-continued

```
Gly Val Arg Val Leu Arg Asp Leu Gly Val Arg Thr Cys Leu Glu Leu
        3380            3385                3390

Gly Pro Asp Gly Val Leu Thr Ala Met Ala Ala Asp Gly Leu Ala Asp
        3395            3400                3405

Thr Pro Ala Asp Ser Ala Ala Gly Ser Pro Val Gly Ser Pro Ala Gly
        3410            3415                3420

Ser Pro Ala Asp Ser Ala Ala Gly Ala Leu Arg Pro Arg Pro Leu Leu
3425            3430            3435                3440

Val Ala Leu Leu Arg Arg Lys Arg Ser Glu Thr Glu Thr Val Ala Asp
            3445            3450                3455

Ala Leu Gly Arg Ala His Ala His Gly Thr Gly Pro Asp Trp His Ala
        3460            3465                3470

Trp Phe Ala Gly Ser Gly Ala His Arg Val Asp Leu Pro Thr Tyr Ser
        3475            3480                3485

Phe Arg Arg Asp Arg Tyr Trp Leu Asp Ala Pro Ala Ala Asp Thr Ala
        3490            3495                3500

Val Asp Thr Ala Gly Leu Gly Leu Gly Thr Ala Asp His Pro Leu Leu
3505            3510            3515                3520

Gly Ala Val Val Ser Leu Pro Asp Arg Asp Gly Leu Leu Leu Thr Gly
            3525            3530                3535

Arg Leu Ser Leu Arg Thr His Pro Trp Leu Ala Asp His Ala Val Leu
        3540            3545                3550

Gly Ser Val Leu Leu Pro Gly Ala Ala Met Val Glu Leu Ala Ala His
        3555            3560                3565

Ala Ala Glu Ser Ala Gly Leu Arg Asp Val Arg Glu Leu Thr Leu Leu
        3570            3575                3580

Glu Pro Leu Val Leu Pro Glu His Gly Gly Val Glu Leu Arg Val Thr
3585            3590            3595                3600

Val Gly Ala Pro Ala Gly Glu Pro Gly Gly Glu Ser Ala Gly Asp Gly
            3605            3610                3615

Ala Arg Pro Val Ser Leu His Ser Arg Leu Ala Asp Ala Pro Ala Gly
        3620            3625                3630

Thr Ala Trp Ser Cys His Ala Thr Gly Leu Leu Ala Thr Asp Arg Pro
        3635            3640                3645

Glu Leu Pro Val Ala Pro Asp Arg Ala Ala Met Trp Pro Pro Gln Gly
        3650            3655                3660

Ala Glu Glu Val Pro Leu Asp Gly Leu Tyr Glu Arg Leu Asp Gly Asn
3665            3670            3675                3680

Gly Leu Ala Phe Gly Pro Leu Phe Gln Gly Leu Asn Ala Val Trp Arg
            3685            3690                3695

Tyr Glu Gly Glu Val Phe Ala Asp Ile Ala Leu Pro Ala Thr Thr Asn
        3700            3705                3710

Ala Thr Ala Pro Ala Thr Ala Asn Gly Gly Gly Ser Ala Ala Ala Ala
        3715            3720                3725

Pro Tyr Gly Ile His Pro Ala Leu Leu Asp Ala Ser Leu His Ala Ile
        3730            3735                3740

Ala Val Gly Gly Leu Val Asp Glu Pro Glu Leu Val Arg Val Pro Phe
3745            3750            3755                3760

His Trp Ser Gly Val Thr Val His Ala Ala Gly Ala Ala Ala Ala Arg
            3765            3770                3775

Val Arg Leu Ala Ser Ala Gly Thr Asp Ala Val Ser Leu Ser Leu Thr
        3780            3785                3790

Asp Gly Glu Gly Arg Pro Leu Val Ser Val Glu Arg Leu Thr Leu Arg
```

```
                    3795                3800                3805

Pro Val Thr Ala Asp Gln Ala Ala Ala Ser Arg Val Gly Gly Leu Met
         3810                3815                3820

His Arg Val Ala Trp Arg Pro Tyr Ala Leu Ala Ser Ser Gly Glu Gln
3825                3830                3835                3840

Asp Pro His Ala Thr Ser Tyr Gly Pro Thr Ala Val Leu Gly Lys Asp
         3845                3850                3855

Glu Leu Lys Val Ala Ala Ala Leu Glu Ser Ala Gly Val Glu Val Gly
             3860                3865                3870

Leu Tyr Pro Asp Leu Ala Ala Leu Ser Gln Asp Val Ala Ala Gly Ala
         3875                3880                3885

Pro Ala Pro Arg Thr Val Leu Ala Pro Leu Pro Ala Gly Pro Ala Asp
         3890                3895                3900

Gly Gly Ala Glu Gly Val Arg Gly Thr Val Ala Arg Thr Leu Glu Leu
3905                3910                3915                3920

Leu Gln Ala Trp Leu Ala Asp Glu His Leu Ala Gly Thr Arg Leu Leu
             3925                3930                3935

Leu Val Thr Arg Gly Ala Val Arg Asp Pro Glu Gly Ser Gly Ala Asp
             3940                3945                3950

Asp Gly Gly Glu Asp Leu Ser His Ala Ala Ala Trp Gly Leu Val Arg
         3955                3960                3965

Thr Ala Gln Thr Glu Asn Pro Gly Arg Phe Gly Leu Leu Asp Leu Ala
         3970                3975                3980

Asp Asp Ala Ser Ser Tyr Arg Thr Leu Pro Ser Val Leu Ser Asp Ala
3985                3990                3995                4000

Gly Leu Arg Asp Glu Pro Gln Leu Ala Leu His Asp Gly Thr Ile Arg
             4005                4010                4015

Leu Ala Arg Leu Ala Ser Val Arg Pro Glu Thr Gly Thr Ala Ala Pro
         4020                4025                4030

Ala Leu Ala Pro Glu Gly Thr Val Leu Leu Thr Gly Gly Thr Gly Gly
         4035                4040                4045

Leu Gly Gly Leu Val Ala Arg His Val Val Gly Glu Trp Gly Val Arg
         4050                4055                4060

Arg Leu Leu Leu Val Ser Arg Arg Gly Thr Asp Ala Pro Gly Ala Asp
4065                4070                4075                4080

Glu Leu Val His Glu Leu Glu Ala Leu Gly Ala Asp Val Ser Val Ala
             4085                4090                4095

Ala Cys Asp Val Ala Asp Arg Glu Ala Leu Thr Ala Val Leu Asp Ala
         4100                4105                4110

Ile Pro Ala Glu His Pro Leu Thr Ala Val His Thr Ala Gly Val
         4115                4120                4125

Leu Ser Asp Gly Thr Leu Pro Ser Met Thr Thr Glu Asp Val Glu His
         4130                4135                4140

Val Leu Arg Pro Lys Val Asp Ala Ala Phe Leu Leu Asp Glu Leu Thr
4145                4150                4155                4160

Ser Thr Pro Ala Tyr Asp Leu Ala Ala Phe Val Met Phe Ser Ser Ala
             4165                4170                4175

Ala Ala Val Phe Gly Gly Ala Gly Gln Gly Ala Tyr Ala Ala Ala Asn
         4180                4185                4190

Ala Thr Leu Asp Ala Leu Ala Trp Arg Arg Arg Ala Ala Gly Leu Pro
         4195                4200                4205

Ala Leu Ser Leu Gly Trp Gly Leu Trp Ala Glu Thr Ser Gly Met Thr
         4210                4215                4220
```

-continued

Gly Glu Leu Gly Gln Ala Asp Leu Arg Arg Met Ser Arg Ala Gly Ile
4225                4230                4235                4240

Gly Gly Ile Ser Asp Ala Glu Gly Ile Ala Leu Leu Asp Ala Ala Leu
            4245                4250                4255

Arg Asp Asp Arg His Pro Val Leu Leu Pro Leu Arg Leu Asp Ala Ala
        4260                4265                4270

Gly Leu Arg Asp Ala Ala Gly Asn Asp Pro Ala Gly Ile Pro Ala Leu
    4275                4280                4285

Phe Arg Asp Val Val Gly Ala Arg Thr Val Arg Ala Arg Pro Ser Ala
4290                4295                4300

Ala Ser Ala Ser Thr Thr Ala Gly Thr Ala Gly Thr Pro Gly Thr Ala
4305                4310                4315                4320

Asp Gly Ala Ala Glu Thr Ala Ala Val Thr Leu Ala Asp Arg Ala Ala
            4325                4330                4335

Thr Val Asp Gly Pro Ala Arg Gln Arg Leu Leu Leu Glu Phe Val Val
        4340                4345                4350

Gly Glu Val Ala Glu Val Leu Gly His Ala Arg Gly His Arg Ile Asp
    4355                4360                4365

Ala Glu Arg Gly Phe Leu Asp Leu Gly Phe Asp Ser Leu Thr Ala Val
4370                4375                4380

Glu Leu Arg Asn Arg Leu Asn Ser Ala Gly Gly Leu Ala Leu Pro Ala
4385                4390                4395                4400

Thr Leu Val Phe Asp His Pro Ser Pro Ala Ala Leu Ala Ser His Leu
            4405                4410                4415

Asp Ala Glu Leu Pro Arg Gly Ala Ser Asp Gln Asp Gly Ala Gly Asn
        4420                4425                4430

Arg Asn Gly Asn Glu Asn Gly Thr Thr Ala Ser Arg Ser Thr Ala Glu
    4435                4440                4445

Thr Asp Ala Leu Leu Ala Gln Leu Thr Arg Leu Glu Gly Ala Leu Val
4450                4455                4460

Leu Thr Gly Leu Ser Asp Ala Pro Gly Ser Glu Glu Val Leu Glu His
4465                4470                4475                4480

Leu Arg Ser Leu Arg Ser Met Val Thr Gly Glu Thr Gly Thr Gly Thr
            4485                4490                4495

Ala Ser Gly Ala Pro Asp Gly Ala Gly Ser Gly Ala Glu Asp Arg Pro
        4500                4505                4510

Trp Ala Ala Gly Asp Gly Ala Gly Gly Gly Ser Glu Asp Gly Ala Gly
    4515                4520                4525

Val Pro Asp Phe Met Asn Ala Ser Ala Glu Glu Leu Phe Gly Leu Leu
4530                4535                4540

Asp Gln Asp Pro Ser Thr Asp
4545                4550

<210> SEQ ID NO 2
<211> LENGTH: 3739
<212> TYPE: PRT
<213> ORGANISM: Streptomyces venezuelae

<400> SEQUENCE: 2

Val Ser Thr Val Asn Glu Glu Lys Tyr Leu Asp Tyr Leu Arg Arg Ala
1               5                   10                  15

Thr Ala Asp Leu His Glu Ala Arg Gly Arg Leu Arg Glu Leu Glu Ala
            20                  25                  30

Lys Ala Gly Glu Pro Val Ala Ile Val Gly Met Ala Cys Arg Leu Pro

-continued

```
               35                  40                  45
Gly Gly Val Ala Ser Pro Glu Asp Leu Trp Arg Leu Val Ala Gly Gly
            50                  55                  60
Glu Asp Ala Ile Ser Glu Phe Pro Gln Asp Arg Gly Trp Asp Val Glu
 65                  70                  75                  80
Gly Leu Tyr Asp Pro Asn Pro Glu Ala Thr Gly Lys Ser Tyr Ala Arg
                85                  90                  95
Glu Ala Gly Phe Leu Tyr Glu Ala Gly Glu Phe Asp Ala Asp Phe Phe
                100                 105                 110
Gly Ile Ser Pro Arg Glu Ala Leu Ala Met Asp Pro Gln Gln Arg Leu
                115                 120                 125
Leu Leu Glu Ala Ser Trp Glu Ala Phe Glu His Ala Gly Ile Pro Ala
            130                 135                 140
Ala Thr Ala Arg Gly Thr Ser Val Gly Val Phe Thr Gly Val Met Tyr
145                 150                 155                 160
His Asp Tyr Ala Thr Arg Leu Thr Asp Val Pro Glu Gly Ile Glu Gly
                165                 170                 175
Tyr Leu Gly Thr Gly Asn Ser Gly Ser Val Ala Ser Gly Arg Val Ala
                180                 185                 190
Tyr Thr Leu Gly Leu Glu Gly Pro Ala Val Thr Val Asp Thr Ala Cys
            195                 200                 205
Ser Ser Ser Leu Val Ala Leu His Leu Ala Val Gln Ala Leu Arg Lys
        210                 215                 220
Gly Glu Val Asp Met Ala Leu Ala Gly Gly Val Thr Val Met Ser Thr
225                 230                 235                 240
Pro Ser Thr Phe Val Glu Phe Ser Arg Gln Arg Gly Leu Ala Pro Asp
                245                 250                 255
Gly Arg Ser Lys Ser Phe Ser Ser Thr Ala Asp Gly Thr Ser Trp Ser
                260                 265                 270
Glu Gly Val Gly Val Leu Leu Val Glu Arg Leu Ser Asp Ala Arg Arg
            275                 280                 285
Lys Gly His Arg Ile Leu Ala Val Val Arg Gly Thr Ala Val Asn Gln
        290                 295                 300
Asp Gly Ala Ser Ser Gly Leu Thr Ala Pro Asn Gly Pro Ser Gln Gln
305                 310                 315                 320
Arg Val Ile Arg Arg Ala Leu Ala Asp Ala Arg Leu Thr Thr Ser Asp
                325                 330                 335
Val Asp Val Val Glu Ala His Gly Thr Gly Thr Arg Leu Gly Asp Pro
                340                 345                 350
Ile Glu Ala Gln Ala Val Ile Ala Thr Tyr Gly Gln Gly Arg Asp Gly
            355                 360                 365
Glu Gln Pro Leu Arg Leu Gly Ser Leu Lys Ser Asn Ile Gly His Thr
        370                 375                 380
Gln Ala Ala Ala Gly Val Ser Gly Val Ile Lys Met Val Gln Ala Met
385                 390                 395                 400
Arg His Gly Val Leu Pro Lys Thr Leu His Val Glu Lys Pro Thr Asp
                405                 410                 415
Gln Val Asp Trp Ser Ala Gly Ala Val Glu Leu Leu Thr Glu Ala Met
                420                 425                 430
Asp Trp Pro Asp Lys Gly Asp Gly Gly Leu Arg Arg Ala Ala Val Ser
            435                 440                 445
Ser Phe Gly Val Ser Gly Thr Asn Ala His Val Val Leu Glu Glu Ala
        450                 455                 460
```

-continued

```
Pro Ala Ala Glu Glu Thr Pro Ala Ser Glu Ala Thr Pro Ala Val Glu
465                 470                 475                 480

Pro Ser Val Gly Ala Gly Leu Val Pro Trp Leu Val Ser Ala Lys Thr
            485                 490                 495

Pro Ala Ala Leu Asp Ala Gln Ile Gly Arg Leu Ala Ala Phe Ala Ser
        500                 505                 510

Gln Gly Arg Thr Asp Ala Ala Asp Pro Gly Ala Val Ala Arg Val Leu
        515                 520                 525

Ala Gly Gly Arg Ala Glu Phe Glu His Arg Ala Val Val Leu Gly Thr
    530                 535                 540

Gly Gln Asp Asp Phe Ala Gln Ala Leu Thr Ala Pro Glu Gly Leu Ile
545                 550                 555                 560

Arg Gly Thr Pro Ser Asp Val Gly Arg Val Ala Phe Val Phe Pro Gly
            565                 570                 575

Gln Gly Thr Gln Trp Ala Gly Met Gly Ala Glu Leu Leu Asp Val Ser
            580                 585                 590

Lys Glu Phe Ala Ala Ala Met Ala Glu Cys Glu Ser Ala Leu Ser Arg
    595                 600                 605

Tyr Val Asp Trp Ser Leu Glu Ala Val Val Arg Gln Ala Pro Gly Ala
    610                 615                 620

Pro Thr Leu Glu Arg Val Asp Val Val Gln Pro Val Thr Phe Ala Val
625                 630                 635                 640

Met Val Ser Leu Ala Lys Val Trp Gln His His Gly Val Thr Pro Gln
                645                 650                 655

Ala Val Val Gly His Ser Gln Gly Glu Ile Ala Ala Tyr Val Ala
                660                 665                 670

Gly Ala Leu Thr Leu Asp Asp Ala Ala Arg Val Val Thr Leu Arg Ser
            675                 680                 685

Lys Ser Ile Ala Ala His Leu Ala Gly Lys Gly Met Ile Ser Leu
    690                 695                 700

Ala Leu Ser Glu Glu Ala Thr Arg Gln Arg Ile Glu Asn Leu His Gly
705                 710                 715                 720

Leu Ser Ile Ala Ala Val Asn Gly Pro Thr Ala Thr Val Val Ser Gly
                725                 730                 735

Asp Pro Thr Gln Ile Gln Glu Leu Ala Gln Ala Cys Glu Ala Asp Gly
            740                 745                 750

Val Arg Ala Arg Ile Ile Pro Val Asp Tyr Ala Ser His Ser Ala His
            755                 760                 765

Val Glu Thr Ile Glu Ser Glu Leu Ala Glu Val Leu Ala Gly Leu Ser
770                 775                 780

Pro Arg Thr Pro Glu Val Pro Phe Phe Ser Thr Leu Glu Gly Ala Trp
785                 790                 795                 800

Ile Thr Glu Pro Val Leu Asp Gly Thr Tyr Trp Tyr Arg Asn Leu Arg
                805                 810                 815

His Arg Val Gly Phe Ala Pro Ala Val Glu Thr Leu Ala Thr Asp Glu
            820                 825                 830

Gly Phe Thr His Phe Ile Glu Val Ser Ala His Pro Val Leu Thr Met
            835                 840                 845

Thr Leu Pro Glu Thr Val Thr Gly Leu Gly Thr Leu Arg Arg Glu Gln
        850                 855                 860

Gly Gly Gln Glu Arg Leu Val Thr Ser Leu Ala Glu Ala Trp Thr Asn
865                 870                 875                 880
```

-continued

```
Gly Leu Thr Ile Asp Trp Ala Pro Val Leu Pro Thr Ala Thr Gly His
            885                 890                 895

His Pro Glu Leu Pro Thr Tyr Ala Phe Gln Arg Arg His Tyr Trp Leu
        900                 905                 910

His Asp Ser Pro Ala Val Gln Gly Ser Val Gln Asp Ser Trp Arg Tyr
    915                 920                 925

Arg Ile Asp Trp Lys Arg Leu Ala Val Ala Asp Ala Ser Glu Arg Ala
    930                 935                 940

Gly Leu Ser Gly Arg Trp Leu Val Val Pro Glu Asp Arg Ser Ala
945                 950                 955                 960

Glu Ala Ala Pro Val Leu Ala Ala Leu Ser Gly Ala Gly Ala Asp Pro
                965                 970                 975

Val Gln Leu Asp Val Ser Pro Leu Gly Asp Arg Gln Arg Leu Ala Ala
            980                 985                 990

Thr Leu Gly Glu Ala Leu Ala Ala Gly Gly Ala Val Asp Gly Val
        995                 1000                1005

Leu Ser Leu Leu Ala Trp Asp Glu Ser Ala His Pro Gly His Pro Ala
    1010                1015                1020

Pro Phe Thr Arg Gly Thr Gly Ala Thr Leu Thr Leu Val Gln Ala Leu
1025                1030                1035                1040

Glu Asp Ala Gly Val Ala Ala Pro Leu Trp Cys Val Thr His Gly Ala
                1045                1050                1055

Val Ser Val Gly Arg Ala Asp His Val Thr Ser Pro Ala Gln Ala Met
            1060                1065                1070

Val Trp Gly Met Gly Arg Val Ala Ala Leu Glu His Pro Glu Arg Trp
        1075                1080                1085

Gly Gly Leu Ile Asp Leu Pro Ser Asp Ala Asp Arg Ala Ala Leu Asp
    1090                1095                1100

Arg Met Thr Thr Val Leu Ala Gly Gly Thr Gly Glu Asp Gln Val Ala
1105                1110                1115                1120

Val Arg Ala Ser Gly Leu Leu Ala Arg Arg Leu Val Arg Ala Ser Leu
                1125                1130                1135

Pro Ala His Gly Thr Ala Ser Pro Trp Trp Gln Ala Asp Gly Thr Val
            1140                1145                1150

Leu Val Thr Gly Ala Glu Glu Pro Ala Ala Ala Glu Ala Ala Arg Arg
        1155                1160                1165

Leu Ala Arg Asp Gly Ala Gly His Leu Leu His Thr Thr Pro Ser
    1170                1175                1180

Gly Ser Glu Gly Ala Glu Gly Thr Ser Gly Ala Ala Glu Asp Ser Gly
1185                1190                1195                1200

Leu Ala Gly Leu Val Ala Glu Leu Ala Asp Leu Gly Ala Thr Ala Thr
                1205                1210                1215

Val Val Thr Cys Asp Leu Thr Asp Ala Glu Ala Ala Arg Leu Leu
            1220                1225                1230

Ala Gly Val Ser Asp Ala His Pro Leu Ser Ala Val Leu His Leu Pro
        1235                1240                1245

Pro Thr Val Asp Ser Glu Pro Leu Ala Ala Thr Asp Ala Asp Ala Leu
    1250                1255                1260

Ala Arg Val Val Thr Ala Lys Ala Thr Ala Ala Leu His Leu Asp Arg
1265                1270                1275                1280

Leu Leu Arg Glu Ala Ala Ala Ala Gly Gly Arg Pro Pro Val Leu Val
                1285                1290                1295

Leu Phe Ser Ser Val Ala Ala Ile Trp Gly Gly Ala Gly Gln Gly Ala
```

-continued

```
             1300            1305            1310
Tyr Ala Ala Gly Thr Ala Phe Leu Asp Ala Leu Ala Gly Gln His Arg
             1315            1320            1325
Ala Asp Gly Pro Thr Val Thr Ser Val Ala Trp Ser Pro Trp Glu Gly
1330            1335            1340
Ser Arg Val Thr Glu Gly Ala Thr Gly Glu Arg Leu Arg Arg Leu Gly
1345            1350            1355            1360
Leu Arg Pro Leu Ala Pro Ala Thr Ala Leu Thr Ala Leu Asp Thr Ala
             1365            1370            1375
Leu Gly His Gly Asp Thr Ala Val Thr Ile Ala Asp Val Asp Trp Ser
             1380            1385            1390
Ser Phe Ala Pro Gly Phe Thr Thr Ala Arg Pro Gly Thr Leu Leu Ala
             1395            1400            1405
Asp Leu Pro Glu Ala Arg Arg Ala Leu Asp Glu Gln Gln Ser Thr Thr
       1410            1415            1420
Ala Ala Asp Asp Thr Val Leu Ser Arg Glu Leu Gly Ala Leu Thr Gly
1425            1430            1435            1440
Ala Glu Gln Gln Arg Arg Met Gln Glu Leu Val Arg Glu His Leu Ala
             1445            1450            1455
Val Val Leu Asn His Pro Ser Pro Glu Ala Val Asp Thr Gly Arg Ala
             1460            1465            1470
Phe Arg Asp Leu Gly Phe Asp Ser Leu Thr Ala Val Glu Leu Arg Asn
             1475            1480            1485
Arg Leu Lys Asn Ala Thr Gly Leu Ala Leu Pro Ala Thr Leu Val Phe
             1490            1495            1500
Asp Tyr Pro Thr Pro Arg Thr Leu Ala Glu Phe Leu Leu Ala Glu Ile
1505            1510            1515            1520
Leu Gly Glu Gln Ala Gly Ala Gly Glu Gln Leu Pro Val Asp Gly Gly
             1525            1530            1535
Val Asp Asp Glu Pro Val Ala Ile Val Gly Met Ala Cys Arg Leu Pro
             1540            1545            1550
Gly Gly Val Ala Ser Pro Glu Asp Leu Trp Arg Leu Val Ala Gly Gly
             1555            1560            1565
Glu Asp Ala Ile Ser Gly Phe Pro Gln Asp Arg Gly Trp Asp Val Glu
       1570            1575            1580
Gly Leu Tyr Asp Pro Asp Pro Asp Ala Ser Gly Arg Thr Tyr Cys Arg
1585            1590            1595            1600
Ala Gly Gly Phe Leu Asp Glu Ala Gly Glu Phe Asp Ala Asp Phe Phe
             1605            1610            1615
Gly Ile Ser Pro Arg Glu Ala Leu Ala Met Asp Pro Gln Gln Arg Leu
             1620            1625            1630
Leu Leu Glu Thr Ser Trp Glu Ala Val Glu Asp Ala Gly Ile Asp Pro
             1635            1640            1645
Thr Ser Leu Gln Gly Gln Gln Val Gly Val Phe Ala Gly Thr Asn Gly
             1650            1655            1660
Pro His Tyr Glu Pro Leu Leu Arg Asn Thr Ala Glu Asp Leu Glu Gly
1665            1670            1675            1680
Tyr Val Gly Thr Gly Asn Ala Ala Ser Ile Met Ser Gly Arg Val Ser
             1685            1690            1695
Tyr Thr Leu Gly Leu Glu Gly Pro Ala Val Thr Val Asp Thr Ala Cys
             1700            1705            1710
Ser Ser Ser Leu Val Ala Leu His Leu Ala Val Gln Ala Leu Arg Lys
             1715            1720            1725
```

-continued

```
Gly Glu Cys Gly Leu Ala Leu Ala Gly Gly Val Thr Val Met Ser Thr
    1730                1735                1740
Pro Thr Thr Phe Val Glu Phe Ser Arg Gln Arg Gly Leu Ala Glu Asp
1745                1750                1755                1760
Gly Arg Ser Lys Ala Phe Ala Ala Ser Ala Asp Gly Phe Gly Pro Ala
            1765                1770                1775
Glu Gly Val Gly Met Leu Leu Val Glu Arg Leu Ser Asp Ala Arg Arg
            1780                1785                1790
Asn Gly His Arg Val Leu Ala Val Val Arg Gly Ser Ala Val Asn Gln
        1795                1800                1805
Asp Gly Ala Ser Asn Gly Leu Thr Ala Pro Asn Gly Pro Ser Gln Gln
    1810                1815                1820
Arg Val Ile Arg Arg Ala Leu Ala Asp Ala Arg Leu Thr Thr Ala Asp
1825                1830                1835                1840
Val Asp Val Val Glu Ala His Gly Thr Gly Thr Arg Leu Gly Asp Pro
            1845                1850                1855
Ile Glu Ala Gln Ala Leu Ile Ala Thr Tyr Gly Gln Gly Arg Asp Thr
            1860                1865                1870
Glu Gln Pro Leu Arg Leu Gly Ser Leu Lys Ser Asn Ile Gly His Thr
        1875                1880                1885
Gln Ala Ala Ala Gly Val Ser Gly Ile Ile Lys Met Val Gln Ala Met
1890                1895                1900
Arg His Gly Val Leu Pro Lys Thr Leu His Val Asp Arg Pro Ser Asp
1905                1910                1915                1920
Gln Ile Asp Trp Ser Ala Gly Thr Val Glu Leu Leu Thr Glu Ala Met
            1925                1930                1935
Asp Trp Pro Arg Lys Gln Glu Gly Gly Leu Arg Arg Ala Ala Val Ser
            1940                1945                1950
Ser Phe Gly Ile Ser Gly Thr Asn Ala His Ile Val Leu Glu Glu Ala
        1955                1960                1965
Pro Val Asp Glu Asp Ala Pro Ala Asp Glu Pro Ser Val Gly Gly Val
    1970                1975                1980
Val Pro Trp Leu Val Ser Ala Lys Thr Pro Ala Ala Leu Asp Ala Gln
1985                1990                1995                2000
Ile Gly Arg Leu Ala Ala Phe Ala Ser Gln Gly Arg Thr Asp Ala Ala
            2005                2010                2015
Asp Pro Gly Ala Val Ala Arg Val Leu Ala Gly Gly Arg Ala Gln Phe
            2020                2025                2030
Glu His Arg Ala Val Ala Leu Gly Thr Gly Gln Asp Asp Leu Ala Ala
        2035                2040                2045
Ala Leu Ala Ala Pro Glu Gly Leu Val Arg Gly Val Ala Ser Gly Val
    2050                2055                2060
Gly Arg Val Ala Phe Val Phe Pro Gly Gln Gly Thr Gln Trp Ala Gly
2065                2070                2075                2080
Met Gly Ala Glu Leu Leu Asp Val Ser Lys Glu Phe Ala Ala Ala Met
            2085                2090                2095
Ala Glu Cys Glu Ala Ala Leu Ala Pro Tyr Val Asp Trp Ser Leu Glu
        2100                2105                2110
Ala Val Val Arg Gln Ala Pro Gly Ala Pro Thr Leu Glu Arg Val Asp
            2115                2120                2125
Val Val Gln Pro Val Thr Phe Ala Val Met Val Ser Leu Ala Lys Val
    2130                2135                2140
```

-continued

```
Trp Gln His His Gly Val Thr Pro Gln Ala Val Val Gly His Ser Gln
2145                2150                2155                2160

Gly Glu Ile Ala Ala Ala Tyr Val Ala Gly Ala Leu Ser Leu Asp Asp
            2165                2170                2175

Ala Ala Arg Val Val Thr Leu Arg Ser Lys Ser Ile Gly Ala His Leu
        2180                2185                2190

Ala Gly Gln Gly Gly Met Leu Ser Leu Ala Leu Ser Glu Ala Ala Val
    2195                2200                2205

Val Glu Arg Leu Ala Gly Phe Asp Gly Leu Ser Val Ala Ala Val Asn
2210                2215                2220

Gly Pro Thr Ala Thr Val Val Ser Gly Asp Pro Thr Gln Ile Gln Glu
2225                2230                2235                2240

Leu Ala Gln Ala Cys Glu Ala Asp Gly Val Arg Ala Arg Ile Ile Pro
            2245                2250                2255

Val Asp Tyr Ala Ser His Ser Ala His Val Glu Thr Ile Glu Ser Glu
        2260                2265                2270

Leu Ala Asp Val Leu Ala Gly Leu Ser Pro Gln Thr Pro Gln Val Pro
    2275                2280                2285

Phe Phe Ser Thr Leu Glu Gly Ala Trp Ile Thr Glu Pro Ala Leu Asp
    2290                2295                2300

Gly Gly Tyr Trp Tyr Arg Asn Leu Arg His Arg Val Gly Phe Ala Pro
2305                2310                2315                2320

Ala Val Glu Thr Leu Ala Thr Asp Glu Gly Phe Thr His Phe Val Glu
            2325                2330                2335

Val Ser Ala His Pro Val Leu Thr Met Ala Leu Pro Glu Thr Val Thr
        2340                2345                2350

Gly Leu Gly Thr Leu Arg Arg Asp Asn Gly Gly Gln His Arg Leu Thr
    2355                2360                2365

Thr Ser Leu Ala Glu Ala Trp Ala Asn Gly Leu Thr Val Asp Trp Ala
    2370                2375                2380

Ser Leu Leu Pro Thr Thr Thr Thr His Pro Asp Leu Pro Thr Tyr Ala
2385                2390                2395                2400

Phe Gln Thr Glu Arg Tyr Trp Pro Gln Pro Asp Leu Ser Ala Ala Gly
            2405                2410                2415

Asp Ile Thr Ser Ala Gly Leu Gly Ala Ala Glu His Pro Leu Leu Gly
        2420                2425                2430

Ala Ala Val Ala Leu Ala Asp Ser Asp Gly Cys Leu Leu Thr Gly Ser
    2435                2440                2445

Leu Ser Leu Arg Thr His Pro Trp Leu Ala Asp His Ala Val Ala Gly
    2450                2455                2460

Thr Val Leu Leu Pro Gly Thr Ala Phe Val Glu Leu Ala Phe Arg Ala
2465                2470                2475                2480

Gly Asp Gln Val Gly Cys Asp Leu Val Glu Glu Leu Thr Leu Asp Ala
            2485                2490                2495

Pro Leu Val Leu Pro Arg Arg Gly Ala Val Arg Val Gln Leu Ser Val
        2500                2505                2510

Gly Ala Ser Asp Glu Ser Gly Arg Arg Thr Phe Gly Leu Tyr Ala His
    2515                2520                2525

Pro Glu Asp Ala Pro Gly Glu Ala Glu Trp Thr Arg His Ala Thr Gly
    2530                2535                2540

Val Leu Ala Ala Arg Ala Asp Arg Thr Ala Pro Val Ala Asp Pro Glu
2545                2550                2555                2560

Ala Trp Pro Pro Pro Gly Ala Glu Pro Val Asp Val Asp Gly Leu Tyr
```

-continued

```
                2565                2570                2575

Glu Arg Phe Ala Ala Asn Gly Tyr Gly Tyr Gly Pro Leu Phe Gln Gly
            2580                2585                2590

Val Arg Gly Val Trp Arg Arg Gly Asp Glu Val Phe Ala Asp Val Ala
        2595                2600                2605

Leu Pro Ala Glu Val Ala Gly Ala Glu Gly Ala Arg Phe Gly Leu His
    2610                2615                2620

Pro Ala Leu Leu Asp Ala Ala Val Gln Ala Ala Gly Ala Gly Gly Ala
2625                2630                2635                2640

Phe Gly Ala Gly Thr Arg Leu Pro Phe Ala Trp Ser Gly Ile Ser Leu
            2645                2650                2655

Tyr Ala Val Gly Ala Thr Ala Leu Arg Val Arg Leu Ala Pro Ala Gly
        2660                2665                2670

Pro Asp Thr Val Ser Val Ser Ala Ala Asp Ser Ser Gly Gln Pro Val
    2675                2680                2685

Phe Ala Ala Asp Ser Leu Thr Val Leu Pro Val Asp Pro Ala Gln Leu
    2690                2695                2700

Ala Ala Phe Ser Asp Pro Thr Leu Asp Ala Leu His Leu Leu Glu Trp
2705                2710                2715                2720

Thr Ala Trp Asp Gly Ala Ala Gln Ala Leu Pro Gly Ala Val Val Leu
            2725                2730                2735

Gly Gly Asp Ala Asp Gly Leu Ala Ala Ala Leu Arg Ala Gly Gly Thr
        2740                2745                2750

Glu Val Leu Ser Phe Pro Asp Leu Thr Asp Leu Val Glu Ala Val Asp
    2755                2760                2765

Arg Gly Glu Thr Pro Ala Pro Ala Thr Val Leu Val Ala Cys Pro Ala
    2770                2775                2780

Ala Gly Pro Gly Gly Pro Glu His Val Arg Glu Ala Leu His Gly Ser
2785                2790                2795                2800

Leu Ala Leu Met Gln Ala Trp Leu Ala Asp Glu Arg Phe Thr Asp Gly
            2805                2810                2815

Arg Leu Val Leu Val Thr Arg Asp Ala Val Ala Ala Arg Ser Gly Asp
        2820                2825                2830

Gly Leu Arg Ser Thr Gly Gln Ala Ala Val Trp Gly Leu Gly Arg Ser
    2835                2840                2845

Ala Gln Thr Glu Ser Pro Gly Arg Phe Val Leu Leu Asp Leu Ala Gly
    2850                2855                2860

Glu Ala Arg Thr Ala Gly Asp Ala Thr Ala Gly Asp Gly Leu Thr Thr
2865                2870                2875                2880

Gly Asp Ala Thr Val Gly Gly Thr Ser Gly Asp Ala Ala Leu Gly Ser
            2885                2890                2895

Ala Leu Ala Thr Ala Leu Gly Ser Gly Glu Pro Gln Leu Ala Leu Arg
        2900                2905                2910

Asp Gly Ala Leu Leu Val Pro Arg Leu Ala Arg Ala Ala Ala Pro Ala
    2915                2920                2925

Ala Ala Asp Gly Leu Ala Leu Ala Asp Gly Leu Ala Ala Leu Pro Leu
    2930                2935                2940

Pro Ala Ala Pro Ala Leu Trp Arg Leu Glu Pro Gly Thr Asp Gly Ser
2945                2950                2955                2960

Leu Glu Ser Leu Thr Ala Ala Pro Gly Asp Ala Glu Thr Leu Ala Pro
            2965                2970                2975

Glu Pro Leu Gly Pro Gly Gln Val Arg Ile Ala Ile Arg Ala Thr Gly
        2980                2985                2990
```

-continued

```
Leu Asn Phe Arg Asp Val Leu Ile Ala Leu Gly Met Tyr Pro Asp Pro
    2995                3000                3005
Ala Leu Met Gly Thr Glu Gly Ala Gly Val Val Thr Ala Thr Gly Pro
    3010                3015                3020
Gly Val Thr His Leu Ala Pro Gly Asp Arg Val Met Gly Leu Leu Ser
3025                3030                3035                3040
Gly Ala Tyr Ala Pro Val Val Ala Asp Ala Arg Thr Val Ala Arg
            3045                3050                3055
Met Pro Glu Gly Trp Thr Phe Ala Gln Gly Ala Ser Val Pro Val Val
            3060                3065                3070
Phe Leu Thr Ala Val Tyr Ala Leu Arg Asp Leu Ala Asp Val Lys Pro
    3075                3080                3085
Gly Glu Arg Leu Leu Val His Ser Ala Ala Gly Gly Val Gly Met Ala
    3090                3095                3100
Ala Val Gln Leu Ala Arg His Trp Gly Val Glu Val His Gly Thr Ala
3105                3110                3115                3120
Ser His Gly Lys Trp Asp Ala Leu Arg Ala Leu Gly Leu Asp Asp Ala
            3125                3130                3135
His Ile Ala Ser Ser Arg Thr Leu Asp Phe Glu Ser Ala Phe Arg Ala
            3140                3145                3150
Ala Ser Gly Gly Ala Gly Met Asp Val Val Leu Asn Ser Leu Ala Arg
    3155                3160                3165
Glu Phe Val Asp Ala Ser Leu Arg Leu Leu Gly Pro Gly Gly Arg Phe
    3170                3175                3180
Val Glu Met Gly Lys Thr Asp Val Arg Asp Ala Glu Arg Val Ala Ala
3185                3190                3195                3200
Asp His Pro Gly Val Gly Tyr Arg Ala Phe Asp Leu Gly Glu Ala Gly
            3205                3210                3215
Pro Glu Arg Ile Gly Glu Met Leu Ala Glu Val Ile Ala Leu Phe Glu
            3220                3225                3230
Asp Gly Val Leu Arg His Leu Pro Val Thr Thr Trp Asp Val Arg Arg
    3235                3240                3245
Ala Arg Asp Ala Phe Arg His Val Ser Gln Ala Arg His Thr Gly Lys
    3250                3255                3260
Val Val Leu Thr Met Pro Ser Gly Leu Asp Pro Glu Gly Thr Val Leu
3265                3270                3275                3280
Leu Thr Gly Gly Thr Gly Ala Leu Gly Gly Ile Val Ala Arg His Val
            3285                3290                3295
Val Gly Glu Trp Gly Val Arg Arg Leu Leu Leu Val Ser Arg Arg Gly
            3300                3305                3310
Thr Asp Ala Pro Gly Ala Gly Glu Leu Val His Glu Leu Glu Ala Leu
            3315                3320                3325
Gly Ala Asp Val Ser Val Ala Ala Cys Asp Val Ala Asp Arg Glu Ala
    3330                3335                3340
Leu Thr Ala Val Leu Asp Ser Ile Pro Ala Glu His Pro Leu Thr Ala
3345                3350                3355                3360
Val Val His Thr Ala Gly Val Leu Ser Asp Gly Thr Leu Pro Ser Met
            3365                3370                3375
Thr Ala Glu Asp Val Glu His Val Leu Arg Pro Lys Val Asp Ala Ala
            3380                3385                3390
Phe Leu Leu Asp Glu Leu Thr Ser Thr Pro Gly Tyr Asp Leu Ala Ala
    3395                3400                3405
```

-continued

```
Phe Val Met Phe Ser Ser Ala Ala Val Phe Gly Gly Ala Gly Gln
    3410                3415                3420

Gly Ala Tyr Ala Ala Ala Asn Ala Thr Leu Asp Ala Leu Ala Trp Arg
3425                3430                3435                3440

Arg Arg Thr Ala Gly Leu Pro Ala Leu Ser Leu Gly Trp Gly Leu Trp
            3445                3450                3455

Ala Glu Thr Ser Gly Met Thr Gly Gly Leu Ser Asp Thr Asp Arg Ser
            3460                3465                3470

Arg Leu Ala Arg Ser Gly Ala Thr Pro Met Asp Ser Glu Leu Thr Leu
        3475                3480                3485

Ser Leu Leu Asp Ala Ala Met Arg Arg Asp Asp Pro Ala Leu Val Pro
        3490                3495                3500

Ile Ala Leu Asp Val Ala Ala Leu Arg Ala Gln Gln Arg Asp Gly Met
3505                3510                3515                3520

Leu Ala Pro Leu Leu Ser Gly Leu Thr Arg Gly Ser Arg Val Gly Gly
            3525                3530                3535

Ala Pro Val Asn Gln Arg Arg Ala Ala Ala Gly Gly Ala Gly Glu Ala
            3540                3545                3550

Asp Thr Asp Leu Gly Gly Arg Leu Ala Ala Met Thr Pro Asp Asp Arg
        3555                3560                3565

Val Ala His Leu Arg Asp Leu Val Arg Thr His Val Ala Thr Val Leu
        3570                3575                3580

Gly His Gly Thr Pro Ser Arg Val Asp Leu Glu Arg Ala Phe Arg Asp
3585                3590                3595                3600

Thr Gly Phe Asp Ser Leu Thr Ala Val Glu Leu Arg Asn Arg Leu Asn
            3605                3610                3615

Ala Ala Thr Gly Leu Arg Leu Pro Ala Thr Leu Val Phe Asp His Pro
            3620                3625                3630

Thr Pro Gly Glu Leu Ala Gly His Leu Leu Asp Glu Leu Ala Thr Ala
        3635                3640                3645

Ala Gly Gly Ser Trp Ala Glu Gly Thr Gly Ser Gly Asp Thr Ala Ser
        3650                3655                3660

Ala Thr Asp Arg Gln Thr Thr Ala Ala Leu Ala Glu Leu Asp Arg Leu
3665                3670                3675                3680

Glu Gly Val Leu Ala Ser Leu Ala Pro Ala Gly Gly Arg Pro Glu
            3685                3690                3695

Leu Ala Ala Arg Leu Arg Ala Leu Ala Ala Ala Leu Gly Asp Asp Gly
            3700                3705                3710

Asp Asp Ala Thr Asp Leu Asp Glu Ala Ser Asp Asp Leu Phe Ser
        3715                3720                3725

Phe Ile Asp Lys Glu Leu Gly Asp Ser Asp Phe
        3730                3735

<210> SEQ ID NO 3
<211> LENGTH: 1562
<212> TYPE: PRT
<213> ORGANISM: Streptomyces venezuelae

<400> SEQUENCE: 3

Met Ala Asn Asn Glu Asp Lys Leu Arg Asp Tyr Leu Lys Arg Val Thr
1               5                   10                  15

Ala Glu Leu Gln Gln Asn Thr Arg Arg Leu Arg Glu Ile Glu Gly Arg
            20                  25                  30

Thr His Glu Pro Val Ala Ile Val Gly Met Ala Cys Arg Leu Pro Gly
        35                  40                  45
```

-continued

```
Gly Val Ala Ser Pro Glu Asp Leu Trp Gln Leu Val Ala Gly Asp Gly
 50                  55                  60

Asp Ala Ile Ser Glu Phe Pro Gln Asp Arg Gly Trp Asp Val Glu Gly
 65                  70                  75                  80

Leu Tyr Asp Pro Asp Pro Asp Ala Ser Gly Arg Thr Tyr Cys Arg Ser
                 85                  90                  95

Gly Gly Phe Leu His Asp Ala Gly Glu Phe Asp Ala Asp Phe Phe Gly
                100                 105                 110

Ile Ser Pro Arg Glu Ala Leu Ala Met Asp Pro Gln Gln Arg Leu Ser
                115                 120                 125

Leu Thr Thr Ala Trp Glu Ala Ile Glu Ser Ala Gly Ile Asp Pro Thr
            130                 135                 140

Ala Leu Lys Gly Ser Gly Leu Gly Val Phe Val Gly Gly Trp His Thr
145                 150                 155                 160

Gly Tyr Thr Ser Gly Gln Thr Thr Ala Val Gln Ser Pro Glu Leu Glu
                165                 170                 175

Gly His Leu Val Ser Gly Ala Ala Leu Gly Phe Leu Ser Gly Arg Ile
                180                 185                 190

Ala Tyr Val Leu Gly Thr Asp Gly Pro Ala Leu Thr Val Asp Thr Ala
                195                 200                 205

Cys Ser Ser Leu Val Ala Leu His Leu Ala Val Gln Ala Leu Arg
210                 215                 220

Lys Gly Glu Cys Asp Met Ala Leu Ala Gly Gly Val Thr Val Met Pro
225                 230                 235                 240

Asn Ala Asp Leu Phe Val Gln Phe Ser Arg Gln Arg Gly Leu Ala Ala
                245                 250                 255

Asp Gly Arg Ser Lys Ala Phe Ala Thr Ser Ala Asp Gly Phe Gly Pro
                260                 265                 270

Ala Glu Gly Ala Gly Val Leu Leu Val Glu Arg Leu Ser Asp Ala Arg
            275                 280                 285

Arg Asn Gly His Arg Ile Leu Ala Val Val Arg Gly Ser Ala Val Asn
            290                 295                 300

Gln Asp Gly Ala Ser Asn Gly Leu Thr Ala Pro His Gly Pro Ser Gln
305                 310                 315                 320

Gln Arg Val Ile Arg Arg Ala Leu Ala Asp Ala Arg Leu Ala Pro Gly
                325                 330                 335

Asp Val Asp Val Val Glu Ala His Gly Thr Gly Thr Arg Leu Gly Asp
                340                 345                 350

Pro Ile Glu Ala Gln Ala Leu Ile Ala Thr Tyr Gly Gln Glu Lys Ser
                355                 360                 365

Ser Glu Gln Pro Leu Arg Leu Gly Ala Leu Lys Ser Asn Ile Gly His
            370                 375                 380

Thr Gln Ala Ala Ala Gly Val Ala Gly Val Ile Lys Met Val Gln Ala
385                 390                 395                 400

Met Arg His Gly Leu Leu Pro Lys Thr Leu His Val Asp Glu Pro Ser
                405                 410                 415

Asp Gln Ile Asp Trp Ser Ala Gly Thr Val Glu Leu Leu Thr Glu Ala
                420                 425                 430

Val Asp Trp Pro Glu Lys Gln Asp Gly Gly Leu Arg Arg Ala Ala Val
                435                 440                 445

Ser Ser Phe Gly Ile Ser Gly Thr Asn Ala His Val Val Leu Glu Glu
450                 455                 460
```

-continued

```
Ala Pro Ala Val Glu Asp Ser Pro Ala Val Glu Pro Ala Gly Gly
465                 470                 475                 480

Gly Val Val Pro Trp Pro Val Ser Ala Lys Thr Pro Ala Ala Leu Asp
            485                 490                 495

Ala Gln Ile Gly Gln Leu Ala Ala Tyr Ala Asp Gly Arg Thr Asp Val
            500                 505                 510

Asp Pro Ala Val Ala Ala Arg Ala Leu Val Asp Ser Arg Thr Ala Met
            515                 520                 525

Glu His Arg Ala Val Ala Val Gly Asp Ser Arg Glu Ala Leu Arg Asp
            530                 535                 540

Ala Leu Arg Met Pro Glu Gly Leu Val Arg Gly Thr Ser Ser Asp Val
545                 550                 555                 560

Gly Arg Val Ala Phe Val Phe Pro Gly Gln Gly Thr Gln Trp Ala Gly
                565                 570                 575

Met Gly Ala Glu Leu Leu Asp Ser Ser Pro Glu Phe Ala Ala Ser Met
            580                 585                 590

Ala Glu Cys Glu Thr Ala Leu Ser Arg Tyr Val Asp Trp Ser Leu Glu
            595                 600                 605

Ala Val Val Arg Gln Glu Pro Gly Ala Pro Thr Leu Asp Arg Val Asp
            610                 615                 620

Val Val Gln Pro Val Thr Phe Ala Val Met Val Ser Leu Ala Lys Val
625                 630                 635                 640

Trp Gln His His Gly Ile Thr Pro Gln Ala Val Val Gly His Ser Gln
                645                 650                 655

Gly Glu Ile Ala Ala Ala Tyr Val Ala Gly Ala Leu Thr Leu Asp Asp
            660                 665                 670

Ala Ala Arg Val Val Thr Leu Arg Ser Lys Ser Ile Ala Ala His Leu
            675                 680                 685

Ala Gly Lys Gly Met Ile Ser Leu Ala Leu Asp Glu Ala Ala Val
            690                 695                 700

Leu Lys Arg Leu Ser Asp Phe Asp Gly Leu Ser Val Ala Ala Val Asn
705                 710                 715                 720

Gly Pro Thr Ala Thr Val Val Ser Gly Asp Pro Thr Gln Ile Glu Glu
                725                 730                 735

Leu Ala Arg Thr Cys Glu Ala Asp Gly Val Arg Ala Arg Ile Ile Pro
            740                 745                 750

Val Asp Tyr Ala Ser His Ser Arg Gln Val Glu Ile Ile Glu Lys Glu
            755                 760                 765

Leu Ala Glu Val Leu Ala Gly Leu Ala Pro Gln Ala Pro His Val Pro
770                 775                 780

Phe Phe Ser Thr Leu Glu Gly Thr Trp Ile Thr Glu Pro Val Leu Asp
785                 790                 795                 800

Gly Thr Tyr Trp Tyr Arg Asn Leu Arg His Arg Val Gly Phe Ala Pro
                805                 810                 815

Ala Val Glu Thr Leu Ala Val Asp Gly Phe Thr His Phe Ile Glu Val
            820                 825                 830

Ser Ala His Pro Val Leu Thr Met Thr Leu Pro Glu Thr Val Thr Gly
            835                 840                 845

Leu Gly Thr Leu Arg Arg Glu Gln Gly Gly Gln Glu Arg Leu Val Thr
            850                 855                 860

Ser Leu Ala Glu Ala Trp Ala Asn Gly Leu Thr Ile Asp Trp Ala Pro
865                 870                 875                 880

Ile Leu Pro Thr Ala Thr Gly His His Pro Glu Leu Pro Thr Tyr Ala
```

```
                    885                 890                 895
Phe Gln Thr Glu Arg Phe Trp Leu Gln Ser Ser Ala Pro Thr Ser Ala
                900                 905                 910
Ala Asp Asp Trp Arg Tyr Arg Val Glu Trp Lys Pro Leu Thr Ala Ser
            915                 920                 925
Gly Gln Ala Asp Leu Ser Gly Arg Trp Ile Val Ala Val Gly Ser Glu
        930                 935                 940
Pro Glu Ala Glu Leu Leu Gly Ala Leu Lys Ala Ala Gly Ala Glu Val
945                 950                 955                 960
Asp Val Leu Glu Ala Gly Ala Asp Asp Arg Glu Ala Leu Ala Ala
                965                 970                 975
Arg Leu Thr Ala Leu Thr Thr Gly Asp Gly Phe Thr Gly Val Val Ser
            980                 985                 990
Leu Leu Asp Asp Leu Val Pro Gln Val Ala Trp Val Gln Ala Leu Gly
                995                1000                1005
Asp Ala Gly Ile Lys Ala Pro Leu Trp Ser Val Thr Gln Gly Ala Val
        1010                1015                1020
Ser Val Gly Arg Leu Asp Thr Pro Ala Asp Pro Asp Arg Ala Met Leu
1025                1030                1035                1040
Trp Gly Leu Gly Arg Val Val Ala Leu Glu His Pro Glu Arg Trp Ala
                1045                1050                1055
Gly Leu Val Asp Leu Pro Ala Gln Pro Asp Ala Ala Ala Leu Ala His
            1060                1065                1070
Leu Val Thr Ala Leu Ser Gly Ala Thr Gly Glu Asp Gln Ile Ala Ile
        1075                1080                1085
Arg Thr Thr Gly Leu His Ala Arg Arg Leu Ala Arg Ala Pro Leu His
    1090                1095                1100
Gly Arg Arg Pro Thr Arg Asp Trp Gln Pro His Gly Thr Val Leu Ile
1105                1110                1115                1120
Thr Gly Gly Thr Gly Ala Leu Gly Ser His Ala Ala Arg Trp Met Ala
                1125                1130                1135
His His Gly Ala Glu His Leu Leu Leu Val Ser Arg Ser Gly Glu Gln
            1140                1145                1150
Ala Pro Gly Ala Thr Gln Leu Thr Ala Glu Leu Thr Ala Ser Gly Ala
        1155                1160                1165
Arg Val Thr Ile Ala Ala Cys Asp Val Ala Asp Pro His Ala Met Arg
    1170                1175                1180
Thr Leu Leu Asp Ala Ile Pro Ala Glu Thr Pro Leu Thr Ala Val Val
1185                1190                1195                1200
His Thr Ala Gly Ala Pro Gly Gly Asp Pro Leu Asp Val Thr Gly Pro
                1205                1210                1215
Glu Asp Ile Ala Arg Ile Leu Gly Ala Lys Thr Ser Gly Ala Glu Val
            1220                1225                1230
Leu Asp Asp Leu Leu Arg Gly Thr Pro Leu Asp Ala Phe Val Leu Tyr
        1235                1240                1245
Ser Ser Asn Ala Gly Val Trp Gly Ser Gly Ser Gln Gly Val Tyr Ala
    1250                1255                1260
Ala Ala Asn Ala His Leu Asp Ala Leu Ala Ala Arg Arg Arg Ala Arg
1265                1270                1275                1280
Gly Glu Thr Ala Thr Ser Val Ala Trp Gly Leu Trp Ala Gly Asp Gly
                1285                1290                1295
Met Gly Arg Gly Ala Asp Asp Ala Tyr Trp Gln Arg Arg Gly Ile Arg
            1300                1305                1310
```

-continued

```
Pro Met Ser Pro Asp Arg Ala Leu Asp Glu Leu Ala Lys Ala Leu Ser
    1315                1320                1325

His Asp Glu Thr Phe Val Ala Val Ala Asp Val Asp Trp Glu Arg Phe
    1330                1335                1340

Ala Pro Ala Phe Thr Val Ser Arg Pro Ser Leu Leu Leu Asp Gly Val
1345                1350                1355                1360

Pro Glu Ala Arg Gln Ala Leu Ala Ala Pro Val Gly Ala Pro Ala Pro
                1365                1370                1375

Gly Asp Ala Ala Val Ala Pro Thr Gly Gln Ser Ser Ala Leu Ala Ala
            1380                1385                1390

Ile Thr Ala Leu Pro Glu Pro Glu Arg Arg Pro Ala Leu Leu Thr Leu
            1395                1400                1405

Val Arg Thr His Ala Ala Ala Val Leu Gly His Ser Ser Pro Asp Arg
    1410                1415                1420

Val Ala Pro Gly Arg Ala Phe Thr Glu Leu Gly Phe Asp Ser Leu Thr
1425                1430                1435                1440

Ala Val Gln Leu Arg Asn Gln Leu Ser Thr Val Val Gly Asn Arg Leu
                1445                1450                1455

Pro Ala Thr Thr Val Phe Asp His Pro Thr Pro Ala Ala Leu Ala Ala
            1460                1465                1470

His Leu His Glu Ala Tyr Leu Ala Pro Ala Glu Pro Ala Pro Thr Asp
        1475                1480                1485

Trp Glu Gly Arg Val Arg Arg Ala Leu Ala Glu Leu Pro Leu Asp Arg
    1490                1495                1500

Leu Arg Asp Ala Gly Val Leu Asp Thr Val Leu Arg Leu Thr Gly Ile
1505                1510                1515                1520

Glu Pro Glu Pro Gly Ser Gly Gly Ser Asp Gly Gly Ala Ala Asp Pro
                1525                1530                1535

Gly Ala Glu Pro Glu Ala Ser Ile Asp Asp Leu Asp Ala Glu Ala Leu
            1540                1545                1550

Ile Arg Met Ala Leu Gly Pro Arg Asn Thr
        1555                1560

<210> SEQ ID NO 4
<211> LENGTH: 1346
<212> TYPE: PRT
<213> ORGANISM: Streptomyces venezuelae

<400> SEQUENCE: 4

Met Thr Ser Ser Asn Glu Gln Leu Val Asp Ala Leu Arg Ala Ser Leu
  1               5                  10                  15

Lys Glu Asn Glu Glu Leu Arg Lys Glu Ser Arg Arg Arg Ala Asp Arg
                20                  25                  30

Arg Gln Glu Pro Met Ala Ile Val Gly Met Ser Cys Arg Phe Ala Gly
            35                  40                  45

Gly Ile Arg Ser Pro Glu Asp Leu Trp Asp Ala Val Ala Ala Gly Lys
        50                  55                  60

Asp Leu Val Ser Glu Val Pro Glu Glu Arg Gly Trp Asp Ile Asp Ser
65                  70                  75                  80

Leu Tyr Asp Pro Val Pro Gly Arg Lys Gly Thr Thr Tyr Val Arg Asn
                85                  90                  95

Ala Ala Phe Leu Asp Asp Ala Ala Gly Phe Asp Ala Ala Phe Phe Gly
                100                 105                 110

Ile Ser Pro Arg Glu Ala Leu Ala Met Asp Pro Gln Gln Arg Gln Leu
```

-continued

```
                115                 120                 125
Leu Glu Ala Ser Trp Glu Val Phe Glu Arg Ala Gly Ile Asp Pro Ala
    130                 135                 140
Ser Val Arg Gly Thr Asp Val Gly Val Tyr Val Gly Cys Gly Tyr Gln
145                 150                 155                 160
Asp Tyr Ala Pro Asp Ile Arg Val Ala Pro Glu Gly Thr Gly Gly Tyr
                165                 170                 175
Val Val Thr Gly Asn Ser Ser Ala Val Ala Ser Gly Arg Ile Ala Tyr
                180                 185                 190
Ser Leu Gly Leu Glu Gly Pro Ala Val Thr Val Asp Thr Ala Cys Ser
                195                 200                 205
Ser Ser Leu Val Ala Leu His Leu Ala Leu Lys Gly Leu Arg Asn Gly
210                 215                 220
Asp Cys Ser Thr Ala Leu Val Gly Gly Val Ala Val Leu Ala Thr Pro
225                 230                 235                 240
Gly Ala Phe Ile Glu Phe Ser Ser Gln Gln Ala Met Ala Ala Asp Gly
                245                 250                 255
Arg Thr Lys Gly Phe Ala Ser Ala Asp Gly Leu Ala Trp Gly Glu
                260                 265                 270
Gly Val Ala Val Leu Leu Leu Glu Arg Leu Ser Asp Ala Arg Arg Lys
                275                 280                 285
Gly His Arg Val Leu Ala Val Val Arg Gly Ser Ala Ile Asn Gln Asp
        290                 295                 300
Gly Ala Ser Asn Gly Leu Thr Ala Pro His Gly Pro Ser Gln Gln Arg
305                 310                 315                 320
Leu Ile Arg Gln Ala Leu Ala Asp Ala Arg Leu Thr Ser Ser Asp Val
                325                 330                 335
Asp Val Val Glu Gly His Gly Thr Gly Thr Arg Leu Gly Asp Pro Ile
                340                 345                 350
Glu Ala Gln Ala Leu Leu Ala Thr Tyr Gly Gln Gly Arg Ala Pro Gly
                355                 360                 365
Gln Pro Leu Arg Leu Gly Thr Leu Lys Ser Asn Ile Gly His Thr Gln
370                 375                 380
Ala Ala Ser Gly Val Ala Gly Val Ile Lys Met Val Gln Ala Leu Arg
385                 390                 395                 400
His Gly Val Leu Pro Lys Thr Leu His Val Asp Glu Pro Thr Asp Gln
                405                 410                 415
Val Asp Trp Ser Ala Gly Ser Val Glu Leu Leu Thr Glu Ala Val Asp
                420                 425                 430
Trp Pro Glu Arg Pro Gly Arg Leu Arg Arg Ala Gly Val Ser Ala Phe
                435                 440                 445
Gly Val Gly Gly Thr Asn Ala His Val Val Leu Glu Glu Ala Pro Ala
450                 455                 460
Val Glu Glu Ser Pro Ala Val Glu Pro Pro Ala Gly Gly Val Val
465                 470                 475                 480
Pro Trp Pro Val Ser Ala Lys Thr Ser Ala Ala Leu Asp Ala Gln Ile
                485                 490                 495
Gly Gln Leu Ala Ala Tyr Ala Glu Asp Arg Thr Asp Val Asp Pro Ala
                500                 505                 510
Val Ala Ala Arg Ala Leu Val Asp Ser Arg Thr Ala Met Glu His Arg
                515                 520                 525
Ala Val Ala Val Gly Asp Ser Arg Glu Ala Leu Arg Asp Ala Leu Arg
        530                 535                 540
```

```
Met Pro Glu Gly Leu Val Arg Gly Thr Val Thr Asp Pro Gly Arg Val
545                 550                 555                 560

Ala Phe Val Phe Pro Gly Gln Gly Thr Gln Trp Ala Gly Met Gly Ala
                565                 570                 575

Glu Leu Leu Asp Ser Ser Pro Glu Phe Ala Ala Met Ala Glu Cys
                580                 585                 590

Glu Thr Ala Leu Ser Pro Tyr Val Asp Trp Ser Leu Glu Ala Val Val
                595                 600                 605

Arg Gln Ala Pro Ser Ala Pro Thr Leu Asp Arg Val Asp Val Val Gln
                610                 615                 620

Pro Val Thr Phe Ala Val Met Val Ser Leu Ala Lys Val Trp Gln His
625                 630                 635                 640

His Gly Ile Thr Pro Glu Ala Val Ile Gly His Ser Gln Gly Glu Ile
                    645                 650                 655

Ala Ala Ala Tyr Val Ala Gly Ala Leu Thr Leu Asp Asp Ala Ala Arg
                660                 665                 670

Val Val Thr Leu Arg Ser Lys Ser Ile Ala Ala His Leu Ala Gly Lys
                675                 680                 685

Gly Gly Met Ile Ser Leu Ala Leu Ser Glu Glu Ala Thr Arg Gln Arg
                690                 695                 700

Ile Glu Asn Leu His Gly Leu Ser Ile Ala Ala Val Asn Gly Pro Thr
705                 710                 715                 720

Ala Thr Val Val Ser Gly Asp Pro Thr Gln Ile Gln Glu Leu Ala Gln
                725                 730                 735

Ala Cys Glu Ala Asp Gly Ile Arg Ala Arg Ile Ile Pro Val Asp Tyr
                740                 745                 750

Ala Ser His Ser Ala His Val Glu Thr Ile Glu Asn Glu Leu Ala Asp
                755                 760                 765

Val Leu Ala Gly Leu Ser Pro Gln Thr Pro Gln Val Pro Phe Phe Ser
770                 775                 780

Thr Leu Glu Gly Thr Trp Ile Thr Glu Pro Ala Leu Asp Gly Gly Tyr
785                 790                 795                 800

Trp Tyr Arg Asn Leu Arg His Arg Val Gly Phe Ala Pro Ala Val Glu
                805                 810                 815

Thr Leu Ala Thr Asp Glu Gly Phe Thr His Phe Ile Glu Val Ser Ala
                820                 825                 830

His Pro Val Leu Thr Met Thr Leu Pro Asp Lys Val Thr Gly Leu Ala
                835                 840                 845

Thr Leu Arg Arg Glu Asp Gly Gly Gln His Arg Leu Thr Thr Ser Leu
850                 855                 860

Ala Glu Ala Trp Ala Asn Gly Leu Ala Leu Asp Trp Ala Ser Leu Leu
865                 870                 875                 880

Pro Ala Thr Gly Ala Leu Ser Pro Ala Val Pro Asp Leu Pro Thr Tyr
                885                 890                 895

Ala Phe Gln His Arg Ser Tyr Trp Ile Ser Pro Ala Gly Pro Gly Glu
                900                 905                 910

Ala Pro Ala His Thr Ala Ser Gly Arg Glu Ala Val Ala Glu Thr Gly
                915                 920                 925

Leu Ala Trp Gly Pro Gly Ala Glu Asp Leu Asp Glu Glu Gly Arg Arg
                930                 935                 940

Ser Ala Val Leu Ala Met Val Met Arg Gln Ala Ala Ser Val Leu Arg
945                 950                 955                 960
```

-continued

Cys Asp Ser Pro Glu Val Pro Val Asp Arg Pro Leu Arg Glu Ile
            965                 970                 975

Gly Phe Asp Ser Leu Thr Ala Val Asp Phe Arg Asn Arg Val Asn Arg
            980                 985                 990

Leu Thr Gly Leu Gln Leu Pro Pro Thr Val Val Phe Glu His Pro Thr
            995                 1000                1005

Pro Val Ala Leu Ala Glu Arg Ile Ser Asp Glu Leu Ala Glu Arg Asn
       1010                1015                1020

Trp Ala Val Ala Glu Pro Ser Asp His Glu Gln Ala Glu Glu Lys
1025                1030                1035                1040

Ala Ala Ala Pro Ala Gly Ala Arg Ser Gly Ala Asp Thr Gly Ala Gly
            1045                1050                1055

Ala Gly Met Phe Arg Ala Leu Phe Arg Gln Ala Val Glu Asp Asp Arg
            1060                1065                1070

Tyr Gly Glu Phe Leu Asp Val Leu Ala Glu Ala Ser Ala Phe Arg Pro
            1075                1080                1085

Gln Phe Ala Ser Pro Glu Ala Cys Ser Glu Arg Leu Asp Pro Val Leu
            1090                1095                1100

Leu Ala Gly Gly Pro Thr Asp Arg Ala Glu Gly Arg Ala Val Leu Val
1105                1110                1115                1120

Gly Cys Thr Gly Thr Ala Ala Asn Gly Gly Pro His Glu Phe Leu Arg
            1125                1130                1135

Leu Ser Thr Ser Phe Gln Glu Glu Arg Asp Phe Leu Ala Val Pro Leu
            1140                1145                1150

Pro Gly Tyr Gly Thr Gly Thr Gly Thr Gly Thr Ala Leu Leu Pro Ala
            1155                1160                1165

Asp Leu Asp Thr Ala Leu Asp Ala Gln Ala Arg Ala Ile Leu Arg Ala
       1170                1175                1180

Ala Gly Asp Ala Pro Val Val Leu Leu Gly His Ser Gly Gly Ala Leu
1185                1190                1195                1200

Leu Ala His Glu Leu Ala Phe Arg Leu Glu Arg Ala His Gly Ala Pro
            1205                1210                1215

Pro Ala Gly Ile Val Leu Val Asp Pro Tyr Pro Pro Gly His Gln Glu
            1220                1225                1230

Pro Ile Glu Val Trp Ser Arg Gln Leu Gly Glu Gly Leu Phe Ala Gly
            1235                1240                1245

Glu Leu Glu Pro Met Ser Asp Ala Arg Leu Leu Ala Met Gly Arg Tyr
       1250                1255                1260

Ala Arg Phe Leu Ala Gly Pro Arg Pro Gly Arg Ser Ser Ala Pro Val
1265                1270                1275                1280

Leu Leu Val Arg Ala Ser Glu Pro Leu Gly Asp Trp Gln Glu Glu Arg
            1285                1290                1295

Gly Asp Trp Arg Ala His Trp Asp Leu Pro His Thr Val Ala Asp Val
            1300                1305                1310

Pro Gly Asp His Phe Thr Met Met Arg Asp His Ala Pro Ala Val Ala
            1315                1320                1325

Glu Ala Val Leu Ser Trp Leu Asp Ala Ile Glu Gly Ile Glu Gly Ala
       1330                1335                1340

Gly Lys
1345

<210> SEQ ID NO 5
<211> LENGTH: 281
<212> TYPE: PRT

<213> ORGANISM: Streptomyces venezuelae

<400> SEQUENCE: 5

```
Val Thr Asp Arg Pro Leu Asn Val Asp Ser Gly Leu Trp Ile Arg Arg
 1               5                  10                  15

Phe His Pro Ala Pro Asn Ser Ala Val Arg Leu Val Cys Leu Pro His
                20                  25                  30

Ala Gly Gly Ser Ala Ser Tyr Phe Phe Arg Phe Ser Glu Glu Leu His
            35                  40                  45

Pro Ser Val Glu Ala Leu Ser Val Gln Tyr Pro Gly Arg Gln Asp Arg
        50                  55                  60

Arg Ala Glu Pro Cys Leu Glu Ser Val Glu Glu Leu Ala Glu His Val
 65                 70                  75                  80

Val Ala Ala Thr Glu Pro Trp Trp Gln Glu Gly Arg Leu Ala Phe Phe
                85                  90                  95

Gly His Ser Leu Gly Ala Ser Val Ala Phe Glu Thr Ala Arg Ile Leu
            100                 105                 110

Glu Gln Arg His Gly Val Arg Pro Glu Gly Leu Tyr Val Ser Gly Arg
        115                 120                 125

Arg Ala Pro Ser Leu Ala Pro Asp Arg Leu Val His Gln Leu Asp Asp
130                 135                 140

Arg Ala Phe Leu Ala Glu Ile Arg Arg Leu Ser Gly Thr Asp Glu Arg
145                 150                 155                 160

Phe Leu Gln Asp Asp Glu Leu Leu Arg Leu Val Leu Pro Ala Leu Arg
                165                 170                 175

Ser Asp Tyr Lys Ala Ala Glu Thr Tyr Leu His Arg Pro Ser Ala Lys
            180                 185                 190

Leu Thr Cys Pro Val Met Ala Leu Ala Gly Asp Arg Asp Pro Lys Ala
        195                 200                 205

Pro Leu Asn Glu Val Ala Glu Trp Arg Arg His Thr Ser Gly Pro Phe
        210                 215                 220

Cys Leu Arg Ala Tyr Ser Gly His Phe Tyr Leu Asn Asp Gln Trp
225                 230                 235                 240

His Glu Ile Cys Asn Asp Ile Ser Asp His Leu Leu Val Thr Arg Gly
                245                 250                 255

Ala Pro Asp Ala Arg Val Val Gln Pro Pro Thr Ser Leu Ile Glu Gly
            260                 265                 270

Ala Ala Lys Arg Trp Gln Asn Pro Arg
        275                 280
```

<210> SEQ ID NO 6
<211> LENGTH: 379
<212> TYPE: PRT
<213> ORGANISM: Streptomyces venezuelae
<220> FEATURE:
<221> NAME/KEY: 251
<222> LOCATION: unsure
<223> OTHER INFORMATION: unsure of amino acid at this position

<400> SEQUENCE: 6

```
Val Ser Ser Arg Ala Glu Thr Pro Arg Val Pro Phe Leu Asp Leu Lys
 1               5                  10                  15

Ala Ala Tyr Glu Glu Leu Arg Ala Glu Thr Asp Ala Ala Ile Ala Arg
                20                  25                  30

Val Leu Asp Ser Gly Arg Tyr Leu Leu Gly Pro Glu Leu Glu Gly Phe
            35                  40                  45
```

```
Glu Ala Glu Phe Ala Ala Tyr Cys Glu Thr Asp His Ala Val Gly Val
        50                  55                  60

Asn Ser Gly Met Asp Ala Leu Gln Leu Ala Leu Arg Gly Leu Gly Ile
 65                  70                  75                  80

Gly Pro Gly Asp Glu Val Ile Val Pro Ser His Thr Tyr Ile Ala Ser
                 85                  90                  95

Trp Leu Ala Val Ser Ala Thr Gly Ala Thr Pro Val Pro Val Glu Pro
            100                 105                 110

His Glu Asp His Pro Thr Leu Asp Pro Leu Leu Val Glu Lys Ala Ile
        115                 120                 125

Thr Pro Arg Thr Arg Ala Leu Leu Pro Val His Leu Tyr Gly His Pro
    130                 135                 140

Ala Asp Met Asp Ala Leu Arg Glu Leu Ala Asp Arg His Gly Leu His
145                 150                 155                 160

Ile Val Glu Asp Ala Ala Gln Ala His Gly Ala Arg Tyr Arg Gly Arg
                165                 170                 175

Arg Ile Gly Ala Gly Ser Ser Val Ala Ala Phe Ser Phe Tyr Pro Gly
            180                 185                 190

Lys Asn Leu Gly Cys Phe Gly Asp Gly Gly Ala Val Val Thr Gly Asp
        195                 200                 205

Pro Glu Leu Ala Glu Arg Leu Arg Met Leu Arg Asn Tyr Gly Ser Arg
    210                 215                 220

Gln Lys Tyr Ser His Glu Thr Lys Gly Thr Asn Ser Arg Leu Asp Glu
225                 230                 235                 240

Met Gln Ala Ala Val Leu Arg Ile Arg Leu Xaa His Leu Asp Ser Trp
                245                 250                 255

Asn Gly Arg Arg Ser Ala Leu Ala Ala Glu Tyr Leu Ser Gly Leu Ala
            260                 265                 270

Gly Leu Pro Gly Ile Gly Leu Pro Val Thr Ala Pro Asp Thr Asp Pro
        275                 280                 285

Val Trp His Leu Phe Thr Val Arg Thr Glu Arg Arg Asp Glu Leu Arg
    290                 295                 300

Ser His Leu Asp Ala Arg Gly Ile Asp Thr Leu Thr His Tyr Pro Val
305                 310                 315                 320

Pro Val His Leu Ser Pro Ala Tyr Ala Gly Glu Ala Pro Pro Glu Gly
                325                 330                 335

Ser Leu Pro Arg Ala Glu Ser Phe Ala Arg Gln Val Leu Ser Leu Pro
            340                 345                 350

Ile Gly Pro His Leu Glu Arg Pro Gln Ala Leu Arg Val Ile Asp Ala
        355                 360                 365

Val Arg Glu Trp Ala Glu Arg Val Asp Gln Ala
    370                 375

<210> SEQ ID NO 7
<211> LENGTH: 382
<212> TYPE: PRT
<213> ORGANISM: Streptomyces venezuelae

<400> SEQUENCE: 7

Val Ala Asp Arg Glu Leu Gly Thr His Leu Leu Glu Thr Arg Gly Ile
  1               5                  10                  15

His Trp Ile His Ala Ala Asn Gly Asp Pro Tyr Ala Thr Val Leu Arg
                 20                  25                  30

Gly Gln Ala Asp Asp Pro Tyr Pro Ala Tyr Glu Arg Val Arg Ala Arg
            35                  40                  45
```

```
Gly Ala Leu Ser Phe Ser Pro Thr Gly Ser Trp Val Thr Ala Asp His
         50                  55                  60

Ala Leu Ala Ala Ser Ile Leu Cys Ser Thr Asp Phe Gly Val Ser Gly
 65                  70                  75                  80

Ala Asp Gly Val Pro Val Pro Gln Gln Val Leu Ser Tyr Gly Glu Gly
                 85                  90                  95

Cys Pro Leu Glu Arg Glu Gln Val Leu Pro Ala Ala Gly Asp Val Pro
                100                 105                 110

Glu Gly Gly Gln Arg Ala Val Val Glu Gly Ile His Arg Glu Thr Leu
            115                 120                 125

Glu Gly Leu Ala Pro Asp Pro Ser Ala Ser Tyr Ala Phe Glu Leu Leu
        130                 135                 140

Gly Gly Phe Val Arg Pro Ala Val Thr Ala Ala Ala Ala Val Leu
145                 150                 155                 160

Gly Val Pro Ala Asp Arg Arg Ala Asp Phe Ala Asp Leu Leu Glu Arg
                165                 170                 175

Leu Arg Pro Leu Ser Asp Ser Leu Leu Ala Pro Gln Ser Leu Arg Thr
            180                 185                 190

Val Arg Ala Ala Asp Gly Ala Leu Ala Glu Leu Thr Ala Leu Leu Ala
        195                 200                 205

Asp Ser Asp Ser Pro Gly Ala Leu Leu Ser Ala Leu Gly Val Thr
210                 215                 220

Ala Ala Val Gln Leu Thr Gly Asn Ala Val Leu Ala Leu Leu Ala His
225                 230                 235                 240

Pro Glu Gln Trp Arg Glu Leu Cys Asp Arg Pro Gly Leu Ala Ala Ala
                245                 250                 255

Ala Val Glu Glu Thr Leu Arg Tyr Asp Pro Pro Val Gln Leu Asp Ala
            260                 265                 270

Arg Val Val Arg Gly Glu Thr Glu Leu Ala Gly Arg Leu Pro Ala
        275                 280                 285

Gly Ala His Val Val Leu Thr Ala Ala Thr Gly Arg Asp Pro Glu
    290                 295                 300

Val Phe Thr Asp Pro Glu Arg Phe Asp Leu Ala Arg Pro Asp Ala Ala
305                 310                 315                 320

Ala His Leu Ala Leu His Pro Ala Gly Pro Tyr Gly Pro Val Ala Ser
                325                 330                 335

Leu Val Arg Leu Gln Ala Glu Val Ala Leu Arg Thr Leu Ala Gly Arg
            340                 345                 350

Phe Pro Gly Leu Arg Gln Ala Gly Asp Val Leu Arg Pro Arg Arg Ala
        355                 360                 365

Pro Val Gly Arg Gly Pro Leu Ser Val Pro Val Ser Ser Ser
    370                 375                 380

<210> SEQ ID NO 8
<211> LENGTH: 426
<212> TYPE: PRT
<213> ORGANISM: Streptomyces venezuelae

<400> SEQUENCE: 8

Met Arg Val Leu Leu Thr Ser Phe Ala His His Thr His Tyr Tyr Gly
 1               5                  10                  15

Leu Val Pro Leu Ala Trp Ala Leu Leu Ala Ala Gly His Glu Val Arg
                20                  25                  30

Val Ala Ser Gln Pro Ala Leu Thr Asp Thr Ile Thr Gly Ser Gly Leu
```

```
                35                  40                  45
Ala Ala Val Pro Val Gly Thr Asp His Leu Ile His Glu Tyr Arg Val
         50                  55                  60

Arg Met Ala Gly Glu Pro Arg Pro Asn His Pro Ala Ile Ala Phe Asp
 65                  70                  75                  80

Glu Ala Arg Pro Glu Pro Leu Asp Trp Asp His Ala Leu Gly Ile Glu
                 85                  90                  95

Ala Ile Leu Ala Pro Tyr Phe Tyr Leu Leu Ala Asn Asn Asp Ser Met
            100                 105                 110

Val Asp Asp Leu Val Asp Phe Ala Arg Ser Trp Gln Pro Asp Leu Val
        115                 120                 125

Leu Trp Glu Pro Thr Thr Tyr Ala Gly Ala Val Ala Ala Gln Val Thr
130                 135                 140

Gly Ala Ala His Ala Arg Val Leu Trp Gly Pro Asp Val Met Gly Ser
145                 150                 155                 160

Ala Arg Arg Lys Phe Val Ala Leu Arg Asp Arg Gln Pro Pro Glu His
                165                 170                 175

Arg Glu Asp Pro Thr Ala Glu Trp Leu Thr Trp Thr Leu Asp Arg Tyr
            180                 185                 190

Gly Ala Ser Phe Glu Glu Leu Leu Thr Gly Gln Phe Thr Ile Asp
        195                 200                 205

Pro Thr Pro Pro Ser Leu Arg Leu Asp Thr Gly Leu Pro Thr Val Gly
    210                 215                 220

Met Arg Tyr Val Pro Tyr Asn Gly Thr Ser Val Val Pro Asp Trp Leu
225                 230                 235                 240

Ser Glu Pro Pro Ala Arg Pro Arg Val Cys Leu Thr Leu Gly Val Ser
                245                 250                 255

Ala Arg Glu Val Leu Gly Gly Asp Gly Val Ser Gln Gly Asp Ile Leu
            260                 265                 270

Glu Ala Leu Ala Asp Leu Asp Ile Glu Leu Val Ala Thr Leu Asp Ala
        275                 280                 285

Ser Gln Arg Ala Glu Ile Arg Asn Tyr Pro Lys His Thr Arg Phe Thr
    290                 295                 300

Asp Phe Val Pro Met His Ala Leu Leu Pro Ser Cys Ser Ala Ile Ile
305                 310                 315                 320

His His Gly Gly Ala Gly Thr Tyr Ala Thr Ala Val Ile Asn Ala Val
                325                 330                 335

Pro Gln Val Met Leu Ala Glu Leu Trp Asp Ala Pro Val Lys Ala Arg
            340                 345                 350

Ala Val Ala Glu Gln Gly Ala Gly Phe Phe Leu Pro Pro Ala Glu Leu
        355                 360                 365

Thr Pro Gln Ala Val Arg Asp Ala Val Val Arg Ile Leu Asp Asp Pro
    370                 375                 380

Ser Val Ala Thr Ala Ala His Arg Leu Arg Glu Glu Thr Phe Gly Asp
385                 390                 395                 400

Pro Thr Pro Ala Gly Ile Val Pro Glu Leu Glu Arg Leu Ala Ala Gln
                405                 410                 415

His Arg Arg Pro Pro Ala Asp Ala Arg His
            420                 425

<210> SEQ ID NO 9
<211> LENGTH: 331
<212> TYPE: PRT
<213> ORGANISM: Streptomyces venezuelae
```

```
<220> FEATURE:
<221> NAME/KEY: 272
<222> LOCATION: unsure
<223> OTHER INFORMATION: unsure of amino acid at this position

<400> SEQUENCE: 9
```

| | | | | | | | | | | | | | | |
|---|---|---|---|---|---|---|---|---|---|---|---|---|---|---|
| Val | Lys | Ser | Ala | Leu | Ser | Asp | Leu | Ala | Phe | Phe | Gly | Gly | Pro | Ala | Ala |
| 1 | | | | 5 | | | | | 10 | | | | | 15 |

Phe Asp Gln Pro Leu Leu Val Gly Arg Pro Asn Arg Ile Asp Arg Ala
            20                  25                  30

Arg Leu Tyr Glu Arg Leu Asp Arg Ala Leu Asp Ser Gln Trp Leu Ser
        35                  40                  45

Asn Gly Gly Pro Leu Val Arg Glu Phe Glu Arg Val Ala Gly Leu
    50                  55                  60

Ala Gly Val Arg His Ala Val Ala Thr Cys Asn Ala Thr Ala Gly Leu
65                  70                  75                  80

Gln Leu Leu Ala His Ala Ala Gly Leu Thr Gly Glu Val Ile Met Pro
                85                  90                  95

Ser Met Thr Phe Ala Ala Thr Pro His Ala Leu Arg Trp Ile Gly Leu
            100                 105                 110

Thr Pro Val Phe Ala Asp Ile Asp Pro Asp Thr Gly Asn Leu Asp Pro
        115                 120                 125

Asp Gln Val Ala Ala Ala Val Thr Pro Arg Thr Ser Ala Val Val Gly
    130                 135                 140

Val His Leu Trp Gly Arg Pro Cys Ala Ala Asp Gln Leu Arg Lys Val
145                 150                 155                 160

Ala Asp Glu His Gly Leu Arg Leu Tyr Phe Asp Ala Ala His Ala Leu
                165                 170                 175

Gly Cys Ala Val Asp Gly Arg Pro Ala Gly Ser Leu Gly Asp Ala Glu
            180                 185                 190

Val Phe Ser Phe His Ala Thr Lys Ala Val Asn Ala Phe Glu Gly Gly
        195                 200                 205

Ala Val Val Thr Asp Asp Ala Asp Leu Ala Ala Arg Ile Arg Ala Leu
    210                 215                 220

His Asn Phe Gly Phe Asp Leu Pro Gly Gly Ser Pro Ala Gly Gly Thr
225                 230                 235                 240

Asn Ala Lys Met Ser Glu Ala Ala Ala Met Gly Leu Thr Ser Leu
                245                 250                 255

Asp Ala Phe Pro Glu Val Ile Asp Arg Asn Arg Arg Asn His Ala Xaa
            260                 265                 270

Tyr Arg Glu His Leu Ala Asp Leu Pro Gly Val Leu Ala Asp His
        275                 280                 285

Asp Arg His Gly Leu Asn Asn His Gln Tyr Val Ile Val Glu Ile Asp
    290                 295                 300

Glu Ala Thr Thr Gly Ile His Arg Asp Leu Val Met Glu Val Leu Lys
305                 310                 315                 320

Ala Glu Gly Val His Thr Arg Ala Tyr Phe Ser
                325                 330

```
<210> SEQ ID NO 10
<211> LENGTH: 485
<212> TYPE: PRT
<213> ORGANISM: Streptomyces venezuelae

<400> SEQUENCE: 10
```

Met Thr Ala Pro Ala Leu Ser Ala Thr Ala Pro Ala Glu Arg Cys Ala

-continued

```
  1               5                  10                  15
His Pro Gly Ala Asp Leu Gly Ala Val His Ala Val Gly Gln Thr
             20                  25                  30
Leu Ala Ala Gly Gly Leu Val Pro Pro Asp Glu Ala Gly Thr Thr Ala
         35                  40                  45
Arg His Leu Val Arg Leu Ala Val Arg Tyr Gly Asn Ser Pro Phe Thr
         50                  55                  60
Pro Leu Glu Glu Ala Arg His Asp Leu Gly Val Asp Arg Asp Ala Phe
 65                  70                  75                  80
Arg Arg Leu Leu Ala Leu Phe Gly Gln Val Pro Glu Leu Arg Thr Ala
                 85                  90                  95
Val Glu Thr Gly Pro Ala Gly Ala Tyr Trp Lys Asn Thr Leu Leu Pro
             100                 105                 110
Leu Glu Gln Arg Gly Val Phe Asp Ala Ala Leu Ala Arg Lys Pro Val
             115                 120                 125
Phe Pro Tyr Ser Val Gly Leu Tyr Pro Gly Pro Thr Cys Met Phe Arg
 130                 135                 140
Cys His Phe Cys Val Arg Val Thr Gly Ala Arg Tyr Asp Pro Ser Ala
 145                 150                 155                 160
Leu Asp Ala Gly Asn Ala Met Phe Arg Ser Val Ile Asp Glu Ile Pro
                 165                 170                 175
Ala Gly Asn Pro Ser Ala Met Tyr Phe Ser Gly Gly Leu Glu Pro Leu
             180                 185                 190
Thr Asn Pro Gly Leu Gly Ser Leu Ala Ala His Ala Thr Asp His Gly
             195                 200                 205
Leu Arg Pro Thr Val Tyr Thr Asn Ser Phe Ala Leu Thr Glu Arg Thr
     210                 215                 220
Leu Glu Arg Gln Pro Gly Leu Trp Gly Leu His Ala Ile Arg Thr Ser
 225                 230                 235                 240
Leu Tyr Gly Leu Asn Asp Glu Glu Tyr Glu Gln Thr Thr Gly Lys Lys
                 245                 250                 255
Ala Ala Phe Arg Arg Val Arg Glu Asn Leu Arg Arg Phe Gln Gln Leu
             260                 265                 270
Arg Ala Glu Arg Glu Ser Pro Ile Asn Leu Gly Phe Ala Tyr Ile Val
             275                 280                 285
Leu Pro Gly Arg Ala Ser Arg Leu Leu Asp Leu Val Asp Phe Ile Ala
 290                 295                 300
Asp Leu Asn Asp Ala Gly Gln Gly Arg Thr Ile Asp Phe Val Asn Ile
 305                 310                 315                 320
Arg Glu Asp Tyr Ser Gly Arg Asp Asp Gly Lys Leu Pro Gln Glu Glu
             325                 330                 335
Arg Ala Glu Leu Gln Glu Ala Leu Asn Ala Phe Glu Glu Arg Val Arg
             340                 345                 350
Glu Arg Thr Pro Gly Leu His Ile Asp Tyr Gly Tyr Ala Leu Asn Ser
             355                 360                 365
Leu Arg Thr Gly Ala Asp Ala Glu Leu Leu Arg Ile Lys Pro Ala Thr
     370                 375                 380
Met Arg Pro Thr Ala His Pro Gln Val Ala Val Gln Val Asp Leu Leu
 385                 390                 395                 400
Gly Asp Val Tyr Leu Tyr Arg Glu Ala Gly Phe Pro Asp Leu Asp Gly
                 405                 410                 415
Ala Thr Arg Tyr Ile Ala Gly Arg Val Thr Pro Asp Thr Ser Leu Thr
             420                 425                 430
```

```
Glu Val Val Arg Asp Phe Val Glu Arg Gly Glu Val Ala Ala Val
            435                 440                 445

Asp Gly Asp Glu Tyr Phe Met Asp Gly Phe Asp Gln Val Val Thr Ala
    450                 455                 460

Arg Leu Asn Gln Leu Glu Arg Asp Ala Ala Asp Gly Trp Glu Glu Ala
465                 470                 475                 480

Arg Gly Phe Leu Arg
                485

<210> SEQ ID NO 11
<211> LENGTH: 237
<212> TYPE: PRT
<213> ORGANISM: Streptomyces venezuelae

<400> SEQUENCE: 11

Val Tyr Glu Val Asp His Ala Asp Val Tyr Asp Leu Phe Tyr Leu Gly
  1               5                  10                  15

Arg Gly Lys Asp Tyr Ala Ala Glu Ala Ser Asp Ile Ala Asp Leu Val
                 20                  25                  30

Arg Ser Arg Thr Pro Glu Ala Ser Ser Leu Leu Asp Val Ala Cys Gly
             35                  40                  45

Thr Gly Thr His Leu Glu His Phe Thr Lys Glu Phe Gly Asp Thr Ala
 50                  55                  60

Gly Leu Glu Leu Ser Glu Asp Met Leu Thr His Ala Arg Lys Arg Leu
 65                  70                  75                  80

Pro Asp Ala Thr Leu His Gln Gly Asp Met Arg Asp Phe Arg Leu Gly
                 85                  90                  95

Arg Lys Phe Ser Ala Val Val Ser Met Phe Ser Ser Val Gly Tyr Leu
            100                 105                 110

Lys Thr Thr Glu Glu Leu Gly Ala Ala Val Ala Ser Phe Ala Glu His
        115                 120                 125

Leu Glu Pro Gly Gly Val Val Val Glu Pro Trp Trp Phe Pro Glu
    130                 135                 140

Thr Phe Ala Asp Gly Trp Val Ser Ala Asp Val Val Arg Arg Asp Gly
145                 150                 155                 160

Arg Thr Val Ala Arg Val Ser His Ser Val Arg Glu Gly Asn Ala Thr
                165                 170                 175

Arg Met Glu Val His Phe Thr Val Ala Asp Pro Gly Lys Gly Val Arg
            180                 185                 190

His Phe Ser Asp Val His Leu Ile Thr Leu Phe His Gln Ala Glu Tyr
        195                 200                 205

Glu Ala Ala Phe Thr Ala Ala Gly Leu Arg Val Glu Tyr Leu Glu Gly
    210                 215                 220

Gly Pro Ser Gly Arg Gly Leu Phe Val Gly Val Pro Ala
225                 230                 235

<210> SEQ ID NO 12
<211> LENGTH: 769
<212> TYPE: PRT
<213> ORGANISM: Streptomyces venezuelae

<400> SEQUENCE: 12

Met Thr Leu Asp Glu Lys Ile Ser Phe Val His Trp Ala Leu Asp Pro
  1               5                  10                  15

Asp Arg Gln Asn Val Gly Tyr Leu Pro Gly Val Pro Arg Leu Gly Ile
                 20                  25                  30
```

```
Pro Glu Leu Arg Ala Ala Asp Gly Pro Asn Gly Ile Arg Leu Val Gly
         35                  40                  45

Gln Thr Ala Thr Ala Leu Pro Ala Pro Val Ala Leu Ala Ser Thr Phe
     50                  55                  60

Asp Asp Thr Met Ala Asp Ser Tyr Gly Lys Val Met Gly Arg Asp Gly
 65                  70                  75                  80

Arg Ala Leu Asn Gln Asp Met Val Leu Gly Pro Met Met Asn Asn Ile
                 85                  90                  95

Arg Val Pro His Gly Gly Arg Asn Tyr Glu Thr Phe Ser Glu Asp Pro
            100                 105                 110

Leu Val Ser Ser Arg Thr Ala Val Ala Gln Ile Lys Gly Ile Gln Gly
        115                 120                 125

Ala Gly Leu Met Thr Thr Ala Lys His Phe Ala Ala Asn Asn Gln Glu
    130                 135                 140

Asn Asn Arg Phe Ser Val Asn Ala Asn Val Asp Glu Gln Thr Leu Arg
145                 150                 155                 160

Glu Ile Glu Phe Pro Ala Phe Glu Ala Ser Ser Lys Ala Gly Ala Gly
                165                 170                 175

Ser Phe Met Cys Ala Tyr Asn Gly Leu Asn Gly Lys Pro Ser Cys Gly
            180                 185                 190

Asn Asp Glu Leu Leu Asn Asn Val Leu Arg Thr Gln Trp Gly Phe Gln
        195                 200                 205

Gly Trp Val Met Ser Asp Trp Leu Ala Thr Pro Gly Thr Asp Ala Ile
    210                 215                 220

Thr Lys Gly Leu Asp Gln Glu Met Gly Val Glu Leu Pro Gly Asp Val
225                 230                 235                 240

Pro Lys Gly Glu Pro Ser Pro Ala Lys Phe Phe Gly Glu Ala Leu
                245                 250                 255

Lys Thr Ala Val Leu Asn Gly Thr Val Pro Glu Ala Ala Val Thr Arg
            260                 265                 270

Ser Ala Glu Arg Ile Val Gly Gln Met Glu Lys Phe Gly Leu Leu Leu
        275                 280                 285

Ala Thr Pro Ala Pro Arg Pro Glu Arg Asp Lys Ala Gly Ala Gln Ala
    290                 295                 300

Val Ser Arg Lys Val Ala Glu Asn Gly Ala Val Leu Leu Arg Asn Glu
305                 310                 315                 320

Gly Gln Ala Leu Pro Leu Ala Gly Asp Ala Gly Lys Ser Ile Ala Val
                325                 330                 335

Ile Gly Pro Thr Ala Val Asp Pro Lys Val Thr Gly Leu Gly Ser Ala
            340                 345                 350

His Val Val Pro Asp Ser Ala Ala Pro Leu Asp Thr Ile Lys Ala
        355                 360                 365

Arg Ala Gly Ala Gly Ala Thr Val Thr Tyr Glu Thr Gly Glu Glu Thr
    370                 375                 380

Phe Gly Thr Gln Ile Pro Ala Gly Asn Leu Ser Pro Ala Phe Asn Gln
385                 390                 395                 400

Gly His Gln Leu Glu Pro Gly Lys Ala Gly Ala Leu Tyr Asp Gly Thr
                405                 410                 415

Leu Thr Val Pro Ala Asp Gly Glu Tyr Arg Ile Ala Val Arg Ala Thr
            420                 425                 430

Gly Gly Tyr Ala Thr Val Gln Leu Gly Ser His Thr Ile Glu Ala Gly
    435                 440                 445
```

-continued

```
Gln Val Tyr Gly Lys Val Ser Ser Pro Leu Leu Lys Leu Thr Lys Gly
            450                 455                 460

Thr His Lys Leu Thr Ile Ser Gly Phe Ala Met Ser Ala Thr Pro Leu
465                 470                 475                 480

Ser Leu Glu Leu Gly Trp Val Thr Pro Ala Ala Asp Ala Thr Ile
                485                 490                 495

Ala Lys Ala Val Glu Ser Ala Arg Lys Ala Arg Thr Ala Val Val Phe
            500                 505                 510

Ala Tyr Asp Asp Gly Thr Glu Gly Val Asp Arg Pro Asn Leu Ser Leu
            515                 520                 525

Pro Gly Thr Gln Asp Lys Leu Ile Ser Ala Val Ala Asp Ala Asn Pro
    530                 535                 540

Asn Thr Ile Val Val Leu Asn Thr Gly Ser Ser Val Leu Met Pro Trp
545                 550                 555                 560

Leu Ser Lys Thr Arg Ala Val Leu Asp Met Trp Tyr Pro Gly Gln Ala
                565                 570                 575

Gly Ala Glu Ala Thr Ala Ala Leu Leu Tyr Gly Asp Val Asn Pro Ser
            580                 585                 590

Gly Lys Leu Thr Gln Ser Phe Pro Ala Ala Glu Asn Gln His Ala Val
            595                 600                 605

Ala Gly Asp Pro Thr Ser Tyr Pro Gly Val Asp Asn Gln Gln Thr Tyr
    610                 615                 620

Arg Glu Gly Ile His Val Gly Tyr Arg Trp Phe Asp Lys Glu Asn Val
625                 630                 635                 640

Lys Pro Leu Phe Pro Phe Gly His Gly Leu Ser Tyr Thr Ser Phe Thr
                645                 650                 655

Gln Ser Ala Pro Thr Val Val Arg Thr Ser Thr Gly Gly Leu Lys Val
            660                 665                 670

Thr Val Thr Val Arg Asn Ser Gly Lys Arg Ala Gly Gln Glu Val Val
            675                 680                 685

Gln Ala Tyr Leu Gly Ala Ser Pro Asn Val Thr Ala Pro Gln Ala Lys
    690                 695                 700

Lys Lys Leu Val Gly Tyr Thr Lys Val Ser Leu Ala Ala Gly Glu Ala
705                 710                 715                 720

Lys Thr Val Thr Val Asn Val Asp Arg Arg Gln Leu Gln Phe Trp Asp
                725                 730                 735

Ala Ala Thr Asp Asn Trp Lys Thr Gly Thr Gly Asn Arg Leu Leu Gln
            740                 745                 750

Thr Gly Ser Ser Ser Ala Asp Leu Arg Gly Ser Ala Thr Val Asn Val
            755                 760                 765

Trp

<210> SEQ ID NO 13
<211> LENGTH: 928
<212> TYPE: PRT
<213> ORGANISM: Streptomyces venezuelae
<220> FEATURE:
<221> NAME/KEY: 694
<222> LOCATION: unsure
<223> OTHER INFORMATION: unsure of amino acid at this position

<400> SEQUENCE: 13

Met Asn Leu Val Glu Arg Asp Gly Glu Ile Ala His Leu Arg Ala Val
  1               5                  10                  15

Leu Asp Ala Ser Ala Ala Gly Asp Gly Thr Leu Leu Leu Val Ser Gly
             20                  25                  30
```

```
Pro Ala Gly Ser Gly Lys Thr Glu Leu Leu Arg Ser Leu Arg Arg Leu
         35                  40                  45

Ala Ala Glu Arg Glu Thr Pro Val Trp Ser Val Arg Ala Leu Pro Gly
     50                  55                  60

Asp Arg Asp Ile Pro Leu Gly Val Leu Cys Gln Leu Leu Arg Ser Ala
 65              70                  75                      80

Glu Gln His Gly Ala Asp Thr Ser Ala Val Arg Asp Leu Leu Asp Ala
                 85                  90                  95

Ala Ser Arg Arg Ala Gly Thr Ser Pro Pro Pro Thr Arg Arg Ser
             100                 105                 110

Ala Ser Thr Arg His Thr Ala Cys Thr Thr Gly Cys Ser Pro Ser Pro
         115                 120                 125

Ala Gly Thr Pro Phe Leu Val Ala Val Asp Asp Leu Thr His Ala Asp
     130                 135                 140

Thr Ala Ser Leu Arg Phe Leu Leu Tyr Cys Ala Ala His His Asp Gln
145                 150                 155                 160

Gly Gly Ile Gly Phe Val Met Thr Glu Arg Ala Ser Gln Arg Ala Gly
                 165                 170                 175

Tyr Arg Val Phe Arg Ala Glu Leu Leu Arg Gln Pro His Cys Arg Asn
             180                 185                 190

Met Trp Leu Ser Gly Leu Pro Pro Ser Gly Val Arg Gln Leu Leu Ala
         195                 200                 205

His Tyr Tyr Gly Pro Glu Ala Ala Glu Arg Arg Ala Pro Ala Tyr His
     210                 215                 220

Ala Thr Thr Gly Gly Asn Pro Leu Leu Leu Arg Ala Leu Thr Gln Asp
225                 230                 235                 240

Arg Gln Ala Ser His Thr Thr Leu Gly Ala Ala Gly Gly Asp Glu Pro
                 245                 250                 255

Val His Gly Asp Ala Phe Ala Gln Ala Val Leu Asp Cys Leu His Arg
             260                 265                 270

Ser Ala Glu Gly Thr Leu Glu Thr Ala Arg Trp Leu Ala Val Leu Glu
         275                 280                 285

Gln Ser Asp Pro Leu Leu Val Glu Arg Leu Thr Gly Thr Thr Ala Ala
     290                 295                 300

Ala Val Glu Arg His Ile Gln Glu Leu Ala Ala Ile Gly Leu Leu Asp
305                 310                 315                 320

Glu Asp Gly Thr Leu Gly Gln Pro Ala Ile Arg Glu Ala Ala Leu Gln
                 325                 330                 335

Asp Leu Pro Ala Gly Glu Arg Thr Glu Leu His Arg Arg Ala Ala Glu
             340                 345                 350

Gln Leu His Arg Asp Gly Ala Asp Glu Asp Thr Val Ala Arg His Leu
         355                 360                 365

Leu Val Gly Gly Ala Pro Asp Ala Pro Trp Ala Leu Pro Leu Leu Glu
     370                 375                 380

Arg Gly Ala Gln Gln Ala Leu Phe Asp Asp Arg Leu Asp Asp Ala Phe
385                 390                 395                 400

Arg Ile Leu Glu Phe Ala Val Arg Ser Ser Thr Asp Asn Thr Gln Leu
                 405                 410                 415

Ala Arg Leu Ala Pro His Leu Val Ala Ala Ser Trp Arg Met Asn Pro
             420                 425                 430

His Met Thr Thr Arg Ala Leu Ala Leu Phe Asp Arg Leu Leu Ser Gly
         435                 440                 445
```

```
-continued

Glu Leu Pro Pro Ser His Pro Val Met Ala Leu Ile Arg Cys Leu Val
    450                 455                 460

Trp Tyr Gly Arg Leu Pro Glu Ala Ala Asp Ala Leu Ser Arg Leu Arg
465                 470                 475                 480

Pro Ser Ser Asp Asn Asp Ala Leu Glu Leu Ser Leu Thr Arg Met Trp
                485                 490                 495

Leu Ala Ala Leu Cys Pro Pro Leu Leu Glu Ser Leu Pro Ala Thr Pro
            500                 505                 510

Glu Pro Glu Arg Gly Pro Val Pro Val Arg Leu Ala Pro Arg Thr Thr
        515                 520                 525

Ala Leu Gln Ala Gln Ala Gly Val Phe Gln Arg Gly Pro Asp Asn Ala
    530                 535                 540

Ser Val Ala Gln Ala Glu Gln Ile Leu Gln Gly Cys Arg Leu Ser Glu
545                 550                 555                 560

Glu Thr Tyr Glu Ala Leu Glu Thr Ala Leu Leu Val Leu Val His Ala
                565                 570                 575

Asp Arg Leu Asp Arg Ala Leu Phe Trp Ser Asp Ala Leu Leu Ala Glu
            580                 585                 590

Ala Val Glu Arg Arg Ser Leu Gly Trp Glu Ala Val Phe Ala Ala Thr
        595                 600                 605

Arg Ala Met Ile Ala Ile Arg Cys Gly Asp Leu Pro Thr Ala Arg Glu
    610                 615                 620

Arg Ala Glu Leu Ala Leu Ser His Ala Ala Pro Glu Ser Trp Gly Leu
625                 630                 635                 640

Ala Val Gly Met Pro Leu Ser Ala Leu Leu Leu Ala Cys Thr Glu Ala
                645                 650                 655

Gly Glu Tyr Glu Gln Ala Glu Arg Val Leu Arg Gln Pro Val Pro Asp
            660                 665                 670

Ala Met Phe Asp Ser Arg His Gly Met Glu Tyr Met His Ala Arg Gly
        675                 680                 685

Arg Tyr Trp Leu Ala Xaa Gly Arg Leu His Ala Ala Leu Gly Glu Phe
    690                 695                 700

Met Leu Cys Gly Glu Ile Leu Gly Ser Trp Asn Leu Asp Gln Pro Ser
705                 710                 715                 720

Ile Val Pro Trp Arg Thr Ser Ala Ala Glu Val Tyr Leu Arg Leu Gly
                725                 730                 735

Asn Arg Gln Lys Ala Arg Ala Leu Ala Glu Ala Gln Leu Ala Leu Val
            740                 745                 750

Arg Pro Gly Arg Ser Arg Thr Arg Gly Leu Thr Leu Arg Val Leu Ala
        755                 760                 765

Ala Ala Val Asp Gly Gln Gln Ala Glu Arg Leu His Ala Glu Ala Val
    770                 775                 780

Asp Met Leu His Asp Ser Gly Asp Arg Leu Glu His Ala Arg Ala Leu
785                 790                 795                 800

Ala Gly Met Ser Arg His Gln Gln Ala Gln Gly Asp Asn Tyr Arg Ala
                805                 810                 815

Arg Met Thr Ala Arg Leu Ala Gly Asp Met Ala Trp Ala Cys Gly Ala
            820                 825                 830

Tyr Pro Leu Ala Glu Glu Ile Val Pro Gly Arg Gly Arg Arg Ala
        835                 840                 845

Lys Ala Val Ser Thr Glu Leu Glu Leu Pro Gly Gly Pro Asp Val Gly
    850                 855                 860

Leu Leu Ser Glu Ala Glu Arg Arg Val Ala Ala Leu Ala Ala Arg Gly
```

```
865                 870                 875                 880
Leu Thr Asn Arg Gln Ile Ala Arg Arg Leu Cys Val Thr Ala Ser Thr
                    885                 890                 895

Val Glu Gln His Leu Thr Arg Val Tyr Arg Lys Leu Asn Val Thr Arg
                900                 905                 910

Arg Ala Asp Leu Pro Ile Ser Leu Ala Gln Asp Lys Ser Val Thr Ala
            915                 920                 925

<210> SEQ ID NO 14
<211> LENGTH: 292
<212> TYPE: PRT
<213> ORGANISM: Streptomyces venezuelae

<400> SEQUENCE: 14

Met Lys Gly Ile Val Leu Ala Gly Gly Ser Gly Thr Arg Leu His Pro
  1               5                  10                  15

Ala Thr Ser Val Ile Ser Lys Gln Ile Leu Pro Val Tyr Asn Lys Pro
                 20                  25                  30

Met Ile Tyr Tyr Pro Leu Ser Val Leu Met Leu Gly Gly Ile Arg Glu
             35                  40                  45

Ile Gln Ile Ile Ser Thr Pro Gln His Ile Glu Leu Phe Gln Ser Leu
         50                  55                  60

Leu Gly Asn Gly Arg His Leu Gly Ile Glu Leu Asp Tyr Ala Val Gln
 65                  70                  75                  80

Lys Glu Pro Ala Gly Ile Ala Asp Ala Leu Leu Val Gly Ala Glu His
                 85                  90                  95

Ile Gly Asp Asp Thr Cys Ala Leu Ile Leu Gly Asp Asn Ile Phe His
            100                 105                 110

Gly Pro Gly Leu Tyr Thr Leu Leu Arg Asp Ser Ile Ala Arg Leu Asp
        115                 120                 125

Gly Cys Val Leu Phe Gly Tyr Pro Val Lys Asp Pro Glu Arg Tyr Gly
    130                 135                 140

Val Ala Glu Val Asp Ala Thr Gly Arg Leu Thr Asp Leu Val Glu Lys
145                 150                 155                 160

Pro Val Lys Pro Arg Ser Asn Leu Ala Val Thr Gly Leu Tyr Leu Tyr
                165                 170                 175

Asp Asn Asp Val Val Asp Ile Ala Lys Asn Ile Arg Pro Ser Pro Arg
            180                 185                 190

Gly Glu Leu Glu Ile Thr Asp Val Asn Arg Val Tyr Leu Glu Arg Gly
        195                 200                 205

Arg Ala Glu Leu Val Asn Leu Gly Arg Gly Phe Ala Trp Leu Asp Thr
    210                 215                 220

Gly Thr His Asp Ser Leu Leu Arg Ala Ala Gln Tyr Val Gln Val Leu
225                 230                 235                 240

Glu Glu Arg Gln Gly Val Trp Ile Ala Gly Leu Glu Ile Ala Phe
                245                 250                 255

Arg Met Gly Phe Ile Asp Ala Gly Ala Cys His Gly Leu Gly Glu Gly
            260                 265                 270

Leu Ser Arg Thr Glu Tyr Gly Ser Tyr Leu Met Glu Ile Ala Gly Arg
        275                 280                 285

Glu Gly Ala Pro
    290

<210> SEQ ID NO 15
<211> LENGTH: 337
```

-continued

```
<212> TYPE: PRT
<213> ORGANISM: Streptomyces venezuelae

<400> SEQUENCE: 15
```

| Val | Arg | Leu | Leu | Val | Thr | Gly | Gly | Ala | Gly | Phe | Ile | Gly | Ser | His | Phe |
|---|---|---|---|---|---|---|---|---|---|---|---|---|---|---|---|
| 1 | | | | 5 | | | | | 10 | | | | | 15 | |
| Val | Arg | Gln | Leu | Leu | Ala | Gly | Ala | Tyr | Pro | Asp | Val | Pro | Ala | Asp | Glu |
| | | | 20 | | | | | 25 | | | | | 30 | | |
| Val | Ile | Val | Leu | Asp | Ser | Leu | Thr | Tyr | Ala | Gly | Asn | Arg | Ala | Asn | Leu |
| | | 35 | | | | | 40 | | | | | 45 | | | |
| Ala | Pro | Val | Asp | Ala | Asp | Pro | Arg | Leu | Arg | Phe | Val | His | Gly | Asp | Ile |
| | 50 | | | | | 55 | | | | | 60 | | | | |
| Arg | Asp | Ala | Gly | Leu | Leu | Ala | Arg | Glu | Leu | Arg | Gly | Val | Asp | Ala | Ile |
| 65 | | | | | 70 | | | | | 75 | | | | | 80 |
| Val | His | Phe | Ala | Ala | Glu | Ser | His | Val | Asp | Arg | Ser | Ile | Ala | Gly | Ala |
| | | | | 85 | | | | | 90 | | | | | 95 | |
| Ser | Val | Phe | Thr | Glu | Thr | Asn | Val | Gln | Gly | Thr | Gln | Thr | Leu | Leu | Gln |
| | | | | 100 | | | | | 105 | | | | | 110 | |
| Cys | Ala | Val | Asp | Ala | Gly | Val | Gly | Arg | Val | Val | His | Val | Ser | Thr | Asp |
| | | | 115 | | | | | 120 | | | | | 125 | | |
| Glu | Val | Tyr | Gly | Ser | Ile | Asp | Ser | Gly | Ser | Trp | Thr | Glu | Ser | Ser | Pro |
| | | 130 | | | | | 135 | | | | | 140 | | | |
| Leu | Glu | Pro | Asn | Ser | Pro | Tyr | Ala | Ala | Ser | Lys | Ala | Gly | Ser | Asp | Leu |
| 145 | | | | | 150 | | | | | 155 | | | | | 160 |
| Val | Ala | Arg | Ala | Tyr | His | Arg | Thr | Tyr | Gly | Leu | Asp | Val | Arg | Ile | Thr |
| | | | | 165 | | | | | 170 | | | | | 175 | |
| Arg | Cys | Cys | Asn | Asn | Tyr | Gly | Pro | Tyr | Gln | His | Pro | Glu | Lys | Leu | Ile |
| | | | | 180 | | | | | 185 | | | | | 190 | |
| Pro | Leu | Phe | Val | Thr | Asn | Leu | Leu | Asp | Gly | Gly | Thr | Leu | Pro | Leu | Tyr |
| | | | 195 | | | | | 200 | | | | | 205 | | |
| Gly | Asp | Gly | Ala | Asn | Val | Arg | Glu | Trp | Val | His | Thr | Asp | Asp | His | Cys |
| | | 210 | | | | | 215 | | | | | 220 | | | |
| Arg | Gly | Ile | Ala | Leu | Val | Leu | Ala | Gly | Gly | Arg | Ala | Gly | Glu | Ile | Tyr |
| 225 | | | | | 230 | | | | | 235 | | | | | 240 |
| His | Ile | Gly | Gly | Gly | Leu | Glu | Leu | Thr | Asn | Arg | Glu | Leu | Thr | Gly | Ile |
| | | | | 245 | | | | | 250 | | | | | 255 | |
| Leu | Leu | Asp | Ser | Leu | Gly | Ala | Asp | Trp | Ser | Ser | Val | Arg | Lys | Val | Ala |
| | | | 260 | | | | | 265 | | | | | 270 | | |
| Asp | Arg | Lys | Gly | His | Asp | Leu | Arg | Tyr | Ser | Leu | Asp | Gly | Gly | Lys | Ile |
| | | 275 | | | | | 280 | | | | | 285 | | | |
| Glu | Arg | Glu | Leu | Gly | Tyr | Arg | Pro | Gln | Val | Ser | Phe | Ala | Asp | Gly | Leu |
| | 290 | | | | | 295 | | | | | 300 | | | | |
| Ala | Arg | Thr | Val | Arg | Trp | Tyr | Arg | Glu | Asn | Arg | Gly | Trp | Trp | Glu | Pro |
| 305 | | | | | 310 | | | | | 315 | | | | | 320 |
| Leu | Lys | Ala | Thr | Ala | Pro | Gln | Leu | Pro | Ala | Thr | Ala | Val | Glu | Val | Ser |
| | | | | 325 | | | | | 330 | | | | | 335 | |
| Ala | | | | | | | | | | | | | | | |

```
<210> SEQ ID NO 16
<211> LENGTH: 332
<212> TYPE: PRT
<213> ORGANISM: Streptomyces venezuelae

<400> SEQUENCE: 16
```

| Ile | Gly | Tyr | Asp | Ser | Ser | Lys | Lys | Gly | Phe | Asp | Gly | Ala | Ser | Cys | Gly |
|---|---|---|---|---|---|---|---|---|---|---|---|---|---|---|---|

```
  1               5                   10                  15
Val Ser Val Ser Ile Gly Ser Gln Ser Pro Asp Ile Ala Gln Gly Val
                    20                  25                  30

Asp Thr Ala Tyr Glu Lys Arg Val Glu Gly Ala Ser Gln Arg Asp Glu
                35                  40                  45

Gly Asp Glu Leu Asp Lys Gln Gly Ala Gly Asp Gln Gly Leu Met Phe
        50                  55                  60

Gly Tyr Ala Ser Asp Glu Thr Pro Glu Leu Met Pro Leu Pro Ile His
 65                  70                  75                  80

Leu Ala His Arg Leu Ser Arg Arg Leu Thr Glu Val Arg Lys Asn Gly
                85                  90                  95

Thr Ile Pro Tyr Leu Arg Pro Asp Gly Lys Thr Gln Val Thr Ile Glu
                100                 105                 110

Tyr Asp Gly Asp Arg Ala Val Arg Leu Asp Thr Val Val Val Ser Ser
                115                 120                 125

Gln His Ala Ser Asp Ile Asp Leu Glu Ser Leu Leu Ala Pro Asp Val
    130                 135                 140

Arg Lys Phe Val Val Glu His Val Leu Ala Gln Leu Val Glu Asp Gly
145                 150                 155                 160

Ile Lys Leu Asp Thr Asp Gly Tyr Arg Leu Leu Val Asn Pro Thr Gly
                165                 170                 175

Arg Phe Glu Ile Gly Gly Pro Met Gly Asp Ala Gly Leu Thr Gly Arg
                180                 185                 190

Lys Ile Ile Ile Asp Thr Tyr Gly Gly Met Ala Arg His Gly Gly Gly
                195                 200                 205

Ala Phe Ser Gly Lys Asp Pro Ser Lys Val Asp Arg Ser Ala Ala Tyr
    210                 215                 220

Ala Met Arg Trp Val Ala Lys Asn Val Val Ala Ala Gly Leu Ala Ser
225                 230                 235                 240

Arg Cys Glu Val Gln Val Ala Tyr Ala Ile Gly Lys Ala Glu Pro Val
                245                 250                 255

Gly Leu Phe Val Glu Thr Phe Gly Thr His Lys Ile Glu Thr Glu Lys
                260                 265                 270

Ile Glu Asn Ala Ile Gly Glu Val Phe Asp Leu Arg Pro Ala Ala Ile
                275                 280                 285

Ile Arg Asp Leu Asp Leu Leu Arg Pro Ile Tyr Ser Gln Thr Ala Ala
                290                 295                 300

Tyr Gly His Phe Gly Arg Glu Leu Pro Asp Phe Thr Trp Glu Arg Thr
305                 310                 315                 320

Asp Arg Val Asp Ala Leu Lys Lys Ala Ala Gly Leu
                325                 330

<210> SEQ ID NO 17
<211> LENGTH: 230
<212> TYPE: PRT
<213> ORGANISM: Streptomyces venezuelae

<400> SEQUENCE: 17

Met Arg Ile Ala Val Thr Gly Ser Ile Ala Thr Asp His Leu Met Thr
 1               5                   10                  15

Phe Pro Gly Arg Phe Ala Glu Gln Ile Leu Pro Asp Gln Leu Ala His
                20                  25                  30

Val Ser Leu Ser Phe Leu Val Asp Thr Leu Asp Ile Arg His Gly Gly
                35                  40                  45
```

-continued

```
Val Ala Ala Asn Ile Ala Tyr Gly Leu Gly Leu Leu Gly Arg Arg Pro
             50                  55                  60

Val Leu Val Gly Ala Val Gly Lys Asp Phe Asp Gly Tyr Gly Gln Leu
 65                  70                  75                  80

Leu Arg Ala Ala Gly Val Asp Thr Asp Ser Val Arg Val Ser Asp Arg
                 85                  90                  95

Gln His Thr Ala Arg Phe Met Cys Thr Thr Asp Glu Asp Gly Asn Gln
                100                 105                 110

Leu Ala Ser Phe Tyr Ala Gly Ala Met Ala Glu Ala Arg Asp Ile Asp
                115                 120                 125

Leu Gly Glu Thr Ala Gly Arg Pro Gly Gly Ile Asp Leu Val Leu Val
            130                 135                 140

Gly Ala Asp Asp Pro Glu Ala Met Val Arg His Thr Arg Val Cys Arg
145                 150                 155                 160

Glu Leu Gly Leu Arg Arg Ala Ala Asp Pro Ser Gln Gln Leu Ala Arg
                    165                 170                 175

Leu Glu Gly Asp Ser Val Arg Glu Leu Val Asp Gly Ala Glu Leu Leu
                180                 185                 190

Phe Thr Asn Ala Tyr Glu Arg Ala Leu Leu Leu Ser Lys Thr Gly Trp
            195                 200                 205

Thr Glu Gln Glu Val Leu Ala Arg Val Gly Thr Trp Ile Thr Thr Leu
    210                 215                 220

Gly Ala Lys Gly Cys Arg
225                 230

<210> SEQ ID NO 18
<211> LENGTH: 416
<212> TYPE: PRT
<213> ORGANISM: Streptomyces venezuelae

<400> SEQUENCE: 18

Val Arg Arg Thr Gln Gln Gly Thr Thr Ala Ser Pro Pro Val Leu Asp
  1               5                  10                  15

Leu Gly Ala Leu Gly Gln Asp Phe Ala Ala Asp Pro Tyr Pro Thr Tyr
             20                  25                  30

Ala Arg Leu Arg Ala Glu Gly Pro Ala His Arg Val Arg Thr Pro Glu
         35                  40                  45

Gly Asp Glu Val Trp Leu Val Val Gly Tyr Asp Arg Ala Arg Ala Val
 50                  55                  60

Leu Ala Asp Pro Arg Phe Ser Lys Asp Trp Arg Asn Ser Thr Thr Pro
 65                  70                  75                  80

Leu Thr Glu Ala Glu Ala Ala Leu Asn His Asn Met Leu Glu Ser Asp
                 85                  90                  95

Pro Pro Arg His Thr Arg Leu Arg Lys Leu Val Ala Arg Glu Phe Thr
                100                 105                 110

Met Arg Arg Val Glu Leu Leu Arg Pro Arg Val Gln Glu Ile Val Asp
            115                 120                 125

Gly Leu Val Asp Ala Met Leu Ala Pro Asp Gly Arg Ala Asp Leu
            130                 135                 140

Met Glu Ser Leu Ala Trp Pro Leu Pro Ile Thr Val Ile Ser Glu Leu
145                 150                 155                 160

Leu Gly Val Pro Glu Pro Asp Arg Ala Ala Phe Arg Val Trp Thr Asp
                    165                 170                 175

Ala Phe Val Phe Pro Asp Asp Pro Ala Gln Ala Gln Thr Ala Met Ala
                180                 185                 190
```

```
Glu Met Ser Gly Tyr Leu Ser Arg Leu Ile Asp Ser Lys Arg Gly Gln
    195                 200                 205

Asp Gly Glu Asp Leu Leu Ser Ala Leu Val Arg Thr Ser Asp Glu Asp
210                 215                 220

Gly Ser Arg Leu Thr Ser Glu Glu Leu Gly Met Ala His Ile Leu
225                 230                 235                 240

Leu Val Ala Gly His Glu Thr Thr Val Asn Leu Ile Ala Asn Gly Met
                245                 250                 255

Tyr Ala Leu Leu Ser His Pro Asp Gln Leu Ala Ala Leu Arg Ala Asp
                260                 265                 270

Met Thr Leu Leu Asp Gly Ala Val Glu Glu Met Leu Arg Tyr Glu Gly
                275                 280                 285

Pro Val Glu Ser Ala Thr Tyr Arg Phe Pro Val Glu Pro Val Asp Leu
290                 295                 300

Asp Gly Thr Val Ile Pro Ala Gly Asp Thr Val Leu Val Val Leu Ala
305                 310                 315                 320

Asp Ala His Arg Thr Pro Glu Arg Phe Pro Asp Pro His Arg Phe Asp
                325                 330                 335

Ile Arg Arg Asp Thr Ala Gly His Leu Ala Phe Gly His Gly Ile His
                340                 345                 350

Phe Cys Ile Gly Ala Pro Leu Ala Arg Leu Glu Ala Arg Ile Ala Val
                355                 360                 365

Arg Ala Leu Leu Glu Arg Cys Pro Asp Leu Ala Leu Asp Val Ser Pro
                370                 375                 380

Gly Glu Leu Val Trp Tyr Pro Asn Pro Met Ile Arg Gly Leu Lys Ala
385                 390                 395                 400

Leu Pro Ile Arg Trp Arg Arg Gly Arg Glu Ala Gly Arg Arg Thr Gly
                405                 410                 415

<210> SEQ ID NO 19
<211> LENGTH: 38506
<212> TYPE: DNA
<213> ORGANISM: Streptomyces venezuelae

<400> SEQUENCE: 19
gatcatgcgg agcactcctt ctctcgtgct cctaccggtg atgtgcgcgc cgaattgatt      60
cgtggagaga tgtcgacagt gtccaagagt gagtccgagg aattcgtgtc cgtgtcgaac     120
gacgccggtt ccgcgcacgg cacagcggaa cccgtcgccg tcgtcggcat ctcctgccgg     180
gtgcccggcg cccgggaccc gagagagttc tgggaactcc tggcggcagg cggccaggcc     240
gtcaccgacg tccccgcgga ccgctggaac gccggcgact tctacgaccc ggaccgctcc     300
gcccccggcc gctcgaacag ccggtggggc gggttcatcg aggacgtcga ccggttcgac     360
gccgccttct tcggcatctc gccccgcgag gccgcggaga tggacccgca gcagcggctc     420
gccctggagc tgggctggga ggccctggag cgcgccggga tcgacccgtc ctcgctcacc     480
ggcacccgca ccggcgtctt cgccggcgcc atctgggacg actacgccac cctgaagcac     540
cgccagggcg cgccgcgat cacccccgcac accgtcaccg gcctccaccg cggcatcatc     600
gcgaaccgac tctcgtacac gctcgggctc cgcggcccca gcatggtcgt cgactccggc     660
cagtcctcgt cgctcgtcgc cgtccacctc ggtgcgaga gcctgcggcg cggcgagtcc     720
gagctcgccc tcgccggcgg cgtctcgctc aacctggtgc cggacagcat catcggggcg     780
agcaagttcg gcggcctctc ccccgacggc cgcgcctaca ccttcgacgc gcgcgccaac     840
```

-continued

```
ggctacgtac gcggcgaggg cggcggtttc gtcgtcctga agcgcctctc ccggaccgtc      900
gccgacggcg acccggtgct cgccgtgatc cggggcagcg ccgtcaacaa cggcggcgcc      960
gcccagggca tgacgacccc cgacgcgcag gcgcaggagg ccgtgctccg cgaggcccac     1020
gagcgggccg gaccgcgcc ggccgacgtg cggtacgtcg agctgcacgg caccggcacc     1080
cccgtgggcg acccgatcga ggccgctgcg ctcggcgccg ccctcggcac cggccgcccg     1140
gccggacagc cgctcctggt cggctcggtc aagacgaaca tcggccacct ggagggcgcg     1200
gccggcatcg ccggcctcat caaggccgtc ctggcggtcc gcggtcgcgc gctgcccgcc     1260
agcctgaact acgagacccc gaacccggcg atcccgttcg aggaactgaa cctccgggtg     1320
aacacggagt acctgccgtg ggagccggag cacgacgggc agcggatggt cgtcggcgtg     1380
tcctcgttcg gcatgggcgg cacgaacgcg catgtcgtgc tcgaagaggc cccggggggtt     1440
gtcgagggtg cttcggtcgt ggagtcgacg gtcggcgggt cggcggtcgg cggcggtgtg     1500
gtgccgtggg tggtgtcggc gaagtccgct gccgcgctga acgcgcagat cgagcggctt     1560
gccgcgttcg cctcgcggga tcgtacggat ggtgtcgacg cgggcgctgt cgatgcgggt     1620
gctgtcgatg cgggtgctgt cgctcgcgta ctggccggcg ggcgtgctca gttcgagcac     1680
cgggccgtcg tcgtcggcag cgggccggac gatctggcgg cagcgctggc cgcgcctgag     1740
ggtctggtcc ggggcgtggc ttccggtgtc gggcgagtgg cgttcgtgtt ccccgggcag     1800
ggcacgcagt gggccggcat gggtgccgaa ctgctggact cttccgcggt gttcgcggcg     1860
gccatggccg aatgcgaggc cgcactctcc ccgtacgtcg actggtcgct ggaggccgtc     1920
gtacggcagg cccccggtgc gcccacgctg gagcgggtcg atgtcgtgca gcctgtgacg     1980
ttcgccgtca tggtctcgct ggctcgcgtg tggcagcacc acgggtgac gccccaggcg     2040
gtcgtcggcc actcgcaggg cgagatcgcc gccgcgtacg tcgccggtgc cctgagcctg     2100
gacgacgccg ctcgtgtcgt gaccctgcgc agcaagtcca tcgccgccca cctcgccggc     2160
aagggcggca tgctgtccct cgcgctgagc gaggacgccg tcctggagcg actggccggg     2220
ttcgacgggc tgtccgtcgc cgctgtgaac gggcccaccg ccaccgtggt ctccggtgac     2280
cccgtacaga tcgaagagct tgctcgggcg tgtgaggccg atgggtccg tgcgcgggtc     2340
attcccgtcg actacgcgtc ccacagccgg caggtcgaga tcatcgagag cgagctcgcc     2400
gaggtcctcg ccgggctcag cccgcaggct ccgcgcgtgc cgttcttctc gacactcgaa     2460
ggcgcctgga tcaccgagcc cgtgctcgac ggcggctact ggtaccgcaa cctgcgccat     2520
cgtgtgggct tcgccccggc cgtcgagacc ctggccaccg acgagggctt cacccacttc     2580
gtcgaggtca gcgcccaccc cgtcctcacc atggccctcc ccgggaccgt caccggtctg     2640
gcgaccctgc gtcgcgacaa cggcggtcag gaccgcctcg tcgctccct cgccgaagca     2700
tgggccaacg gactcgcggt cgactggagc ccgctcctcc cctccgcgac cggccaccac     2760
tccgacctcc ccacctacgc gttccagacc gagcgccact ggctgggcga gatcgaggcg     2820
ctcgcccgg cggcgagcc ggcggtgcag cccgccgtcc tccgcacgga gcggccgag     2880
ccggcggagc tcgaccggga cgagcagctg cgcgtgatcc tggacaaggt ccgggcgcag     2940
acggcccagg tgctggggta cgcgacaggc gggcagatcg aggtcgaccg gaccttccgt     3000
gaggccggtt gcacctccct gaccggcgtg gacctgcgca accggatcaa cgccgccttc     3060
ggcgtacgga tggcgccgtc catgatcttc gacttcccca cccccgaggc tctcgcggag     3120
cagctgctcc tcgtcgtgca cggggaggcg gcggcgaacc cggccggtgc ggagccggct     3180
ccggtggcgg cggccggtgc cgtcgacgag ccggtggcga tcgtcggcat ggcctgccgc     3240
```

```
ctgcccggtg gggtcgcctc gccggaggac ctgtggcggc tggtggccgg cggcggggac      3300
gcgatctcgg agttcccgca ggaccgcggc tgggacgtgg aggggctgta ccacccggat      3360
cccgagcacc ccggcacgtc gtacgtccgc cagggcggtt tcatcgagaa cgtcgccggc      3420
ttcgacgcgg ccttcttcgg gatctcgccg cgcgaggccc tcgccatgga cccgcagcag      3480
cggctcctcc tcgaaacctc ctgggaggcc gtcgaggacg ccgggatcga cccgacctcc      3540
ctgcggggac ggcaggtcgg cgtcttcact ggggcgatga cccacgagta cgggccgagc      3600
ctgcgggacg gcggggaagg cctcgacggc tacctgctga ccggcaacac ggccagcgtg      3660
atgtcgggcc gcgtctcgta cacactcggc cttgagggcc ccgccctgac ggtggacacg      3720
gcctgctcgt cgtcgctggt cgccctgcac ctcgccgtgc aggccctgcg caagggcgag      3780
gtcgacatgg cgctcgccgg cggcgtggcc gtgatgccca cgcccgggat gttcgtcgag      3840
ttcagccggc agcgcgggct ggccggggac ggccggtcga aggcgttcgc cgcgtcggcg      3900
gacggcacca gctggtccga gggcgtcggc gtcctcctcg tcgagcgcct gtcggacgcc      3960
cgccgcaacg gacaccaggt cctcgcggtc gtccgcggca cgccgtgaa ccaggacggc       4020 gcgagcaacg gcctcacggc tccgaacggg ccctcgcagc agcgcgtcat ccggcgcgcg      4080
ctggcggacc cccggctgac gacctccgac gtggacgtcg tcgaggcaca cggcacgggc      4140
acgcgactcg gcgacccgat cgaggcgcag gccctgatcg ccacctacgg ccagggccgt      4200
gacgacgaac agccgctgcg cctcgggtcg ttgaagtcca acatcgggca cacccaggcc      4260
gcggccggcg tctccggtgt catcaagatg gtccaggcga tgcgccacgg actgctgccg      4320
aagacgctgc acgtcgacga gccctcggac cagatcgact ggtcggctgg cgccgtggaa      4380
ctcctcaccg aggccgtcga ctggccggag aagcaggacg cgggctgcg ccgggccgcc       4440 gtctcctcct cgggatcag cggcaccaat gcgcatgtgg tgctcgaaga ggcccccggtg      4500 gttgtcgagg gtgcttcggt cgtcgagccg tcggttggcg ggtcggcggt cggcggcggt      4560
gtgacgcctt gggtggtgtc ggcgaagtcc gctgccgcgc tcgacgcgca gatcgagcgg      4620
cttgccgcat tcgcctcgcg ggatcgtacg gatgacgccg acgccggtgc tgtcgacgcg      4680
ggcgctgtcg ctcacgtact ggctgacggg cgtgctcagt tcgagcaccg ggccgtcgcg      4740
ctcggcgccg gggcggacga cctcgtacag gcgctggccg atccggacgg gctgatacgc      4800
ggaacggctt ccggtgtcgg gcgagtggcg ttcgtgttcc ccggtcaggg cacgcagtgg      4860
gctggcatgg gtgccgaact gctggactct tccgcggtgt tcgcggcggc catggccgag      4920
tgtgaggccg cgctgtcccc gtacgtcgac tggtcgctgg aggccgtcgt acggcaggcc      4980
cccggtgcgc ccacgctgga gcgggtcgat gtcgtgcagc ctgtgacgtt cgccgtcatg      5040
gtctcgctgg ctcgcgtgtg gcagcaccac ggtgtgacgc cccaggcggt cgtcggccac      5100
tcgcagggcg agatcgccgc cgcgtacgtc gccggagccc tgcccctgga cgacgccgcc      5160
cgcgtcgtca ccctgcgcag caagtccatc gccgcccacc tcgccggcaa gggcggcatg      5220
ctgtccctcg cgctgaacga ggacgccgtc ctggagcgac tgagtgactt cgacgggctg      5280
tccgtcgccg ccgtcaacgg gcccaccgcc actgtcgtgt cgggtgaccc cgtacagatc      5340
gaagagcttg ctcaggcgtg caaggcggac ggattccgcg cgcggatcat tcccgtcgac      5400
tacgcgtccc acagccggca ggtcgagatc atcgagagcg agctcgccca ggtcctcgcc      5460
ggtctcagcc cgcaggcccc gcgcgtgccg ttcttctcga cgctcgaagg cacctggatc      5520
accgagcccg tcctcgacgg cacctactgg taccgcaacc tccgtcaccg cgtcggcttc      5580
```

```
gcccccgcca tcgagaccct ggccgtcgac gagggcttca cgcacttcgt cgaggtcagc   5640
gcccaccccg tcctcaccat gaccctcccc gagaccgtca ccggcctcgg caccctccgt   5700
cgcgaacagg gaggccaaga gcgtctggtc acctcgctcg ccgaggcgtg ggtcaacggg   5760
cttccgtgg  catggacttc gctcctgccc gccacggcct cccgcccgg  tctgcccacc   5820
tacgccttcc aggccgagcg ctactggctc gagaacactc ccgccgccct ggccaccggc   5880
gacgactggc gctaccgcat cgactggaag cgcctcccgg ccgccgaggg gtccgagcgc   5940
accggcctgt ccgccgcctg gctcgccgtc acgccggagg accactccgc gcaggccgcc   6000
gccgtgctca ccgcgctggt cgacgccggg gcgaaggtcg aggtgctgac ggccggggcg   6060
gacgacgacc gtgaggccct cgccgccggg ctcaccgcac tgacgaccgg tgacggcttc   6120
accggcgtgg tctcgctcct cgacggactc gtaccgcagg tcgcctgggt ccaggcgctc   6180
ggcgacgccg gaatcaaggc gcccctgtgg tccgtcaccc agggcgcggt ctccgtcgga   6240
cgtctcgaca ccccgccga  ccccgaccgg gccatgctct gggcctcgg  ccgcgtcgtc   6300
gcccttgagc accccgaacg ctgggccggc ctcgtcgacc tccccgccca gcccgatgcc   6360
gccgccctcg cccacctcgt caccgcactc tccggcgcca ccggcgagga ccagatcgcc   6420
atccgcacca ccggactcca cgcccgccgc ctcgcccgcg caccctcca  cggacgtcgg   6480
cccacccgcg actggcagcc ccacggcacc gtcctcatca ccggcggcac cggagccctc   6540
ggcagccacg ccgcacgctg gatggcccac cacggagccg aacacctcct cctcgtcagc   6600
cgcagcggcg aacaagcccc cggagccacc caactcaccg ccgaactcac cgcatcgggc   6660
gcccgcgtca ccatcgccgc ctgcgacgtc gccgaccccc acgccatgcg caccctcctc   6720
gacgccatcc ccgccgagac gcccctcacc gccgtcgtcc acaccgccgg cgcgctcgac   6780
gacggcatcg tggacacgct gaccgccgag caggtccggc gggcccaccg tgcgaaggcc   6840
gtcgcgcct  cggtgctcga cgagctgacc cggacctcg  acctcgacgc gttcgtgctc   6900
ttctcgtccg tgtcgagcac tctgggcatc cccggtcagg gcaactacgc cccgcacaac   6960
gcctacctcg acgccctcgc ggctcgccgc cgggccaccg gccggtccgc cgtctcggtg   7020
gcctggggac cgtgggacgg tggcggcatg gccgccggtg acgcgtggc  cgagcggctg   7080
cgcaaccacg gcgtgcccgg catggacccg gaactcgccc tggccgcact ggagtccgcg   7140
ctcggccggg acgagaccgc gatcaccgtc gcggacatcg actggaccg  cttctacctc   7200
gcgtactcct ccggtcgccc gcagcccctc gtcgaggagc tgcccgaggt gcggcgcatc   7260
atcgacgcac gggacagcgc cacgtccgga cagggcggga gctccgccca gggcgccaac   7320
cccctggccg agcggctggc cgccgcggct ccggcgagc  gtacggagat cctcctcggt   7380
ctcgtacggg cgcaggccgc cgccgtgctc cggatgcgtt cgccggagga cgtcgccgcc   7440
gaccgcgcct tcaaggacat cggcttcgac tcgctcgccg tgtcgagct  cgcaacagg   7500
ctgaccgggg cgaccgggct ccagctgccc gcgacgctcg tcttcgacca cccgacgccg   7560
ctggccctcg tgtcgctgct ccgcagcgag ttcctcggtg acgaggagac ggcggacgcc   7620
cggcggtccg cggcgctgcc cgcgactgtc ggtgccggtc cggcgccgg  cgccggcacc   7680
gatgccgacg acgatccgat cgcgatcgtc gcgatgagct gccgctaccc cggtgacatc   7740
cgcagcccgg aggacctgtg gcggatgctg tccgagggcg gcgagggcat cacgccgttc   7800
ccaccgacc  gcggctggga cctcgacggc ctgtacgacg ccgacccgga cgcgctcggc   7860
agggcgtacg tccgcgaggg cgggttcctg cacgacgcgg ccgagttcga cgcggagttc   7920
ttcggcgtct cgccgcgcga ggcgctggcc atggacccgc agcagcggat gctcctgacg   7980
```

```
acgtcctggg aggccttcga gcgggccggc atcgagccgg catcgctgcg cggcagcagc    8040
accggtgtct tcatcggcct ctcctaccag gactacgcgg cccgcgtccc gaacgccccg    8100
cgtggcgtgg agggttacct gctgaccggc agcacgccga gcgtcgcgtc gggccgtatc    8160
gcgtacacct tcggtctcga agggcccgcg acgaccgtcg acaccgcctg ctcgtcgtcg    8220
ctgaccgccc tgcacctggc ggtgcgggcg ctgcgcagcg gcgagtgcac gatggcgctc    8280
gccggtggcg tggcgatgat ggcgaccccg cacatgttcg tggagttcag ccgtcagcgg    8340
gcgctcgccc cggacggccg cagcaaggcc ttctcggcgg acgccgacgg gttcggcgcc    8400
gcggagggcg tcggcctgct gctcgtggag cggctctcgg acgcgcggcg caacggtcac    8460
ccggtgctcg ccgtggtccg cggtaccgcc gtcaaccagg acggcgccag caacgggctg    8520
accgcgccca acggaccctc gcagcagcgg gtgatccggc aggcgctcgc cgacgcccgg    8580
ctggcacccg cgacatcga cgccgtcgag acgcacggca cgggaacctc gctgggcgac    8640
cccatcgagg cccagggcct ccaggccacg tacggcaagg agcggcccgc ggaacggccg    8700
ctcgccatcg gctccgtgaa gtccaacatc ggacacaccc aggccgcggc cggtgcggcg    8760
ggcatcatca agatggtcct cgcgatgcgc cacggcaccc tgccgaagac cctccacgcc    8820
gacgagccga gcccgcacgt cgactgggcg aacagcggcc tggccctcgt caccgagccg    8880
atcgactggc cggccggcac cggtccgcgc cgcgccgccg tctcctcctt cggcatcagc    8940
gggacgaacg cgcacgtcgt gctggagcag gcgccggatg ctgctggtga ggtgcttggg    9000
gccgatgagg tgcctgaggt gtctgagacg gtagcgatgg ctgggacggc tgggacctcc    9060
gaggtcgctg agggctctga ggcctccgag gcccccgcgg ccccccggcag ccgtgaggcg    9120 tccctccccg ggcacctgcc ctgggtgctg tccgccaagg acgagcagtc gctgcgcggc    9180
caggccgccg ccctgcacgc gtggctgtcc gagcccgccg ccgacctgtc ggacgcggac    9240
ggaccggccc gcctgcggga cgtcgggtac acgctcgcca cgagccgtac cgccttcgcg    9300
caccgcgccg ccgtgaccgc cgccgaccgg gacgggttcc tggacgggct ggccacgctg    9360
gcccagggcg gcacctcggc ccacgtccac ctggacaccg cccgggacgg caccaccgcg    9420
ttcctcttca ccggccaggg cagtcagcgc cccggcgccg gccgtgagct gtacgaccgg    9480
caccccgtct tcgcccgggc gctcgacgag atctgcgccc acctcgacgg tcacctcgaa    9540
ctgcccctgc tcgacgtgat gttcgcggcc gagggcagcg cggaggccgc gctgctcgac    9600
gagacgcggt acacgcagtg cgcgctgttc gccctggagg tcgcgctctt ccggctcgtc    9660
gagagctggg gcatgcggcc ggccgcactg ctcggtcact cggtcggcga gatcgccgcc    9720
gcgcacgtcg ccggtgtgtt ctcgctcgcc gacgccgccc gctggtcgc cgcgcgcggc    9780 cggctcatgc aggagctgcc cgccggtggc gcgatgctcg ccgtccaggc gcggaggac    9840 gagatccgct gtggctgga gacggaggag cggtacgcgg gacgtctgga cgtcgccgcc    9900
gtcaacggcc ccgaggccgc cgtcctgtcc ggcgacgcgg acgcggcgcg ggaggcggag    9960
gcgtactggt ccgggctcgg ccgcaggacc cgcgcgctgc gggtcagcca cgccttccac    10020
tccgcgcaca tggacggcat gctcgacggg ttccgcgccg tcctggagac ggtggagttc    10080
cggcgcccct ccctgaccgt ggtctcgaac gtcaccggcc tggccgccgg cccggacgac    10140
ctgtgcgacc ccgagtactg gtccggcac gtccgcggca ccgtccgctt cctcgacggc    10200
gtccgtgtcc tgcgcgacct cggcgtgcgg acctgcctgg agctgggccc cgacgggtc    10260 ctcaccgcca tggcggccga cggcctcgcg gacaccccg cggattccgc tgccggctcc    10320
```

```
cccgtcggct ctcccgccgg ctctcccgcc gactccgccg ccggcgcgct ccggccccgg   10380
ccgctgctcg tggcgctgct gcgccgcaag cggtcggaga ccgagaccgt cgcggacgcc   10440
ctcggcaggg cgcacgccca cggcaccgga cccgactggc acgcctggtt cgccggctcc   10500
ggggcgcacc gcgtggacct gcccacgtac tccttccggc gcgaccgcta ctggctggac   10560
gccccggcgg ccgacaccgc ggtggacacc gccggcctcg gtctcggcac cgccgaccac   10620
ccgctgctcg gcgccgtggt cagccttccg gaccgggacg gcctgctgct caccggccgc   10680
ctctccctgc gcacccaccc gtggctcgcg gaccacgccg tcctggggag cgtcctgctc   10740
cccggcgccg cgatggtcga actcgccgcg cacgctgcgg agtccgccgg tctgcgtgac   10800
gtgcgggagc tgaccctcct tgaaccgctg gtactgcccg agcacggtgg cgtcgagctg   10860
cgcgtgacgg tcgggcgcc ggccggagag cccggtggcg agtcggccgg ggacggcgca   10920
cggcccgtct ccctccactc gcggctcgcc gacgcgcccg ccgtaccgc ctggtcctgc   10980
cacgcgaccg gtctgctggc caccgaccgg cccgagcttc ccgtcgcgcc cgaccgtgcg   11040
gccatgtggc cgccgcaggg cgccgaggag gtgccgctcg acggtctcta cgagcggctc   11100
gacgggaacg gcctcgcctt cggtccgctg ttccaggggc tgaacgcggt gtggcggtac   11160
gagggtgagg tcttcgccga catcgcgctc cccgccacca cgaatgcgac cgcgcccgcg   11220
accgcgaacg gcggcgggag tgcggcggcg gcccctacg gcatccaccc cgccctgctc   11280
gacgcttcgc tgcacgccat cgcggtcggc ggtctcgtcg acgagcccga gctcgtccgc   11340
gtccccttcc actggagcgg tgtcaccgtg cacgcggccg gtgccgcggc ggcccgggtc   11400
cgtctcgcct ccgcggggac ggacgccgtc tcgctgtccc tgacggacgg cgagggacgc   11460
ccgctggtct ccgtggaacg gctcacgctg cgcccggtca ccgccgatca ggcggcggcg   11520
agccgcgtcg gcgggctgat gcaccgggtg gcctggcgtc cgtacgccct cgcctcgtcc   11580
ggcgaacagg acccgcacgc cacttcgtac gggccgaccg ccgtcctcgg caaggacgag   11640
ctgaaggtcg ccgccgccct ggagtccgcg ggcgtcgaag tcgggctcta ccccgacctg   11700
gccgcgctgt cccaggacgt ggcggccggc gccccggcgc ccgtaccgt ccttgcgccg   11760
ctgcccgcgg gtcccgccga cggcggcgcg gagggtgtac ggggcacggt ggcccggacg   11820
ctggagctgc tccaggcctg gctggccgac gagcacctcg cgggcacccg cctgctcctg   11880
gtcacccgcg gtgcggtgcg ggaccccgag gggtccggcg ccgacgatgg cggcgaggac   11940
ctgtcgcacg cggccgcctg gggtctcgta cggaccgcgc agaccgagaa ccccggccgc   12000
ttcggccttc tcgacctggc cgacgacgcc tcgtcgtacc ggaccctgcc gtcggtgctc   12060
tccgacgcgg gcctgcgcga cgaaccgcag ctcgccctgc acgacggcac catcaggctg   12120
gcccgcctgg cctccgtccg gcccgagacc ggcaccgccg caccggcgct cgccccggag   12180
ggcacggtcc tgctgaccgg cggcaccggc ggcctgggcg gactggtcgc ccggcacgtg   12240
gtgggcgagt ggggcgtacg acgcctgctg ctggtgagcc ggcggggcac ggacgccccg   12300
ggcgccgacg agctcgtgca cgagctggag gccctgggag ccgacgtctc ggtgccgcg   12360
tgcgacgtcg ccgaccgcga agccctcacc gccgtactcg acgccatccc cgccgaacac   12420
ccgctcaccg cggtcgtcca cacggcaggc gtcctctccg acggcaccct ccgtccatg   12480
acgacggagg acgtggaaca cgtactgcgg cccaaggtcg acgccgcgtt cctcctcgac   12540
gaactcacct cgacgcccgc atacgacctg gcagcgttcg tcatgttctc ctccgccgcc   12600
gccgtcttcg gtgcgcgggg gcaggcgcc tacgccgccg ccaacgccac cctcgacgcc   12660
ctcgcctggc gccgcgggc agccggactc cccgccctct ccctcggctg gggcctctgg   12720
```

```
gccgagacca gcggcatgac cggcgagctc ggccaggcgg acctgcgccg gatgagccgc  12780
gcgggcatcg gcgggatcag cgacgccgag ggcatcgcgc tcctcgacgc cgccctccgc  12840
gacgaccgcc acccggtcct gctgcccctg cggctcgacg ccgccgggct gcgggacgcg  12900
gccgggaacg acccggccgg aatcccggcg ctcttccggg acgtcgtcgg cgccaggacc  12960
gtccgggccc ggccgtccgc ggcctccgcc tcgacgacga ccgggacggc cggcacgccg  13020
gggacggcgg acgcgcggc ggaaacggcg gcggtcacgc tcgccgaccg gccgccacc   13080 gtggacgggc ccgcacggca gcgcctgctg ctcgagttcg tcgtcggcga ggtcgccgaa  13140
gtactcggcc acgcccgcgg tcaccggatc gacgccgaac ggggcttcct cgacctcggc  13200
ttcgactccc tgaccgccgt cgaactccgc aaccggctca actccgccgg tggcctcgcc  13260
ctcccggcga ccctggtctt cgaccaccca agcccggcgg cactcgcctc ccacctggac  13320
gccgagctgc cgcgcggcgc ctcggaccag gacggagccg ggaaccggaa cgggaacgag  13380
aacgggacga cggcgtcccg gagcaccgcc gagacggacg cgctgctggc acaactgacc  13440
cgcctggaag gcgccttggt gctgacgggc ctctcggacg cccccgggag cgaagaagtc  13500
ctggagcacc tgcggtccct gcgctcgatg gtcacgggcg agaccgggac cgggaccgcg  13560
tccggagccc cggacggcgc cgggtccggc gccgaggacc ggccctgggc ggccggggac  13620
ggagccgggg gcgggagtga ggacggcgcg ggagtgccgg acttcatgaa cgcctcggcc  13680
gaggaactct tcgcctcct cgaccaggac cccagcacgg actgatccct gccgcacggt  13740
cgcctcccgc cccggacccc gtcccgggca cctcgactcg aatcacttca tgcgcgcctc  13800
gggcgcctcc aggaactcaa ggggacagcg tgtccacggt gaacgaagag aagtacctcg  13860
actacctgcg tcgtgccacg gcggacctcc acgaggcccg tggccgcctc cgcgagctgg  13920
aggcgaaggc gggcgagccg gtggcgatcg tcggcatggc ctgccgcctg cccggcggcg  13980
tcgcctcgcc cgaggacctg tggcggctgg tggccggcgg cgaggacgcg atctcggagt  14040
tcccccagga ccgcggctgg gacgtggagg gcctgtacga cccgaacccg gaggccacgg  14100
gcaagagtta cgcccgcgag gccggattcc tgtacgaggc gggcgagttc gacgccgact  14160
tcttcgggat ctcgccgcgc gaggccctcg ccatggaccc gcagcagcgt ctcctcctgg  14220
aggcctcctg ggaggcgttc gagcacgccg ggatcccggc ggccaccgcg cgcggcacct  14280
cggtcggcgt cttcaccggc gtgatgtacc acgactacgc cacccgtctc accgatgtcc  14340
cggagggcat cgagggctac ctgggcaccg gcaactccgg cagtgtcgcc tcgggccgcg  14400
tcgcgtacac gcttggcctg gaggggccgg ccgtcacggt cgacaccgcc tgctcgtcct  14460
cgctggtcgc cctgcacctc gccgtgcagg ccctgcgcaa gggcgaggtc gacatggcgc  14520
tcgccggcgg cgtgacggtc atgtcgacgc ccagcacctt cgtcgagttc agccgtcagc  14580
gcgggctggc gccggacggc cggtcgaagt ccttctcgtc gacggccgac ggcaccagct  14640
ggtccgaggg cgtcggcgtc ctcctcgtcg agcgcctgtc cgacgcgcgt cgcaagggcc  14700
atcggatcct cgccgtggtc cggggcaccg ccgtcaacca ggacgcgcc agcagcggcc  14760 tcacggctcc gaacgggccg tcgcagcagc gcgtcatccg acgtgccctg cggacgccc   14820 ggctcacgac ctccgacgtg gacgtcgtcg aggcccacgg cacgggtacg cgactcggcg  14880
acccgatcga ggcgcaggcc gtcatcgcca cgtacgggca gggccgtgac ggcgaacagc  14940
cgctgcgcct cgggtcgttg aagtccaaca tcggacacac ccaggccgcc gccggtgtct  15000
ccggcgtgat caagatggtc caggcgatgc gccacggcgt cctgccgaag acgctccacg  15060
```

```
tggagaagcc gacggaccag gtggactggt ccgcgggcgc ggtcgagctg ctcaccgagg    15120
ccatggactg gccggacaag ggcgacggcg gactgcgcag ggccgcggtc tcctccttcg    15180
gcgtcagcgg gacgaacgcg cacgtcgtgc tcgaagaggc cccggcggcc gaggagaccc    15240
ctgcctccga ggcgaccccg gccgtcgagc cgtcggtcgg cgccggcctg gtgccgtggc    15300
tggtgtcggc gaagactccg gccgcgctgg acgcccagat cggacgcctc gccgcgttcg    15360
cctcgcaggg ccgtacggac gccgccgatc cgggcgcggt cgctcgcgta ctggccggcg    15420
ggcgcgccga gttcgagcac cgggccgtcg tgctcggcac cggacaggac gatttcgcgc    15480
aggcgctgac cgctccggaa ggactgatac gcggcacgcc ctcggacgtg gccgggtgg    15540 cgttcgtgtt ccccggtcag ggcacgcagt gggccgggat gggcgccgaa ctcctcgacg    15600
tgtcgaagga gttcgcggcg gccatggccg agtgcgagag cgcgctctcc cgctatgtcg    15660
actggtcgct ggaggccgtc gtccggcagg cgccgggcgc gcccacgctg gagcgggtcg    15720
acgtcgtcca gcccgtgacc ttcgctgtca tggtttcgct ggcgaaggtc tggcagcacc    15780
acggcgtgac gccgcaggcc gtcgtcggcc actcgcaggg cgagatcgcc gccgcgtacg    15840
tcgccggtgc cctcaccctc gacgacgccg cccgcgtcgt caccctgcgc agcaagtcca    15900
tcgccgccca cctcgccggc aagggcggca tgatctccct cgccctcagc gaggaagcca    15960
cccggcagcg catcgagaac ctccacggac tgtcgatcgc cgccgtcaac ggccccaccg    16020
ccaccgtggt ttcgggcgac cccacccaga tccaagagct cgctcaggcg tgtgaggccg    16080
acggggtccg cgcacggatc atccccgtcg actacgcctc ccacagcgcc cacgtcgaga    16140
ccatcgagag cgaactcgcc gaggtcctcg ccgggctcag cccgcggaca cctgaggtgc    16200
cgttcttctc gacactcgaa ggcgcctgga tcaccgagcg ggtgctcgac ggcacctact    16260
ggtaccgcaa cctccgccac cgcgtcggct tcgccccgc cgtcgagacc ctcgccaccg    16320
acgaaggctt cacccacttc atcgaggtca gcgcccaccc cgtcctcacc atgaccctcc    16380
ccgagaccgt caccggcctc ggcaccctcc gccgcgaaca gggaggccag gagcgtctgg    16440
tcacctcact cgccgaagcc tggaccaacg gcctcaccat cgactgggcg cccgtcctcc    16500
ccaccgcaac cggccaccac cccgagctcc ccacctacgc cttccagcgc cgtcactact    16560
ggctccacga ctcccccgcc gtccaggget ccgtgcagga ctcctggcgc taccgcatcg    16620
actggaagcg cctcgcggtc gccgacgcgt ccgagcgcgc cgggctgtcc gggcgctggc    16680
tcgtcgtcgt ccccgaggac cgttccgccg aggccgcccc ggtgctcgcc gcgctgtccg    16740
gcgccggcgc cgaccccgta cagctggacg tgtccccgct gggcgaccgg cagcggctcg    16800
ccgcgacgct gggcgaggcc ctggcggcgg ccggtggagc cgtcgacggc gtcctctcgc    16860
tgctcgcgtg ggacgagagc gcgcacccce gccacccege ccccttcace cggggcaccg    16920 gcgccaccct caccctggtg caggcgctgg aggacgccgg cgtcgccgcc ccgctgtggt    16980
gcgtgaccca cggcgcggtg tccgtcggcc gggccgacca cgtcacctcc cccgcccagg    17040
ccatggtgtg gggcatgggc cggtcgccg ccctggagca ccccgagcgg tggggcggcc    17100
tgatcgacct gccctcggac gccgaccggg cggccctgga ccgcatgacc acggtcctcg    17160
ccggcggtac gggtgaggac caggtcgcgg tacgcgcctc cgggctgctc gcccgccgcc    17220
tcgtccgcgc ctccctcccg gcgcacggca cggcttcgcc gtggtggcag gccgacggca    17280
cggtgctcgt caccggtgcc gaggagcctg cggccgccga ggccgacgc cggctggccc    17340 gcgacggcgc cggacacctc ctcctccaca ccacccccto cggcagcgaa ggcgccgaag    17400
gcacctccgg tgccgccgag gactccggcc tcgccgggct cgtcgccgaa ctcgcggacc    17460
```

```
tgggcgcgac ggccaccgtc gtgacctgcg acctcacgga cgcggaggcg gccgcccggc  17520
tgctcgccgg cgtctccgac gcgcacccgc tcagcgccgt cctccacctg ccgcccaccg  17580
tcgactccga gccgctcgcc gcgaccgacg cggacgcgct cgcccgtgtc gtgaccgcga  17640
aggccaccgc cgcgctccac ctggaccgcc tcctgcggga ggccgcggct gccggaggcc  17700
gtccgcccgt cctggtcctc ttctcctcgg tcgccgcgat ctggggcggc gccggtcagg  17760
gcgcgtacgc cgccggtacg gccttcctcg acgccctcgc cggtcagcac cgggccgacg  17820
gccccaccgt gacctcggtg gcctggagcc cctgggaggg cagccgcgtc accgagggtg  17880
cgaccgggga gcggctgcgc cgcctcggcc tgcgcccct cgccccgcg acggcgctca  17940 ccgccctgga caccgcgctc ggccacgcg acaccgccgt cacgatcgcc gacgtcgact  18000
ggtcgagctt cgcccccggc ttcaccacgg cccggccggg caccctcctc gccgatctgc  18060
ccgaggcgcg ccgcgcgctc gacgagcagc agtcgacgac ggccgccgac gacaccgtcc  18120
tgagccgcga gctcggtgcg ctcaccggcg ccgaacagca gcgccgtatg caggagttgg  18180
tccgcgagca cctcgccgtg gtcctcaacc accctcccc cgaggccgtc gacacggggc  18240
gggccttccg tgacctcgga ttcgactcgc tgacggcggt cgagctccgc aaccgcctca  18300
agaacgccac cggcctggcc ctcccggcca ctctggtctt cgactacccg acccccccgga  18360 cgctggcgga gttcctcctc gcggagatcc tgggcgagca ggccggtgcc ggcgagcagc  18420
ttccggtgga cggcggggtc gacgacgagc ccgtcgcgat cgtcggcatg gcgtgccgcc  18480
tgccgggcgg tgtcgcctcg ccggaggacc tgtggcggct ggtggccggc ggcgaggacg  18540
cgatctccgg cttcccgcag gaccgcggct gggacgtgga ggggctgtac gacccggacc  18600
cggacgcgtc cgggcggacg tactgccgtg ccggtggctt cctcgacgag gcgggcgagt  18660
tcgacgccga cttcttcggg atctcgccgc gcgaggccct cgccatggac ccgcagcagc  18720
ggctcctcct ggagacctcc tgggaggccg tcgaggacgc cgggatcgac ccgacctccc  18780
ttcaggggca gcaggtcggc gtgttcgcgg gcaccaacgg cccccactac gagccgctgc  18840
tccgcaacac cgccgaggat cttgagggtt acgtcgggac gggcaacgcc gccagcatca  18900
tgtcgggccg tgtctcgtac accctcggcc tggagggccc ggccgtcacg gtcgacaccg  18960
cctgctcctc ctcgctggtc gccctgcacc tcgccgtgca ggccctgcgc aagggcgaat  19020
gcggactggc gctcgcgggc ggtgtgacgg tcatgtcgac gcccacgacg ttcgtggagt  19080
tcagccggca gcgcgggctc gcggaggacg gccggtcgaa ggcgttcgcc gcgtcggcgg  19140
acggcttcgg cccggcggag ggcgtcggca tgctcctcgt cgagcgcctg tcggacgccc  19200
gccgcaacgg acaccgtgtg ctggcggtcg tgcgcggcag cgccggtcaac caggacgcg  19260 cgagcaacgg cctgaccgcc cgaacgggc cctcgcagca gcgcgtcatc cggcgcgcgc  19320
tcgcggacgc ccgactgacg accgccgacg tggacgtcgt cgaggcccac ggcacgggca  19380
cgcgactcgg cgacccgatc gaggcacagg ccctcatcgc cacctacggc caggggcgcg  19440
acaccgaaca gccgctgcgc ctgggtcgt tgaagtccaa catcggacac acccaggccg  19500
ccgccggtgt ctccggcatc atcaagatgg tccaggcgat gcgccacggc gtcctgccga  19560
agacgctcca cgtggaccgg ccgtcggacc agatcgactg gtcggcgggc acgtcgagc  19620 tgctcaccga ggccatggac tggccgagga agcaggaggg cgggctgcgc cgcgcggccg  19680
tctcctcctt cggcatcagc ggcacgaacg cgcacatcgt gctcgaagaa gccccggtcg  19740
acgaggacgc cccggcggac gagccgtcgg tcggcggtgt ggtgccgtgg ctcgtgtccg  19800
```

```
cgaagactcc ggccgcgctg gacgcccaga tcggacgcct cgccgcgttc gcctcgcagg   19860
gccgtacgga cgccgccgat ccgggcgcgg tcgctcgcgt actggccggc gggcgtgcgc   19920
agttcgagca ccgggccgtc gcgctcggca cggacagga cgacctggcg gccgcactgg    19980
ccgcgcctga gggtctggtc cggggtgtgg cctccggtgt gggtcgagtg gcgttcgtgt   20040
tcccgggaca gggcacgcag tgggccggga tgggtgccga actcctcgac gtgtcgaagg   20100
agttcgcggc ggccatggcc gagtgcgagg ccgcgctcgc tccgtacgtg gactggtcgc   20160
tggaggccgt cgtccgacag gccccgcgcg cgcccacgct ggagcgggtc gatgtcgtcc   20220
agcccgtgac gttcgccgtc atggtctcgc tggcgaaggt ctggcagcac cacggggtga   20280
ccccgcaagc cgtcgtcggc cactcgcagg gcgagatcgc cgccgcgtac gtcgccggtg   20340
ccctgagcct ggacgacgcc gctcgtgtcg tgaccctgcg cagcaagtcc atcggcgccc   20400
acctcgcggg ccaggcggc atgctgtccc tcgcgctgag cgaggcggcc gttgtggagc    20460
gactggccgg gttcgacggg ctgtccgtcg ccgccgtcaa cgggcctacc gccaccgtgg   20520
tttcgggcga cccgacccag atccaagagc tcgctcaggc gtgtgaggcc gacgggtcc    20580 gcgcacggat catccccgtc gactacgcct cccacagcgc ccacgtcgag accatcgaga   20640
gcgaactcgc cgacgtcctg gcggggttgt cccccagac accccaggtc ccttcttct    20700 ccaccctcga aggcgcctgg atcaccgaac ccgccctcga cggcggctac tggtaccgca   20760
acctccgcca tcgtgtgggc ttcgccccgg ccgtcgaaac cctggccacc gacgaaggct   20820
tcacccactt cgtcgaggtc agcgcccacc ccgtcctcac catggccctg cccgagaccg   20880
tcaccggcct cggcaccctc cgccgtgaca acggcggaca gcaccgcctc accacctccc   20940
tcgccgaggc ctgggccaac ggcctcaccg tcgactgggc ctctctcctc cccaccacga   21000 ccaccaccc cgatctgccc acctacgcct tccagaccga gcgctactgg ccgcagcccg   21060
acctctccgc cgccggtgac atcacctccg ccggtctcgg ggcggccgag cacccgctgc   21120
tcggcgcggc cgtggcgctc gcggactccg acggctgcct gctcacgggg agcctctccc   21180
tccgtacgca ccccctggctg gcggaccacg cggtggccgg caccgtgctg ctgccggga   21240 cggcgttcgt ggagctggcg ttccgagccg gggaccaggt cggttgcgat ctggtcgagg   21300 agctcacccct cgacgcgccg ctcgtgctgc ccgtcgtgg cgcggtccgt gtgcagctgt   21360
ccgtcggcgc gagcgacgag tccgggcgtc gtaccttcgg gctctacgcg cacccggagg   21420
acgcgccggg cgaggcggag tggacgcggc acgccaccgg tgtgctggcc gcccgtgcgg   21480
accgcaccgc cccgtcgcc gacccggagg cctggccgcc gcgggcgcc gagccggtgg    21540 acgtggacgt tctgtacgag cgcttcgcgg cgaacggcta cggctacggc cccctcttcc   21600
agggcgtccg tggtgtctgg cggcgtggcg acgaggtgtt cgccgacgtg gccctgccgg   21660
ccgaggtcgc cggtgccgag ggcgcgcggt tcggccttca cccggcgctg ctcgacgccg   21720
ccgtgcaggc ggccggtgcg ggcgggggcgt tcggcgcggg cacgcggctg ccgttcgcct   21780
ggagcgggat ctccctgtac gcggtcggcg ccacgcccct ccgcgtgcgg ctggcccccg   21840
ccggcccgga cacggtgtcc gtgagcgccg ccgactcctc cgggcagccg gtgttcgccg   21900
cggactccct cacggtgctg cccgtcgacc ccgcgcagct ggcggccttc agcgacccga   21960
ctctggacgc gctgcacctg ctggagtgga ccgcctggga cggtgccgcg caggccctgc   22020
ccggcgcggt cgtgctgggc ggcgacgccg acggtctcgc cgcggcgctg cgcgccggtg   22080
gcaccgaggt cctgtccttc ccggaccttta cggacctggt ggaggccgtc gaccggggcg   22140 agacccggc cccggcgacc gtcctggtgg cctgccccgc cgccggcccc ggtgggccgg   22200
```

```
agcatgtccg cgaggccctg cacgggtcgc tcgcgctgat gcaggcctgg ctggccgacg   22260
agcggttcac cgatgggcgc ctggtgctcg tgacccgcga cgcggtcgcc gcccgttccg   22320
gcgacggcct gcggtccacg ggacaggccg ccgtctgggg cctcgccgg tccgcgcaga   22380 cggagagccc gggccggttc gtcctgctcg acctcgccgg ggaagcccgg acggccgggg   22440
acgccaccgc cggggacggc ctgacgaccg gggacgccac cgtcggcggc acctctggag   22500
acgccgccct cggcagcgcc ctcgcgaccg ccctcggctc gggcgagccg cagctcgccc   22560
tccgggacgg ggcgctcctc gtaccccgcc tggcgcgggc cgccgcgccc gccgcggccg   22620
acggcctcgc cgcggccgac ggcctcgccg ctctgccgct gcccgccgct ccggccctct   22680
ggcgtctgga gcccggtacg gacggcagcc tggagagcct cacggcggcg cccggcgacg   22740
ccgagaccct cgccccggag ccgctcggcc cgggacaggt ccgcatcgcg atccgggcca   22800
ccggtctcaa cttccgcgac gtcctgatcg ccctcggcat gtaccccgat ccggcgctga   22860
tgggcaccga gggagccggc gtggtcaccg cgaccggccc cggcgtcacg cacctcgccc   22920
ccggcgaccg ggtcatgggc ctgctctccg gcgcgtacgc cccggtcgtc gtggcggacg   22980
cgcggaccgt cgcgcggatg cccgaggggt ggacgttcgc ccagggcgcc tccgtgccgg   23040
tggtgttcct gacggccgtc tacgccctgc gcgacctggc ggacgtcaag cccggcgagc   23100
gcctcctggt ccactccgcc gccggtggcg tgggcatggc cgccgtgcag ctcgcccggc   23160 actgggcgt ggaggtccac ggcacggcga gtcacgggaa gtgggacgcc ctgcgcgcgc   23220
tcggcctgga cgacgcgcac atcgcctcct cccgcaccct ggacttcgag tccgcgttcc   23280
gtgccgcttc cggcggggcg ggcatggacg tcgtactgaa ctcgctcgcc cgcgagttcg   23340
tcgacgcctc gctgcgcctg ctcgggccgg gcggccggtt cgtggagatg gggaagaccg   23400
acgtccgcga cgcggagcgg gtcgccgccg accaccccgg tgtcggctac cgcgccttcg   23460
acctgggcga ggccgggccg gagcggatcg gcgagatgct cgccgaggtc atcgccctct   23520
tcgaggacgg ggtgctccgg cacctgcccg tcacgacctg gacgtgcgc cgggcccgcg   23580 acgccttccg gcacgtcagc caggcccgcc acacgggcaa ggtcgtcctc acgatgccgt   23640
cgggcctcga cccggagggt acggtcctgc tgaccggcgg caccggtgcg ctgggggca   23700 tcgtggcccg gcacgtggtg ggcgagtggg gcgtacgacg cctgctgctc gtgagccggc   23760
ggggcacgga cgccccgggc gccggcgagc tcgtgcacga gctggaggcc ctgggagccg   23820
acgtctcggt ggccgcgtgc gacgtcgccg accgcgaagc cctcaccgcc gtactcgact   23880
cgatccccgc cgaacacccg ctcaccgcgc tcgtccacac ggcaggcgtc ctctccgacg   23940
gcaccctccc ctcgatgaca gcggaggatg tggaacacgt actgcgtccc aaggtcgacg   24000
ccgcgttcct cctcgacgaa ctcacctcga cgcccggcta cgacctggca gcgttcgtca   24060
tgttctcctc cgccgccgcc gtcttcggtg gcgcggggca gggcgcctac gccgccgcca   24120
acgccaccct cgacgccctc gcctggcgcc gccggacagc cggactcccc gccctctccc   24180
tcggctgggg cctctgggcc gagaccagcg gcatgaccgg cggactcagc gacaccgacc   24240
gctcgcggct ggcccgttcc ggggcgacgc ccatggacag cgagctgacc ctgtccctcc   24300 tggacgcgg catgcgccgc gacgaccgg cgctcgtccc gatcgccctg gacgtcgccg   24360
cgctccgcgc ccagcagcgc gacggcatgc tggcgccgct gctcagcggg ctcacccgcg   24420
gatcgcgggt cggcggcgcg ccggtcaacc agcgcagggc agccgccgga ggcgcgggcg   24480
aggcggacac ggacctcggc gggcggctcg ccgcgatgac accggacgac cgggtcgcgc   24540
```

-continued

```
acctgcggga cctcgtccgt acgcacgtgg cgaccgtcct gggacacggc accccgagcc   24600
gggtggacct ggagcgggcc ttccgcgaca ccggtttcga ctcgctcacc gccgtcgaac   24660
tccgcaaccg tctcaacgcc gcgaccgggc tgccggctgcc ggccacgctg gtcttcgacc   24720
accccacccc gggggagctc gccgggcacc tgctcgacga actcgccacg gccgcgggcg   24780
ggtcctgggc ggaaggcacc gggtccggag acacggcctc ggcgaccgat cggcagacca   24840
cggcggccct cgccgaactc gaccggctgg aaggcgtgct cgcctccctc gcgcccgccg   24900
ccggcggccg tccggagctc gccgcccggc tcagggcgct ggccgcggcc ctgggggacg   24960
acggcgacga cgccaccgac ctggacgagg cgtccgacga cgacctcttc tccttcatcg   25020
acaaggagct gggcgactcc gacttctgac ctgcccgaca ccaccggcac caccggcacc   25080
accagccccc ctcacacacg gaacacggaa cggacaggcg agaacgggag ccatggcgaa   25140
caacgaagac aagctccgcg actacctcaa gcgcgtcacc gccgagctgc agcagaacac   25200
caggcgtctg cgcgagatcg agggacgcac gcacgagccg gtggcgatcg tgggcatggc   25260
ctgccgcctg ccgggcggtg tcgcctcgcc cgaggacctg tggcagctgg tggccggggga   25320 cggggacgcg atctcggagt tcccgcagga ccgcggctgg gacgtggagg ggctgtacga   25380
ccccgacccg gacgcgtccg gcaggacgta ctgccggtcc ggcggattcc tgcacgacgc   25440
cggcgagttc gacgccgact tcttcgggat ctcgccgcgc gaggccctcg ccatggaccc   25500
gcagcagcga ctgtccctca ccaccgcgtg ggaggcgatc gagagcgcgg gcatcgaccc   25560
gacggccctg aagggcagcg gcctcggcgt cttcgtcggc ggctggcaca ccggctacac   25620
ctcggggcag accaccgccg tgcagtcgcc cgagctggag ggccacctgg tcagcggcgc   25680
ggcgctgggc ttcctgtccg gccgtatcgc gtacgtcctc ggtacggacg accggcccct   25740
gaccgtggac acggcctgct cgtcctcgct ggtcgccctg cacctcgccg tgcaggccct   25800
ccgcaagggc gagtgcgaca tggccctcgc cggtggtgtc acggtcatgc ccaacgggga   25860
cctgttcgtg cagttcagcc ggcagcgcgg gctggccgcg gacggccggt cgaaggcgtt   25920
cgccacctcg gcggacggct tcggccccgc ggagggcgcc ggagtcctgc tggtggagcg   25980
cctgtcggac gcccgccgca acggacaccg gatcctcgcg gtcgtccgcg gcagcgcggt   26040
caaccaggac ggcgccagca acggcctcac ggctccgcac gggccctccc agcagcgcgt   26100
catccgacgg gccctggcgg acgcccggct cgcgccgggt gacgtggacg tcgtcgaggc   26160
gcacggcacg ggcacgcggc tcggcgaccc gatcgaggcg caggccctca tcgccaccta   26220
cggccaggag aagagcagcg aacagccgct gaggctgggc gcgttgaagt cgaacatcgg   26280
gcacacgcag gccgcggccg gtgtcgcagg tgtcatcaag atggtccagg cgatgcgcca   26340
cggactgctg ccgaagacgc tgcacgtcga cgagccctcg gaccagatcg actggtcggc   26400
gggcacggtg gaactcctca ccgaggccgt cgactggccg gagaagcagg acggcgggct   26460
gcgccgcgcg gctgtctcct ccttcggcat cagcgggacg aacgcgcacg tcgtcctgga   26520
ggaggccccg gcggtcgagg actccccggc cgtcgagccg ccggccggtg gcggtgtggt   26580
gccgtggccg gtgtccgcga agactccggc cgcgctggac gcccagatcg ggcagctcgc   26640
cgcgtacgcg gacggtcgta cggacgtgga tccggcggtg gccgcccgcg ccctggtcga   26700
cagccgtacg gcgatggagc accgcgcggt cgcgtcggc gacagccggg aggcactgcg   26760
ggacgccctg cggatgccgg aaggactggt acgcggcacg tcctcggacg tgggccgggt   26820
ggcgttcgtc ttccccggcc agggcacgca gtgggccggc atgggcgccg aactccttga   26880
cagctcaccg gagttcgctg cctcgatggc cgaatgcgag accgcgctct cccgctacgt   26940
```

-continued

```
cgactggtct cttgaagccg tcgtccgaca ggaacccggc gcacccacgc tcgaccgcgt   27000
cgacgtcgtc cagcccgtga ccttcgctgt catggtctcg ctggcgaagg tctggcagca   27060
ccacggcatc acccccagg ccgtcgtcgg ccactcgcag ggcgagatcg ccgccgcgta    27120
cgtcgccggt gcactcaccc tcgacgacgc cgcccgcgtc gtcaccctgc gcagcaagtc   27180
catcgccgcc cacctcgccg gcaagggcgg catgatctcc ctcgccctcg acgaggcggc   27240
cgtcctgaag cgactgagcg acttcgacgg actctccgtc gccgccgtca acggccccac   27300
cgccaccgtc gtctccggcg acccgaccca gatcgaggaa ctcgcccgca cctgcgaggc   27360
cgacggcgtc cgtgcgcgga tcatcccggt cgactacgcc tcccacagcc ggcaggtcga   27420
gatcatcgag aaggagctgg ccgaggtcct cgccggactc gccccgcagg ctccgcacgt   27480
gccgttcttc tccaccctcg aaggcacctg gatcaccgag ccggtgctcg acggcaccta   27540
ctggtaccgc aacctgcgcc atcgcgtggg cttcgccccc gccgtggaga ccttggcggt   27600
tgacggcttc acccacttca tcgaggtcag cgcccacccc gtcctcacca tgaccctccc   27660
cgagaccgtc accggcctcg gcaccctccg ccgcgaacag ggaggccagg agcgtctggt   27720
cacctcactc gccgaagcct gggccaacgg cctcaccatc gactgggcgc ccatcctccc   27780
caccgcaacc ggccaccacc ccgagctccc cacctacgcc ttccagaccg agcgcttctg   27840
gctgcagagc tccgcgccca ccagcgccgc cgacgactgg cgttaccgcg tcgagtggaa   27900
gccgctgacg gcctccggcc aggcggacct gtccgggcgg tggatcgtcg ccgtcgggag   27960
cgagccagaa gccgagctgc tgggcgcgct gaaggccgcg ggagcggagg tcgacgtact   28020
ggaagccggg gcggacgacg accgtgaggc cctcgccgcc cggctcaccg cactgacgac   28080
cggcgacggc ttcaccggcg tggtctcgct cctcgacgac ctcgtgccac aggtcgcctg   28140
ggtgcaggca ctcggcgacg ccggaatcaa ggcgcccctg tggtccgtca cccagggcgc   28200
ggtctccgtc ggacgtctcg acacccccgc cgaccccgac cgggccatgc tctggggcct   28260
cggccgcgtc gtcgcccttg agcacccccga acgctgggcc ggcctcgtcg acctccccgc   28320
ccagcccgat gccgccgccc tcgcccacct cgtcaccgca ctctccggcg ccaccggcga   28380
ggaccagatc gccatccgca ccaccggact ccacgcccgc cgcctcgccc gcgcacccct   28440
ccacggacgt cggcccaccc gcgactggca gccccacggc accgtcctca tcaccggcgg   28500
caccggagcc ctcggcagcc acgccgcacg ctggatggcc caccacgag ccgaacacct    28560 cctcctcgtc agccgcagcg gcgaacaagc ccccggagcc acccaactca ccgccgaact   28620
caccgcatcg ggcgcccgcg tcaccatcgc cgcctgcgac gtcgccgacc cccacgccat   28680
gcgcaccctc ctcgacgcca tccccgccga gacgcccctc accgccgtcg tccacaccgc   28740
cggcgcaccg ggcggcgatc cgctggacgt caccggcccg gaggacatcg cccgcatcct   28800
gggcgcgaag acgagcggcg ccgaggtcct cgacgacctg ctccgcggca ctccgctgga   28860
cgccttcgtc ctctactcct cgaacgccgg ggtctggggc agcggcagcc agggcgtcta   28920
cgcggcggcc aacgcccacc tcgacgcgct cgccgcccgg cgccgcgccc ggggcgagac   28980
ggcgacctcg gtcgcctggg gcctctgggc cggcgacggc atgggccggg gcgccgacga   29040
cgcgtactgg cagcgtcgcg gcatccgtcc gatgagcccc gaccgcgccc tggacgaact   29100
ggccaaggcc ctgagccacg acgagacctt cgtcgccgtg ccgatgtcg actgggagcg    29160 gttcgcgccc gcgttcacgg tgtccgtcc cagccttctg ctcgacgcg tcccggaggc     29220 ccggcaggcg ctcgccgcac ccgtcggtgc cccggctccc ggcgacgccg ccgtggcgcc   29280
```

```
gaccgggcag tcgtcggcgc tggccgcgat caccgcgctc cccgagcccg agcgccggcc   29340
ggcgctcctc accctcgtcc gtacccacgc ggcggccgta ctcggccatt cctcccccga   29400
ccgggtggcc cccggccgtg ccttcaccga gctcggcttc gactcgctga cggccgtgca   29460
gctccgcaac cagctctcca cggtggtcgg caacaggctc cccgccacca cggtcttcga   29520
ccacccgacg cccgccgcac tcgccgcgca cctccacgag gcgtacctcg caccggccga   29580
gccggccccg acggactggg aggggcgggt gcgccgggcc ctggccgaac tgcccctcga   29640
ccggctgcgg gacgcggggg tcctcgacac cgtcctgcgc ctcaccggca tcgagcccga   29700
gccgggttcc ggcggttcgg acggcggcgc cgccgaccct ggtgcggagc cggaggcgtc   29760
gatcgacgac ctggacgccg aggccctgat ccggatggct ctcggccccc gtaacacctg   29820
acccgaccgc ggtcctgccc cacgcgccgc accccgcgca tcccgcgcac cacccgcccc   29880
cacacgccca caaccccatc cacgagcgga agaccacacc cagatgacga gttccaacga   29940
acagttggtg gacgctctgc gcgcctctct caaggagaac gaagaactcc ggaaagagag   30000
ccgtcgccgg gccgaccgtc ggcaggagcc catggcgatc gtcggcatga gctgccggtt   30060
cgcgggcgga atccggtccc ccgaggacct ctggacgcc gtcgccgcgg gcaaggacct   30120
ggtctccgag gtaccggagg agcgcggctg ggacatcgac tccctctacg acccggtgcc   30180
cgggcgcaag ggcacgacgt acgtccgcaa cgccgcgttc ctcgacgacg ccgccggatt   30240
cgacgcggcc ttcttcggga tctcgccgcg cgaggccctc gccatggacc cgcagcagcg   30300
gcagctcctc gaagcctcct gggaggtctt cgagcgggcc ggcatcgacc ccgcgtcggt   30360
ccgcggcacc gacgtcggcg tgtacgtggg ctgtggctac caggactacg cgccggacat   30420
ccgggtcgcc cccgaaggca ccggcggtta cgtcgtcacc ggcaactcct ccgccgtggc   30480
ctccgggcgc atcgcgtact ccctcggcct ggagggaccc gccgtgaccg tggacacggc   30540
gtgctcctct tcgctcgtcg ccctgcacct cgccctgaag ggcctgcgga acggcgactg   30600
ctcgacggca ctcgtgggcg gcgtggccgt cctcgcgacg ccgggcgcgt tcatcgagtt   30660
cagcagccag caggccatgg ccgccgacgg ccggaccaag ggcttcgcct cggcggcgga   30720
cggcctcgcc tggggcgagg gcgtcgccgt actcctcctc gaacggctct ccgacgcgcg   30780
gcgcaagggc caccgggtcc tggccgtcgt gcgcggcagc gccatcaacc aggacggcgc   30840
gagcaacggc ctcacggctc cgcacgggcc ctcccagcag cgcctgatcc gccaggccct   30900
ggccgacgcg cggctcacgt cgagcgacgt ggacgtcgtg gagggccacg gcacggggac   30960
ccgtctcggc gacccgatcg aggcgcaggc gctgctcgcc acgtacgggc aggggcgcgc   31020
cccggggcag ccgctgcggc tggggacgct gaagtcgaac atcgggcaca cgcaggccgc   31080
ttcgggtgtc gccggtgtca tcaagatggt gcaggcgctg cgccacgggg tgctgccgaa   31140
gaccctgcac gtggacgagc cgacggacca ggtcgactgg tcggccggtt cggtcgagct   31200
gctcaccgag gccgtggact ggccggagcg gccgggccgg ctccgccggg cgggcgtctc   31260
cgcgttcggc gtgggcggga cgaacgcgca cgtcgtcctg gaggaggccc cggcggtcga   31320
ggagtcccct gccgtcgagc cgccggccgg tggcggcgtg gtgccgtggc cggtgtccgc   31380
gaagacctcg gccgcactgg acgcccagat cgggcagctc gccgcatacg cggaagaccg   31440
cacggacgtg gatccggcgg tggccgcccg cgccctggtc gacagccgta cggcgatgga   31500
gcaccgcgcg gtcgcggtcg gcgacagccg ggaggcactg cgggacgccc tgcggatgcc   31560
ggaaggactg gtacggggca cggtcaccga tccgggccgg gtggcgttcg tcttccccgg   31620
ccagggcacg cagtgggccg gcatgggcgc cgaactcctc gacagctcac ccgaattcgc   31680
```

```
cgccgccatg gccgaatgcg agaccgcact ctccccgtac gtcgactggt ctctcgaagc   31740
cgtcgtccga caggctccca gcgcaccgac actcgaccgc gtcgacgtcg tccagcccgt   31800
caccttcgcc gtcatggtct ccctcgccaa ggtctggcag caccacggca tcaccccga    31860 ggccgtcatc ggccactccc agggcgagat cgccgccgcg tacgtcgccg gtgccctcac   31920
cctcgacgac gccgctcgtg tcgtgaccct ccgcagcaag tccatcgccg cccacctcgc   31980
cggcaagggc ggcatgatct ccctcgccct cagcgaggaa gccacccggc agcgcatcga   32040
gaacctccac ggactgtcga tcgccgccgt caacgggcct accgccaccg tggtttcggg   32100
cgaccccacc cagatccaag aacttgctca ggcgtgtgag gccgacggca tccgcgcacg   32160
gatcatcccc gtcgactacg cctcccacag cgcccacgtc gagaccatcg agaacgaact   32220
cgccgacgtc ctggcggggt tgtccccca  gacacccag  gtcccttct  tctccaccct   32280 cgaaggcacc tggatcaccg aacccgccct cgacggcggc tactggtacc gcaacctccg   32340
ccatcgtgtg ggcttcgccc cggccgtcga gaccctcgcc accgacgaag gcttcaccca   32400
cttcatcgag gtcagcgccc accccgtcct caccatgacc ctccccgaca aggtcaccgg   32460
cctggccacc ctccgacgcg aggacggcgg acagcaccgc ctcaccacct cccttgccga   32520
ggcctgggcc aacggcctcg ccctcgactg ggcctccctc ctgcccgcca cgggcgccct   32580
cagccccgcc gtccccgacc tcccgacgta cgccttccag caccgctcgt actggatcag   32640
ccccgcgggt cccggcgagg cgcccgcgca caccgcttcc gggcgcgagg ccgtcgccga   32700 gacgggctc  gcgtggggcc cgggtgccga ggacctcgac gaggagggcc ggcgcagcgc   32760
cgtactcgcg atggtgatgc ggcaggcggc ctccgtgctc cggtgcgact cgcccgaaga   32820
ggtccccgtc gaccgcccgc tgcgggagat cggcttcgac tcgctgaccg ccgtcgactt   32880
ccgcaaccgc gtcaaccggc tgaccggtct ccagctgccg cccaccgtcg tgttcgagca   32940
cccgacgccc gtcgcgctcg ccgagcgcat cagcgacgag ctggccgagc ggaactgggc   33000
cgtcgccgag ccgtcggatc acgagcaggc ggaggaggaa aaggccgccg ctccggcggg   33060
ggcccgctcc ggggccgaca ccggcgccgg cgccgggatg ttccgcgccc tgttccggca   33120
ggccgtggag gacgaccggt acggcgagtt cctcgacgtc ctcgccgaag cctccgcgtt   33180
ccgcccgcag ttcgcctcgc ccgaggcctg ctcggagcgg ctcgacccgg tgctgctcgc   33240
cggcggtccg acggaccggg cggaaggccg tgccgttctc gtcggctgca ccggcaccgc   33300
ggcgaacggc ggcccgcacg agttcctgcg gctcagcacc tccttccagg aggagcggga   33360
cttcctcgcc gtacctctcc ccggctacgg cacgggtacg ggcaccggca cggccctcct   33420
cccggccgat ctcgacaccg cgctcgacgc ccaggcccgg gcgatcctcc gggccgccgg   33480
ggacgccccg gtcgtcctgc tcgggcactc cggcggcgcc ctgctcgcgc acgagctggc   33540
cttccgcctg gagcgggcgc acggcgcgcc gccggccggg atcgtcctgg tcgacccta   33600 tccgccgggc catcaggagc ccatcgaggt gtggagcagg cagctgggcg agggcctgtt   33660
cgcgggcgag ctggagccga tgtccgatgc gcggctgctg gccatgggcc ggtacgcgcg   33720
gttcctcgcc ggcccgcggc cgggccgcag cagcgcgccc gtgcttctgg tccgtgcctc   33780
cgaaccgctg ggcgactggc aggaggagcg gggcgactgg cgtgcccact gggaccttcc   33840
gcacaccgtc gcggacgtgc cgggcgacca cttcacgatg atgcgggacc acgcgccggc   33900
cgtcgccgag gccgtcctct cctggctcga cgccatcgag gcatcgagg  gggcgggcaa   33960 gtgaccgaca gacctctgaa cgtggacagc ggactgtgga tccggcgctt ccaccccgcg   34020
```

```
ccgaacagcg cggtgcggct ggtctgcctg ccgcacgccg gcggctccgc cagctacttc   34080
ttccgcttct cggaggagct gcacccctcc gtcgaggccc tgtcggtgca gtatccgggc   34140
cgccaggacc ggcgtgccga gccgtgtctg gagagcgtcg aggagctcgc cgagcatgtg   34200
gtcgcggcca ccgaaccctg gtggcaggag ggccggctgg ccttcttcgg gcacagcctc   34260
ggcgcctccg tcgccttcga gacggcccgc atcctggaac agcggcacgg ggtacggccc   34320
gagggcctgt acgtctccgg tcggcgcgcc ccgtcgctgg cgccggaccg gctcgtccac   34380
cagctggacg accgggcgtt cctggccgag atccggcggc tcagcggcac cgacgagcgg   34440
ttcctccagg acgacgagct gctgcggctg gtgctgcccg cgctgcgcag cgactacaag   34500
gcggcggaga cgtacctgca ccggccgtcc gccaagctca cctgcccggt gatggccctg   34560
gccggcgacc gtgacccgaa ggcgccgctg aacgaggtgg ccgagtggcg tcggcacacc   34620
agcgggccgt tctgcctccg ggcgtactcc ggcggccact tctacctcaa cgaccagtgg   34680
cacgagatct gcaacgacat ctccgaccac ctgctcgtca cccgcggcgc gcccgatgcc   34740
cgcgtcgtgc agcccccgac cagccttatc gaaggagcgg cgaagagatg cagaaccca   34800 cggtgaccga cgacctgacg ggggccctca cgcagccccc gctgggccgc accgtccgcg   34860
cggtggccga ccgtgaactc ggcacccacc tcctggagac ccgcggcatc cactggatcc   34920
acgccgcgaa cggcgacccg tacgccaccg tgctgcgcgg ccaggcggac gacccgtatc   34980
ccgcgtacga gcgggtgcgt gcccgcggcg cgctctcctt cagcccgacg ggcagctggg   35040
tcaccgccga tcacgccctg gcggcgagca tcctctgctc gacggacttc ggggtctccg   35100
gcgccgacgg cgtcccggtg ccgcagcagg tcctctcgta cggggagggc tgtccgctgg   35160
agcgcgagca ggtgctgccg gcggccggtg acgtgccgga gggcgggcag cgtgccgtgg   35220 tcgagggat ccaccgggag acgctggagg gtctcgcgcc ggacccgtcg gcgtcgtacg   35280
ccttcgagct gctgggcggt ttcgtccgcc cggcggtgac ggccgctgcc gccgccgtgc   35340
tgggtgttcc cgcggaccgg cgcgcggact cgcggatct gctggagcgg ctccggccgc   35400
tgtccgacag cctgctggcc ccgcagtccc tgcggacggt acgggcggcg gacggcgcgc   35460
tggccgagct cacggcgctg ctcgccgatt cggacgactc ccccggggcc ctgctgtcgg   35520
cgctcggggt caccgcagcc gtccagctca cggggaacgc ggtgctcgcg ctcctcgcgc   35580
atcccgagca gtggcgggag ctgtgcgacc ggcccgggct cgcggcggcc gcggtggagg   35640
agaccctccg ctacgacccg ccggtgcagc tcgacgcccg ggtggtccgc ggggagacgg   35700
agctggcggg ccggcggctg ccggccgggg cgcatgtcgt cgtcctgacc gccgcgaccg   35760
gccgggaccc ggaggtcttc acggaccggg agcgcttcga cctcgcgcgc cccgacgccg   35820
ccgcgcacct cgcgctgcac cccgccggtc cgtacgcccc ggtggcgtcc ctggtccggc   35880
ttcaggcgga ggtcgcgctg cggacccgtg ccgggcgttt cccgggctg cggcaggcgg   35940 gggacgtgct ccgcccccgc cgcgcgcctg tcggccgcgg gccgctgagc gtcccggtca   36000
gcagctcctg agacaccggg gccccggtcc gccggccc ccttcggacg gaccggacgg   36060
ctcggaccac ggggacggct cagaccgtcc cgtgtgtccc cgtccggctc ccgtccgccc   36120
catcccgccc ctccaccggc aaggaaggac acgacgccat gcgcgtcctg ctgacctcgt   36180
tcgcacatca cacgcactac tacggcctgg tgcccctggc ctgggcgctg ctcgccgccg   36240
ggcacgaggt gcgggtcgcc agccagcccg cgctcacgga caccatcacc gggtccgggc   36300
tcgccgcggt gccggtcggc accgaccacc tcatccacga gtaccgggtg cggatggcgg   36360
gcgagccgcg cccgaaccat ccggcgatcg ccttcgacga ggcccgtccc gagccgctgg   36420
```

```
actgggacca cgccctcggc atcgaggcga tcctcgcccc gtacttctat ctgctcgcca    36480
acaacgactc gatggtcgac gacctcgtcg acttcgcccg gtcctggcag ccggacctgg    36540
tgctgtggga gccgacgacc tacgcgggcg ccgtcgccgc ccaggtcacc ggtgccgcgc    36600
acgcccgggt cctgtggggg cccgacgtga tgggcagcgc ccgccgcaag ttcgtcgcgc    36660
tgcgggaccg gcagccgccc gagcaccgcg aggaccccac cgcggagtgg ctgacgtgga    36720
cgctcgaccg gtacgcgccc tccttcgaag aggagctgct caccggccag ttcacgatcg    36780
acccgacccc gccgagcctg cgcctcgaca cgggcctgcc gaccgtcggg atgcgttatg    36840
ttccgtacaa cggcacgtcg gtcgtgccgg actggctgag tgagccgccc gcgcggcccc    36900
gggtctgcct gaccctcggc gtctccgcgc gtgaggtcct cggcggcgac ggcgtctcgc    36960
agggcgacat cctggaggcg ctcgccgacc tcgacatcga gctcgtcgcc acgctcgacg    37020
cgagtcagcg cgccgagatc cgcaactacc gaagcacac ccggttcacg gacttcgtgc     37080
cgatgcacgc gctcctgccg agctgctcgg cgatcatcca ccacggcggg gcgggcacct    37140
acgcgaccgc cgtgatcaac gcggtgccgc aggtcatgct cgccgagctg tgggacgcgc    37200
cggtcaaggc gcgggccgtc gccgagcagg gggcggggtt cttcctgccg ccggccgagc    37260
tcacgccgca ggccgtgcgg gacgccgtcg tccgcatcct cgacgacccc tcggtcgcca    37320
ccgccgcgca ccggctgcgc gaggagacct tcggcgaccc caccccggcc gggatcgtcc    37380
ccgagctgga gcggctcgcc gcgcagcacc gccgcccgcc ggccgacgcc cggcactgag    37440
ccgcacccct cgccccaggc ctcacccctg tatctgcgcc gggggacgcc cccggcccac    37500
cctccgaaag accgaaagca ggagcaccgt gtacgaagtc gaccacgccg acgtctacga    37560
cctcttctac ctgggtcgcg gcaaggacta cgccgccgag gcctccgaca tcgccgacct    37620
ggtgcgctcc cgtaccccg aggcctcctc gctcctggac gtggcctgcg gtacgggcac    37680
gcatctggag cacttcacca aggagttcgg cgacaccgcc ggcctggagc tgtccgagga    37740
catgctcacc cacgcccgca gcggctgccg acgccacg ctccaccagg gcgacatgcg     37800
ggacttccgg ctcggccgga agttctccgc cgtggtcagc atgttcagct ccgtcggcta    37860
cctgaagacg accgaggaac tcggcgcggc cgtcgcctcg ttcgcggagc acctggagcc    37920
cggtggcgtc gtcgtcgtcg agccgtggtg gttcccggag accttcgccg acggctgggt    37980
cagcgccgac gtcgtccgcc gtgacgggcg caccgtggcc cgtgtctcgc actcggtgcg    38040
ggagggaac gcgacgcgca tggaggtcca cttcaccgtg gccgacccgg caagggcgt     38100
gcggcacttc tccgacgtcc atctcatcac cctgttccac caggccgagt acgaggccgc    38160
gttcacggcc gccgggctgc gcgtcgagta cctggagggc ggccgtcgg gccgtggcct     38220
cttcgtcggc gtccccgcct gagcaccgcc caagaccccc cggggcggga cgtcccgggt    38280
gcaccaagca aagagagaga acgaaccgt gacaggtaag acccgaatac cgcgtgtccg     38340
ccgcggccgc accacgccca gggccttcac cctggccgtc gtcggcaccc tgctggcggg    38400
caccaccgtg gcggccgccg ctcccggcgc cgccgacacg gccaatgttc agtacacgag    38460
ccgggcggcg gagctcgtcg cccagatgac gctcgacgag aagatc                   38506
```

<210> SEQ ID NO 20
<211> LENGTH: 2401
<212> TYPE: DNA
<213> ORGANISM: Streptomyces venezuelae

<400> SEQUENCE: 20

-continued

```
cgtggcggcc gccgctcccg gcgccgccga cacggccaat gttcagtaca cgagccgggc      60
ggcggagctc gtcgcccaga tgacgctcga cgagaagatc agcttcgtcc actgggcgct     120
ggaccccgac cggcagaacg tcggctacct tcccggcgtg ccgcgtctgg gcatcccgga     180
gctgcgtgcc gccgacggcc cgaacggcat ccgcctggtg gggcagaccg ccaccgcgct     240
gcccgcgccg gtcgccctgg ccagcacctt cgacgacacc atggccgaca gctacggcaa     300
ggtcatgggc cgcgacggtc gcgcgctcaa ccaggacatg gtcctgggcc cgatgatgaa     360
caacatccgg gtgccgcacg gcggccggaa ctacgagacc ttcagcgagg accccctggt     420
ctcctcgcgc accgcggtcg cccagatcaa gggcatccag ggtgcgggtc tgatgaccac     480
ggccaagcac ttcgcggcca acaaccagga gaacaaccgc ttctccgtga cgccaatgt      540
cgacgagcag acgctccgcg agatcgagtt cccggcgttc gaggcgtcct ccaaggccgg     600
cgcgggctcc ttcatgtgtg cctacaacgg cctcaacggg aagccgtcct gcggcaacga     660
cgagctcctc aacaacgtgc tgcgcacgca gtggggcttc cagggctggg tgatgtccga     720
ctggctcgcc accccgggca ccgacgccat caccaagggc ctcgaccagg agatgggcgt     780
cgagctcccc ggcgacgtcc cgaagggcga gccctcgccg ccggccaagt tcttcggcga     840
ggcgctgaag acgccgtcc tgaacggcac ggtccccgag gcggccgtga cgcggtcggc      900
ggagcggatc gtcggccaga tggagaagtt cggtctgctc ctcgccactc cggcgccgcg     960
gcccgagcgc gacaaggcgg gtgcccaggc ggtgtcccgc aaggtcgccg agaacggcgc    1020
ggtgctcctg cgcaacgagg gccaggccct gccgctcgcc ggtgacgccg gcaagagcat    1080
cgcggtcatc ggcccgacgg ccgtcgaccc caaggtcacc ggcctgggca gcgcccacgt    1140
cgtcccggac tcgcggcgg cgccactcga caccatcaag gcccgcgcgg gtgcgggtgc     1200
gacggtgacg tacgagacgg gtgaggagac cttcgggacg cagatcccgg cggggaacct    1260
cagcccggcg ttcaaccagg gccaccagct cgagccgggc aaggcggggg cgctgtacga    1320
cggcacgctg accgtgcccg ccgacggcga gtaccgcatc gcggtccgtg ccaccggtgg    1380
ttacgccacg gtgcagctcg gcagccacac catcgaggcc ggtcaggtct acggcaaggt    1440
gagcagcccg ctcctcaagc tgaccaaggg cacgcacaag ctcacgatct cgggcttcgc    1500
gatgagtgcc accccgctct ccctggagct gggctgggtn acgccggcgg cggccgacgc    1560
gacgatcgcg aaggccgtgg agtcggcgcg gaaggcccgt acggcggtcg tcttcgccta    1620
cgacgacggc accgagggcg tcgaccgtcc gaacctgtcg ctgccgggta cgcaggacaa    1680
gctgatctcg gctgtcgcgg acgccaaccc gaacacgatc gtggtcctca caccggttc     1740
gtcggtgctg atgccgtggc tgtccaagac ccgcgcggtc ctggacatgt ggtacccggg    1800
ccaggcgggc gccgaggcca ccgccgcgct gctctacggt gacgtcaacc cgagcggcaa    1860
gctcacgcag agcttcccgg ccgccgagaa ccagcacgcg gtcgccggcg acccgaccag    1920
ctacccgggc gtcgacaacc agcagacgta ccgcgagggc atccacgtcg ggtaccgctg    1980
gttcgacaag gagaacgtca agccgctgtt cccgttcggg cacggcctgt cgtacacctc    2040
gttcacgcag agcgccccga ccgtcgtgcg tacgtccacg ggtggtctga aggtcacggt    2100
cacggtccgc aacagcggga agcgcgccgg ccaggaggtc gtccaggcgt acctcggtgc    2160
cagcccgaac gtgacggctc cgcaggcgaa gaagaagctc gtgggctaca cgaaggtctc    2220
gctcgccgcg ggcgaggcga agacggtgac ggtgaacgtc gaccgccgtc agctgcagtt    2280
ctgggatgcc gccacggaca actggaagac gggaacgggc aaccgcctcc tgcagaccgg    2340
ttcgtcctcc gccgacctgc ggggcagcgc cacggtcaac gtctggtgac gtgacgccgt    2400
``` g                                                                          2401

<210> SEQ ID NO 21
<211> LENGTH: 5970
<212> TYPE: DNA
<213> ORGANISM: Streptomyces venezuelae

<400> SEQUENCE: 21

| | | | | | |
|---|---|---|---|---|---|
| ggcgagaagt | aggcgcgggt | gtgcacgcct | tcggccttca | ggacctccat | gacgaggtcg       60 |
| cggtggatgc | cggtggtggc | ctcgtcgatc | tcgacgatca | cgtactggtg | gttgttgagg      120 |
| ccgtggcggt | cgtggtcggc | gacgaggacg | ccggggaggt | ccgcgaggtg | ctcgcggtag      180 |
| scggcgtggt | tgcgccggtt | ccggtcgatg | acctcgggaa | acgcgtcgag | ggaggtgagg      240 |
| cccatggcgg | cggcggcctc | gctcatcttg | gcgttggtcc | cgccggcggg | gctgccgccg      300 |
| ggcaggtcga | agccgaagtt | gtggagggcg | cggatccggg | cggcgaggtc | ggcgtcgtcg      360 |
| gtgacgacgg | cgccgccctc | gaaggcgttg | acggccttgg | tggcgtggaa | gctgaagacc      420 |
| tcggcgtcgc | cgaggctgcc | ggcgggccgg | ccgtcgaccg | cgcagccgag | ggcgtgcgcg      480 |
| gcgtcgaagt | acagccgcag | gccgtgctcg | tcggcgacct | tccgcagctg | gtcggcggcg      540 |
| caggggcggc | cccagaggtg | gacgccgacg | acggccgagg | tgcggggtgt | gaccgcggcg      600 |
| gccacctggt | ccgggtcgag | gttgccggtg | tccggtcga  | tgtcggcgaa | gaccggggtg      660 |
| aggccgatcc | agcgcagtgc | gtgcggggtg | gcggcgaacg | tcatcgacgg | catgatcact      720 |
| tcgccggtga | ggccggcggc | gtgcgcgagg | agctggagcc | cggccgtggc | gttgcaggtg      780 |
| gccacggcat | gccggacccc | ggcgagcccg | gcgacgcgct | cctcgaactc | gcggacgagc      840 |
| gggccgccgt | tggacagcca | ctggctgtcg | agggcccggt | cgagccgctc | gtacagcctg      900 |
| gcgcggtcga | tgcggttggg | ccgccccacg | aggagcggct | ggtcgaaagc | ggcggggccg      960 |
| ccgaagaatg | cgaggtcgga | taaggcgctt | ttcacggatg | ttccctccgg | gccaccgtca     1020 |
| cgaaatgatt | cgccgatccg | ggaatcccga | acgaggtcgc | cgcgctccac | cgtgacgtac     1080 |
| gacgagatgg | tcgattgtgg | tggtcgattt | cgggggact  | ctaatccgcg | cggaacggga     1140 |
| ccgacaagag | cacgctatgc | gctctcgatg | tgcttcggat | cacatccgcc | tccgggtat      1200 |
| tccatcggcg | gcccgaatgt | gatgatcctt | gacaggatcc | gggaatcagc | cgagccgccg     1260 |
| ggagggccgg | ggcgcgctcc | gcggaagagt | acgtgtgaga | agtcccgttc | ctcttcccgt     1320 |
| ttccgttccg | cttccggccc | ggtctggagt | tctccgtgcg | ccgtacccag | cagggaacga     1380 |
| ccgcttctcc | cccggtactc | gacctcgggg | ccctggggca | ggatttcgcg | gccgatccgt     1440 |
| atccgacgta | cgcgagactg | cgtgccgagg | gtccggccca | ccggtgcgc  | accccgagg      1500 |
| gggacgaggt | gtggctggtc | gtcggctacg | accgggcgcg | ggcggtcctc | gccgatcccc     1560 |
| ggttcagcaa | ggactggcgc | aactccacga | ctcccctgac | cgaggccgag | gccgcgctca     1620 |
| accacaacat | gctggagtcc | gacccgccgg | ggcacacccg | gctgcgcaag | ctggtggccc     1680 |
| gtgagttcac | catgcgccgg | gtcgagttgc | tgcggccccg | ggtccaggag | atcgtcgacg     1740 |
| ggctcgtgga | cgccatgctg | gcggcgcccg | acggccgcgc | cgatctgatg | gagtccctgg     1800 |
| cctggccgct | gccgatcacc | gtgatctccg | aactcctcgg | cgtgcccgag | ccggaccgcg     1860 |
| ccgccttccg | cgtctggacc | gacgccttcg | tcttcccgga | cgatcccgcc | caggcccaga     1920 |
| ccgccatggc | cgagatgagc | ggctatctct | cccggctcat | cgactccaag | cgcgggcagg     1980 |
| acggcgagga | cctgctcagc | gcgctcgtgc | ggaccagcga | cgaggacggc | tcccggctga     2040 |

```
cctccgagga gctgctcggt atggcccaca tcctgctcgt cgcggggcac gagaccacgg    2100
tcaatctgat cgccaacggc atgtacgcgc tgctctcgca ccccgaccag ctggccgccc    2160
tgcgggccga catgacgctc ttggacgcg cggtggagga gatgttgcgc tacgagggcc    2220
cggtggaatc cgcgacctac cgcttccgg tcgagcccgt cgacctggac ggcacggtca    2280
tcccggccgt tgacacggtc ctcgtcgtcc tggccgacgc ccaccgcacc cccgagcgct    2340
tcccggaccc gcaccgcttc gacatccgcc gggacaccgc cggccatctc gccttcggcc    2400
acggcatcca cttctgcatc ggcgcccct tggcccggtt ggaggcccgg atcgccgtcc    2460
gcgcccttct cgaacgctgc ccggacctcg ccctggacgt ctcccccggc gaactcgtgt    2520
ggtatccgaa cccgatgatc cgcgggctca aggccctgcc gatccgctgg cggcgaggac    2580
gggaggcggg ccgccgtacc ggttgaaccc gcacgtcacc cattacgact ccttgtcacg    2640
gaagccccgg atcggtcccc cctcgccgta caagacctg gttagagtga tggaggacga    2700
cgaagggttc ggcgcccgga cgaggggga cttccgcgat gaatctggtg gaacgcgacg    2760
gggagatagc ccatctcagg gccgttcttg acgcatccgc cgcaggtgac gggacgctct    2820
tactcgtctc cggaccggcc ggcagcggga agacggagct gctgcggtcg ctccgccggc    2880
tggccgccga gcgggagacc cccgtctggt cggtccgggc gctgccgggt gaccgcgaca    2940
tccccctggg cgtcctctgc cagttactcc gcagcgccga caacacggt gccgacacct    3000 ccgccgtccg cgacctgctg gacgccgcct cgcggcgggc cggaacctca cctcccccgc    3060
cgacgcgccg ctccgcgtcg acgagacaca ccgcctgcac gactggctgc tctccgtctc    3120
ccgccggcac cccgttcctc gtcgccgtcg acgacctgac ccacgccgac accgcgtccc    3180
tgaggttcct cctgtactgc gccgcccacc acgaccaggg cggcatcggc ttcgtcatga    3240
ccgagcgggc ctcgcagcgc gccggatacc gggtgttccg cgccgagctg ctccgccagc    3300
cgcactgccg caacatgtgg ctctccgggc ttcccccag cggggtacgc cagttactcg    3360
cccactacta cggccccgag gccgccgagc ggcgggcccc cgcgtaccac gcgacgaccg    3420
gcgggaaccc gctgctcctg cgggcgctga cccaggaccg gcaggcctcc cacaccaccc    3480
tcggcgcggc cggcggcgac gagcccgtcc acggcgacgc cttcgcccag gccgtcctcg    3540
actgcctgca ccgcagcgcc gagggcacac tggagaccgc ccgctggctc gcggtcctcg    3600
aacagtccga cccgctcctg gtggagcggc tcacgggaac gaccgccgcc gccgtcgagc    3660
gccacatcca ggagctcgcc gccatcggcc tcctggacga ggacggcacc ctgggacagc    3720
ccgcgatccg cgaggccgcc ctccaggacc tgccggccgg cgagcgcacc gaactgcacc    3780
ggcgcgccgc ggagcagctg caccgggacg gcgccgacga ggacaccgtg gcccgccacc    3840
tgctggtcgg cggcgccccc gacgctccct gggcgctgcc cctgctcgaa cggggcgcgc    3900
agcaggccct gttcgacgac cgactcgacg acgccttccg gatcctcgag ttcgccgtgc    3960
ggtcgagcac cgacaacacc cagctggccc gcctcgcccc acacctggtc gcggcctcct    4020
ggcggatgaa cccgcacatg acgacccggg ccctcgcact cttcgaccgg ctcctgagcg    4080
gtgaactgcc gcccagccac ccggtcatgg ccctgatccg ctgcctcgtc tggtacggnc    4140
ggctgcccga ggccgccgac gcgctgtccc ggctgcggcc cagctccgac aacgatgcct    4200
tggagctgtc gctcacccgg atgtggctcg cggcgctgtg cccgccgctc ctggagtccc    4260
tgccggccac gccggagccg gagcggggtc ccgtccccgt acggctcgcg ccgcggacga    4320
ccgcgctcca ggcccaggcc ggcgtcttcc agcggggccc ggacaacgcc tcggtcgcgc    4380
aggccgaaca gatcctgcag ggctgccggc tgtcggagga gacgtacgag gccctggaga    4440
```

```
cggccctctt ggtcctcgtc cacgccgacc ggctcgaccg ggcgctgttc tggtcggacg      4500
ccctgctcgc cgaggccgtg gagcggcggt cgctcggctg ggaggcggtc ttcgccgcga      4560
cccgggcgat gatcgcgatc cgctgcgcg  acctcccgac ggcgcgggag cgggccgagc      4620
tggcgctctc ccacgcggcg ccggagagct ggggcctcgc cgtgggcatg cccctctccg      4680
cgctgctgct cgcctgcacg gaggccgcg  agtacgaaca ggcggagcgg gtcctgcggc      4740
agccggtgcc ggacgcgatg ttcgactcgc ggcacggcat ggagtacatg cacgcccggg      4800 ccgctactg  gctggcganc ggccggctgc acgcggcgct gggcgagttc atgctctgcg      4860
gggagatcct gggcagctgg aacctcgacc agccctcgat cgtgccctgg cggacctccg      4920
ccgccgaggt gtacctgcgg ctcggcaacc gccagaaggc cagggcgctg ccgaggcccc     4980
agctcgccct ggtgcggccc gggcgctccc gcacccgggg tctcacccty cgggtcctgg      5040
cggcggcggt ggacgccag  caggcggagc ggctgcacgc cgaggcggtc gacatgctgc      5100
acgacagcgg cgaccggctc gaacacgccc gcgcgctcgc cgggatgagc cgccaccagc      5160
aggcccaggg ggacaactac cgggcgagga tgacggcgcg gctcgccggc gacatggcgt      5220
gggcctgcgg cgcgtacccg ctggccgagg agatcgtgcc gggccgcggc ggccgccggg      5280
cgaaggcggt gagcacggag ctggaactgc cgggcggccc ggacgtcggc ctgctctcgg      5340
aggccgaacg ccgggtggcg gccctggcag cccgaggatt gacgaaccgc cagatagcgc      5400
gccggctctg cgtcaccgcg agcacggtcg aacagcacct gacgcgcgtc taccgcaaac      5460
tgaacgtgac ccgccgagca gacctcccga tcagcctcgc ccaggacaag tccgtcacgg      5520
cctgagccac ccccggtgtc cccgtgcgac gacccgccgc acgggccacc gggcccgccg      5580
ggacacgccg gtgcgacacg ggggcgcgcc aggtgccatg gggacctccg tgaccgcccg      5640
aggcgcccga ggcgcccggt gcggcacccg gagacgccag gaccgccggg accaccggag      5700
acgccaggga ccgctgggga caccgggacc tcagggaccg ccgggaccgc ccgagttgca      5760
cccggtgcgc ccggggacac cagaccgccg ggaccacccg agggtgcccg gtgtggcccc      5820
ggcggccggg gtgtccttca tcggtgggcc ttcatcggca ggaggaagcg accgtgagac      5880
ccgtcgtgcc gtcggcgatc agccgcctgt acgggcgtcg gactccctgg cggtcccgga      5940
cccgtcgtac gggctcgcgg gacccggtgc                                      5970

<210> SEQ ID NO 22
<211> LENGTH: 3292
<212> TYPE: DNA
<213> ORGANISM: Streptomyces venezuelae

<400> SEQUENCE: 22 acccccaaa  ggggtggtga cactcccct  gcgcagcccc tagcgccccc ctaactcgcc        60
acgccgaccg ttatcaccgg cgccctgctg ctagtttccg agaatgaagg gaatagtcct       120
ggccggcggg agcggaactc ggctgcatcc ggcgacctcg gtcatttcga agcagattct       180
tccggtctac aacaaaccga tgatctacta tccgctgtcg gttctcatgc tcggcggtat       240
tcgcgagatt caaatcatct cgaccccca  gcacatcgaa ctcttccagt cgcttctcgg       300
aaacggcagg cacctgggaa tagaactcga ctatgcggtc cagaaagagc ccgcaggaat       360
cgcggacgca cttctcgtcg gagccgagca catcggcgac gacacctgcg ccctgatcct       420
gggcgacaac atcttccacg ggcccggcct ctacacgctc ctgcgggaca gcatcgcgcg       480
cctcgacggc tgcgtgctct tcggctaccc ggtcaaggac cccgagcggt acggcgtcgc       540
```

```
cgaggtggac gcgacgggcc ggctgaccga cctcgtcgag aagcccgtca agccgcgctc    600
caacctcgcc gtcaccggcc tctacctcta cgacaacgac gtcgtcgaca tcgccaagaa    660
catccggccc tcgccgcgcg gcgagctgga gatcaccgac gtcaaccgcg tctacctgga    720
gcggggccgg gccgaactcg tcaacctggg ccgcggcttc gcctggctgg acaccggcac    780
ccacgactcg ctcctgcggg ccgcccagta cgtccaggtc ctggaggagc ggcagggcgt    840
ctggatcgcg ggccttgagg agatcgcctt ccgcatgggc ttcatcgacg ccgaggcctg    900
tcacggcctg ggagaaggcc tctcccgcac cgagtacgag agctatctga tggagatcgc    960
cggccgcgag ggagccccgt gagggcacct cgcggccgac gcgttccacg accgacagc   1020 gccaccgaca gtgcgaccca caccgcgacc cgcaccgcca ccgacagtgc gacccacacc   1080
gcgacctaca gcgcgaccga aggaagacg gcagtgcggc ttctggtgac cggaggtgcg   1140
ggcttcatcg gctcgcactt cgtgcggcag ctcctcgccg gggcgtaccc cgacgtgccc   1200
gccgatgagg tgatcgtcct ggacagcctc acctacgcgg gcaaccgcgc caacctcgcc   1260
ccggtggacg cggaccccgcg actgcgcttc gtccacggcg acatccgcga cgccggcctc   1320
ctcgcccggg aactgcgcgg cgtggacgcc atcgtccact tcgcggccga gagccacgtg   1380
gaccgctcca tcgcgggcgc gtccgtgttc accgagacca acgtgcaggg cacgcagacg   1440
ctgctccagt gcgccgtcga cgccggcgtc ggccgggtcg tgcacgtctc caccgacgag   1500
gtgtacgggt cgatcgactc cggctcctgg accgagagca gccgctgga gcccaactcg   1560 ccctacgcgg cgtccaaggc cggctccgac ctcgttgccc gcgcctacca ccggacgtac   1620
ggcctcgacg tacgatcac ccgctgctgc aacaactacg gccgtacca gcaccccgag   1680 aagctcatcc ccctcttcgt gacgaacctc ctcgacggcg gacgctccc gctgtacggc   1740 gacggcgcga acgtccgcga gtgggtgcac accgacgacc actgccgggg catcgcgctc   1800
gtcctcgcgg cggccgggc cggcgagatc taccacatcg gcggcggcct ggagctgacc   1860
aaccgcgaac tcaccggcat cctcctggac tcgctcggcg ccgactggtc ctcggtccgg   1920
aagtcgccga ccgcaaggg ccacgacctg cgctactccc tcgacggcgg caagatcgag   1980
cgcgagctcg gctaccgccc gcaggtctcc ttcgcggacg gcctcgcgcg gaccgtccgc   2040
tggtaccggg agaaccgcgg ctggtgggag ccgctcaagg cgaccgcccc gcagctgccc   2100
gccaccgccg tggaggtgtc cgcgtgagca gccgcgccga cccccccgc gtccccttcc   2160 tcgacctcaa ggccgcctac gaggagctcc gcgcggagac cgacgccgcg atcgcccgcg   2220
tcctcgactc ggggcgctac ctcctcggac ccgaactcga aggattcgag cggagttcg   2280 ccgcgtactg cgagacggac cacgccgtcg gcgtgaacag cgggatggac gccctccagc   2340
tcgccctccg cggcctcggc atcggacccg gggacgaggt gatcgtcccc tcgcacacgt   2400
acatcgccag ctggctcgcg gtgtccgcca ccggcgcgac cccgtgccc gtcgagccgc   2460 acgaggacca cccaccctg gacccgctgc tcgtcgagaa ggcgatcacc cccgcaccc   2520 gggcgctcct cccgtccac ctctacgggc acccgccga catggacgcc ctccgcgagc   2580
tcgcggaccg gcacggcctg cacatcgtcg aggacgccgc gcaggccac ggcgcccgct   2640 accggggccg gcgatcggc gccgggtcgt cggtggccgt gttcagcttc tacccgggca   2700
agaacctcgg ctgcttcggc gacggcggcg ccgtcgtcac cggcgacccc gagctcgccg   2760
aacggctccg gatgctccgc aactacggct cgcggcagaa gtacagccac gagacgaagg   2820
gcaccaactc ccgcctggac gagatgcagg ccgccgtgct gcggatccgg ctcgnccacc   2880
tggacagctg gaacggccgc aggtcggcgc tggccgcgga gtacctctcc gggctcgccg   2940
```

```
gactgcccgg catcggcctg ccggtgaccg cgcccgacac cgacccggtc tggcacctct    3000
tcaccgtgcg caccgagcgc cgcgacgagc tgcgcagcca cctcgacgcc cgcggcatcg    3060
acaccctcac gcactacccg gtacccgtgc acctctcgcc cgcctacgcg ggcgaggcac    3120
cgccggaagg ctcgctcccg cgggccgaga gcttcgcgcg gcaggtcctc agcctgccga    3180
tcggcccgca cctggagcgc ccgcaggcgc tgcggtgat cgacgccgtg cgcgaatggg    3240
ccgagcgggt cgaccaggcc tagtcaggtg gtccggtaga cccagcaggc cg           3292

<210> SEQ ID NO 23
<211> LENGTH: 1693
<212> TYPE: DNA
<213> ORGANISM: Streptomyces venezuelae

<400> SEQUENCE: 23
atgcggcacc ccttggcgcc gagcgtggtg atccaggtgc cgacccgggc gagcacctcc      60
tgctcggtcc agcccgtctt gctgagcagc agcgcccgct cgtaggcgtt cgtgaacagc     120
agctcggctc cgtcgacgag ctcccggacg ctgtcgccct ccagccgggc gagctgctgc     180 gagggtccg cggcccggcg gaggcccagc tcgcggcaga cccgcgtgtg ccgcaccatc     240
gcctcggggt cgtccgcgcc gacgaggacg aggtcgatcc cgccgggccg gccggccgtc     300
tcgcccaggt cgatgtcgcg cgcctcggcc atcgcgcccg cgtagaacga ggcgagctga     360
ttgccgtcct cgtcggtggt gcacatgaag cgggcggtgt gctgacggtc cgacacccgc     420
acggagtcgg tgtcgacgcc cgcggcgcgg agcagctgcc cgtacccgtc gaagtccttg     480
ccgacggcgc cgacgaggac ggggcggcga ccgagcaggc cgaggccgta cgcgatgttg     540
gcggcgacgc cgccgtgccg gatgtccagg gtgtcgacga ggaacgacag ggacacgtgg     600
gcgagctggt ccggcaggat ctgctcggcg aagcggcccg ggaaggtcat caggtggtcg     660
gtggcgatcg acccggtgac ggctatacgc atgtcagagc cccgcggcct tcttcagggc     720
gtccacgcgg tcggtgcgct cccaggtgaa gtccggcagc tcgcgccga agtggccgta     780 ggcggcggtc tgggagtaga tcgggcggag caggtcgagg tcgcggatga tcgcggccgg     840
gcggaggtcg aagacctcgc cgatggcgtt ctcgatcttc tcggtctcga tcttgtgggt     900
gccgaaggtc tcgacgaaga ggccgacggg ctcggccttg ccgatcgcgt acgcgacctg     960
gacctcgcag cgcgaggcga accggcggc gacgacgttc ttcgccaccc agcgcatcgc    1020
gtacgcggcg gagcggtcga ccttcgacgg gtccttgccg gagaaggcgc cgccaccgtg    1080
gcgggccatg ccgccgtagg tgtcgatgat gatcttgcgg ccggtgaggc cggcgtcgcc    1140
catcgggccg ccgatctcga agcgaccggt cgggttcacg agcaggcggt agccgtcggt    1200
gtcgagcttg atgccgtcct cgacgagctg cgcaagcacg tgctcgacga cgaacttccg    1260
cacgtcgggg gcgagcagcg actccaggtc gatgtccgag gcgtgctgcg aggagacgac    1320
gaccgtgtcg agacggaccg ccctgtcgcc gtcgtactcg atggtgacct gggtcttgcc    1380
gtcgggacgc aggtacggga tggtcccgtt cttgcgacc tcggtcaggc ggcgcgagag    1440
acggtgcgcg aggtggatcg gcagcggcat cagctcgggc gtctcgtccg aggcatagcc    1500
gaacatcagg ccctggtcac cggcgccctg cttgtcgagc tcgtccccct cgtcccgctg    1560
ggaggcaccc tcgacccgct tctcgtacgc ggtgtcgaca ccctgggcga tgtccgggga    1620
ctgcgacccg atggacaccg acacgccgca ggaggcgccg tcgaagccct tcttcgagga    1680
gtcgtacccg atc                                                       1693
```

<210> SEQ ID NO 24
<211> LENGTH: 1565
<212> TYPE: DNA
<213> ORGANISM: Streptomyces venezuelae

<400> SEQUENCE: 24

```
ccccgctcgc ggcccccccag acatccacgc ccacgattgg acgctcccga tgaccgcccc      60
cgccctctcc gccaccgccc cggccgaacg ctgcgcgcac cccggagccg atctgggggc     120
ggcggtccac gccgtcggcc agaccctcgc gccggcggc ctcgtgccgc ccgacgaggc      180
cggaacgacc gcccgccacc tcgtccggct cgccgtgcgc tacggcaaca gccccttcac     240
cccgctggag gaggcccgcc acgacctggg cgtcgaccgg gacgccttcc ggcgcctcct     300
cgccctgttc gggcaggtcc cggagctccg caccgcggtc gagaccggcc ccgccggggc     360
gtactggaag aacaccctgc tcccgctcga cagcgcggt gtcttcgacg cggcgctcgc      420
caggaagccc gtcttcccgt acagcgtcgg cctctacccc ggcccgacct gcatgttccg     480
ctgccacttc tgcgtccgtg tgaccggcgc ccgctacgac ccgtccgccc tcgacgccgg     540
caacgccatg ttccggtcgg tcatcgacga gatacccgcg ggcaacccct cggcgatgta     600
cttctccggc ggcctggagc cgctcaccaa ccccggcctc gggagcctgg ccgcgcacgc     660
caccgaccac ggcctgcggc ccaccgtcta cacgaactcc ttcgcgctca ccgagcgcac     720
cctggagcgc cagcccggcc tctggggcct gcacgccatc cgcacctcgc tctacggcct     780
caacgacgag gagtacgagc agaccaccgg caagaaggcc gccttccgcc gcgtccgcga     840
gaacctgcgc cgcttccagc agctgcgcgc cgagcgcgag tcgccgatca acctcggctt     900
cgcctacatc gtgctcccgg gccgtgcctc ccgcctgctc gacctggtcg acttcatcgc     960
cgacctcaac gacgccgggc agggcaggac gatcgacttc gtcaacattc gcgaggacta    1020
cagcggccgt gacgacggca agctgccgca ggaggagcgg gccgagctcc aggaggccct    1080
caacgccttc gaggagcggg tccgcgagcg caccccgga ctccacatcg actacggcta     1140
cgccctgaac agcctgcgca ccggggccga cgccgaactg ctgcggatca gcccgccac     1200
catgcggccc accgcgcacc cgcaggtcgc ggtgcaggtc gatctcctcg cgacgtgta     1260
cctgtaccgc gaggccggct tccccgacct ggacggcgcg accgctaca tcgcgggccg     1320
cgtgaccccc gacacctccc tcaccgaggt cgtcagggac ttcgtcgagc gcggcggcga    1380
ggtggcggcc gtcgacggcg acgagtactt catggacggc ttcgatcagg tcgtcaccgc    1440
ccgcctgaac cagctggagc gcgacgccgc ggacggctgg gaggaggccc gcggcttcct    1500
gcgctgaccc gcacccgccc cgatcccccc gatccccccc ccacgatccc cccacctgag    1560
ggccc                                                                1565
```

<210> SEQ ID NO 25
<211> LENGTH: 31
<212> TYPE: DNA
<213> ORGANISM: Streptomyces venezuelae

<400> SEQUENCE: 25

```
ccctgcagcg gcaaggaagg acacgacgcc a                                      31
```

<210> SEQ ID NO 26
<211> LENGTH: 32
<212> TYPE: DNA
<213> ORGANISM: Streptomyces venezuelae

<400> SEQUENCE: 26

```
aggtctagag ctcagtgccg ggcgtcggcc gg                                    32

<210> SEQ ID NO 27
<211> LENGTH: 37
<212> TYPE: DNA
<213> ORGANISM: Streptomyces venezuelae

<400> SEQUENCE: 27
ttgcatgcat atgcgccgta cccagcaggg aacgacc                               37

<210> SEQ ID NO 28
<211> LENGTH: 38
<212> TYPE: DNA
<213> ORGANISM: Streptomyces venezuelae

<400> SEQUENCE: 28
ttgaattctc aactagtacg gcggcccgcc tcccgtcc                              38

<210> SEQ ID NO 29
<211> LENGTH: 29
<212> TYPE: DNA
<213> ORGANISM: Streptomyces venezuelae

<400> SEQUENCE: 29
ctagtatgca tcatcatcat catcattaa                                        29

<210> SEQ ID NO 30
<211> LENGTH: 29
<212> TYPE: DNA
<213> ORGANISM: Streptomyces venezuelae

<400> SEQUENCE: 30
aattttaatg atgatgatga tgatgcata                                        29

<210> SEQ ID NO 31
<211> LENGTH: 18
<212> TYPE: DNA
<213> ORGANISM: Streptomyces venezuelae

<400> SEQUENCE: 31
tcctctagac gtttccgt                                                    18

<210> SEQ ID NO 32
<211> LENGTH: 21
<212> TYPE: DNA
<213> ORGANISM: Streptomyces venezuelae

<400> SEQUENCE: 32
tgaagcttga attcaaccgg t                                                21

<210> SEQ ID NO 33
<211> LENGTH: 27
<212> TYPE: DNA
<213> ORGANISM: Streptomyces venezuelae

<400> SEQUENCE: 33
tttatgcatc ccgcgggtcc cggcgag                                          27

<210> SEQ ID NO 34
<211> LENGTH: 27
<212> TYPE: DNA
<213> ORGANISM: Streptomyces venezuelae
```

```
<400> SEQUENCE: 34
tcagaattct gtcggtcact tgcccgc                                              27
```

RECOMBINANT NARBONOLIDE POLYKETIDE SYNTHASE

CROSS-REFERENCE TO RELATED APPLICATIONS

This application claims priority under 35 U.S.C. §120 to and is a divisional application of U.S. Ser. No. 09/320,878 filed May 27, 1999, now U.S. Pat. No. 6,117,659 which is a continuation-in-part of U.S. Ser. No. 09/141,908, filed Aug. 28, 1998, which is a continuation-in-part of U.S. Ser. No. 09/073,538, filed May 6, 1998, which is a continuation-in-part of U.S. Ser. No. 08/846,247, filed Apr. 30, 1997 now U.S. Pat. No. 6,391,594. This application also claims priority under 35 U.S.C. §119(e) to U.S. provisional application Ser. Nos. 60/134,990, filed May 20, 1999; 60/119,139, filed Feb. 8, 1999; 60/100,880, filed Sep. 22, 1998; and 60/087,080, filed May 28, 1998. Each of the above patent applications is incorporated herein by reference.

REFERENCE TO GOVERNMENT FUNDING

This invention was supported in part by SBIR grant 1R43-CA75792-01. The U.S. government has certain rights in this invention.

FIELD OF THE INVENTION

The present invention provides recombinant methods and materials for producing polyketides by recombinant DNA technology. More specifically, it relates to narbonolides and derivatives thereof. The invention relates to the fields of agriculture, animal husbandry, chemistry, medicinal chemistry, medicine, molecular biology, pharmacology, and veterinary technology.

BACKGROUND OF THE INVENTION

Polyketides represent a large family of diverse compounds synthesized from 2-carbon units through a series of condensations and subsequent modifications. Polyketides occur in many types of organisms, including fungi and mycelial bacteria, in particular, the actinomycetes. There is a wide variety of polyketide structures, and the class of polyketides encompasses numerous compounds with diverse activities. Tetracycline, erythromycin, FK506, FK520, narbomycin, picromycin, rapamycin, spinocyn, and tylosin, are examples of such compounds. Given the difficulty in producing polyketide compounds by traditional chemical methodology, and the typically low production of polyketides in wild-type cells, there has been considerable interest in finding improved or alternate means to produce polyketide compounds. See PCT publication Nos. WO 93/13663; WO 95/08548; WO 96/40968; WO 97/02358; and WO 98/27203; U.S. Pat. Nos. 4,874,748; 5,063,155; 5,098,837; 5,149,639; 5,672,491; and 5,712,146; Fu et al., 1994, *Biochemistry* 33: 9321–9326; McDaniel et al., 1993, *Science* 262: 1546–1550; and Rohr, 1995, *Angew. Chem. Int. Ed. Engl.* 34(8): 881–888, each of which is incorporated herein by reference.

Polyketides are synthesized in nature by polyketide synthase (PKS) enzymes. These enzymes, which are complexes of multiple large proteins, are similar to the synthases that catalyze condensation of 2-carbon units in the biosynthesis of fatty acids. PKS enzymes are encoded by PKS genes that usually consist of three or more open reading frames (ORFs). Two major types of PKS enzymes are known; these differ in their composition and mode of synthesis. These two major types of PKS enzymes are commonly referred to as Type I or "modular" and Type II "iterative" PKS enzymes.

Modular PKSs are responsible for producing a large number of 12, 14, and 16-membered macrolide antibiotics including methymycin, erythromycin, narbomycin, picromycin, and tylosin. These large multifunctional enzymes (>300,000 kDa) catalyze the biosynthesis of polyketide macrolactones through multistep pathways involving decarboxylative condensations between acyl thioesters followed by cycles of varying $\beta$-carbon processing activities (see O'Hagan, D. *The polyketide metabolites*; E. Horwood: New York, 1991, incorporated herein by reference). The modular PKS are generally encoded in multiple ORFs. Each ORF typically comprises two or more "modules" of ketosynthase activity, each module of which consists of at least two (if a loading module) and more typically three or more enzymatic activities or "domains."

During the past half decade, the study of modular PKS function and specificity has been greatly facilitated by the plasmid-based *Streptomyces coelicolor* expression system developed with the 6-deoxyerythronolide B (6-dEB) synthase (DEBS) genes (see Kao et al., 1994, *Science*, 265: 509–512, McDaniel et al., 1993, *Science* 262: 1546–1557, and U.S. Pat. Nos. 5,672,491 and 5,712,146, each of which is incorporated herein by reference). The advantages to this plasmid-based genetic system for DEBS were that it overcame the tedious and limited techniques for manipulating the natural DEBS host organism, *Saccharopolyspora erythraea*, allowed more facile construction of recombinant PKSs, and reduced the complexity of PKS analysis by providing a "clean" host background. This system also expedited construction of the first combinatorial modular polyketide library in Streptomyces (see PCT publication No. WO 98/49315, incorporated herein by reference).

The ability to control aspects of polyketide biosynthesis, such as monomer selection and degree of $\beta$-carbon processing, by genetic manipulation of PKSs has stimulated great interest in the combinatorial engineering of novel antibiotics (see Hutchinson, 1998, *Curr. Opin. Microbiol.* 31: 319–329; Carreras and Santi, 1998, *Curr. Opin. Biotech.* 9: 403–411; and U.S. Pat. Nos. 5,712,146 and 5,672,491, each of which is incorporated herein by reference). This interest has resulted in the cloning, analysis, and manipulation by recombinant DNA technology of genes that encode PKS enzymes. The resulting technology allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters. It has been possible to manipulate modular PKS genes other than the narbonolide PKS using generally known recombinant techniques to obtain altered and hybrid forms. See, e.g., U.S. Pat. Nos. 5,672,491 and 5,712,146 and PCT publication No. WO 98/49315. See Lau et al., 1999, "Dissecting the role of acyltransferase domains of modular polyketide synthases in the choice and stereochemical fate of extender units" *Biochemistry* 38(5): 1643–1651, and Gokhale et al., Apr. 16, 1999, Dissecting and Exploiting Intermodular Communication in Polyketide Synthases", *Science* 284: 482–485.

The present invention provides methods and reagents relating to the modular PKS gene cluster for the polyketide antibiotics known as narbomycin and picromycin. Narbomycin is produced in *Streptomyces narbonensis*, and both narbomycin and picromycin are produced in *S. venezuelae*. These species are unique among macrolide producing organisms in that they produce, in addition to the 14-membered macrolides narbomycin and picromycin (picromycin is shown in FIG. 1, compound 1), the 12-membered macrolides neomethymycin and methymycin (methymycin is shown in FIG. 1, compound 2). Narbomycin differs from picromycin only by lacking the hydroxyl at position 12. Based on the structural similarities between picromycin and methymycin, it was speculated that methymycin would result from premature cyclization of a hexaketide intermediate in the picromycin pathway.

Glycosylation of the C5 hydroxyl group of the polyketide precursor, narbonolide, is achieved through an endogenous desosaminyl transferase to produce narbomycin. In *Streptomyces venezuelae*, narbomycin is then converted to picromycin by the endogenously produced narbomycin hydroxylase. (See FIG. 1) Thus, as in the case of other macrolide antibiotics, the macrolide product of the narbonolide PKS is further modified by hydroxylation and glycosylation. FIG. 1 also shows the metabolic relationships of the compounds discussed above.

Picromycin (FIG. 1, compound 1) is of particular interest because of its close structural relationship to ketolide compounds (e.g. HMR 3004, FIG. 1, compound 3). The ketolides are a new class of semi-synthetic macrolides with activity against pathogens resistant to erythromycin (see Agouridas et al., 1998, *J. Med. Chem.* 41: 4080–4100, incorporated herein by reference). Thus, genetic systems that allow rapid engineering of the narbonolide PKS would be valuable for creating novel ketolide analogs for pharmaceutical applications. Furthermore, the production of picromycin as well as novel compounds with useful activity could be accomplished if the heterologous expression of the narbonolide PKS in *Streptomyces lividans* and other host cells were possible. The present invention meets these and other needs.

DISCLOSURE OF THE INVENTION

The present invention provides recombinant methods and materials for expressing PKSs derived in whole and in part from the narbonolide PKS and other genes involved in narbomycin and picromycin biosynthesis in recombinant host cells. The invention also provides the polyketides derived from the narbonolide PKS. The invention provides the complete PKS gene cluster that ultimately results, in *Streptomyces venezuelae*, in the production of picromycin. The ketolide product of this PKS is narbonolide. Narbonolide is glycosylated to obtain narbomycin and then hydroxylated at C12 to obtain picromycin. The enzymes responsible for the glycosylation and hydroxylation are also provided in recombinant form by the invention.

Thus, in one embodiment, the invention is directed to recombinant materials that contain nucleotide sequences encoding at least one domain, module, or protein encoded by a narbonolide PKS gene. The recombinant materials may be "isolated." The invention also provides recombinant materials useful for conversion of ketolides to antibiotics. These materials include recombinant DNA compounds that encode the C12hydroxylase (the picK gene), the desosamine biosynthesis and desosaminyl transferase enzymes, and the beta-glucosidase enzyme involved in picromycin biosynthesis in *S. venezuelae* and the recombinant proteins that can be produced from these nucleic acids in the recombinant host cells of the invention.

In one embodiment, the invention provides a recombinant expression system that comprises a heterologous promoter positioned to drive expression of the narbonolide PKS, including a "hybrid" narbonolide PKS. In a preferred embodiment, the promoter is derived from a PKS gene. In a related embodiment, the invention provides recombinant host cells comprising the vector that produces narbonolide. In a preferred embodiment, the host cell is *Streptomyces lividans* or *S. coelicolor.*

In another embodiment, the invention provides a recombinant expression system that comprises the desosamine biosynthetic genes as well as the desosaminyl transferase gene. In a related embodiment, the invention provides recombinant host cells comprising a vector that produces the desosamine biosynthetic gene products and desosaminyl transferase gene product. In a preferred embodiment, the host cell is *Streptomyces lividans* or *S. coelicolor.*

In another embodiment, the invention provides a method for desosaninylating polyketide compounds in recombinant host cells, which method comprises expressing the PKS for the polyketide and the desosaminyl transferase and desosamine biosynthetic genes in a host cell. In a preferred embodiment, the host cell expresses a beta-glucosidase gene as well. This preferred method is especially advantageous when producing desosaminylated polyketides in Streptomyces host cells, because such host cells typically glucosylate desosamine residues of polyketides, which can decrease desired activity, such as antibiotic activity. By coexpression of beta-glucosidase, the glucose residue is removed from the polyketide.

In another embodiment, the invention provides the picK hydroxylase gene in recombinant form and methods for hydroxylating polyketides with the recombinant gene product. The invention also provides polyketides thus produced and the antibiotics or other useful compounds derived therefrom.

In another embodiment, the invention provides a recombinant expression system that comprises a promoter positioned to drive expression of a "hybrid" PKS comprising all or part of the narbonolide PKS and at least a part of a second PKS, or comprising a narbonolide PKS modified by deletions, insertions and/or substitutions. In a related embodiment, the invention provides recombinant host cells comprising the vector that produces the hybrid PKS and its corresponding polyketide. In a preferred embodiment, the host cell is *Streptomyces lividans* or *S. coelicolor.*

In a related embodiment, the invention provides recombinant materials for the production of libraries of polyketides wherein the polyketide members of the library are synthesized by hybrid PKS enzymes of the invention. The resulting polyketides can be further modified to convert them to other useful compounds, such as antibiotics, typically through hydroxylation and/or glycosylation. Modified macrolides provided by the invention that are useful intermediates in the preparation of antibiotics are of particular benefit.

In another related embodiment, the invention provides a method to prepare a nucleic acid that encodes a modified PKS, which method comprises using the narbonolide PKS encoding sequence as a scaffold and modifying the portions of the nucleotide sequence that encode enzymatic activities, either by mutagenesis, inactivation. insertion, or replacement. The thus modified narbonolide PKS encoding nucleotide sequence can then be expressed in a suitable host cell and the cell employed to produce a polyketide different from that produced by the narbonolide PKS. In addition, portions of the narbonolide PKS coding sequence can be inserted into other PKS coding sequences to modify the products thereof The narbonolide PKS can itself be manipulated, for example, by fusing two or more of its open reading frames, particularly those for extender modules 5 and 6, to make more efficient the production of 14-membered as opposed to 12-membered macrolides.

In another related embodiment, the invention is directed to a multiplicity of cell colonies, constituting a library of colonies, wherein each colony of the library contains an expression vector for the production of a modular PKS derived in whole or in part from the narbonolide PKS. Thus, at least a portion of the modular PKS is identical to that found in the PKS that produces narbonolide and is identifiable as such. The derived portion can be prepared synthetically or directly from DNA derived from organisms that produce narbonolide. In addition, the invention provides methods to screen the resulting polyketide and antibiotic libraries.

The invention also provides novel polyketides and antibiotics or other useful compounds derived therefrom. The compounds of the invention can be used in the manufacture of another compound. In a preferred embodiment, the antibiotic compounds of the invention are formulated in a mixture or solution for administration to an animal or human.

These and other embodiments of the invention are described in more detail in the following description, the examples, and claims set forth below.

MODES OF CARRYING OUT THE INVENTION

Figure 1:
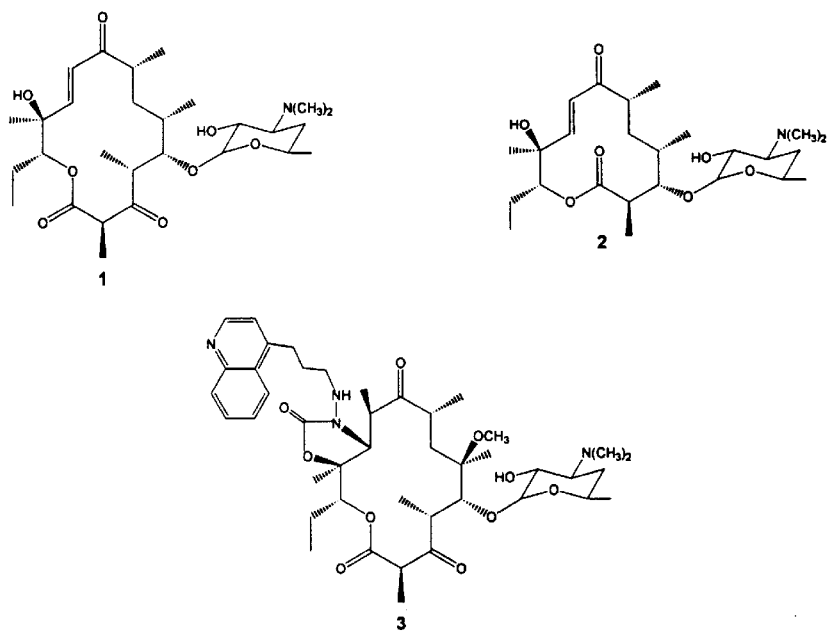
FIG. 1 shows the structures of picromycin (compound 1), methymycin (compound 2), and the ketolide HMR 3004 (compound 3) and the relationship of several compounds related to picromycin.
Figure 1:
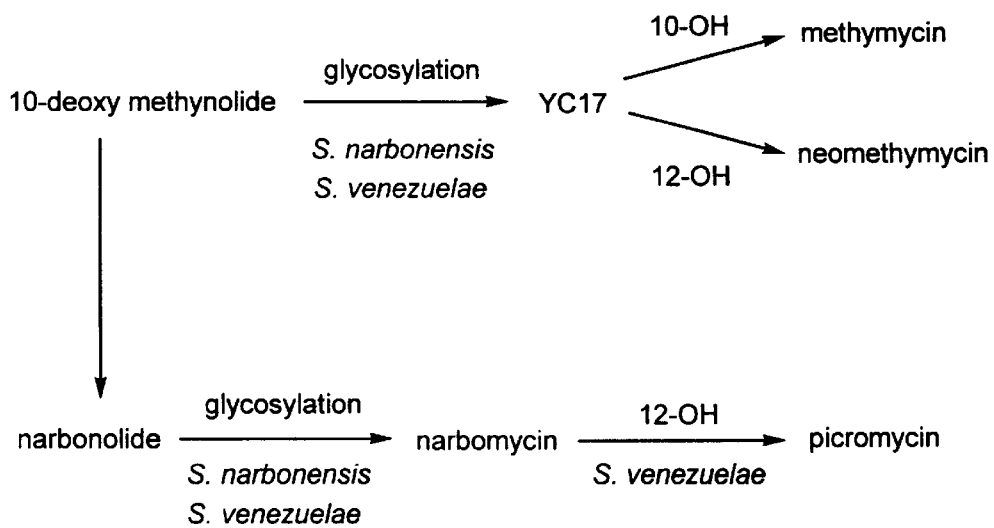

The present invention provides useful compounds and methods for producing polyketides in recombinant host cells. As used herein, the term recombinant refers to a compound or composition produced by human intervention. The invention provides recombinant DNA compounds encoding all or a portion of the narbonolide PKS. The invention also provides recombinant DNA compounds encoding the enzymes that catalyze the further modification of the ketolides produced by the narbonolide PKS. The invention provides recombinant expression vectors useful in producing the narbonolide PKS and hybrid PKSs composed of a portion of the narbonolide PKS in recombinant host cells. Thus, the invention also provides the narbonolide PKS, hybrid PKSs, and polyketide modification enzymes in recombinant form. The invention provides the polyketides produced by the recombinant PKS and polyketide modification enzymes. In particular, the invention provides methods for producing the polyketides 10-deoxymethynolide, narbonolide, YC17, narbomycin, methymycin, neomethymycin, and picromycin in recombinant host cells.

To appreciate the many and diverse benefits and applications of the invention, the description of the invention below is organized as follows. First, a general description of polyketide biosynthesis and an overview of the synthesis of narbonolide and compounds derived therefrom in Streptomyces venezuelae are provided. This general description and overview are followed by a detailed description of the invention in six sections. In Section I, the recombinant narbonolide PKS provided by the invention is described. In Section II, the recombinant desosamine biosynthesis genes, the desosaminyl transferase gene, and the beta-glucosidase gene provided by the invention are described. In Section III, the recombinant picK hydroxylase gene provided by the invention is described. In Section IV, methods for heterologous expression of the narbonolide PKS and narbonolide modification enzymes provided by the invention are described. In Section V, the hybrid PKS genes provided by the invention and the polyketides produced thereby are described. In Section VI, the polyketide compounds provided by the invention and pharmaceutical compositions of those compounds are described. The detailed description is followed by a variety of working examples illustrating the invention.

The narbonolide synthase gene, like other PKS genes, is composed of coding sequences organized in a loading module, a number of extender modules, and a thioesterase domain. As described more fully below, each of these domains and modules is a polypeptide with one or more specific functions. Generally, the loading module is responsible for binding the first building block used to synthesize the polyketide and transferring it to the first extender module. The building blocks used to form complex polyketides are typically acylthioesters, most commonly acetyl, propionyl, malonyl, methylmalonyl, and ethylmalonyl CoA. Other building blocks include amino acid like acylthioesters. PKSs catalyze the biosynthesis of polyketides through repeated, decarboxylative Claisen condensations between the acylthioester building blocks. Each module is responsible for binding a building block, performing one or more functions on that building block, and transferring the resulting compound to the next module. The next module, in turn, is responsible for attaching the next building block and transferring the growing compound to the next module until synthesis is complete. At that point, an enzymatic thioesterase activity cleaves the polyketide from the PKS. See, generally, FIG. 5.

Such modular organization is characteristic of the modular class of PKS enzymes that synthesize complex polyketides and is well known in the art. The polyketide known as 6-deoxyerythronolide B is a classic example of this type of complex polyketide. The genes, known as eryAI, eryAII, and eryAIII (also referred to herein as the DEBS genes, for the proteins, known as DEBS1, DEBS2, and DEBS3, that comprise the 6-dEB synthase), that code for the multi-subunit protein known as DEBS that synthesizes 6-dEB, the precursor polyketide to erythromycin, are described in U.S. Pat. No. 5,824,513, incorporated herein by reference. Recombinant methods for manipulating modular PKS genes are described in U.S. Pat. Nos. 5,672,491; 5,843,718; 5,830,750; and 5,712,146; and in PCT publication Nos. WO 98/49315 and WO 97/02358, each of which is incorporated herein by reference.

The loading module of DEBS consists of two domains, an acyl-transferase (AT) domain and an acyl carrier protein (ACP) domain. Each extender module of DEBS, like those of other modular PKS enzymes, contains a ketosynthase (KS), AT, and ACP domains, and zero, one, two, or three domains for enzymatic activities that modify the beta-carbon of the growing polyketide chain. A module can also contain domains for other enzymatic activities, such as, for example, a methyltransferase or dimethyltransferase activity. Finally, the releasing domain contains a thioesterase and, often, a cyclase activity.

The AT domain of the loading module recognizes a particular acyl-CoA (usually acetyl or propionyl but sometimes butyryl) and transfers it as a thiol ester to the ACP of the loading module. Concurrently, the AT on each of the extender modules recognizes a particular extender-CoA (malonyl or alpha-substituted malonyl, i.e., methylmalonyl, ethylmalonyl, and carboxylglycolyl) and transfers it to the ACP of that module to form a thioester. Once the PKS is primed with acyl- and malonyl-ACPs, the acyl group of the loading module migrates to form a thiol ester (trans-esterification) at the KS of the first extender module; at this stage, extender module 1 possesses an acyl-KS adjacent to a malonyl (or substituted malonyl) ACP. The acyl group derived from the loading module is then covalently attached to the alpha-carbon of the malonyl group to form a carbon-carbon bond, driven by concomitant decarboxylation, and generating a new acyl-ACP that has a backbone two carbons longer than the loading unit (elongation or extension). The growing polyketide chain is transferred from the ACP to the KS of the next module, and the process continues.

The polyketide chain, growing by two carbons each module, is sequentially passed as covalently bound thiol esters from module to module, in an assembly line-like process. The carbon chain produced by this process alone would possess a ketone at every other carbon atom, producing a polyketone, from which the name polyketide arises. Most commonly, however, additional enzymatic activities modify the beta keto group of each two-carbon unit just after it has been added to the growing polyketide chain, but before it is transferred to the next module. Thus, in addition to the minimal module containing KS, AT, and ACP domains necessary to form the carbon-carbon bond, modules may contain a ketoreductase (KR) that reduces the keto group to an alcohol. Modules may also contain a KR plus a dehydratase (DH) that dehydrates the alcohol to a double bond. Modules may also contain a KR, a DH, and an enoylreductase (ER) that converts the double bond to a saturated single bond using the beta carbon as a methylene function. As noted above, modules may contain additional enzymatic activities as well.

Once a polyketide chain traverses the final extender module of a PKS, it encounters the releasing domain or thioesterase found at the carboxyl end of most PKSs. Here, the polyketide is cleaved from the enzyme and cyclyzed. The resulting polyketide can be modified further by tailoring enzymes; these enzymes add carbohydrate groups or methyl groups, or make other modifications, i.e., oxidation or reduction, on the polyketide core molecule.

While the above description applies generally to modular PKS enzymes, there are a number of variations that exist in nature. For example, some polyketides, such as epothilone, incorporate a building block that is derived from an amino acid. PKS enzymes for such polyketides include an activity that functions as an amino acid ligase or as a non-ribosomal peptide synthetase (NRPS). Another example of a variation, which is actually found more often than the two domain loading module construct found in DEBS, occurs when the loading module of the PKS is not composed of an AT and an ACP but instead utilizes an inactivated KS, an AT, and an ACP. This inactivated KS is in most instances called $KS^Q$, where the superscript letter is the abbreviation for the amino acid, glutamine, that is present instead of the active site cysteine required for activity. For example, the narbonolide PKS loading module contains a $KS^Q$. Yet another example of a variation has been mentioned above in the context of modules that include a methyltransferase or dimethyltransferase activity; modules can also include an epimerase activity. These variations will be described further below in specific reference to the narbonolide PKS and the various recombinant and hybrid PKSs provided by the invention.

With this general description of polyketide biosynthesis, one can better appreciate the biosynthesis of narbonolide related polyketides in *Streptomyces venezuelae* and *S. narbonensis*. The narbonolide PKS produces two polyketide products, narbonolide and 10-deoxymethynolide. Narbonolide is the polyketide product of all six extender modules of the narbonolide PKS. 10-deoxymethynolide is the polyketide product of only the first five extender modules of the narbonolide PKS. These two polyketides are desosaminylated to yield narbomycin and YC17, respectively. These two glycosylated polyketides are the final products produced in *S. narbonensis*. In *S. venezuelae*, these products are hydroxylated by the picK gene product to yield picromycin and either methymycin (hydroxylation at the C10 position of YC17) or neomethymycin (hydroxylation at the C12 position of YC17). (See FIG. 1) The present invention provides the genes required for the biosynthesis of all of these polyketides in recombinant form.

Section I: The Narbonolide PKS

Figure 4:
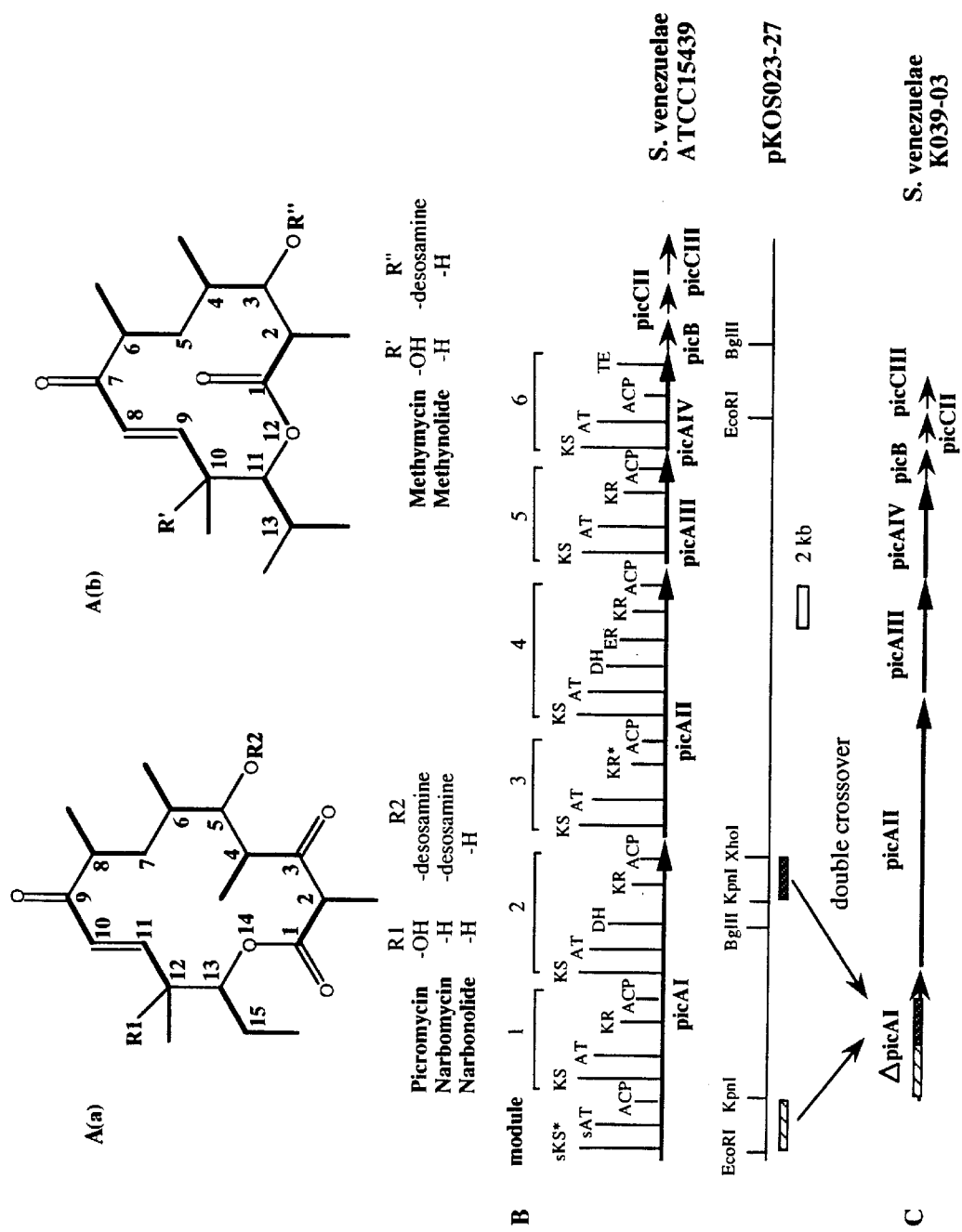
FIG. 4 has three parts. In Part A, the structures of picromycin (A(a)) and methymycin (A(b)) are shown, as well as the related structures of narbomycin, narbonolide, and methynolide. In the structures, the bolded lines indicate the two or three carbon chains produced by each module (loading and extender) of the narbonolide PKS. Part B shows the organization of the narbonolide PKS genes on the chromosome of Streptomyces venezuelae, including the location of the various module encoding sequences (the loading module domains are identified as sKS*, sAT, and sACP), as well as the picB thioesterase gene and two desosamine biosynthesis genes (picCII and picCIII). Part C shows the engineering of the S. venezuelae host of the invention in which the picAI gene has been deleted. In the Figure, ACP is acyl carrier protein; AT is acyltransferase; DH is dehydratase; ER is enoylreductase; KR is ketoreductase; KS is ketosynthase; and TE is thioesterase.

The narbonolide PKS is composed of a loading module, six extender modules, and two thioesterase domains one of which is on a separate protein. FIG. 4, part B, shows the organization of the narbonolide PKS genes on the *Streptomyces venezuelae* chromosome, as well as the location of the module encoding sequences in those genes, and the various domains within those modules. In the Figure, the loading module is not numbered, and its domains are indicated as sKS*, sAT, and ACP. Also shown in the Figure, part A, are the structures of picromycin and methymycin.

The loading and six extender modules and the thioesterase domain of the narbonolide PKS reside on four proteins, designated PICAI, PICAII, PICAIII, and PICAIV. PICAI includes the loading module and extender modules 1 and 2 of the PKS. PICAII includes extender modules 3 and 4. PICAIII includes extender module 5. PICAIV includes extender module 6 and a thioesterase domain. There is a second thioesterase domain (TEII) on a separate protein, designated PICB. The amino acid sequences of these proteins are shown below.

Amino acid sequence of narbonolide synthase subunit 1, PICAI (SEQ ID NO:1)

```
   1 MSTVSKSESE EFVSVSNDAG SAHGTAEPVA VVGISCRVPG ARDPREFWEL LAAGGQAVTD
  61 VPADRWNAGD FYDPDRSAPG RSNSRWGGFI EDVDRFDAAF FGISPREAAE MDPQQRLALE
 121 LGWEALERAG IDPSSLTGTR TGVFAGAIWD DYATLKHRQG GAAITPHTVT GLHRGIIANR
 181 LSYTLGLRGP SMVVDSGQSS SLVAVHLACE SLRRGESELA LAGGVSLNLV PDSIIGASKF
 241 GGLSPDGRAY TFDARANGYV RGEGGGFVVL KRLSRAVADG DPVLAVIRGS AVNNGGAAQG
 301 MTTPDAQAQE AVLREAHERA GTAPADVRYV ELHGTGTPVG DPIEAAALGA ALGTGRPAGQ
 361 PLLVGSVKTN IGHLEGAAGI AGLIKAVLAV RGRALPASLN YETPNPAIPF EELNLRVNTE
 421 YLPWEPEHDG QRMVVGVSSF GMGGTNAHVV LEEAPGVVEG ASVVESTVGG SAVGGGVVPW
 481 VVSAKSAAAL DAQIERLAAF ASRDRTDGVD AGAVDAGAVD AGAVARVLAG GRAQFEHRAV
 541 VVGSGPDDLA AALAAPEGLV RGVASGVGRV AFVFPGQGTQ WAGMGAELLD SSAVFAAAMA
 601 ECEAALSPYV DWSLEAVVRQ APGAPTLERV DVVQPVTFAV MVSLARVWQH HGVTPQAVVG
 661 HSQGEIAAAY VAGALSLDDA ARVVTLRSKS IAAHLAGKGG MLSLALSEDA VLERLAGFDG
 721 LSVAAVNGPT ATVVSGDPVQ IEELARACEA DGVRARVIPV DYASHSRQVE IIESELAEVL
 781 AGLSPQAPRV PFFSTLEGAW ITEPVLDGGY WYRNLRHRVG FAPAVETLAT DEGFTHFVEV
 841 SAHPVLTMAL PGTVTGLATL RRDNGGQDRL VASLAEAWAN GLAVDWSPLL PSATGHHSDL
 901 PTYAFQTERH WLGEIEALAP AGEPAVQPAV LRTEAAEPAE LDRDEQLRVI LDKVRAQTAQ
 961 VLGYATGGQI EVDRTFREAG CTSLTGVDLR NRINAAFGVR MAPSMIFDFP TPEALAEQLL
1021 LVVHGEAAAN PAGAEPAPVA AAGAVDEPVA IVGMACRLPG GVASPEDLWR LVAGGGDAIS
1081 EFPQDRGWDV EGLYHPDPEH PGTSYVRQGG FIENVAGFDA AFFGISPREA LAMDPQQRLL
1141 LETSWEAVED AGIDPTSLRG RQVGVFTGAM THEYGPSLRD GGEGLDGYLL TGNTASVMSG
1201 RVSYTLGLEG PALTVDTACS SSLVALHLAV QALRKGEVDM ALAGGVAVMP TPGMFVEFSR
1261 QRGLAGDGRS KAFAASADGT SWSEGVGVLL VERLSDARRN GHQVLAVVRG SAVNQDGASN
1321 GLTAPNGPSQ QRVIRRALAD ARLTTSDVDV VEAHGTGTRL GDPIEAQALI ATYGQGRDDE
1381 QPLRLGSLKS NIGHTQAAAG VSGVIKMVQA MRHGLLPKTL HVDEPSDQID WSAGAVELLT
1441 EAVDWPEKQD GGLRRAAVSS FGISGTNAHV VLEEAPVVVE GASVVEPSVG GSAVGGGVTP
1501 WVVSAKSAAA LDAQIERLAA FASRDRTDDA DAGAVDAGAV AHVLADGRAQ FEHRAVALGA
1561 GADDLVQALA DPDGLIRGTA SGVGRVAFVF PGQGTQWAGM GAELLDSSAV FAAAMAECEA
1621 ALSPYVDWSL EAVVRQAPGA PTLERVDVVQ PVTFAVMVSL ARVWQHHGVT PQAVVGHSQG
1681 EIAAAYVAGA LPLDDAARVV TLRSKSIAAH LAGKGGMLSL ALNEDAVLER LSDFDGLSVA
1741 AVNGPTATVV SGDPVQIEEL AQACKADGFR ARIIPVDYAS HSRQVEIIES ELAQVLAGLS
1801 PQAPRVPFFS TLEGTWITEP VLDGTYWYRN LRHRVGFAPA IETLAVDEGF THFVEVSAHP
1861 VLTMTLPETV TGLGTLRREQ GGQERLVTSL AEAWVNGLPV AWTSLLPATA SRPGLPTYAF
1921 QAERYWLENT PAALATGDDW RYRIDWKRLP AAEGSERTGL SGRWLAVTPE DHSAQAAAVL
1981 TALVDAGAKV EVLTAGADDD REALAARLTA LTTGDGFTGV VSLLDGLVPQ VAWVQALGDA
2041 GIKAPLWSVT QGAVSVGRLD TPADPDRAML WGLGRVVALE HPERWAGLVD LPAQPDAAAL
2101 AHLVTALSGA TGEDQIAIRT TGLHARRLAR APLHGRRPTR DWQPHGTVLI TGGTGALGSH
2161 AARWMAHHGA EHLLLVSRSG EQAPGATQLT AELTASGARV TIAACDVADP HAMRTLLDAI
```

-continued

```
2221 PAETPLTAVV HTAGALDDGI VDTLTAEQVR RAHRAKAVGA SVLDELTRDL DLDAFVLFSS
2281 VSSTLGIPGQ GNYAPHNAYL DALAARRRAT GRSAVSVAWG PWDGGGMAAG DGVAERLRNH
2341 GVPGMDPELA LAALESALGR DETAITVADI DWDRFYLAYS SGRPQPLVEE LPEVRRIIDA
2401 RDSATSGQGG SSAQGANPLA ERLAAAAPGE RTEILLGLVR AQAAAVLRMR SPEDVAADRA
2461 FKDIGFDSLA GVELRNRLTR ATGLQLPATL VFDHPTPLAL VSLLRSEFLG DEETADARRS
2521 AALPATVGAG AGAGAGTDAD DDPIAIVAMS CRYPGDIRSP EDLWRMLSEG GEGITPFPTD
2581 RGWDLDGLYD ADPDALGRAY VREGGFLHDA AEFDAEFFGV SPREALAMDP QQRMLLTTSW
2641 EAFERAGIEP ASLRGSSTGV FIGLSYQDYA ARVPNAPRGV EGYLLTGSTP SVASGRIAYT
2701 FGLEGPATTV DTACSSSLTA LHLAVRALRS GECTMALAGG VAMMATPHMF VEFSRQRALA
2761 PDGRSKAFSA DADGFGAAEG VGLLLVERLS DARRNGHPVL AVVRGTAVNQ DGASNGLTAP
2821 NGPSQQRVIR QALADARLAP GDIDAVETHG TGTSLGDPIE AQGLQATYGK ERPAERPLAI
2881 GSVKSNIGHT QAAAGAAGII KMVLAMRHGT LPKTLHADEP SPHVDWANSG LALVTEPIDW
2941 PAGTGPRRAA VSSFGISGTN AHVVLEQAPD AAGEVLGADE VPEVSETVAM AGTAGTSEVA
3001 EGSEASEAPA APGSREASLP GHLPWVLSAK DEQSLRGQAA ALHAWLSEPA ADLSDADGPA
3061 RLRDVGYTLA TSRTAFAHRA AVTAADRDGF LDGLATLAQG GTSAHVHLDT ARDGTTAFLF
3121 TGQGSQRPGA GRELYDRHPV FARALDEICA HLDGHLELPL LDVMFAAEGS AEAALLDETR
3181 YTQCALFALE VALFRLVESW GMRPAALLGH SVGEIAAAHV AGVFSLADAA RLVAARGRLM
3241 QELPAGGAML AVQAAEDEIR VWLETEERYA GRLDVAAVNG PEAAVLSGDA DAAREAEAYW
3301 SGLGRRTRAL RVSHAFHSAH MDGMLDGFRA VLETVEFRRP SLTVVSNVTG LAAGPDDLCD
3361 PEYWVRHVRG TVRFLDGVRV LRDLGVRTCL ELGPDGVLTA MAADGLADTP ADSAAGSPVG
3421 SPAGSPADSA AGALRPRPLL VALLRRKRSE TETVADALGR AHAHGTGPDW HAWFAGSGAH
3481 RVDLPTYSFR RDRYWLDAPA ADTAVDTAGL GLGTADHPLL GAVVSLPDRD GLLLTGRLSL
3541 RTHPWLADHA VLGSVLLPGA AMVELAAHAA ESAGLRDVRE LTLLEPLVLP EHGGVELRVT
3601 VGAPAGEPGG ESAGDGARPV SLHSRLADAP AGTAWSCHAT GLLATDRPEL PVAPDRAAMW
3661 PPQGAEEVPL DGLYERLDGN GLAFGPLFQG LNAVWEYEGE VFADIALPAT TNATAPATAN
3721 GGGSAAAAPY GIHPALLDAS LHAIAVGGLV DEPELVRVPF HWSGVTVHAA GAAAARVRLA
3781 SAGTDAVSLS LTDGEGRPLV SVERLTLRPV TADQAAASRV GGLMHRVAWR PYALASSGEQ
3841 DPHATSYGPT AVLGKDELKV AAALESAGVE VGLYPDLAAL SQDVAAGAPA PRTVLAPLPA
3901 GPADGGAEGV RGTVARTLEL LQAWLADEHL AGTRLLLVTR GAVRDPEGSG ADDGGEDLSH
3961 AAAWGLVRTA QTENPGRFGL LDLADDASSY RTLPSVLSDA GLRDEPQLAL HDGTIRLARL
4021 ASVRPETGTA APALAPEGTV LLTGGTGGLG GLVARHVVGE WGVRRLLLVS RRGTDAPGAD
4081 ELVHELEALG ADVSVAACDV ADREALTAVL DAIPAEHPLT AVVHTAGVLS DGTLPSMTTE
4141 DVEHVLRPKV DAAFLLDELT STPAYDLAAF VMFSSAAAVF GGAGQGAYAA ANATLDALAW
4201 RRRAAGLPAL SLGWGLWAET SGMTGELGQA DLRRMSRAGI GGISDAEGIA LLDAALRDDR
4261 HPVLLPLRLD AAGLRDAAGN DPAGIPALFR DVVGARTVRA RPSAASASTT AGTAGTPGTA
4321 DGAAETAAVT LADRAATVDG PARQRLLLEF VVGEVAEVLG HARGHRIDAE RGFLDLGFDS
4381 LTAVELRNRL NSAGGLALPA TLVFDHPSPA ALASHLDAEL PRGASDQDGA GNRNGNENGT
4441 TASRSTAETD ALLAQLTRLE GALVLTGLSD APGSEEVLEH LRSLRSMVTG ETGTGTASGA
4501 PDGAGSGAED RPWAAGDGAG GGSEDGAGVP DFMNASAEEL FGLLDQDPST D
(SEQ ID NO:1)
```

Amino acid sequence of narbonolide synthase subunit 2, PICAII (SEQ ID NO:2)

```
   1 VSTVNEEKYL DYLRRATADL HEARGRLREL EAKAGEPVAI VGMACRLPGG VASPEDLWRL
  61 VAGGEDAISE FPQDRGWDVE GLYDPNPEAT GKSYAREAGF LYEAGEFDAD FFGISPREAL
 121 AMDPQQRLLL EASWEAFEHA GIPAATARGT SVGVFTGVMY HDYATRLTDV PEGIEGYLGT
 181 GNSGSVASGR VAYTLGLEGP AVTVDTACSS SLVALHLAVQ ALRKGEVDMA LAGGVTVMST
 241 PSTFVEFSRQ RGLAPDGRSK SFSSTADGTS WSEGVGVLLV ERLSDARRKG HRILAVVRGT
 301 AVNQDGASSG LTAPNGPSQQ RVIRRALADA RLTTSDVDVV EAHGTGTRLG DPIEAQAVIA
 361 TYGQGRDGEQ PLRLGSLKSN IGHTQAAAGV SGVIKMVQAM RHGVLPKTLH VEKPTDQVDW
 421 SAGAVELLTE AMDWPDKGDG GLRRAAVSSF GVSGTNAHVV LEEAPAAEET PASEATPAVE
 481 PSVGAGLVPW LVSAKTPAAL DAQIGRLAAF ASQGRTDAAD PGAVARVLAG GRAEFEHRAV
 541 VLGTGQDDFA QALTAPEGLI RGTPSDVGRV AFVFPGQGTQ WAGMGAELLD VSKEFAAAMA
 601 ECESALSRYV DWSLEAVVRQ APGAPTLERV DVVQPVTFAV MVSLAKVWQH HGVTPQAVVG
 661 HSQGEIAAAY VAGALTLDDA ARVVTLRSKS IAAHLAGKGG MISLALSEEA TRQRIENLHG
 721 LSIAAVNGPT ATVVSGDPTQ IQELAQACEA DGVRARIIPV DYASHSAHVE TIESELAEVL
 781 AGLSPRTPEV PFFSTLEGAW ITEPVLDGTY WYRNLRHRVG FAPAVETLAT DEGFTHFIEV
 841 SAHPVLTMTL PETVTGLGTL RREQGGQERL VTSLAEAWTN GLTIDWAPVL PTATGHHPEL
 901 PTYAFQRRHY WLHDSPAVQG SVQDSWRYRI DWKRLAVADA SERAGLSGRW LVVVPEDRSA
 961 EAAPVLAALS GAGADPVQLD VSPLGDRQRL AATLGEALAA AGGAVDGVLS LLAWDESAHP
1021 GHPAPFTRGT GATLTLVQAL EDAGVAAPLW CVTHGAVSVG RADHVTSPAQ AMVWGMGRVA
1081 ALEHPERWGG LIDLPSDADR AALDRMTTVL AGGTGEDQVA VRASGLLARR LVRASLPAHG
1141 TASPWWQADG TVLVTGAEEP AAAEAARRLA RDGAGHLLLH TTPSGSEGAE GTSGAAEDSG
1201 LAGLVAELAD LGATATVVTC DLTDAEAAAR LLAGVSDAHP LSAVLHLPPT VDSEPLAATD
1261 ADALARVVTA KATAALHLDR LLREAAAAGG RPPVLVLFSS VAAIWGGAGQ GAYAAGTAFL
1321 DALAGQHRAD GPTVTSVAWS PWEGSRVTEG ATGERLRRLG LRPLAPATAL TALDTALGHG
1381 DTAVTIADVD WSSFAPGFTT ARPGTLLADL PEARRALDEQ QSTTAADDTV LSRELGALTG
1441 AEQQRRMQEL VREHLAVVLN HPSPEAVDTG RAFRDLGFDS LTAVELRNRL KNATGLALPA
1501 TLVFDYPTPR TLAEFLLAEI LGEQAGAGEQ LPVDGGVDDE PVAIVGMACR LPGGVASPED
1561 LWRLVAGGED AISGFPQDRG WDVEGLYDPD PDASGRTYCR AGGFLDEAGE FDADFFGISP
1621 REALAMDPQQ RLLLETSWEA VEDAGIDPTS LQGQQVGVFA GTNGPHYEPL LRNTAEDLEG
1681 YVGTGNAASI MSGRVSYTLG LEGPAVTVDT ACSSSLVALH LAVQALRKGE CGLALAGGVT
1741 VMSTPTTFVE FSRQRGLAED GRSKAFAASA DGFGPAEGVG MLLVERLSDA RRNGHRVLAV
1801 VRGSAVNQDG ASNGLTAPNG PSQQRVIRRA LADARLTTAD VDVVEAHGTG TRLGDPIEAQ
1861 ALIATYGQGR DTEQPLRLGS LKSNIGHTQA AAGVSGIIKM VQAMRHGVLP KTLHVDRPSD
1921 QIDWSAGTVE LLTEAMDWPR KQEGGLRRAA VSSFGISGTN AHIVLEEAPV DEDAPADEPS
1981 VGGVVPWLVS AKTPAALDAQ IGRLAAFASQ GRTDAADPGA VARVLAGGRA QFEHRAVALG
2041 TGQDDLAAAL AAPEGLVRGV ASGVGRVAFV FPGQGTQWAG MGAELLDVSK EFAAAMAECE
2101 AALAPYVDWS LEAVVRQAPG APTLERVDVV QPVTFAVMVS LAKVWQHHGV TPQAVVGHSQ
2161 GEIAAAYVAG ALSLDDAARV VTLRSKSIGA HLAGQGGMLS LALSEAAVVE RLAGFDGLSV
2221 AAVNGPTATV VSGDPTQIQE LAQACEADGV RARIIPVDYA SHSAHVETIE SELADVLAGL
```

```
-continued
2281 SPQTPQVPFF STLEGAWITE PALDGGYWYR NLRHRVGFAP AVETLATDEG FTHFVEVSAH
2341 PVLTMALPET VTGLGTLRRD NGGQHRLTTS LAEAWANGLT VDWASLLPTT TTHPDLPTYA
2401 FQTERYWPQP DLSAAGDITS AGLGAAEHPL LGAAVALADS DGCLLTGSLS LRTHPWLADH
2461 AVAGTVLLPG TAFVELAFRA GDQVGCDLVE ELTLDAPLVL PRRGAVRVQL SVGASDESGR
2521 RTFGLYAHPE DAPGEAEWTR HATGVLAARA DRTAPVADPE AWPPPGAEPV DVDGLYERFA
2581 ANGYGYGPLF QGVRGVWRRG DEVFADVALP AEVAGAEGAR FGLHPALLDA AVQAAGAGGA
2641 FGAGTRLPFA WSGISLYAVG ATALRVRLAP AGPDTVSVSA ADSSGQPVFA ADSLTVLPVD
2701 PAQLAAFSDP TLDALHLLEW TAWDGAAQAL PGAVVLGGDA DGLAAALRAG GTEVLSFPDL
2761 TDLVEAVDRG ETPAPATVLV ACPAAGPGGP EHVREALHGS LALMQAWLAD ERFTDGRLVL
2821 VTRDAVAARS GDGLRSTGQA AVWGLGRSAQ TESPGRFVLL DLAGEARTAG DATAGDGLTT
2881 GDATVGGTSG DAALGSALAT ALGSGEPQLA LRDGALLVPR LARAAAPAAA DGLAAADGLA
2941 ALPLPAAPAL WRLEPGTDGS LESLTAAPGD AETLAPEPLG PGQVRIAIRA TGLNFRDVLI
3001 ALGMYPDPAL MGTEGAGVVT ATGPGVTHLA PGDRVMGLLS GAYAPVVVAD ARTVARMPEG
3061 WTFAQGASVP VVFLTAVYAL RDLADVKPGE RLLVHSAAGG VGMAAVQLAR HWGVEVHGTA
3121 SHGKWDALRA LGLDDAHIAS SRTLDFESAF RAASGGAGMD VVLNSLAREF VDASLRLLGP
3181 GGRFVEMGKT DVRDAERVAA DHPGVGYRAF DLGEAGPERI GEMLAEVIAL FEDGVLRHLP
3241 VTTWDVRRAR DAFRHVSQAR HTGKVVLTMP SGLDPEGTVL LTGGTGALGG IVARHVVGEW
3301 GVRRLLLVSR RGTDAPGAGE LVHELEALGA DVSVAACDVA DREALTAVLD SIPAEHPLTA
3361 VVHTAGVLSD GTLPSMTAED VEHVLRPKVD AAFLLDELTS TPGYDLAAFV MFSSAAAVFG
3421 GAGQGAYAAA NATLDALAWR RRTAGLPALS LGWGLWAETS GMTGGLSDTD RSRLARSGAT
3481 PMDSELTLSL LDAAMRRDDP ALVPIALDVA ALRAQQRDGM LAPLLSGLTR GSRVGGAPVN
3541 QRRAAAGGAG EADTDLGGRL AAMTPDDRVA HLRDLVRTHV ATVLGHGTPS RVDLERAFRD
3601 TGFDSLTAVE LRNRLNAATG LRLPATLVFD HPTPGELAGH LLDELATAAG GSWAEGTGSG
3661 DTASATDRQT TAALAELDRL EGVLASLAPA AGGRPELAAR LRALAAALGD DGDDATDLDE
3721 ASDDDLFSFI DKELGDSDF (SEQ ID NO:2)
```

Amino acid sequence of narbonolide synthase subunit 3, PICAIII (SEQ ID NO:3)

```
   1 MANNEDKLRD YLKRVTAELQ QNTRRLREIE GRTHEPVAIV GMACRLPGGV ASPEDLWQLV
  61 AGDGDAISEF PQDRGWDVEG LYDPDPDASG RTYCRSGGFL HDAGEFDADF FGISPREALA
 121 MDPQQRLSLT TAWEAIESAG IDPTALKGSG LGVFVGGWHT GYTSGQTTAV QSPELEGHLV
 181 SGAALGFLSG RIAYVLGTDG PALTVDTACS SSLVALHLAV QALRKGECDM ALAGGVTVMP
 241 NADLFVQFSR QRGLAADGRS KAFATSADGF GPAEGAGVLL VERLSDARRN GHRILAVVRG
 301 SAVNQDGASN GLTAPHGPSQ QRVIRRALAD ARLAPGDVDV VEAHGTGTRL GDPIEAQALI
 361 ATYGQEKSSE QPLRLGALKS NIGHTQAAAG VAGVIKMVQA MRHGLLPKTL HVDEPSDQID
 421 WSAGTVELLT EAVDWPEKQD GGLRRAAVSS FGISGTNAHV VLEEAPAVED SPAVEPPAGG
 481 GVVPWPVSAK TPAALDAQIG QLAAYADGRT DVDPAVAARA LVDSRTAMEH RAVAVGDSRE
 541 ALRDALRMPE GLVRGTSSDV GRVAFVFPGQ GTQWAGMGAE LLDSSPEFAA SMAECETALS
 601 RYVDWSLEAV VRQEPGAPTL DRVDVVQPVT FAVMVSLAKV WQHHGITPQA VVGHSQGEIA
 661 AAYVAGALTL DDAARVVTLR SKSIAAHLAG KGGMISLALD EAAVLKRLSD FDGLSVAAVN
```

```
 721 GPTATVVSGD PTQIEELART CEADGVRARI IPVDYASHSR QVEIIRKELA EVLAGLAPQA

781 PHVPFFSTLE GTWITEPVLD GTYWYRNLRH RVGFAPAVET LAVDGFTHFI EVSAHPVLTM

841 TLPETVTGLG TLRREQGGQE RLVTSLAEAW ANGLTIDWAP ILPTATGHHP ELPTYAFQTE

901 RFWLQSSAPT SAADDWRYRV EWKPLTASGQ ADLSGRWIVA VGSEPEAELL GALKAAGAEV

961 DVLEAGADDD REALAARLTA LTTGDGFTGV VSLLDDLVPQ VAWVQALGDA GIKAPLWSVT

1021 QGAVSVGRLD TPADPDRAML WGLGRVVALE HPERWAGLVD LPAQPDAAAL AHLVTALSGA

1081 TGEDQIAIRT TGLHARRLAR APLHGRRPTR DWQPHGTVLI TGGTGALGSH AARWMAHHGA

1141 EHLLLVSRSG EQAPGATQLT AELTASGARV TIAACDVADP HAMRTLLDAI PAETPLTAVV

1201 HTAGAPGGDP LDVTGPEDIA RILGAKTSGA EVLDDLLRGT PLDAFVLYSS NAGVWGSGSQ

1261 GVYAAANAHL DALAARRRAR GETATSVAWG LWAGDGMGRG ADDAYWQRRG IRPMSPDRAL

1321 DELAKALSHD ETFVAVADVD WERFAPAFTV SRPSLLLDGV PEARQALAAP VGAPAPGDAA

1381 VAPTGQSSAL AAITALPEPE RRPALLTLVR THAAAVLGHS SPDRVAPGRA FTRLGFDSLT

1441 AVQLRNQLST VVGNRLPATT VFDHPTPAAL AAHLHEAYLA PAEPAPTDWE GRVRRALAEL

1501 PLDRLRDAGV LDTVLRLTGI EPEPGSGGSD GGAADPGAEP EASIDDLDAE ALIRMALGPR 1561 (SEQ ID NO:3)
```

Amino acid sequence of narbonolide synthase subunit 4, PICAIV (SEQ ID NO:4)

```
   1 MTSSNEQLVD ALRASLKENE ELRKESRRRA DRRQEPMAIV GMSCRFAGGI RSPEDLWDAV

61 AAGKDLVSEV PEERGWDIDS LYDPVPGRKG TTYVRNAAFL DDAAGFDAAF FGISPREALA

121 MDPQQRQLLE ASWEVFERAG IDPASVRGTD VGVYVGCGYQ DYAPDIRVAP EGTGGYVVTG

181 NSSAVASGRI AYSLGLEGPA VTVDTACSSS LVALHLALKG LRNGDCSTAL VGGVAVLATP

241 GAFIEFSSQQ AMAADGRTKG FASAADGLAW GEGVAVLLLE RLSDARRKGH RVLAVVRGSA

301 INQDGASNGL TAPHGPSQQR LIRGALADAR LTSSDVDVVE GHGTGTRLGD PIEAQALLAT

361 YGQGRAPGQP LRLGTLKSNI GHTQAASGVA GVIKMVQALR HGVLPKTLHV DEPTDQVDWS

421 AGSVELLTEA VDWPERPGRL RRAGVSAFGV GGTNAHVVLE EAPAVEESPA VEPPAGGGVV

481 PWPVSAKTSA ALDAQIGQLA AYAEDRTDVD PAVAARALVD SRTAMEHRAV AVGDSREALR

541 DALRMPEGLV RGTVTDPGRV AFVFPGQGTQ WAGMGAELLD SSPEFAAAMA ECETALSPYV

601 DWSLEAVVRQ APSAPTLDRV DVVQPVTFAV MVSLAKVWQH HGITPEAVIG HSQGEIAAAY

661 VAGALTLDDA ARVVTLRSKS IAAHLAGKGG MISLALSEEA TRQRIENLHG LSIAAVNGPT

721 ATVVSGDPTQ IQELAQACEA DGIRARIIPV DYASFSAHVE TIENELADVL AGLSPQTPQV

781 PFFSTLEGTW ITEPALDGGY WYRNLRHRVG FAPAVETLAT DEGFTHFIEV SAHPVLTMTL

841 PDKVTGLATL RREDGGQHRL TTSLAEAWAN GLALDWASLL PATGALSPAV PDLPTYAFQH

901 RSYWISPAGP GEAPAHTASG REAVAETGLA WGPGAEDLDE EGRRSAVLAM VMRQAASVLR

961 CDSPEEVPVD RPLREIGFDS LTAVDFRNRV NRLTGLQLPP TVVFEHPTPV ALAERISDEL

1021 AERNWAVAEP SDHEQAEEEK AAAPAGARSG ADTGAGAGMF RALFRQAVED DRYGEFLDVL

1081 AEASAFRPQF ASPEACSERL DPVLLAGGPT DRAEGRAVLV GCTGTAANGG PHEFLRLSTS

1141 FQEERDFLAV PLPGYGTGTG TGTALLPADL DTALDAQARA ILRAAGDAPV VLLGHSGGAL

1201 LAHELAFRLE RAHGAPPAGI VLVDPYPPGH QEPIEVWSRQ LGEGLFAGEL EPMSDARLLA
```

-continued

```
1261 MGRYARFLAG PRPGRSSAPV LLVRASEPLG DWQEERGDWR AHWDLPHTVA DVPGDHFTMM

1321 RDHAPAVAEA VLSWLDAIEG IEGAGK (SEQ ID NO:4)
```

Amino acid sequence of typeII thioesterase, PICB (SEQ ID NO:5)

```
  1 VTDRPLNVDS GLWIRRFHPA PNSAVRLVCL PHAGGSASYF FRFSEELHPS VEALSVQYPG

61 RQDRRAEPCL ESVEELAEHV VAATEPWWQE GRLAFFGHSL GASVAFETAR ILEQRHGVRP

121 EGLYVSGRRA PSLAPDRLVH QLDDRAFLAE IRRLSGTDER FLQDDELLRL VLPALRSDTK

181 AAETYLHRPS AKLTCPVMAL AGDRDPKAPL NEVAEWRRHT SGPFCLRAYS GGHFYLNDQW

241 HEICNDISDH LLVTRGAPDA RVVQPPTSLI EGAAKRWQNP R (SEQ ID NO:5)
```

Figure 2:
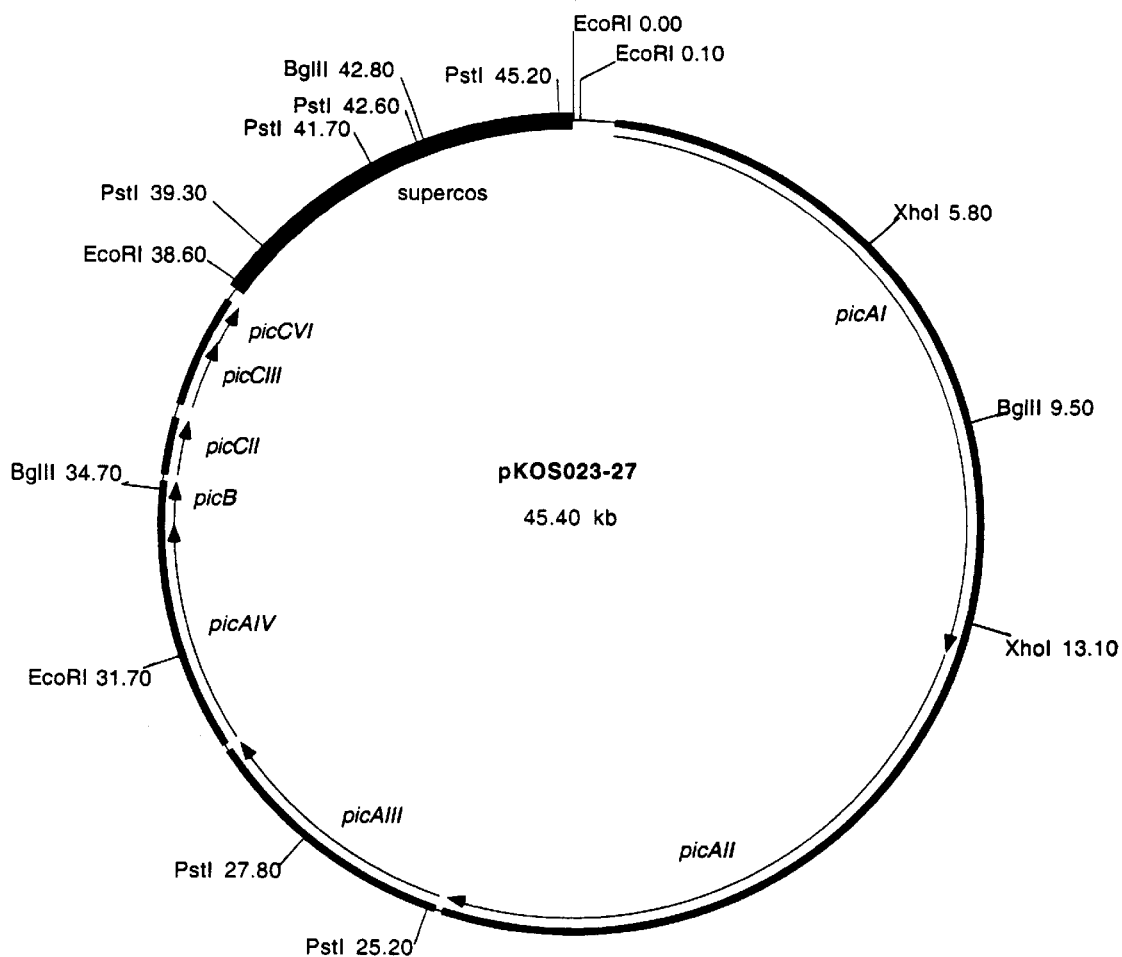
FIG. 2 shows a restriction site and function map of cosmid pKOS023-27.

The DNA encoding the above proteins can be isolated in recombinant form from the recombinant cosmid pKOS023-27 of the invention, which was deposited with the American Type Culture Collection under the terms of the Budapest Treaty on Aug. 20, 1998 and is available under accession number ATCC 203141. Cosmid pKOS023-27 contains an insert of *Streptomyces venezuelae* DNA of 38506 nucleotides. The complete sequence of the insert from cosmid pKOS023-27 is shown below. The location of the various ORFs in the insert, as well as the boundaries of the sequences that encode the various domains of the multiple modules of the PKS, are summarized in the Table below. FIG. 2 shows a restriction site and function map of pKOS023-27, which contains the complete coding sequence for the four proteins that constitute narbonolide PKS and four additional ORFs. One of these additional ORFs encodes the picB gene product, the type II thioesterase mentioned above. PICB shows a high degree of similarity to other type II thioesterases, with an identity of 51%, 49%, 45% and 40% as compared to those of *Amycolatopsis mediterranae, S. griseus, S. fradiae* and *Saccharopolyspora erythraea*, respectively. The three additional ORFs in the cosmid pKOS023-27 insert DNA sequence, from the picCII, picCIII, and picCVI, genes, are involved in desosamine biosynthesis and transfer and described in the following section.

| From Nucleotide | To Nucleotide | Description |
| --- | --- | --- |
| 70 | 13725 | picAI |
| 70 | 13725 | narbonolide synthase 1 (PICAI) |
| 148 | 3141 | loading module |
| 148 | 1434 | KS loading module |
| 1780 | 2802 | AT loading module |
| 2869 | 3141 | ACP loading module |
| 3208 | 7593 | extender module 1 |
| 3208 | 4497 | KS1 |
| 4828 | 5847 | AT1 |
| 6499 | 7257 | KR1 |
| 7336 | 7593 | ACP1 |
| 7693 | 13332 | extender module 2 |
| 7693 | 8974 | KS2 |
| 9418 | 10554 | AT2 |
| 10594 | 11160 | DH2 |
| 12175 | 12960 | KR2 |
| 13063 | 13332 | ACP2 |
| 13830 | 25049 | picAII |
| 13830 | 25049 | narbonolide synthase 2 (PICAII) |
| 13935 | 18392 | extender module 3 |
| 13935 | 15224 | KS3 |
| 15540 | 16562 | AT3 |
| 17271 | 18071 | KR3 (inactive) |
| 18123 | 18392 | ACP3 |
| 18447 | 24767 | extender module 4 |
| 18447 | 19736 | KS4 |
| 20031 | 21050 | AT4 |
| 21093 | 21626 | DH4 |
| 22620 | 23588 | ER4 |
| 23652 | 24423 | KR4 |
| 24498 | 24765 | ACP4 |
| 25133 | 29821 | picAIII |
| 25133 | 29821 | narbonolide synthase 3 (PICAIII) |
| 25235 | 29567 | extender module 5 |
| 25235 | 26530 | KS5 |
| 26822 | 27841 | AT5 |
| 28474 | 29227 | KR5 |
| 29302 | 29569 | ACP5 |
| 29924 | 33964 | picAIV |
| 29924 | 33964 | narbonolide synthase 4 (PICAIV) |
| 30026 | 32986 | extender module 6 |
| 30026 | 31312 | KS6 |
| 31604 | 32635 | AT6 |
| 32708 | 32986 | ACP6 |
| 33068 | 33961 | PKS thioesterase domain |
| 33961 | 34806 | picB |
| 33961 | 34806 | typeII thioesterase homolog |
| 34863 | 36011 | picCII |
| 34863 | 36011 | 4-keto-6-deoxyglucose isomerase |
| 36159 | 37439 | picCIII |
| 36159 | 37439 | desosaminyl transferase |
| 37529 | 38242 | picCVI |
| 37529 | 38242 | 3-amino dimethyltransferase |

DNA Sequence of the Insert DNA in Cosmid pKOS023-27
(SEQ ID NO:19)

DNA Sequence of the Insert DNA in Cosmid pKOS023-27 (SEQ ID NO:19)

(SEQ ID NO:19)

```
   1 GATCATGCGG AGCACTCCTT CTCTCGTGCT CCTACCGGTG ATGTGCGCGC CGAATTGATT
  61 CGTGGAGAGA TGTCGACAGT GTCCAAGAGT GAGTCCGAGG AATTCGTGTC CGTGTCGAAC
 121 GACGCCGGTT CCGCGCACGG CACAGCGGAA CCCGTCGCCG TCGTCGGCAT CTCCTGCCGG
 181 GTGCCCGGCG CCCGGGACCC GAGAGAGTTC TGGGAACTCC TGGCGGCAGG CGGCCAGGCC
 241 GTCACCGACG TCCCCGCGGA CCGCTGGAAC GCCGGCGACT TCTACGACCC GGACCGCTCC
 301 GCCCCCGGCC GCTCGAACAG CCGGTGGGGC GGGTTCATCG AGGACGTCGA CCGGTTCGAC
 361 GCCGCCTTCT TCGGCATCTC GCCCCGCGAG GCCGCGGAGA TGGACCCGCA GCAGCGGCTC
 421 GCCCTGGAGC TGGGCTGGGA GGCCCTGGAG CGCGCCGGGA TCGACCCGTC CTCGCTCACC
 481 GGCACCCGCA CCGGCGTCTT CGCCGGCGCC ATCTGGGACG ACTACGCCAC CCTGAAGCAC
 541 CGCCAGGGCG GCGCCGCGAT CACCCCGCAC ACCGTCACCG GCCTCCACCG CGGCATCATC
 601 GCGAACCGAC TCTCGTACAC GCTCGGGCTC CGCGGCCCCA GCATGGTCGT CGACTCCGGC
 661 CAGTCCTCGT CGCTCGTCGC CGTCCACCTC GCGTGCGAGA GCCTGCGGCG CGGCGAGTCC
 721 GAGCTCGCCC TCGCCGGCGG CGTCTCGCTC AACCTGGTGC CGGACAGCAT CATCGGGGCG
 781 AGCAAGTTCG GCGGCCTCTC CCCCGACGGC CGCGCCTACA CCTTCGACGC GCGCGCCAAC
 841 GGCTACGTAC GCGGCGAGGG CGGCGGTTTC GTCGTCCTGA AGCGCCTCTC CCGGGCCGTC
 901 GCCGACGGCG ACCCGGTGCT CGCCGTGATC CGGGGCAGCG CCGTCAACAA CGGCGGCGCC
 961 GCCCAGGGCA TGACGACCCC CGACGCGCAG GCGCAGGAGG CCGTGCTCCG CGAGGCCCAC
1021 GAGCGGGCCG GGACCGCGCC GGCCGACGTG CGGTACGTCG AGCTGCACGG CACCGGCACC
1081 CCCGTGGGCG ACCCGATCGA GGCCGCTGCG CTCGGCGCCG CCCTCGGCAC CGGCCGCCCG
1141 GCCGGACAGC CGCTCCTGGT CGGCTCGGTC AAGACGAACA TCGGCCACCT GGAGGGCGCG
1201 GCCGGCATCG CCGGCCTCAT CAAGGCCGTC CTGGCGGTCC GCGGTCGCGC GCTGCCCGCC
1261 AGCCTGAACT ACGAGACCCC GAACCCGGCG ATCCCGTTCG AGGAACTGAA CCTCCGGGTG
1321 AACACGGAGT ACCTGCCGTG GGAGCCGGAG CACGACGGGC AGCGGATGGT CGTCGGCGTG
1381 TCCTCGTTCG GCATGGGCGG CACGAACGCG CATGTCGTGC TCGAAGAGGC CCCGGGGGTT
1441 GTCGAGGGTG CTTCGGTCGT GGAGTCGACG GTCGGCGGGT CGGCGGTCGG CGGCGGTGTG
1501 GTGCCGTGGG TGGTGTCGGC GAAGTCCGCT GCCGCGCTGG ACGCGCAGAT CGAGCGGCTT
1561 GCCGCGTTCG CCTCGCGGGA TCGTACGGAT GGTGTCGACG CGGGCGCTGT CGATGCGGGT
1621 GCTGTCGATG CGGGTGCTGT CGCTCGCGTA CTGGCCGGCG GCGTGCTCA GAACGAGCAC
1681 CGGGCCGTCG TCGTCGGCAG CGGGCCGGAC GATCTGGCGG CAGCGCTGGC CGCGCTTGAG
1741 GGTCTGGTCC GGGGCGTGGC TTCCGGTGTC GGGCGAGTGG CGTTCGTGTT CCCCGGGCAG
1801 GGCACGCAGT GGGCCGGCAT GGGTGCCGAA CTGCTGGACT CTTCCGCGGT GTTCGCGGCG
1861 GCCATGGCCC AATGCGAGGC CGCACTCTCC CCGTACGTCG ACTGGTCGCT GGAGGCCGTC
1921 GTACGGCAGG CCCCCGGTGC GCCCACGCTG GAGCGGGTCG ATGTCGTGCA GCCTGTGACG
1981 TTCGCCGTCA TGGTCTCGCT GGCTCGCGTG TGGCAGCACC ACGGGGTGAC GCCCCAGGCG
2041 GTCGTCGGCC ACTCGCAGGG CGAGATCGCC GCCGCGTACG TCGCCGGTGC CCTGAGCCTG
2101 GACGACGCCG CTCGTGTCGT GACCCTGCGC AGCAAGTCCA TCGCCGCCCA CCTCGCCGGC
```

| DNA Sequence of the Insert DNA in Cosmid pKOS023-27 (SEQ ID NO:19) |
|---|
| 2161 AAGGGCGGCA TGCTGTCCCT CGCGCTGAGC GAGGACGCCG TCCTGGAGCG ACTGGCCGGG |
| 2221 TTCGACGGGC TGTCCGTCGC CGCTGTGAAC GGGCCCACCG CCACCGTGGT CTCCGGTGAC |
| 2281 CCCGTACAGA TCGAAGAGCT TGCTCGGGCG TGTGAGGCCG ATGGGGTCCG TGCGCGGGTC |
| 2341 ATTCCCGTCG ACTACGCGTC CCACAGCCGG CAGGTCGAGA TCATCGAGAG CGAGCTCGCC |
| 2401 GAGGTCCTCG CCGGGCTCAG CCCGCAGGCT CCGCGCGTGC CGTTCTTCTC GACACTCGAA |
| 2461 GGCGCCTGGA TCACCGAGCC CGTGCTCGAC GGCGGCTACT GGTACCGCAA CCTGCGCCAT |
| 2521 CGTGTGGGCT TCGCCCCGGC CGTCGAGACC CTGGCCACCG ACGAGGGCTT CACCCACTTC |
| 2581 GTCGAGGTCA GCGCCCACCC CGTCCTCACC ATGGCCCTCC CCGGGACCGT CACCGGTCTG |
| 2641 GCGACCCTGC GTCGCGACAA CGGCGGTCAG GACCGCCTCG TCGCCTCCCT CGCCGAAGCA |
| 2701 TGGGCCAACG GACTCGCGGT CGACTGGAGC CCGCTCCTCC CCTCCGCGAC CGGCCACCAC |
| 2761 TCCGACCTCC CCACCTACGC GTTCCAGACC GAGCGCCACT GGCTGGGCGA GATCGAGGCG |
| 2821 CTCGCCCCGG CGGGCGAGCC GGCGGTGCAG CCCGCCGTCC TCCGCACGGA GGCGGCCGAG |
| 2881 CCGGCGGAGC TCGACCGGGA CGAGCAGCTG CGCGTGATCC TGGACAAGGT CCGGGCGCAG |
| 2941 ACGGCCCAGG TGCTGGGGTA CGCGACAGGC GGGCAGATCG AGGTCGACCG GACCTTCCGT |
| 3001 GAGGCCGGTT GCACCTCCCT GACCGGCGTG GACCTGCGCA ACCGGATCAA CGCCGCCTTC |
| 3061 GGCGTACGGA TGGCGCCGTC CATGATCTTC GACTTCCCCA CCCCCGAGGC TCTCGCGGAG |
| 3121 CAGCTGCTCC TCGTCGTGCA CGGGGAGGCG GCGGCGAACC CGGCCGGTGC GGAGCCGGCT |
| 3181 CCGGTGGCGG CGGCCGGTGC CGTCGACGAG CCGGTGGCGA TCGTCGGCAT GGCCTGCCGC |
| 3241 CTGCCCGGTG GGGTCGCCTC GCCGGAGGAC CTGTGGCGGC TGGTGGCCGG CGGCGGGGAC |
| 3301 GCGATCTCGG AGTTCCCGCA GGACCGCGGC TGGGACGTGG AGGGGCTGTA CCACCCGGAT |
| 3361 CCCGAGCACC CCGGCACGTC GTACGTCCGC CAGGGCGGTT TCATCGAGAA CGTCGCCGGC |
| 3421 TTCGACGCGG CCTTCTTCGG GATCTCGCCG CGCGAGGCCC TCGCCATGGA CCCGCAGCAG |
| 3481 CGGCTCCTCC TCGAAACCTC CTGGGAGGCC GTCGAGGACG CCGGGATCGA CCCGACCTCC |
| 3541 CTGCGGGGAC GGCAGGTCGG CGTCTTCACT GGGGCGATGA CCCACGAGTA CGGGCCGAGC |
| 3601 CTGCGGGACG CGCGGGAAGG CCTCGACGGC TACCTGCTGA CCGGCAACAC GGCCAGCGTG |
| 3661 ATGTCGGGCC GCGTCTCGTA CACACTCGGC CTTGAGGGCC CCGCCCTGAC GGTGGACACG |
| 3721 GCCTGCTCGT CGTCGCTGGT CGCCCTGCAC CTCGCCGTGC AGGCCCTGCG CAAGGGCGAG |
| 3781 GTCGACATGG CGCTCGCCGG CGGCGTGGCC GTGATGCCCA CGCCCGGGAT GTTCGTCGAG |
| 3841 TTCAGCCGGC AGCGCGGGCT GGCCGGGGAC GGCCGGTCGA AGGCGTTCGC CGCGTCGGCG |
| 3901 GACGGCACCA GCTGGTCCGA GGGCGTCGGC GTCCTCCTCG TCGAGCGCCT GTCGGACGCC |
| 3961 CGCCGCAACG GACACCAGGT CCTCGCGGTC GTCCGCGGCA GCGCCGTGAA CCAGGACGGC |
| 4021 GCGAGCAACG GCCTCACGGC TCCGAACGGG CCCTCGCAGC AGCGCGTCAT CCGGCGCGCG |
| 4081 CTGGCGGACG CCCGGCTGAC GACCTCCGAC GTGGACGTCG TCGAGGCACA CGGCACGGGC |
| 4141 ACGCGACTCG GCGACCCGAT CGAGGCGCAG GCCCTGATCG CCACCTACGG CCAGGGCCGT |
| 4201 GACGACGAAC AGCCGCTGCG CCTCGGGTCG TTGAAGTCCA ACATCGGGCA CACCCAGGCC |
| 4261 GCGGCCGGCG TCTCCGGTGT CATCAAGATG GTCCAGGCGA TGCGCCACGG ACTGCTGCCG |
| 4321 AAGACGCTGC ACGTCGACGA GCCCTCGGAC CAGATCGACT GGTCGGCTGG CGCCGTGGAA |
| 4381 CTCCTCACCG AGGCCGTCGA CTGGCCGGAG AAGCAGGACG CGGGCTGCG CCGGGCCGCC |
| 4441 GTCTCCTCCT TCGGGATCAG CGGCACCAAT GCGCATGTGG TGCTCGAAGA GGCCCCGGTG |

DNA Sequence of the Insert DNA in Cosmid pKOS023-27 (SEQ ID NO:19)

```
4501 GTTGTCGAGG GTGCTTCGGT CGTCGAGCCG TCGGTTGGCG GGTCGGCGGT CGGCGGCGGT
4561 GTGACGCCTT GGGTGGTGTC GGCGAAGTCC GCTGCCGCGC TCGACGCGCA GATCGAGCGG
4621 CTTGCCGCAT TCGCCTCGCG GGATCGTACG GATGACGCCG ACGCCGGTGC TGTCGACGCG
4681 GGCGCTGTCG CTCACGTACT GGCTGACGGG CGTGCTCAGT TCGAGCACCG GGCCGTCGCG
4741 CTCGGCGCCG GGGCGGACGA CCTCGTACAG GCGCTGGCCG ATCCGGACGG GCTCATACGC
4801 GGAACGGCTT CCGGTGTCGG GCGAGTGGCG TTCGTGTTCC CCGGTCAGGG CACGCAGTGG
4861 GCTGGCATGG GTGCCGAACT GCTGGACTCT TCCGCGGTGT TCGCGGCGGC CATGGCCGAG
4921 TGTGAGGCCG CGCTGTCCCC GTACGTCGAC TGGTCGCTGG AGGCCGTCGT ACGGCAGGCC
4981 CCCGGTGCGC CCACGCTGGA GCGGGTCGAT GTCGTGCAGC CTGTGACGTT CGCCGTCATG
5041 GTCTCGCTGG CTCGCGTGTG GCAGCACCAC GGTGTGACGC CCCAGGCGGT CGTCGGCCAC
5101 TCGCAGGGCG AGATCGCCGC CGCGTACGTC GCCGGAGCCC TGCCCCTGGA CGACGCCGCC
5161 CGCGTCGTCA CCCTGCGCAG CAAGTCCATC GCCGCCCACC TCGCCGGCAA GGGCGGCATG
5221 CTGTCCCTCG CGCTGAACGA GGACGCCGTC CTGGAGCGAC TGAGTGACTT CGACGGGCTG
5281 TCCGTCGCCG CCGTCAACGG GCCCACCGCC ACTGTCGTGT CGGGTGACCC CGTACAGATC
5341 GAAGAGCTTG CTCAGGCGTG CAAGGCGGAC GGATTCCGCG CGCGGATCAT TCCCGTCGAC
5401 TACGCGTCCC ACAGCCGGCA GGTCGAGATC ATCGAGAGCG AGCTCGCCCA GGTCCTCGCC
5461 GGTCTCAGCC CGCAGGCCCC GCGCGTGCCG TTCTTCTCGA CGCTCGAAGG CACCTGGATC
5521 ACCGAGCCCG TCCTCGACGG CACCTACTGG TACCGCAACC TCCGTCACCG CGTCGGCTTC
5581 GCCCCCGCCA TCGAGACCCT GGCCGTCGAC GAGGGCTTCA CGCACTTCGT CGAGGTCAGC
5641 GCCCACCCCG TCCTCACCAT GACCCTCCCC GAGACCGTCA CCGGCCTCGG CACCCTCCGT
5701 CGCGAACAGG GAGGCCAAGA GCGTCTGGTC ACCTCGCTCG CCGAGGCGTG GGTCAACGGG
5761 CTTCCCGTGG CATGGACTTC GCTCCTGCCC GCCACGGCCT CCCGCCCCGG TCTGCCCACC
5821 TACGCCTTCC AGGCCGAGCG CTACTGGCTC GAGAACACTC CCGCCGCCCT GGCCACCGGC
5881 GACGACTGGC GCTACCGCAT CGACTGGAAG CGCCTCCCGG CCGCCGAGGG GTCCGAGCGC
5941 ACCGGCCTGT CCGGCCGCTG GCTCGCCGTC ACGCCGGAGG ACCACTCCGC GCAGGCCGCC
6001 GCCGTGCTCA CCGCGCTGGT CGACGCCGGG GCGAAGGTCG AGGTGCTGAC GGCCGGGGCG
6061 GACGACGACC GTGAGGCCCT CGCCGCCCGG CTCACCGCAC TGACGACCGG TGACGGCTTC
6121 ACCGGCGTGG TCTCGCTCCT CGACGGACTC GTACCGCAGG TCGCCTGGGT CCAGGCGCTC
6181 GGCGACGCCG GAATCAAGGC GCCCCTGTGG TCCGTCACCC AGGGCGCGGT CTCCGTCGGA
6241 CGTCTCGACA CCCCCGCCGA CCCCGACCGG GCCATGCTCT GGGGCCTCGG CCGCGTCGTC
6301 GCCCTTGAGC ACCCCGAACG CTGGGCCGGC CTCGTCGACC TCCCCGCCCA GCCCGATGCC
6361 GCCGCCCTCG CCCACCTCGT CACCGCACTC TCCGGCGCCA CCGGCGAGGA CCAGATCGCC
6421 ATCCGCACCA CCGGACTCCA CGCCCGCCGC CTCGCCCGCG CACCCCTCCA CGGACGTCGG
6481 CCCACCCGCG ACTGGCAGCC CCACGGCACC GTCCTCATCA CCGGCGGCAC CGGAGCCCTC
6541 GGCAGCCACG CCGCACGCTG GATGGCCCAC CACGGAGCCG AACACCTCCT CCTCGTCAGC
6601 CGCAGCGGCG AACAAGCCCC CGGAGCCACC CAACTCACCG CCGAACTCAC CGCATCGGGC
6661 GCCCGCGTCA CCATCGCCGC CTGCGACGTC GCCGACCCCC ACGCCATGCG CACCCTCCTC
6721 GACGCCATCC CCGCCGAGAC GCCCCTCACC GCCGTCGTCC ACACCGCCGG CGCGCTCGAC
```

DNA Sequence of the Insert DNA in Cosmid pKOS023-27 (SEQ ID NO:19)

```
6781 GACGGCATCG TGGACACGCT GACCGCCGAG CAGGTCCGGC GGGCCCACCG TGCGAAGGCC
6841 GTCGGCGCCT CGGTGCTCGA CGAGCTGACC CGGGACCTCG ACCTCGACGC GTTCGTGCTC
6901 TTCTCGTCCG TGTCGAGCAC TCTGGGCATC CCCGGTCAGG GCAACTACGC CCCGCACAAC
6961 GCCTACCTCG ACGCCCTCGC GGCTCGCCGC CGGGCCACCG GCCGGTCCGC CGTCTCGGTG
7021 GCCTGGGGAC CGTGGGACGG TGGCGGCATG GCCGCCGGTG ACGGCGTGGC CGAGCGGCTG
7081 CGCAACCACG GCGTGCCCGG CATGGACCCG GAACTCGCCC TGGCCGCACT GGAGTCCGCG
7141 CTCGGCCGGG ACGAGACCGC GATCACCGTC GCGGACATCG ACTGGGACCG CTTCTACCTC
7201 GCGTACTCCT CCGGTCGCCC GCAGCCCCTC GTCGAGGAGC TGCCCGAGGT GCGGCGCATC
7261 ATCGACGCAC GGGACAGCGC CACGTCCGGA CAGGGCGGGA GCTCCGCCCA GGGCGCCAAC
7321 CCCCTGGCCG AGCGGCTGGC CGCCGCGGCT CCCGGCGAGC GTACGGAGAT CCTCCTCGGT
7381 CTCGTACGGG CGCAGGCCGC CGCCGTGCTC CGGATGCGTT CGCCGGAGGA CGTCGCCGCC
7441 GACCGCGCCT TCAAGGACAT CGGCTTCGAC TCGCTCGCCG GTGTCGAGCT GCGCAACAGG
7501 CTGACCCGGG CGACCGGGCT CCAGCTGCCC GCGACGCTCG TCTTCGACCA CCCGACGCCG
7561 CTGGCCCTCG TGTCGCTGCT CCGCAGCGAG TTCCTCGGTG ACGAGGAGAC GGCGGACGCC
7621 CGGCGGTCCG CGGCGCTGCC CGCGACTGTC GGTGCCGGTG CCGGCGCCGG CGCCGGCACC
7681 GATGCCGACG ACGATCCGAT CGCGATCGTC GCGATGAGCT GCCGCTACCC CGGTGACATC
7741 CGCAGCCCGG AGGACCTGTG GCGGATGCTG TCCGAGGGCG GCGAGGGCAT CACGCCGTTC
7801 CCCACCGACC GCGGCTGGGA CCTCGACGGC CTGTACGACG CCGACCCGGA CGCGCTCGGC
7861 AGGGCGTACG TCCGCGAGGG CGGGTTCCTG CACGACGCGG CCGAGTTCGA CGCGGAGTTC
7921 TTCGGCGTCT CGCCGCGCGA GGCGCTGGCC ATGGACCCGC AGCAGCGGAT GCTAATGACG
7981 ACGTCCTGGG AGGCCTTCGA GCGGGCCGGC ATCGAGCCGG CATCGCTGCG CGGCAGCAGC
8041 ACCGGTGTCT TCATCGGCCT CTCCTACCAG GACTACGCGG CCCGCGTCCC GAACGCCCCG
8101 CGTGGCGTGG AGGGTTACCT GCTGACCGGC AGCACGCCGA GCGTCGCGTC GGGCCGTATC
8161 GCGTACACCT TCGGTCTCGA AGGGCCCGCG ACGACCGTCG ACACCGCCTG CTCGTCGTCG
8221 CTGACCGCCC TGCACCTGGC GGTGCGGGCG CTGCGCAGCG GCGAGTGCAC GATGGCGCTC
8281 GCCGGTGGCG TGGCGATGAT GGCGACCCCG CACATGTTCG TGGAGTTCAG CCGTCAGCGG
8341 GCGCTCGCCC CGGACGGCCG CAGCAAGGCC TTCTCGGCGG ACGCCGACGG GTTCGGCGCC
8401 GCGGAGGGCG TCGGCCTGCT GCTCGTGGAG CGGCTCTCGG ACGCGCGGCG CAACGGTCAC
8461 CCGGTGCTCG CCGTGGTCCG CGGTACCGCC GTCAACCAGG ACGGCGCCAG CAACGGGCTG
8521 ACCGCGCCCA ACGGACCCTC GCAGCAGCGG GTGATCCGGC AGGCGCTCGC CGACGCCCGG
8581 CTGGCACCCG CGACATCGA CGCCGTCGAG ACGCACGGCA CGGGAACCTC GCTGGGCGAC
8641 CCCATCGAGG CCCAGGGCCT CCAGGCCACG TACGGCAAGG AGCGGCCCGC GGAACGGCCG
8701 CTCGCCATCG GCTCCGTGAA GTCCAACATC GGACACACCC AGGCCGCGGC CGGTGCGGCG
8761 GGCATCATCA AGATGGTCCT CGCGATGCGC CACGGCACCC TGCCGAAGAC CCTCCACGCC
8821 GACGAGCCGA GCCCGCACGT CGACTGGGCG AACAGCGGCC TGGCCCTCGT CACCGAGCCG
8881 ATCGACTGGC CGGCCGGCAC CGGTCCGCGC CGCGCCGCCG TCTCCTCCTT CGGCATCAGC
8941 GGGACGAACG CGCACGTCGT GCTGGAGCAG GCGCCGGATG CTGCTGGTGA GGTGCTTGGG
9001 GCCGATGAGG TGCCTGAGGT GTCTGAGACG GTAGCGATGG CTGGGACGGC TGGGACCTCC
9061 GAGGTCGCTG AGGGCTCTGA GGCCTCCGAG GCCCCCGCGG CCCCCGGCAG CCGTGAGGCG
```

DNA Sequence of the Insert DNA in Cosmid pKOS023-27 (SEQ ID NO:19)

```
 9121 TCCCTCCCCG GCACCTGCC CTGGGTGCTG TCCGCCAAGG ACGAGCAGTC GCTGCGCGGC
 9181 CAGGCCGCCG CCCTGCACGC GTGGCTGTCC GAGCCCGCCG CCGACCTGTC GGACGCGGAC
 9241 GGACCGGCCC GCCTGCGGGA CGTCGGGTAC ACGCTCGCCA CGAGCCGTAC CGCCTTCGCG
 9301 CACCGCGCCG CCGTGACCGC CGCCGACCGG GACGGGTTCC TGGACGGGCT GGCCACGCTG
 9361 GCCCAGGGCG GCACCTCGGC CCACGTCCAC CTGGACACCG CCCGGGACGG CACCACCGCG
 9421 TTCCTCTTCA CCGGCCAGGG CAGTCAGCGC CCCGGCGCCG GCCGTGAGCT GTACGACCGG
 9481 CACCCCGTCT TCGCCCGGGC GCTCGACGAG ATCTGCGCCC ACCTCGACGG TCACCTCGAA
 9541 CTGCCCCTGC TCGACGTGAT GTTCGCGGCC GAGGGCAGCG CGGAGGCCGC GCTGCTCGAC
 9601 GAGACGCGGT ACACGCAGTG CGCGCTGTTC GCCCTGGAGG TCGCGCTCTT CCGGCTCGTC
 9661 GAGAGCTGGG GCATGCGGCC GGCCGCACTG CTCGGTCACT CGGTCGGCGA GATCGCCGCC
 9721 GCGCACGTCG CCGGTGTGTT CTCGCTCGCC GACGCCGCCC GCCTGGTCGC CGCGCGCGGC
 9781 CGGCTCATGC AGGAGCTGCC CGCCGGTGGC GCGATGCTCG CCGTCCAGGC CGCGGAGGAC
 9841 GAGATCCGCG TGTGGCTGGA GACGGAGGAG CGGTACGCGG GACGTCTGGA CGTCGCCGCC
 9901 GTCAACGGCC CCGAGGCCGC CGTCCTGTCC GGCGACGCGG ACGCGGCGCG GGAGGCGGAG
 9961 GCGTACTGGT CCGGGCTCGG CCGCAGGACC CGCGCGCTGC GGGTCAGCCA CGCCTTCCAC
10021 TCCGCGCACA TGGACGGCAT GCTCGACGGG TTCCGCGCCG TCCTGGAGAC GGTGGAGTTC
10081 CGGCGCCCCT CCCTGACCGT GGTCTCGAAC GTCACCGGCC TGGCCGCCGG CCCGGACGAC
10141 CTGTGCGACC CCGAGTACTG GGTCCGGCAC GTCCGCGGCA CCGTCCGCTT CCTCGACGGC
10201 GTCCGTGTCC TGCGCGACCT CGGCGTGCGG ACCTGCCTGG AGCTGGGCCC CGACGGGGTC
10261 CTCACCGCCA TGGCGGCCGA CGGCCTCGCG GACACCCCCG CGGATTCCGC TGCCGGCTCC
10321 CCCGTCGGCT CTCCCGCCGG CTCTCCCGCC GACTCCGCCG CCGGCGCGCT CCGGCCCCGG
10381 CCGCTGCTCG TGGCGCTGCT GCGCCGCAAG CGGTCGGAGA CCGAGACCGT CGCGGACGCC
10441 CTCGGCAGGG CGCACGCCCA CGGCACCGGA CCCGACTGGC ACGCCTGGTT CGCCGGCTCC
10501 GGGGCGCACC GCGTGGACCT GCCCACGTAC TCCTTCCGGC GCGACCGCTA CTGGCTGGAC
10561 GCCCCGGCGG CCGACACCGC GGTGGACACC GCCGGCCTCG GTCTCGGCAC CGCCGACCAC
10621 CCGCTGCTCG GCGCCGTGGT CAGCCTTCCG GACCGGGACG GCCTGCTGCT CACCGGCCGC
10681 CTCTCCCTGC GCACCCACCC GTGGCTCGCG GACCACGCCG TCCTGGGGAG CGTCCTGCTC
10741 CCCGGCGCCG CGATGGTCGA ACTCGCCGCG CACGCTGCGG AGTCCGCCGG TCTGAGTGAC
10801 GTGCGGGAGC TGACCCTCCT TGAACCGCTG GTACTGCCCG AGCACGGTGG CGTCGAGCTG
10861 CGCGTGACGG TCGGGGCGCC GGCCGGAGAG CCCGGTGGCG AGTCGGCCGG GGACGGCGCA
10921 CGGCCCGTCT CCCTCCACTC GCGGCTCGCC GACGCGCCCG CCGGTACCGC CTGGTCCTGC
10981 CACGCGACCG GTCTGCTGGC CACCGACCGG CCCGAGCTTC CCGTCGCGCC CGACCGTGCG
11041 GCCATGTGGC CGCCGCAGGG CGCCGAGGAG GTGCCGCTCG ACGGTCTCTA CGAGCGGCTC
11101 GACGGGAACG GCCTCGCCTT CGGTCCGCTG TTCCAGGGGC TGAACGCGGT GTGGCGGTAC
11161 GAGGGTGAGG TCTTCGCCGA CATCGCGCTC CCCGCCACCA CGAATGCGAC CGCGCCCGCG
11221 ACCGCGAACG GCGGCGGGAG TGCGGCGGCG GCCCCCTACG GCATCCACCC CGCCCTGCTC
11281 GACGCTTCGC TGCACGCCAT CGCGGTCGGC GGTCTCGTCG ACGAGCCCGA GCTCGTCCGC
11341 GTCCCCTTCC ACTGGAGCGG TGTCACCGTG CACGCGGCCG GTGCCGCGGC GGCCCGGGTC
```

DNA Sequence of the Insert DNA in Cosmid pKOS023-27 (SEQ ID NO:19)

```
11401 CGTCTCGCCT CCGCGGGGAC GGACGCCGTC TCGCTGTCCC TGACGGACGG CGAGGGACGC
11461 CCGCTGGTCT CCGTGGAACG GCTCACGCTG CGCCCGGTCA CCGCCGATCA GGCGGCGGCG
11521 AGCCGCGTCG GCGGGCTGAT GCACCGGGTG GCCTGGCGTC CGTACGCCCT CGCCTCGTCC
11581 GGCGAACAGG ACCCGCACGC CACTTCGTAC GGGCCGACCG CCGTCCTCGG CAAGGACGAG
11641 CTGAAGGTCG CCGCCGCCCT GGAGTCCGCG GCGTCGAAG TCGGGCTCTA CCCCGACCTG
11701 GCCGCGCTGT CCCAGGACGT GGCGGCCGGC GCCCCGGCGC CCCGTACCGT CCTTGCGCCG
11761 CTGCCCGCGG GTCCCGCCGA CGGCGGCGCG GAGGGTGTAC GGGGCACGGT GGCCCGGACG
11821 CTGGAGCTGC TCCAGGCCTG GCTGGCCGAC GAGCACCTCG CGGGCACCCG CCTGCTCCTG
11881 GTCACCCGCG GTGCGGTGCG GGACCCCGAG GGGTCCGGCG CCGACGATGG CGGCGAGGAC
11941 CTGTCGCACG CGGCCGCCTG GGGTCTCGTA CGGACCGCGC AGACCGAGAA CCCCGGCCGC
12001 TTCGGCCTTC TCGACCTGGC CGACGACGCC TCGTCGTACC GGACCCTGCC GTCGGTGCTC
12061 TCCGACGCGG GCCTGCGCGA CGAACCGCAG CTCGCCCTGC ACGACGGCAC CATCAGGCTG
12121 GCCCGCCTGG CCTCCGTCCG GCCCGAGACC GGCACCGCCG CACCGGCGCT CGCCCCGGAG
12181 GGCACGGTCC TGCTGACCGG CGGCACCGGC GGCCTGGGCG GACTGGTCGC CCGGCACGTG
12241 GTGGGCGAGT GGGGCGTACG ACGCCTGCTG CTGGTGAGCC GGCGGGGCAC GGACGCCCCG
12301 GGCGCCGACG AGCTCGTGCA CGAGCTGGAG GCCCTGGGAG CCGACGTCTC GGTGGCCGCG
12361 TGCGACGTCG CCGACCGCGA AGCCCTCACC GCCGTACTCG ACGCCATCCC CGCCGAACAC
12421 CCGCTCACCG CGGTCGTCCA CACGGCAGGC GTCCTCTCCG ACGGCACCCT CCCGTCCATG
12481 ACGACGGAGG ACGTGGAACA CGTACTGCGG CCCAAGGTCG ACGCCGCGTT CCTCCTCGAC
12541 GAACTCACCT CGACGCCCGC ATACGACCTG GCAGCGTTCG TCATGTTCTC CTCCGCCGCC
12601 GCCGTCTTCG GTGGCGCGGG GCAGGGCGCC TACGCCGCCG CCAACGCCAC CCTCGACGCC
12661 CTCGCCTGGC GCCGCCGGGC AGCCGGACTC CCCGCCCTCT CCCTCGGCTG GGGCCTCTGG
12721 GCCGAGACCA GCGGCATGAC CGGCGAGCTC GGCCAGGCGG ACCTGCGCCG GATGAGCCGC
12781 GCGGGCATCG GCGGGATCAG CGACGCCGAG GGCATCGCGC TCCTCGACGC CGCCCTCCGC
12841 GACGACCGCC ACCCGGTCCT GCTGCCCCTG CGGCTCGACG CCGCCGGGCT GCGGGACGCG
12901 GCCGGGAACG ACCCGGCCGG AATCCCGGCG CTCTTCCGGG ACGTCGTCGG CGCCAGGACC
12961 GTCCGGGCCC GGCCGTCCGC GGCCTCCGCC TCGACGACAG CCGGGACGGC CGGCACGCCG
13021 GGGACGGCGG ACGGCGCGGC GGAAACGGCG GCGGTCACGC TCGCCGACCG GGCCGCCACC
13081 GTGGACGGGC CCGCACGGCA GCGCCTGCTG CTCGAGTTCG TCGTCGGCGA GGTCGCCGAA
13141 GTACTCGGCC ACGCCCGCGG TCACCGGATC GACGCCGAAC GGGGCTTCCT CGACCTCGGC
13201 TTCGACTCCC TGACCGCCGT CGAACTCCGC AACCGGCTCA ACTCCGCCGG TGGCCTCGCC
13261 CTCCCGGCGA CCCTGGTCTT CGACCACCCA AGCCCGGCGG CACTCGCCTC CCACCTGGAC
13321 GCCGAGCTGC CGCGCGGCGC CTCGGACCAG GACGGAGCCG GAACCGGAA CGGGAACGAG
13381 AACGGGACGA CGGCGTCCCG GAGCACCGCC GAGACGGACG CGCTGCTGGC ACAACTGACC
13441 CGCCTGGAAG GCGCCTTGGT GCTGACGGGC CTCTCGGACG CCCCCGGGAG CGAAGAAGTC
13501 CTGGAGCACC TGCGGTCCCT GCGCTCGATG GTCACGGGCG AGACCGGGAC CGGGACCGCG
13561 TCCGAGCCCC CGGACGGCGC CGGGTCCGGC GCCGAGGACC GGCCCTGGGC GGCCGGGGAC
13621 GGAGCCGGGG GCGGGAGTGA GGACGGCGCG GGAGTGCCGG ACTTCATGAA CGCCTCGGCC
13681 GAGGAACTCT TCGGCCTCCT CGACCAGGAC CCCAGCACGG ACTGATCCCT GCCGCACGGT
```

-continued

| DNA Sequence of the Insert DNA in Cosmid pKOS023-27 (SEQ ID NO:19) |
|---|

```
13741 CGCCTCCCGC CCCGGACCCC GTCCCGGGCA CCTCGACTCG AATCACTTCA TGCGCGCCTC

13801 GGGCGCCTCC AGGAACTCAA GGGGACAGCG TGTCCACGGT GAACGAAGAG AAGTACCTCG

13861 ACTACCTGCG TCGTGCCACG GCGGACCTCC ACGAGGCCCG TGGCCGCCTC CGCGAGCTGG

13921 AGGCGAAGGC GGGCGAGCCG GTGGCGATCG TCGGCATGGC CTGCCGCCTG CCCGGCGGCG

13981 TCGCCTCGCC CGAGGACCTG TGGCGGCTGG TGGCCGGCGG CGAGGACGCG ATCTCGGAGT

14041 TCCCCCAGGA CCGCGGCTGG GACGTGGAGG GCCTGTACGA CCCGAACCCG GAGGCCACGG

14101 GCAAGAGTTA CGCCCGCGAG GCCGGATTCC TGTACGAGGC GGGCGAGTTC GACGCCGACT

14161 TCTTCGGGAT CTCGCCGCGC GAGGCCCTCG CCATGGACCC GCAGCAGCGT CTCCTCCTGG

14221 AGGCCTCCTG GGAGGCGTTC GAGCACGCCG GGATCCCGGC GGCCACCGCG CGCGGCACCT

14281 CGGTCGGCGT CTTCACCGGC GTGATGTACC ACGACTACGC CACCCGTCTC ACCGATGTCC

14341 CGGAGGGCAT CGAGGGCTAC CTGGGCACCG GCAACTCCGG CAGTGTCGCC TCGGGCCGCG

14401 TCGCGTACAC GCTTGGCCTG GAGGGGCCGG CCGTACGGT CGACACCGCC TGCTCGTCCT

14461 CGCTGGTCGC CCTGCACCTC GCCGTGCAGG CCCTGCGCAA GGGCGAGGTC GACATGGCGC

14521 TCGCCGGCGG CGTGACGGTC ATGTCGACGC CCAGCACCTT CGTCGAGTTC AGCCGTCAGC

14581 GCGGGCTGGC GCCGGACGGC CGGTCGAAGT CCTTCTCGTC GACGGCCGAC GGCACCAGCT

14641 GGTCCGAGGG CGTCGGCGTC CTCCTCGTCG AGCGCCTGTC CGACGCGCGT CGCAAGGGCC

14701 ATCGGATCCT CGCCGTGGTC CGGGGCACCG CCGTCAACCA GGACGGCGCC AGCAGCGGCC

14761 TCACGGCTCC GAACGGGCCG TCGCAGCAGC GCGTCATCCG ACGTGCCCTG GCGGACGCCC

14821 GGCTCACGAC CTCCGACGTG GACGTCGTCG AGGCCCACGG CACGGGTACG CGACTCGGCG

14881 ACCCGATCGA GGCGCAGGCC GTCATCGCCA CGTACGGGCA GGGCCGTGAC GGCGAACAGC

14941 CGCTGCGCCT CGGGTCGTTG AAGTCCAACA TCGGACACAC CCAGGCCGCC GCCGGTGTCT

15001 CCGGCGTGAT CAAGATGGTC CAGGCGATGC GCCACGGCGT CCTGCCGAAG ACGCTCCACG

15061 TGGAGAAGCC GACGGACCAG GTGGACTGGT CCGCGGGCGC GGTCGAGCTG CTCACCGAGG

15121 CCATGGACTG GCCGGACAAG GGCGACGGCG GACTGCGCAG GGCCGCGGTC TCCTCCTTCG

15181 GCGTCAGCGG GACGAACGCG CACGTCGTGC TCGAAGAGGC CCCGGCGGCC GAGGAGACCC

15241 CTGCCTCCGA GGCGACCCCG GCCGTCGAGC CGTCGGTCGG CGCCGGCCTG GTGCCGTGGC

15301 TGGTGTCGGC GAAGACTCCG GCCGCGCTGG ACGCCCAGAT CGGACGCCTC GCCGCGTTCG

15361 CCTCGCAGGG CCGTACGGAC GCCGCCGATC CGGGCGCGGT CGCTCGCGTA CTGGCCGGCG

15421 GGCGCGCCGA GTTCGAGCAC CGGGCCGTCG TGCTCGGCAC CGGACAGGAC GATTTCGCGC

15481 AGGCGCTGAC CGCTCCGGAA GGACTGATAC GCGGCACGCC CTCGGACGTG GCCGGGTGG

15541 CGTTCGTGTT CCCCGGTCAG GGCACGCAGT GGGCCGGGAT GGGCGCCGAA CTCCTCGACG

15601 TGTCGAAGGA GTTCGCGGCG GCCATGGCCG AGTGCGAGAG CGCGCTCTCC CGCTATGTCG

15661 ACTGGTCGCT GGAGGCCGTC GTCCGGCAGG CGCCGGGCGC GCCCACGCTG GAGCGGGTCG

15721 ACGTCGTCCA GCCCGTGACC TTCGCTGTCA TGGTTTCGCT GGCGAAGGTC TGGCAGCACC

15781 ACGGCGTGAC GCCGCAGGCC GTCGTCGGCC ACTCGCAGGG CGAGATCGCC GCCGCGTACG

15841 TCGCCGGTGC CCTCACCCTC GACGACGCCG CCCGCGTCGT CACCCTGCGC AGCAAGTCCA

15901 TCGCCGCCCA CCTCGCCGGC AAGGGCGGCA TGATCTCCCT CGCCCTCAGC GAGGAAGCCA

15961 CCCGGCAGCG CATCGAGAAC CTCCACGGAC TGTCGATCGC CGCCGTCAAC GGCCCCACCG
```

| DNA Sequence of the Insert DNA in Cosmid pKOS023-27 (SEQ ID NO:19) |
|---|
| 16021 CCACCGTGGT TTCGGGCGAC CCCACCCAGA TCCAAGAGCT CGCTCAGGCG TGTGAGGCCG |
| 16081 ACGGGGTCCG CGCACGGATC ATCCCCGTCG ACTACGCCTC CCACAGCGCC CACGTCGAGA |
| 16141 CCATCGAGAG CGAACTCGCC GAGGTCCTCG CCGGGCTCAG CCCGCGGACA CCTGAGGTGC |
| 16201 CGTTCTTCTC GACACTCGAA GGCGCCTGGA TCACCGAGCC GGTGCTCGAC GGCACCTACT |
| 16261 GGTACCGCAA CCTCCGCCAC CGCGTCGGCT TCGCCCCCGC CGTCGAGACC CTCGCCACCG |
| 16321 ACGAAGGCTT CACCCACTTC ATCGAGGTCA GCGCCCACCC CGTCCTCACC ATGACCCTCC |
| 16381 CCGAGACCGT CACCGGCCTC GGCACCCTCC GCCGCGAACA GGGAGGCCAG GAGCGTCTGG |
| 16441 TCACCTCACT CGCCGAAGCC TGGACCAACG GCCTCACCAT CGACTGGGCG CCCGTCCTCC |
| 16501 CCACCGCAAC CGGCCACCAC CCCGAGCTCC CCACCTACGC CTTCCAGCGC CGTCACTACT |
| 16561 GGCTCCACGA CTCCCCCGCC GTCCAGGGCT CCGTGCAGGA CTCCTGGCGC TACCGCATCG |
| 16621 ACTGGAAGCG CCTCGCGGTC GCCGACGCGT CCGAGCGCGC CGGGCTGTCC GGGCGCTGGC |
| 16681 TCGTCGTCGT CCCCGAGGAC CGTTCCGCCG AGGCCGCCCC GGTGCTCGCC GCGCTGTCCG |
| 16741 GCGCCGGCGC CGACCCCGTA CAGCTGGACG TGTCCCCGCT GGGCGACCGG CAGCGGCTCG |
| 16801 CCGCGACGCT GGGCGAGGCC CTGGCGGCGG CCGGTGGAGC CGTCGACGGC GTCCTCTCGC |
| 16861 TGCTCGCGTG GGACGAGAGC GCGCACCCCG GCCACCCCGC CCCCTTCACC CGGGGCACCG |
| 16921 GCGCCACCCT CACCCTGGTG CAGGCGCTGG AGGACGCCGG CGTCGCCGCC CCGCTGTGGT |
| 16981 GCGTGACCCA CGGCGCGGTG TCCGTCGGCC GGGCCGACCA CGTCACCTCC CCCGCCCAGG |
| 17041 CCATGGTGTG GGGCATGGGC CGGGTCGCCG CCCTGGAGCA CCCCGAGCGG TGGGGCGGCC |
| 17101 TGATCGACCT GCCCCTCGGAC GCCGACCGGG CGGCCCTGGA CCGCATGACC ACGGTCCTCG |
| 17161 CCGGCGGTAC GGGTGAGGAC CAGGTCGCGG TACGCGCCTC CGGGCTGCTC GCCCGCCGCC |
| 17221 TCGTCCGCGC CTCCCTCCCG GCGCACGGCA CGGCTTCGCC GTGGTGGCAG GCCGACGGCA |
| 17281 CGGTGCTCGT CACCGGTGCC GAGGAGCCTG CGGCCGCCGA GGCCGCACGC CGGCTGGCCC |
| 17341 GCGACGGCGC CGGACACCTC CTCCTCCACA CCACCCCCTC CGGCAGCGAA GGCGCCGAAG |
| 17401 GCACCTCCGG TGCCGCCGAG GACTCCGGCC TCGCCGGGCT CGTCGCCGAA CTCGCGGACC |
| 17461 TGGGCGCGAC GGCCACCGTC GTGACCTGCG ACCTCACGGA CGCGGAGGCG GCCGCCCGGC |
| 17521 TGCTCGCCGG CGTCTCCGAC GCGCACCCGC TCAGCGCCGT CCTCCACCTG CCGCCCACCG |
| 17581 TCGACTCCGA GCCGCTCGCC GCGACCGACG CGGACGCGCT CGCCCGTGTC GTGACCGCGA |
| 17641 AGGCCACCGC CGCGCTCCAC CTGGACCGCC TCCTGCGGGA GGCCGCGGCT GCCGGAGGCC |
| 17701 GTCCGCCCGT CCTGGTCCTC TTCTCCTCGG TCGCCGCGAT CTGGGCGGC GCCGGTCAGG |
| 17761 GCGCGTACGC CGCCGGTACG GCCTTCCTCG ACGCCCTCGC CGGTCAGCAC CGGGCCGACG |
| 17821 GCCCCACCGT GACCTCGGTG GCCTGGAGCC CCTGGGAGGG CAGCCGCGTC ACCGAGGGTG |
| 17881 CGACCGGGGA GCGGCTGCGC CGCCTCGGCC TGCGCCCCCT CGCCCCGCG ACGGCGCTCA |
| 17941 CCGCCCTGGA CACCGCGCTC GGCCACGGCG ACACCGCCGT CACGATCGCC GACGTCGACT |
| 18001 GGTCGAGCTT CGCCCCCGGC TTCACCACGG CCCGGCCGGG CACCCTCCTC GCCGATCTGC |
| 18061 CCGAGGCGCG CCGCGCGCTC GACGAGCAGC AGTCGACGAC GGCCGCCGAC GACACCGTCC |
| 18121 TGAGCCGCGA GCTCGGTGCG CTCACCGGCG CCGAACAGCA GCGCCGTATG CAGGAGTTGG |
| 18181 TCCGCGAGCA CCTCGCCGTG GTCCTCAACC ACCCCTCCCC CGAGGCCGTC GACACGGGGC |
| 18241 GGGCCTTCCG TGACCTCGGA TTCGACTCGC TGACGGCGGT CGAGCTCCGC AACCGCCTCA |
| 18301 AGAACGCCAC CGGCCTGGCC CTCCCGGCCA CTCTGGTCTT CGACTACCCG ACCCCCCGGA |

-continued

DNA Sequence of the Insert DNA in Cosmid pKOS023-27 (SEQ ID NO:19)

```
18361 CGCTGGCGGA GTTCCTCCTC GCGGAGATCC TGGGCGAGCA GGCCGGTGCC GGCGAGCAGC
18421 TTCCGGTGGA CGGCGGGGTC GACGACGAGC CCGTCGCGAT CGTCGGCATG GCGTGCCGCC
18481 TGCCGGGCGG TGTCGCCTCG CCGGAGGACC TGTGGCGGCT GGTGGCCGGC GGCGAGGACG
18541 CGATCTCCGG CTTCCCGCAG GACCGCGGCT GGGACGTGGA GGGGCTGTAC GACCCGGACC
18601 CGGACGCGTC CGGGCGGACG TACTGCCGTG CCGGTGGCTT CCTCGACGAG GCGGGCGAGT
18661 TCGACGCCGA CTTCTTCGGG ATCTCGCCGC GCGAGGCCCT CGCCATGGAC CCGCAGCAGC
18721 GGCTCCTCCT GGAGACCTCC TGGGAGGCCG TCGAGGACGC CGGGATCGAC CCGACCTCCC
18781 TTCAGGGGCA GCAGGTCGGC GTGTTCGCGG GCACCAACGG CCCCCACTAC GAGCCGCTGC
18841 TCCGCAACAC CGCCGAGGAT CTTGAGGGTT ACGTCGGGAC GGGCAACGCC GCCAGCATCA
18901 TGTCGGGCCG TGTCTCGTAC ACCCTCGGCC TGGAGGGCCC GGCCGTCACG GTCGACACCG
18961 CCTGCTCCTC CTCGCTGGTC GCCCTGCACC TCGCCGTGCA GGCCCTGCGC AAGGGCGAAT
19021 GCGGACTGGC GCTCGCGGGC GGTGTGACGG TCATGTCGAC GCCCACGACG TTCGTGGAGT
19081 TCAGCCGGCA GCGCGGGCTC GCGGAGGACG GCCGGTCGAA GGCGTTCGCC GCGTCGGCGG
19141 ACGGCTTCGG CCCGGCGGAG GGCGTCGGCA TGCTCCTCGT CGAGCGCCTG TCGGACGCCC
19201 GCCGCAACGG ACACCGTGTG CTGGCGGTCG TGCGCGGCAG CGCGGTCAAC CAGGACGGCG
19261 CGAGCAACGG CCTGACCGCC CCGAACGGGC CCTCGCAGCA GCGCGTCATC CGGCGCGCGC
19321 TCGCGGACGC CCGACTGACG ACCGCCGACG TGGACGTCGT CGAGGCCCAC GGCACGGGCA
19381 CGCGACTCGG CGACCCGATC GAGGCACAGG CCCTCATCGC CACCTACGGC CAGGGGCGCG
19441 ACACCGAACA GCCGCTGCGC CTGGGGTCGT TGAAGTCCAA CATCGGACAC ACCCAGGCCG
19501 CCGCCGGTGT CTCCGGCATC ATCAAGATGG TCCAGGCGAT GCGCCACGGC GTCCTGCCGA
19561 AGACGCTCCA CGTGGACCGG CCGTCGGACC AGATCGACTG GTCGGCGGGC ACGGTCGAGC
19621 TGCTCACCGA GGCCATGGAC TGGCCGAGGA AGCAGGAGGG CGGGCTGCGC CGCGCGGCCG
19681 TCTCCTCCTT CGGCATCAGC GGCACGAACG CGCACATCGT GCTCGAAGAA GCCCCGGTCG
19741 ACGAGGACGC CCCGGCGGAC GAGCCGTCGG TCGGCGGTGT GGTGCCGTGG CTCGTGTCCG
19801 CGAAGACTCC GGCCGCGCTG GACGCCCAGA TCGGACGCCT CGCCGCGTTC GCCTCGCAGG
19861 GCCGTACGGA CGCCGCCGAT CCGGGCGCGG TCGCTCGCGT ACTGGCCGGC GGGCGTGCGC
19921 AGTTCGAGCA CCGGGCCGTC GCGCTCGGCA CCGGACAGGA CGACCTGGCG GCCGCACTGG
19981 CCGCGCCTGA GGGTCTGGTC CGGGGTGTGG CCTCCGGTGT GGGTCGAGTG GCGTTCGTGT
20041 TCCCGGGACA GGGCACGCAG TGGGCCGGGA TGGGTGCCGA ACTCCTCGAC GTGTCGAAGG
20101 AGTTCGCGGC GGCCATGGCC GAGTGCGAGG CCGCGCTCGC TCCGTACGTG GACTGGTCGC
20161 TGGAGGCCGT CGTCCGACAG GCCCCCGGCG CGCCCACGCT GGAGCGGGTC GATGTCGTCC
20221 AGCCCGTGAC GTTCGCCGTC ATGGTCTCGC TGGCGAAGGT CTGGCAGCAC CACGGGGTGA
20281 CCCCGCAAGC CGTCGTCGGC CACTCGCAGG GCGAGATCGC CGCCGCGTAC GTCGCCGGTG
20341 CCCTGAGCCT GGACGACGCC GCTCGTGTCG TGACCCTGCG CAGCAAGTCC ATCGGCGCCC
20401 ACCTCGCGGG CCAGGCGGC ATGCTGTCCC TCGCGCTGAG CGAGGCGGCC GTTGTGGAGC
20461 GACTGGCCGG GTTCGACGGG CTGTCCGTCG CCGCCGTCAA CGGGCCTACC GCCACCGTGG
20521 TTTCGGGCGA CCCGACCCAG ATCCAAGAGC TCGCTCAGGC GTGTGAGGCC GACGGGGTCC
20581 GCGCACGGAT CATCCCCGTC GACTACGCCT CCCACAGCGC CCACGTCGAG ACCATCGAGA
```

| DNA Sequence of the Insert DNA in Cosmid pKOS023-27 (SEQ ID NO:19) |
|---|
| 20641 GCGAACTCGC CGACGTCCTG GCGGGGTTGT CCCCCCAGAC ACCCCAGGTC CCCTTCTTCT |
| 20701 CCACCCTCGA AGGCGCCTGG ATCACCGAAC CCGCCCTCGA CGGCGGCTAC TGGTACCGCA |
| 20761 ACCTCCGCCA TCGTGTGGGC TTCGCCCCGG CCGTCGAAAC CCTGGCCACC GACGAAGGCT |
| 20821 TCACCCACTT CGTCGAGGTC AGCGCCCACC CCGTCCTCAC CATGGCCCTG CCCGAGACCG |
| 20881 TCACCGGCCT CGGCACCCTC CGCCGTGACA ACGGCGGACA GCACCGCCTC ACCACCTCCC |
| 20941 TCGCCGAGGC CTGGGCCAAC GGCCTCACCG TCGACTGGGC CTCTCTCCTC CCCACCACGA |
| 21001 CCACCCACCC CGATCTGCCC ACCTACGCCT TCCAGACCGA GCGCTACTGG CCGCAGCCCG |
| 21061 ACCTCTCCGC CGCCGGTGAC ATCACCTCCG CCGGTCTCGG GGCGGCCGAG CACCCGCTGC |
| 21121 TCGGCGCGGC CGTGGCGCTC GCGGACTCCG ACGGCTGCCT GCTCACGGGG AGCCTCTCCC |
| 21181 TCCGTACGCA CCCCTGGCTG GCGGACCACG CGGTGGCCGG CACCGTGCTG CTGCCGGGAA |
| 21241 CGGCGTTCGT GGAGCTGGCG TTCCGAGCCG GGACCAGGT CGGTTGCGAT CTGGTCGAGG |
| 21301 AGCTCACCCT CGACGCGCCG CTCGTGCTGC CCCGTCGTGG CGCGGTCCGT GTGCAGCTGT |
| 21361 CCGTCGGCGC GAGCGACGAG TCCGGGCGTC GTACCTTCGG GCTCTACGCG CACCCGGAGG |
| 21421 ACGCGCCGGG CGAGGCGGAG TGGACGCGGC ACGCCACCGG TGTGCTGGCC GCCCGTGCGG |
| 21481 ACCGCACCGC CCCCGTCGCC GACCCGGAGG CCTGGCCGCC GCCGGGCGCC GAGCCGGTGG |
| 21541 ACGTGGACGG TCTGTACGAG CGCTTCGCGG CGAACGGCTA CGGCTACGGC CCCCTCTTCC |
| 21601 AGGGCGTCCG TGGTGTCTGG CGGCGTGGCG ACGAGGTGTT CGCCGACGTG GCCCTGCCGG |
| 21661 CCGAGGTCGC CGGTGCCGAG GGCGCGCGGT TCGGCCTTCA CCCGGCGCTG CTCGACGCCG |
| 21721 CCGTGCAGGC GGCCGGTGCG GGCGGGGCGT TCGGCGCGGG CACGCGGCTG CCGTTCGCCT |
| 21781 GGAGCGGGAT CTCCCTGTAC GCGGTCGGCG CCACCGCCCT CCGCGTGCGG CTGGCCCCCG |
| 21841 CCGGCCCGGA CACGGTGTCC GTGAGCGCCC CGACTCCTC CGGGCAGCCG GTGTTCGCCG |
| 21901 CGGACTCCCT CACGGTGCTG CCCGTCGACC CCGCGCAGCT GGCGGCCTTC AGCGACCCGA |
| 21961 CTCTGGACGC GCTGCACCTG CTGGAGTGGA CCGCCTGGGA CGGTGCCGCG CAGGCCCTGC |
| 22021 CCGGCGCGGT CGTGCTGGGC GGCGACGCCG ACGGTCTCGC CGCGGCGCTG CGCGCCGGTG |
| 22081 GCACCGAGGT CCTGTCCTTC CCGGACCTTA CGGACCTGGT GGAGGCCGTC GACCGGGGCG |
| 22141 AGACCCCGGC CCCGGCGACC GTCCTGGTGG CCTGCCCCGC CGCCGGCCCC GGTGGGCCGG |
| 22201 AGCATGTCCG CGAGGCCCTG CACGGGTCGC TCGCGCTGAT GCAGGCCTGG CTGGCCGACG |
| 22261 AGCGGTTCAC CGATGGGCGC CTGGTGCTCG TGACCCGCGA CGCGGTCGCC GCCCGTTCCG |
| 22321 GCGACGGCCT GCGGTCCACG GGACAGGCCG CCGTCTGGGG CCTCGGCCGG TCCGCGCAGA |
| 22381 CGGAGAGCCC GGGCCGGTTC GTCCTGCTCG ACCTCGCCGG GGAAGCCCGG ACGGCCGGGG |
| 22441 ACGCCACCGC CGGGGACGGC CTGACGACCG GGACGCCAC CGTCGGCGGC ACCTCTGGAG |
| 22501 ACGCCGCCCT CGGCAGCGCC CTCGCGACCG CCCTCGGCTC GGGCGAGCCG CAGCTCGCCC |
| 22561 TCCGGGACGG GGCGCTCCTC GTACCCCGCC TGGCGCGGGC CGCCGCGCCC GCCGCGGCCG |
| 22621 ACGGCCTCGC CGCGGCCGAC GGCCTCGCCG CTCTGCCGCT GCCCGCCGCT CCGGCCCTCT |
| 22681 GGCGTCTGGA GCCCGGTACG GACGGCAGCC TGGAGAGCCT CACGGCGGCG CCCGGCGACG |
| 22741 CCGAGACCCT CGCCCCGGAG CCGCTCGGCC CGGGACAGGT CCGCATCGCG ATCCGGGCCA |
| 22801 CCGGTCTCAA CTTCCGCGAC GTCCTGATCG CCCTCGGCAT GTACCCCGAT CCGGCGCTGA |
| 22861 TGGGCACCGA GGGAGCCGGC GTGGTCACCG CGACCGGCCC CGGCGTCACG CACCTCGCCC |
| 22921 CCGGCGACCG GGTCATGGGC CTGCTCTCCG GCGCGTACGC CCCGGTCGTC GTGGCGGACG |

DNA Sequence of the Insert DNA in Cosmid pKOS023-27 (SEQ ID NO:19)

```
22981 CGCGGACCGT CGCGCGGATG CCCGAGGGGT GGACGTTCGC CCAGGGCGCC TCCGTGCCGG
23041 TGGTGTTCCT GACGGCCGTC TACGCCCTGC GCGACCTGGC GGACGTCAAG CCCGGCGAGC
23101 GCCTCCTGGT CCACTCCGCC GCCGGTGGCG TGGGCATGGC CGCCGTGCAG CTCGCCCGGC
23161 ACTGGGGCGT GGAGGTCCAC GGCACGGCGA GTCACGGGAA GTGGGACGCC CTGCGCGCGC
23221 TCGGCCTGGA CGACGCGCAC ATCGCCTCCT CCCGCACCCT GGACTTCGAG TCCGCGTTCC
23281 GTGCCGCTTC CGGCGGGGCG GGCATGGACG TCGTACTGAA CTCGCTCGCC CGCGAGTTCG
23341 TCGACGCCTC GCTGCGCCTG CTCGGGCCGG GCGGCCGGTT CGTGGAGATG GGGAAGACCG
23401 ACGTCCGCGA CGCGGAGCGG GTCGCCGCCG ACCACCCCGG TGTCGGCTAC CGCGCCTTCG
23461 ACCTGGGCGA GGCCGGGCCG GAGCGGATCG GCGAGATGCT CGCCGAGGTC ATCGCCCTCT
23521 TCGAGGACGG GGTGCTCCGG CACCTGCCCG TCACGACCTG GGACGTGCGC CGGGCCCGCG
23581 ACGCCTTCCG GCACGTCAGC CAGGCCCGCC ACACGGGCAA GGTCGTCCTC ACGATGCCGT
23641 CGGGCCTCGA CCCGGAGGGT ACGGTCCTGC TGACCGGCGG CACCGGTGCG CTGGGGGGCA
23701 TCGTGGCCCG GCACGTGGTG GGCGAGTGGG GCGTACGACG CCTGCTGCTC GTGAGCCGGC
23761 GGGGCACGGA CGCCCCGGGC GCCGGCGAGC TCGTGCACGA GCTGGAGGCC CTGGGAGCCG
23821 ACGTCTCGGT GGCCGCGTGC GACGTCGCCG ACCGCGAAGC CCTCACCGCC GTACTCGACT
23881 CGATCCCCGC CGAACACCCG CTCACCGCGG TCGTCCACAC GGCAGGCGTC CTCTCCGACG
23941 GCACCCTCCC CTCGATGACA GCGGAGGATG TGGAACACGT ACTGCGTCCC AAGGTCGACG
24001 CCGCGTTCCT CCTCGACGAA CTCACCTCGA CGCCCGGCTA CGACCTGGCA GCGTTCGTCA
24061 TGTTCTCCTC CGCCGCCGCC GTCTTCGGTG GCGCGGGGCA GGGCGCCTAC GCCGCCGCCA
24121 ACGCCACCCT CGACGCCCTC GCCTGGCGCC GCCGGACAGC CGGACTCCCC GCCCTCTCCC
24181 TCGGCTGGGG CCTCTGGGCC GAGACCAGCG GCATGACCGG CGGACTCAGC GACACCGACC
24241 GCTCGCGGCT GGCCCGTTCC GGGGCGACGC CCATGGACAG CGAGCTGACC CTGTCCCTCC
24301 TGGACGCGGC CATGCGCCGC GACGACCCGG CGCTCGTCCC GATCGCCCTG GACGTCGCCG
24361 CGCTCCGCGC CCAGCAGCGC GACGGCATGC TGGCGCCGCT GCTCAGCGGG CTCACCCGCG
24421 GATCGCGGGT CGGCGGCGCG CCGGTCAACC AGCGCAGGGC AGCCGCCGGA GGCGCGGGCG
24481 AGGCGGACAC GGACCTCGGC GGGCGGCTCG CCGCGATGAC ACCGGACGAC CGGGTCGCGC
24541 ACCTGCGGGA CCTCGTCCGT ACGCACGTGG CGACCGTCCT GGGACACGGC ACCCCGAGCC
24601 GGGTGGACCT GGAGCGGGCC TTCCGCGACA CCGGTTTCGA CTCGCTCACC GCCGTCGAAC
24661 TCCGCAACCG TCTCAACGCC GCGACCGGGC TGCGGCTGCC GGCCACGCTG GTCTTCGACC
24721 ACCCCACCCC GGGGGAGCTC GCCGGGCACC TGCTCGACGA ACTCGCCACG GCCGCGGGCG
24781 GGTCCTGGGC GGAAGGCACC GGGTCCGGAG ACACGGCCTC GGCGACCGAT CGGCAGACCA
24841 CGGCGGCCCT CGCCGAACTC GACCGGCTGG AAGGCGTGCT CGCCTCCCTC GCGCCCGCCG
24901 CCGGCGGCCT CCGGAGCTC GCCGCCCGGC TCAGGGCGCT GGCCGCGGCC CTGGGGGACG
24961 ACGGCGACGA CGCCACCGAC CTGGACGAGG CGTCCGACGA CGACCTCTTC TCCTTCATCG
25021 ACAAGGAGCT GGGCGACTCC GACTTCTGAC CTGCCCGACA CCACCGGCAC CACCGGCACC
25081 ACCAGCCCCC CTCACACACG GAACACGGAA CGGACAGGCG AGAACGGGAG CCATGGCGAA
25141 CAACGAAGAC AAGCTCCGCG ACTACCTCAA GCGCGTCACC GCCGAGCTGC AGCAGAACAC
25201 CAGGCGTCTG CGCGAGATCG AGGGACGCAC GCACGAGCCG GTGGCGATCG TGGGCATGGC
```

DNA Sequence of the Insert DNA in Cosmid pKOS023-27 (SEQ ID NO:19)

```
25261 CTGCCGCCTG CCGGGCGGTG TCGCCTCGCC CGAGGACCTG TGGCAGCTGG TGGCCGGGGA
25321 CGGGGACGCG ATCTCGGAGT TCCCGCAGGA CCGCGGCTGG GACGTGGAGG GGCTGTACGA
25381 CCCCGACCCG GACGCGTCCG GCAGGACGTA CTGCCGGTCC GGCGGATTCC TGCACGACGC
25441 CGGCGAGTTC GACGCCGACT TCTTCGGGAT CTCGCCGCGC GAGGCCCTCG CCATGGACCC
25501 GCAGCAGCGA CTGTCCCTCA CCACCGCGTG GGAGGCGATC GAGAGCGCGG GCATCGACCC
25561 GACGGCCCTG AAGGGCAGCG GCCTCGGCGT CTTCGTCGGC GGCTGGCACA CCGGCTACAC
25621 CTCGGGGCAG ACCACCGCCG TGCAGTCGCC CGAGCTGGAG GGCCACCTGG TCAGCGGCGC
25681 GGCGCTGGGC TTCCTGTCCG GCCGTATCGC GTACGTCCTC GGTACGGACG GACCGGCCCT
25741 GACCGTGGAC ACGGCCTGCT CGTCCTCGCT GGTCGCCCTG CACCTCGCCG TGCAGGCCCT
25801 CCGCAAGGGC GAGTGCGACA TGGCCCTCGC CGGTGGTGTC ACGGTCATGC CAACGCGGA
25861 CCTGTTCGTG CAGTTCAGCC GGCAGCGCGG GCTGGCCGCG GACGGCCGGT CGAAGGCGTT
25921 CGCCACCTCG GCGGACGGCT TCGGCCCCGC GGAGGGCGCC GGAGTCCTGC TGGTGGAGCG
25981 CCTGTCGGAC GCCCGCCGCA ACGGACACCG GATCCTCGCG GTCGTCCGCG GCAGCGCGGT
26041 CAACCAGGAC GGCGCCAGCA ACGGCCTCAC GGCTCCGCAC GGGCCCTCCC AGCAGCGCGT
26101 CATCCGACGG GCCCTGGCGG ACGCCCGGCT CGCGCCGGGT GACGTGGACG TCGTCGAGGC
26161 GCACGGCACG GGCACGCGGC TCGGCGACCC GATCGAGGCG CAGGCCCTCA TCGCCACCTA
26221 CGGCCAGGAG AAGAGCAGCG AACAGCCGCT GAGGCTGGGC GCGTTGAAGT CGAACATCGG
26281 GCACACGCAG GCCGCGGCCG GTGTCGCAGG TGTCATCAAG ATGGTCCAGG CGATGCGCCA
26341 CGGACTGCTG CCGAAGACGC TGCACGTCGA CGAGCCCTCG GACCAGATCG ACTGGTCGGC
26401 GGGCACGGTG GAACTCCTCA CCGAGGCCGT CGACTGGCCG GAGAAGCAGG ACGGCGGGCT
26461 GCGCCGCGCG GCTGTCTCCT CCTTCGGCAT CAGCGGGACG AACGCGCACG TCGTCCTGGA
26521 GGAGGCCCCG GCGGTCGAGG ACTCCCCGGC CGTCGAGCCG CCGGCCGGTG GCGGTGTGGT
26581 GCCGTGGCCG GTGTCCGCGA AGACTCCGGC CGCGCTGGAC GCCCACATCG GCAGCTCGC
26641 CGCGTACGCG GACGGTCGTA CGGACGTGGA TCCGGCGGTG GCCGCCCGCG CCCTGGTCGA
26701 CAGCCGTACG GCGATGGAGC ACCGCGCGGT CGCGGTCGGC GACAGCCGGG AGGCACTGCG
26761 GGACGCCCTG CGGATGCCGG AAGGACTGGT ACGCGGCACG TCCTCGGACG TGGGCCGGGT
26821 GGCGTTCGTC TTCCCCGGCC AGGGCACGCA GTGGGCCGGC ATGGGCGCCG AACTCCTTAG
26881 CAGCTCACCG GAGTTCGCTG CCTCGATGGC CGAATGCGAG ACCGCGCTCT CCCGCTACGT
26941 CGACTGGTCT CTTGAAGCCG TCGTCCGACA GGAACCCGGC GCACCCACGC TCGACCGCGT
27001 CGACGTCGTC CAGCCCGTGA CCTTCGCTGT CATGGTCTCG CTGGCGAAGG TCTGGCAGCA
27061 CCACGGCATC ACCCCCCAGG CCGTCGTCGG CCACTCGCAG GGCGAGATCG CCGCCGCGTA
27121 CGTCGCCGGT GCACTCACCC TCGACGACGC CGCCCGCGTC GTCACCCTGC GCAGCAAGTC
27181 CATCGCCGCC CACCTCGCCG GCAAGGGCGG CATGATCTCC CTCGCCCTCG ACGAGGCGGC
27241 CGTCCTGAAG CGACTGAGCG ACTTCGACGG ACTCTCCGTC GCCGCCGTCA ACGGCCCCAC
27301 CGCCACCGTC GTCTCCGGCG ACCCGACCCA GATCGAGGAA CTCGCCCGCA CCTGCGAGGC
27361 CGACGGCGTC CGTGCGCGGA TCATCCCGGT CGACTACGCC TCCCACAGCC GGCAGGTCGA
27421 GATCATCGAG AAGGAGCTGG CCGAGGTCCT CGCCGGACTC GCCCCGCAGG CTCCGCACGT
27481 GCCGTTCTTC TCCACCCTCG AAGGCACCTG GATCACCGAG CCGGTGCTCG ACGGCACCTA
27541 CTGGTACCGC AACCTGCGCC ATCGCGTGGG CTTCGCCCCC GCCGTGGAGA CCTTGGCGGT
```

-continued

DNA Sequence of the Insert DNA in Cosmid pKOS023-27 (SEQ ID NO:19)

```
27601 TGACGGCTTC ACCCACTTCA TCGAGGTCAG CGCCCACCCC GTCCTCACCA TGACCCTCCC
27661 CGAGACCGTC ACCGGCCTCG GCACCCTCCG CCGCGAACAG GGAGGCCAGG AGCGTCTGGT
27721 CACCTCACTC GCCGAAGCCT GGGCCAACGG CCTCACCATC GACTGGGCGC CCATCCTCCC
27781 CACCGCAACC GGCCACCACC CCGAGCTCCC CACCTACGCC TTCCAGACCG AGCGCTTCTG
27841 GCTGCAGAGC TCCGCGCCCA CCAGCGCCGC CGACGACTGG CGTTACCGAG TCGAGTGGAA
27901 GCCGCTGACG GCCTCCGGCC AGGCGGACCT GTCCGGGCGG TGGATCGTCG CCGTCGGGAG
27961 CGACGGAGAA GCCGAGCTGC TGGGCGCGCT GAAGGCCGCG GGAGCGGAGG TCGACGTACT
28021 GGAAGCCGGG GCGGACGACG ACCGTGAGGC CCTCGCCGCC CGGCTCACCG CACTGACGAC
28081 CGGCGACGGC TTCACCGGCG TGGTCTCGCT CCTCGACGAC CTCGTGCCAC AGGTCGCCTG
28141 GGTGCAGGCA CTCGGCGACG CCGGAATCAA GGCGCCCCTG TGGTCCGTCA CCCAGGGCGC
28201 GGTCTCCGTC GGACGTCTCG ACACCCCCGC CGACCCCGAC CGGGCCATGC TCTGGGCCT
28261 CGGCCGCGTC GTCGCCCTTG AGCACCCCGA ACGCTGGGCC GGCCTCGTCG ACCTCCCCGC
28321 CCAGCCCGAT GCCGCCGCCC TCGCCCACCT CGTCACCGCA CTCTCCGGCG CCACCGGCGA
28381 GGACCAGATC GCCATCCGCA CCACCGGACT CCACGCCCGC CGCCTCGCCC GCGCACCCCT
28441 CCACGGACGT CGGCCCACCC GCGACTGGCA GCCCCACGGC ACCGTCCTCA TCACCGGCGG
28501 CACCGGAGCC CTCGGCAGCC ACGCCGCACG CTGGATGGCC CACCACGGAG CCGAACACCT
28561 CCTCCTCGTC AGCCGCAGCG GCGAACAAGC CCCCGGAGCC ACCCAACTCA CCGCCGAACT
28621 CACCGCATCG GGCGCCCGCG TCACCATCGC CGCCTGCGAC GTCGCCGACC CCACGCCAT
28681 GCGCACCCTC CTCGACGCCA TCCCCGCCGA CGCCCCTC ACCGCCGTCG TCCACACCGC
28741 CGGCGCACCG GCGGCGATC CGCTGGACGT CACCGGCCCG GAGGACATCG CCCGCATCCT
28801 GGGCGCGAAG ACGAGCGGCG CCGAGGTCCT CGACGACCTG CTCCGCGGCA CTCCGCTGGA
28861 CGCCTTCGTC CTCTACTCCT CGAACGCCGG GGTCTGGGGC AGCGGCAGCC AGGGCGTCTA
28921 CGCGGCGGCC AACGCCCACC TCGACGCGCT CGCCGCCCGG CGCCGCGCCC GGGGCGAGAC
28981 GGCGACCTCG GTCGCCTGGG GCCTCTGGGC CGGCGACGGC ATGGGCCGGG GCGCCGACGA
29041 CGCGTACTGG CAGCGTCGCG GCATCCGTCC GATGAGCCCC GACCGCGCCC TGGACGAACT
29101 GGCCAAGGCC CTGAGCCACG ACGAGACCTT CGTCGCCGTG GCCGATGTCG ACTGGGAGCG
29161 GTTCGCGCCC GCGTTCACGG TGTCCCGTCC CAGCCTTCTG CTCGACGGCG TCCCGGAGGC
29221 CCGGCAGGCG CTCGCCGCAC CCGTCGGTGC CCCGGCTCCC GGCGACGCCC CGTGGCGCC
29281 GACCGGGCAG TCGTCGGCGC TGGCCGCGAT CACCGCGCTC CCCGAGCCCG AGCGCCGGCC
29341 GGCGCTCCTC ACCCTCGTCC GTACCCACGC GGCGGCCGTA CTCGGCCATT CCTCCCCCGA
29401 CCGGGTGGCC CCCGGCCGTG CCTTCACCGA GCTCGGCTTC GACTCGCTGA CGGCCGTGCA
29461 GCTCCGCAAC CAGCTCTCCA CGGTGGTCGG CAACAGGCTC CCCGCCACCA CGGTCTTCGA
29521 CCACCCGACG CCCGCCGCAC TCGCCGCGCA CCTCCACGAG GCGTACCTCG CACCGGCCGA
29581 GCCGGCCCCG ACGGACTGGG AGGGGCGGGT GCGCCGGGCC CTGGCCGAAC TGCCCCTCGA
29641 CCGGCTGCGG GACGCGGGGG TCCTCGACAC CGTCCTGCGC CTCACCGGCA TCGAGCCCGA
29701 GCCGGGTTCC GGCGGTTCGG ACGGCGGCGC CGCCGACCCT GGTGCGGAGC CGGAGGCGTC
29761 GATCGACGAC CTGGACGCCG AGGCCCTGAT CCGGATGGCT CTCGGCCCCC GTAACACCTG
29821 ACCCGACCGC GGTCCTGCCC CACGCGCCGC ACCCCGCGCA TCCCGCGCAC CACCCGCCCC
```

-continued

DNA Sequence of the Insert DNA in Cosmid pKOS023-27 (SEQ ID NO:19)

```
29881 CACACGCCCA CAACCCCATC CACGAGCGGA AGACCACACC CAGCTGACGA GTTCCAACGA
29941 ACAGTTGGTG GACGCTCTGC GCGCCTCTCT CAAGGAGAAC GAAGAACTCC GGAAAGAGAG
30001 CCGTCGCCGG GCCGACCGTC GGCAGGAGCC CATGGCGATC GTCGGCATGA GCTGCCGGTT
30061 CGCGGGCGGA ATCCGGTCCC CCGAGGACCT CTGGGACGCC GTCGCCGCGG GCAAGGACCT
30121 GGTCTCCGAG GTACCGGAGG AGCGCGGCTG GACATCGAC TCCCTCTACG ACCCGGTGCC
30181 CGGGCGCAAG GGCACGACGT ACGTCCGCAA CGCCGCGTTC CTCGACGACG CCGCCGGATT
30241 CGACGCGGCC TTCTTCGGGA TCTCGCCGCG CGAGGCCCTC GCCATGGACC CGCAGCAGCG
30301 GCAGCTCCTC GAAGCCTCCT CCCACCTCTT CGAGCGGGCC GGCATCGACC CCGCGTCGGT
30361 CCGCGGCACC GACGTCGGCG TGTACGTGGG CTGTGGCTAC CAGGACTACG CGCCGGACAT
30421 CCGGGTCGCC CCCGAAGGCA CCGGCGGTTA CGTCGTCACC GGCAACTCCT CCGCCGTGGC
30481 CTCCGGGCGC ATCGCGTACT CCCTCGGCCT GGAGGGACCC GCCGTGACCG TGGACACGGC
30541 GTGCTCCTCT TCGCTCGTCG CCCTGCACCT CGCCCTGAAG GGCCTGCGGA ACGGCGACTG
30601 CTCGACGGCA CTCGTGGGCG GCGTGGCCGT CCTCGCGACG CCGGGCGCGT TCATCGAGTT
30661 CAGCAGCCAG CAGGCCATGG CCGCCGACGG CCGGACCAAG GGCTTCGCCT CGGCGGCGGA
30721 CGGCCTCGCC TGGGGCGAGG GCGTCGCCGT ACTCCTCCTC GAACGGCTCT CCGACGCGCG
30781 GCGCAAGGGC CACCGGGTCC TGGCCGTCGT GCGCGGCAGC GCCATCAACC AGGACGGCGC
30841 GAGCAACGGA CTCACGGCTC CGCACGGGCC CTCCCAGCAG CGCCTCATCC GCCAGGCCCT
30901 GGCCGACGCG CGGCTCACGT CGAGCGACGT GGACGTCGTG GAGGGCCACG GCACGGGGAC
30961 CCGTCTCGGC GACCCGATCG AGGCGCAGGC GCTGCTCGCC ACGTACGGGC AGGGGCGCGC
31021 CCCGGGGCAG CCGCTGCGGC TGGGGACGCT GAAGTCGAAC ATCGGGCACA CGCAGGCCGC
31081 TTCGGGTGTC GCCGGTGTCA TCAAGATGGT GCAGGCGCTG CGCCACGGGG TGCTGCCGAA
31141 GACCCTGCAC GTGGACGAGC CGACGGACCA GGTCGACTGG TCGGCCGGTT CGGTCGAGCT
31201 GCTCACCGAG GCCGTGGACT GGCCGGAGCG GCCGGGCCGG CTCCGCCGGG CGGGCGTCTC
31261 CGCGTTCGGC GTGGGCGGGA CGAACGCGCA CGTCGTCCTG GAGGAGGCCC CGGCGGTCGA
31321 GGAGTCCCCT GCCGTCGAGC CGCCGGCCGG TGGCGGCGTG GTGCCGTGGC CGGTGTCCGC
31381 GAAGACCTCG GCCGCACTGG ACGCCCAGAT CGGGCAGCTC GCCGCATACG CGGAAGACCG
31441 CACGGACGTG GATCCGGCGG TGGCCGCCCG CGCCCTGGTC GACAGCCGTA CGGCGATGGA
31501 GCACCGCGCG GTCGCGGTCG GCGACAGCCG GGAGGCACTG CGGGACGCCC TGCGGATGCC
31561 GGAAGGACTG GTACGGGGCA CGGTCACCGA TCCGGGCCGG GTGGCGTTCG TCTTCCCCGG
31621 CCAGGGCACG CAGTGGGCCG GCATGGGCGC CGAACTCCTC GACAGCTCAC CCGAATTCGC
31681 CGCCGCCATG GCCGAATGCG AGACCGCACT CTCCCCGTAC GTCGACTGGT CTCTCGAAGC
31741 CGTCGTCCGA CAGGCTCCCA GCGCACCGAC CATCGACCGC GTCGACGTCG TCCAGCCCGT
31801 CACCTTCGCC GTCATGGTCT CCCTCGCCAA GGTCTGGCAG CACCACGGCA TCACCCCCGA
31861 GGCCGTCATC GGCCACTCCC AGGGCGAGAT CGCCGCCGCG TACGTCGCCG GTGCCCTCAC
31921 CCTCGACGAC GCCGCTCGTG TCGTGACCCT CCGCAGCAAG TCCATCGCCG CCCACCTCGC
31981 CGGCAAGGGC GGCATGATCT CCCTCGCCCT CAGCGAGGAA GCCACCCGGC AGCGCATCGA
32041 GAACCTCCAC GGACTGTCGA TCGCCGCCGT CAACGGGCCT ACCGCCACCG TGGTTTCGGG
32101 CGACCCCACC CAGATCCAAG AACTTGCTCA GGCGTGTGAG GCCGACGGCA TCCGCGCACG
32161 GATCATCCCC GTCGACTACG CCTCCCACAG CGCCCACGTC GAGACCATCG AGAACGAACT
```

DNA Sequence of the Insert DNA in Cosmid pKOS023-27 (SEQ ID NO:19)

```
32221 CGCCGACGTC CTGGCGGGGT TGTCCCCCCA GACACCCCAG GTCCCCTTCT TCTCCACCCT
32281 CGAAGGCACC TGGATCACCG AACCCGCCCT CGACGGCGGC TACTGGTACC GCAACCTCCG
32341 CCATCGTGTG GGCTTCGCCC CGGCCGTCGA GACCCTCGCC ACCGACGAAG GCTTCACCCA
32401 CTTCATCGAG GTCAGCGCCC ACCCCGTCCT CACCATGACC CTCCCCGACA AGGTCACCGG
32461 CCTGGCCACC CTCCGACGCG AGGACGGCGG ACAGCACCGC CTCACCACCT CCCTTGCCGA
32521 GGCCTGGGCC AACGGCCTCG CCCTCGACTG GGCCTCCCTC CTGCCCGCCA CGGGCGCCCT
32581 CAGCCCCGCC GTCCCCGACC TCCCGACGTA CGCCTTCCAG CACCGCTCGT ACTGGATCAG
32641 CCCCGCGGGT CCCGGCGAGG CGCCCGCGCA CACCGCTTCC GGGCGCGAGG CCGTCGCCGA
32701 GACGGGGCTC GCGTGGGGCC CGGGTGCCGA GGACCTCGAC GAGGAGGGCC GGCGCAGCGC
32761 CGTACTCGCG ATGGTGATGC GGCAGGCGGC CTCCGTGCTC CGGTGCGACT CGCCCGAAGA
32821 GGTCCCCGTC GACCGCCCGC TGCGGGAGAT CGGCTTCGAC TCGCTGACCG CCGTCGACTT
32881 CCGCAACCGC GTCAACCGGC TGACCGGTCT CCAGCTGCCG CCCACCGTCG TGTTCGAGCA
32941 CCCGACGCCC GTCGCGCTCG CCGAGCGCAT CAGCGACGAG CTGGCCGAGC GGAACTGGGC
33001 CGTCGCCGAG CCGTCGGATC ACGAGCAGGC GGAGGAGGAG AAGGCCGCCG CTCCGGCGGG
33061 GGCCCGCTCC GGGGCCGACA CCGGCGCCGG CGCCGGGATG TTCCGCGCCC TGTTCCGGCA
33121 GGCCGTGGAG GACGACCGGT ACGGCGAGTT CCTCGACGTC CTCGCCGAAG CCTCCGCGTT
33181 CCGCCCGCAG TTCGCCTCGC CCGAGGCCTG CTCGGAGCGG CTCGACCCGG TGCTGCTCGC
33241 CGGCGGTCCG ACGGACCGGG CGGAAGGCCG TGCCGTTCTC GTCGGCTGCA CCGGCACCGC
33301 GGCGAACGGC GGCCCGCACG AGTTCCTGCG GCTCAGCACC TCCTTCCAGG AGGAGCGGGA
33361 CTTCCTCGCC GTACCTCTCC CCGGCTACGG CACGGGTACG GGCACCGGCA CGGCCCTCCT
33421 CCCGGCCGAT CTCGACACCG CGCTCGACGC CCAGGCCCGG GCGATCCTCC GGGCCGCCGG
33481 GGACGCCCCG GTCGTCCTGC TCGGGCACTC CGGCGGCGCC CTGCTCGCGC ACGAGCTGGC
33541 CTTCCGCCTG GAGCGGGCGC ACGGCGCGCC GCCGGCCGGG ATCGTCCTGG TCGACCCCTA
33601 TCCGCCGGGC CATCAGGAGC CCATCGAGGT GTGGAGCAGG CAGCTGGGCG AGGGCCTGTT
33661 CGCGGGCGAG CTGGAGCCGA TGTCCGATGC GCGGCTGCTG GCCATGGGCC GGTACGCGCG
33721 GTTCCTCGCC GGCCCGCGGC CGGGCCGCAG CAGCGCGCCC GTGCTTCTGG TCCGTGCCTC
33781 CGAACCGCTG GGCGACTGGC AGGAGGAGCG GGGCGACTGG CGTGCCCACT GGGACCTTCC
33841 GCACACCGTC GCGGACGTGC CGGGCGACCA CTTCACGATG ATGCGGGACC ACGCGCCGGC
33901 CGTCGCCGAG GCCGTCCTCT CCTGGCTCGA CGCCATCGAG GCATCGAGG GGGCGGGCAA
33961 GTGACCGACA GACCTCTGAA CGTGGACAGC GGACTGTGGA TCCGGCGCTT CCACCCCGCG
34021 CCGAACAGCG CGGTGCGGCT GGTCTGCCTG CCGCACGCCG GCGGCTCCGC CAGCTACTTC
34081 TTCCGCTTCT CGGAGGAGCT GCACCCCTCC GTCGAGGCCC TGTCGGTGCA GTATCCGGGC
34141 CGCCAGGACC GGCGTGCCGA GCCGTGTCTG GAGAGCGTCG AGGAGCTCGC CGAGCATGTG
34201 GTCGCGGCCA CCGAACCCTG GTGGCAGGAG GGCCGGCTGG CCTTCTTCGG GCACAGCCTC
34261 GGCGCCTCCG TCGCCTTCGA GACGGCCCGC ATCCTGGAAC AGCGGCACGG GGTACGGCCC
34321 GAGGGCCTGT ACGTCTCCGG TCGGCGCGCC CCGTCGCTGG CGCCGGACCG GCTCGTCCAC
34381 CAGCTGGACG ACCGGGCGTT CCTGGCCGAG ATCCGGCGGC TCAGCGGCAC CGACGAGCGG
34441 TTCCTCCAGG ACGACGAGCT GCTGCGGCTG GTGCTGCCCG CGCTGCGCAG CGACTACAAG
```

| DNA Sequence of the Insert DNA in Cosmid pKOS023-27 (SEQ ID NO:19) |
|---|
| 34501 GCGGCGGAGA CGTACCTGCA CCGGCCGTCC GCCAAGCTCA CCTGCCCGGT GATGGCCCTG |
| 34561 GCCGGCGACC GTGACCCGAA GGCGCCGCTG AACGAGGTGG CCGAGTGGCG TCGGCACACC |
| 34621 AGCGGGCCGT TCTGCCTCCG GGCGTACTCC GGCGGCCACT TCTACCTCAA CGACCAGTGG |
| 34681 CACGAGATCT GCAACGACAT CTCCGACCAC CTGCTCGTCA CCCGCGGCGC GCCCGATGCC |
| 34741 CGCGTCGTGC AGCCCCCGAC CAGCCTTATC GAAGGAGCGG CGAAGAGATG GCAGAACCCA |
| 34801 CGGTGACCGA CGACCTGACG GGGGCCCTCA CGCAGCCCCC GCTGGGCCGC ACCGTCCGCG |
| 34861 CGGTGGCCGA CCGTGAACTC GGCACCCACC TCCTGGAGAC CCGCGGCATC CACTGGATCC |
| 34921 ACGCCGCGAA CGGCGACCCG TACGCCACCG TGCTGCGCGG CCAGGCGGAC GACCCGTATC |
| 34981 CCGCGTACGA GCGGGTGCGT GCCCGCGGCG CGCTCTCCTT CAGCCCGACG GGCAGCTGGG |
| 35041 TCACCGCCGA TCACGCCCTG GCGGCGAGCA TCCTCTGCTC CAGCCACTTC GGGGTCTCCG |
| 35101 GCGCCGACGG CGTCCCGGTG CCGCAGCAGG TCCTCTCGTA CGGGGAGGGC TGTCCGCTGG |
| 35161 AGCGCGAGCA GGTGCTGCCG GCGGCCGGTG ACGTGCCGGA GGGCGGGCAG CGTGCCGTGG |
| 35221 TCGAGGGGAT CCACCGGGAG ACGCTGGAGG GTCTCGCGCC GGACCCGTCG GCGTCGTACG |
| 35281 CCTTCGAGCT GCTGGGCGGT TTCGTCCGCC CGGCGGTGAC GGCCGCTGCC GCCGCCGTGC |
| 35341 TGGGTGTTCC CGCGGACCGG CGCGCGGACT TCGCGGATCT GCTGGAGCGG CTCCGGCCGC |
| 35401 TGTCCGACAG CCTGCTGGCC CCGCAGTCCC TGCGGACGGT ACGGGCGGCG GACGGCGCGC |
| 35461 TGGCCGAGCT CACGGCGCTG CTCGCCGATT CGGACGACTC CCCCGGGGCC CTGCTGTCGG |
| 35521 CGCTCGGGGT CACCGCAGCC GTCCAGCTCA CCGGGAACGC GGTGCTCGCG CTCCTCGCGC |
| 35581 ATCCCGAGCA GTGGCGGGAG CTGTGCGACC GGCCCGGGCT CGCGGCGGCC GCGGTGGAGG |
| 35641 AGACCCTCCG CTACGACCCG CCGGTGCAGC TCGACGCCCG GGTGGTCCGC GGGGAGACGG |
| 35701 AGCTGGCGGG CCGGCGGCTG CCGGCCGGGG CGCATGTCGT CGTCCTGACC GCCGCGACCG |
| 35761 GCCGGGACCC GGAGGTCTTC ACGGACCCGG AGCGCTTCGA CCTCGCGCGC CCCGACGCCG |
| 35821 CCGCGCACCT CGCGCTGCAC CCCGCCGGTC CGTACGGCCC GGTGGCGTCC CTGGTCCGGC |
| 35881 TTCAGGCGGA GGTCGCGCTG CGGACCCTGG CCGGGCGTTT CCCCGGGCTG CGGCAGGCGG |
| 35941 GGGACGTGCT CCGCCCCGC CGCGCGCCTG TCGGCCGCGG GCCGCTGAGC GTCCCGGTCA |
| 36001 GCAGCTCCTG AGACACCGGG GCCCCGGTCC GCCCGGCCCC CCTTCGGACG GACCGGACGG |
| 36061 CTCGGACCAC GGGGACGGCT CAGACCGTCC CGTGTGTCCC CGTCCGGCTC CCGTCCGCCC |
| 36121 CATCCCGCCC CTCCACCGGC AAGGAAGGAC ACGACGCCAT GCGCGTCCTG CTGACCTCGT |
| 36181 TCGCACATCA CACGCACTAC TACGGCCTGG TGCCCCTGGC CTGGGCGCTG CTCGCCGCCG |
| 36241 GGCACGAGGT GCGGGTCGCC AGCCAGCCCG CGCTCACGGA CACCATCACC GGGTCCGGGC |
| 36301 TCGCCGCGGT GCCGGTCGGC ACCGACCACC TCATCCACGA GTACCGGGTG CGGATGGCGG |
| 36361 GCGAGCCGCG CCCGAACCAT CCGGCGATCG CCTTCGACGA GGCCCGTCCC GAGCCGCTGG |
| 36421 ACTGGGACCA CGCCCTCGGC ATCGAGGCGA TCCTCGCCCC GTACTTCTAT CTGCTCGCCA |
| 36481 ACAACGACTC GATGGTCGAC GACCTCGTCG ACTTCGCCCG GTCCTGGCAG CCGGACCTGG |
| 36541 TGCTGTGGGA GCCGACGACC TACGGGGCG CCGTCGCCGC CCAGGTCACC GGTGCCGCGC |
| 36601 ACGCCCGGGT CCTGTGGGGG CCCGACGTGA TGGGCAGCGC CCGCCGCAAG TTCGTCGCGC |
| 36661 TGCGGGACCG GCAGCCGCCC GAGCACCGCG AGGACCCCAC CGCGGAGTGG CTGACGTGGA |
| 36721 CGCTCGACCG GTACGGCGCC TCCTTCGAAG AGGAGCTGCT CACCGGCCAG TTCACGATCG |
| 36781 ACCCGACCCC GCCGAGCCTG CGCCTCGACA CGGGCCTGCC GACCGTCGGG ATGCGTTATG |

-continued

DNA Sequence of the Insert DNA in Cosmid pKOS023-27 (SEQ ID NO:19)

```
36841 TTCCGTACAA CGGCACGTCG GTCGTGCCGG ACTGGCTGAG TGAGCCGCCC GCGCGGCCCC
36901 GGGTCTGCCT GACCCTCGGC GTCTCCGCGC GTGAGGTCCT CGGCGGCGAC GGCGTCTCGC
36961 AGGGCGACAT CCTGGAGGCG CTCGCCGACC TCGACATCGA GCTCGTCGCC ACGCTCGACG
37021 CGAGTCAGCG CGCCGAGATC CGCAACTACC CGAAGCACAC CCGGTTCACG GACTTCGTGC
37081 CGATGCACGC GCTCCTGCCG AGCTGCTCGG CGATCATCCA CCACGGCGGG GCGGGCACCT
37141 ACGCGACCGC CGTGATCAAC GCGGTGCCGC AGGTCATGCT CGCCGAGCTG TGGGACGCGC
37201 CGGTCAAGGC GCGGGCCGTC GCCGAGCAGG GGGCGGGGTT CTTCCTGCCG CCGGCCGAGC
37261 TCACGCCGCA GGCCGTGCGG GACGCCGTCG TCCGCATCCT CGACGACCCC TCGGTCGCCA
37321 CCGCCGCGCA CCGGCTGCGC GAGGAGACCT TCGGCGACCC CACCCCGGCC GGGATCGTCC
37381 CCGAGCTGGA GCGGCTCGCC GCGCAGCACC GCCGCCCGCC GGCCGACGCC CGGCACTGAG
37441 CCGCACCCCT CGCCCCAGGC CTCACCCCTG TATCTGCGCC GGGGACGCC CCCGGCCCAC
37501 CCTCCGAAAG ACCGAAAGCA GGAGCACCGT GTACGAAGTC GACCACGCCG ACGTCTACGA
37561 CCTCTTCTAC CTGGGTCGCG GCAAGGACTA CGCCGCCGAG GCCTCCGACA TCGCCGACCT
37621 GGTGCGCTCC CGTACCCCCG AGGCCTCCTC GCTCCTGGAC GTGGCCTGCG GTACGGGCAC
37681 GCATCTGGAG CACTTCACCA AGGAGTTCGG CGACACCGCC GGCCTGGAGC TGTCCGAGGA
37741 CATGCTCACC CACGCCCGCA AGCGGCTGCC CGACGCCACG CTCCACCAGG GCGACATGCG
37801 GGACTTCCGG CTCGGCCGGA AGTTCTCCGC CGTGGTCAGC CTGTTCAGCT CCGTCGGCTA
37861 CCTGAAGACG ACCGAGGAAC TCGGCGCGGC CGTCGCCTCG TTCGCGGAGC ACCTGGAGCC
37921 CGGTGGCGTC GTCGTCGTCG AGCCGTGGTG GTTCCCGGAG ACCTTCGCCG ACGGCTGGGT
37981 CAGCGCCGAC GTCGTCCGCC GTGACGGGCG CACCGTGGCC CGTGTCTCGC ACTCGGTGCG
38041 GGAGGGGAAC GCGACGCGCA TGGAGGTCCA CTTCACCGTG GCCGACCCGG GCAAGGGCGT
38101 GCGGCACTTC TCCGACGTCC ATCTCATCAC CCTGTTCCAC CAGGCCGAGT ACGAGGCCGC
38161 GTTCACGGCC GCCGGGCTGC GCGTCGAGTA CCTGGAGGGC GGCCCGTCGG GCCGTGGCCT
38221 CTTCGTCGGC GTCCCCGCCT GAGCACCGCC CAAGACCCCC CGGGGCGGGA CGTCCCGGGT
38281 GCACCAAGCA AAGAGAGAGA AACGAACCGT GACAGGTAAG ACCCGAATAC CGCGTGTCCG
38341 CCGCGGCCGC ACCACGCCCA GGGCCTTCAC CCTGGCCGTC GTCGGCACCC TGCTGGCGGG
38401 CACCACCGTG GCGGCCGCCG CTCCCGGCGC CGCCGACACG GCCAATGTTC AGTACACGAG
38461 CCGGGCGGCG GAGCTCGTCG CCCAGATGAC GCTCGACGAG AAGATC
```

Those of skill in the art will recognize that, due to the degenerate nature of the genetic code, a variety of DNA compounds differing in their nucleotide sequences can be used to encode a given amino acid sequence of the invention. The native DNA sequence encoding the narbonolide PKS of *Streptomyces venezuelae* is shown herein merely to illustrate a preferred embodiment of the invention, and the invention includes DNA compounds of any sequence that encode the amino acid sequences of the polypeptides and proteins of the invention. In similar fashion, a polypeptide can typically tolerate one or more amino acid substitutions, deletions, and insertions in its amino acid sequence without loss or significant loss of a desired activity. The present invention includes such polypeptides with alternate amino acid sequences, and the amino acid sequences shown merely illustrate preferred embodiments of the invention.

The recombinant nucleic acids, proteins, and peptides of the invention are many and diverse. To facilitate an understanding of the invention and the diverse compounds and methods provided thereby, the following description of the various regions of the narbonolide PKS and corresponding coding sequences is provided.

The loading module of the narbonolide PKS contains an inactivated KS domain, an AT domain, and an ACP domain. The AT domain of the loading module binds propionyl CoA. Sequence analysis of the DNA encoding the KS domain indicates that this domain is enzymatically inactivated, as a critical cysteine residue in the motif TVDACSSSL, which is highly conserved among KS domains, is replaced by a glutamine and so is referred to as a $KS^Q$ domain. Such inactivated KS domains are also found in the PKS enzymes that synthesize the 1 6-membered macrolides carbomycin, spiromycin, tylosin, and niddamycin. While the KS domain is inactive for its usual function in extender modules, it is believed to serve as a decarboxylase in the loading module.

The present invention provides recombinant DNA compounds that encode the loading module of the narbonolide PKS and useful portions thereof. These recombinant DNA compounds are useful in the construction of PKS coding sequences that encode all or a portion of the narbonolide PKS and in the construction of hybrid PKS encoding DNA compounds of the invention, as described in the section concerning hybrid PKSs below. To facilitate description of the invention, reference to a PKS, protein, module, or domain herein can also refer to DNA compounds comprising coding sequences therefor and vice versa. Also, reference to a heterologous PKS refers to a PKS or DNA compounds comprising coding sequences therefor from an organism other than *Streptomyces venezuelae*. In addition, reference to a PKS or its coding sequence includes reference to any portion thereof.

The present invention provides recombinant DNA compounds that encode one or more of the domains of each of the six extender modules (modules 1–6, inclusive) of the narbonolide PKS. Modules 1 and 5 of the narbonolide PKS are functionally similar. Each of these extender modules contains a KS domain, an AT domain specific for methylmalonyl CoA, a KR domain, and an ACP domain. Module 2 of the narbonolide PKS contains a KS domain, an AT domain specific for malonyl CoA, a KR domain, a DH domain, and an ACP domain. Module 3 differs from extender modules 1 and 5 only in that it contains an inactive ketoreductase domain. Module 4 of the narbonolide PKS contains a KS domain, an AT domain specific for methylmalonyl CoA, a KR domain, a DH domain, an ER domain, and an ACP domain. Module 6 of the narbonolide PKS contains a KS domain, an AT domain specific for methylmalonyl CoA, and an ACP domain. The approximate boundaries of these "domains" is shown in Table 1.

In one important embodiment, the invention provides a recombinant narbonolide PKS that can be used to express only narbonolide (as opposed to the mixture of narbonolide and 10-deoxymethynolide that would otherwise be produced) in recombinant host cells. This recombinant narbonolide PKS results from a fusion of the coding sequences of the picAIII and picAIV genes so that extender modules 5 and 6 are present on a single protein. This recombinant PKS can be constructed on the *Streptomyces venezuelae* or *S. narbonensis* chromosome by homologous recombination. Alternatively, the recombinant PKS can be constructed on an expression vector and introduced into a heterologous host cell. This recombinant PKS is preferred for the expression of narbonolide and its glycosylated and/or hydroxylated derivatives, because a lesser amount or no 10-deoxymethynolide is produced from the recombinant PKS as compared to the native PKS. In a related embodiment, the invention provides a recombinant narbonolide PKS in which the picAIV gene has been rendered inactive by an insertion, deletion, or replacement. This recombinant PKS of the invention is useful in the production of 10-deoxymethynolide and its derivatives without production of narbonolide.

In similar fashion, the invention provides recombinant narbonolide PKS in which any of the domains of the native PKS have been deleted or rendered inactive to make the corresponding narbonolide or 10-deoxymethynolide derivative. Thus, the invention also provides recombinant narbonolide PKS genes that differ from the narbonolide PKS gene by one or more deletions. The deletions can encompass one or more modules and/or can be limited to a partial deletion within one or more modules. When a deletion encompasses an entire module, the resulting narbonolide derivative is at least two carbons shorter than the polyketide produced from the PKS encoded by the gene from which deleted PKS gene and corresponding polyketide were derived. When a deletion is within a module, the deletion typically encompasses a KR, DH, or ER domain, or both DH and ER domains, or both KR and DH domains, or all three KR, DH, and ER domains.

This aspect of the invention is illustrated in FIG. 4, parts B and C, which shows how a vector of the invention, plasmid pKOS039-16 (not shown), was used to delete or "knock out" the picAI gene from the *Streptomyces venezuelae* chromosome. Plasmid pKOS039-16 comprises two segments (shown as cross-hatched boxes in FIG. 4, part B) of DNA flanking the picAI gene and isolated from cosmid pKOS023-27 (shown as a linear segment in the Figure) of the invention. When plasmid pKOS039-16 was used to transform *S. venezuelae* and a double crossover homologous recombination event occurred, the picAI gene was deleted. The resulting host cell, designated K039-03 in the Figure, does not produce picromycin unless a functional picAI gene is introduced.

This *Streptomyces venezuelae* K039-03 host cell and corresponding host cells of the invention are especially useful for the production of polyketides produced from hybrid PKS or narbonolide PKS derivatives. Especially preferred for production in this host cell are narbonolide derivatives produced by PKS enzymes that differ from the narbonolide PKS only in the loading module and/or extender modules 1 and/or 2. These are especially preferred, because one need only introduce into the host cell the modified picAI gene or other corresponding gene to produce the desired PKS and corresponding polyketide. These host cells are also preferred for desosaminylating polyketides in accordance with the method of the invention in which a polyketide is provided to an *S. venezuelae* cell and desosaminylated by the endogenous desosamine biosynthesis and desosaminyl transferase gene products.

The recombinant DNA compounds of the invention that encode each of the domains of each of the modules of the narbonolide PKS are also useful in the construction of expression vectors for the heterologous expression of the narbonolide PKS and for the construction of hybrid PKS expression vectors, as described further below.

Section II: The Genes for Desosamine Biosynthesis and Transfer and for Beta-glucosidase Narbonolide and 10-deoxymethynolide are desosaminylated in *Streptomyces venezuelae* and *S. narbonensis* to yield narbomycin and YC-17, respectively. This conversion requires the biosynthesis of desosamine and the transfer of the desosamine to the substrate polyketides by the enzyme desosaminyl transferase. Like other Streptomyces, *S. venezuelae* and *S. narbonensis* produce glucose and a glucosyl transferase enzyme that glucosylates desosamine at the 2' position. However, *S. venezuelae* and *S. narbonensis* also produce a beta-glucosidase, which removes the glucose residue from the desosamine. The present invention provides recombinant DNA compounds and expression vectors for each of the desosamine biosynthesis enzymes, desosaminyl transferase, and beta-glucosidase.

As noted above, cosmid pKOS023-27 contains three ORFs that encode proteins involved in desosamine biosynthesis and transfer. The first ORF is from the picCII gene, also known as des VIII, a homologue of eryCII, believed to encode a 4-keto-6-deoxyglucose isomerase. The second ORF is from the picCIII gene, also known as des VII, a homologue of eryCIII, which encodes a desosaminyl transferase. The third ORF is from the picCVI gene, also known as desVI a homologue of eryCVI, which encodes a 3-amino dimethyltransferase.

Figure 3:
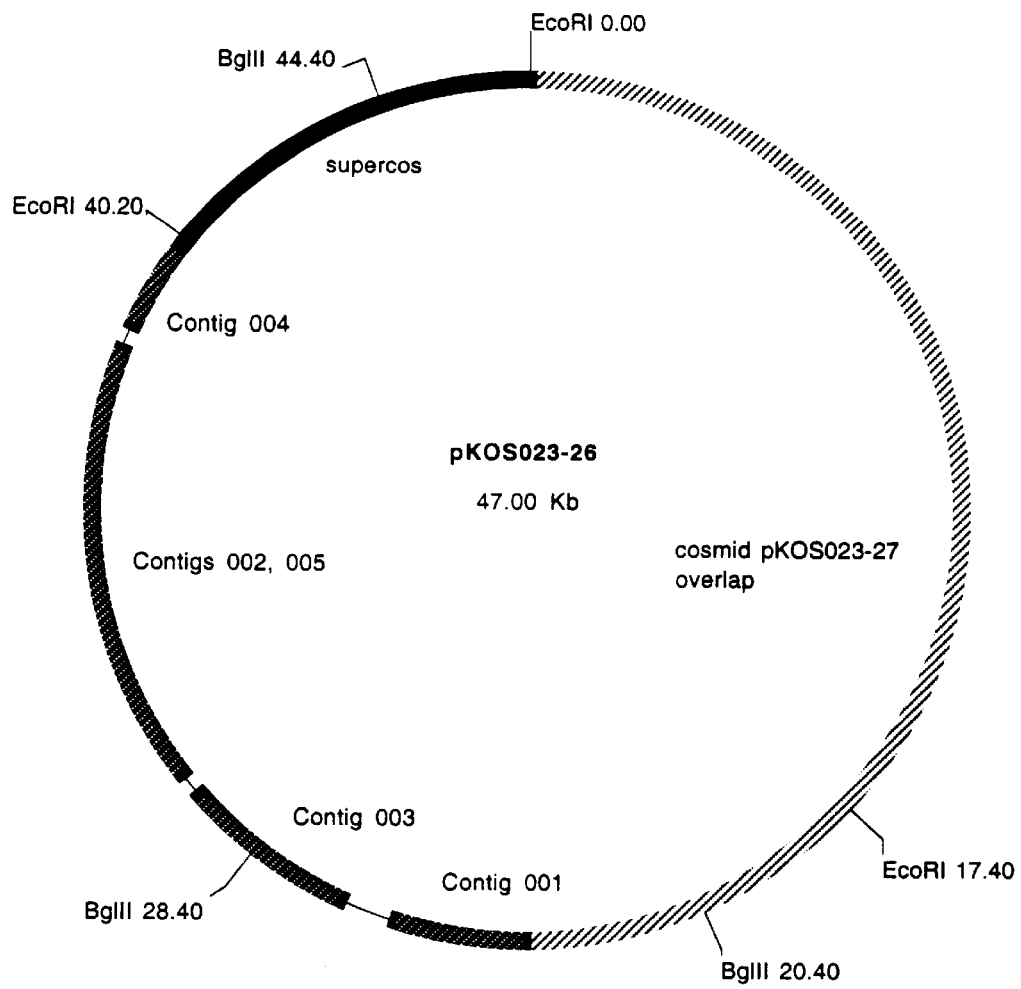
FIG. 3 shows a restriction site and function map of cosmid pKOS023-26.

The three genes above and the remaining desosamine biosynthetic genes can be isolated from cosmid pKOS023-26, which was deposited with the American Type Culture Collection on Aug. 20, 1998 under the Budapest Treaty and is available under the accession number ATCC 203141. FIG. 3 shows a restriction site and function map of cosmid pKOS023-26. This cosmid contains a region of overlap with cosmid pKOS023-27 representing nucleotides 14252 to nucleotides 38506 of pKOS023-27.

The remaining desosamine biosynthesis genes on cosmid pKOS023-26 include the following genes. ORF11, also known as desR, encodes beta-glucosidase and has no ery gene homologue. The picCI gene, also known as desV, is a homologue of eryCI. ORF14, also known as desIV, has no known ery gene homologue and encodes an NDP glucose 4,6-dehydratase. ORF13, also known as desIII, has no known ery gene homologue and encodes an NDP glucose synthase. The picCV gene, also known as desII, a homologue of eryCV is required for desosamine biosynthesis. The picCIV gene also known as desI, is a homologue of eryCIV, and its product is believed to be a 3,4-dehydratase. Other ORFs on cosmid pKOS023-26 include ORF12, believed to be a regulatory gene; ORF15, which encodes an S-adenosyl methionine synthase; and ORF16, which is a homolog of the *M. tuberculosis* cbhK gene. Cosmid pKOS023-26 also encodes the picK gene, which encodes the cytochrome P450 hydroxylase that hydroxylates the C12 of narbomycin and the C10 and C12 positions of YC-17. This gene is described in more detail in the following section.

Below, the amino acid sequences or partial amino acid sequences of the gene products of the desosamine biosynthesis and transfer and beta-glucosidase genes are shown. These amino acid sequences are followed by the DNA sequences that encode them.

Amino acid sequence of PICCI (desk) (SEQ ID NO:6)

```
  1 VSSRAETPRV PFLDLKAAYE ELRAETDAAI ARVLDSGRYL LGPELEGFEA EFAAYCETDH
 61 AVGVNSGMDA LQLALRGLGI GPGDEVIVPS HTYIASWLAV SATGATPVPV EPHEDHPTLD
121 PLLVEKAITP RTRALLPVHL YGHPADMDAL RELADRHGLH IVEDAAQAHG ARYRGRRIGA
181 GSSVAAFSFY PGKNLGCFGD GGAVVTGDPE LAERLRMLRN YGSRQKYSHE TKGTNSRLDE
241 MQAAVLRIRL XHLDSWNGRR SALAAEYLSG LAGLPGIGLP VTAPDTDPVW HLFTVRTERR
301 DELRSHLDAR GIDTLTHYPV PVHLSPAYAG EAPPEGSLPR AESFARQVLS LPIGPHLERP
361 QALRVIDAVR EWAERVDQA  (SEQ ID NO:6)
```

Amino acid sequence of 3-keto-6-deoxyglucose isomerase, PICCII (desVIII) (SEQ ID NO:7)

```
  1 VADRELGTHL LETRGIHWIH AANGDPYATV LRGQADDPYP AYERVRARGA LSFSPTGSWV
 61 TADHALAASI LCSTDFGVSG ADGVPVPQQV LSYGEGCPLE REQVLPAAGD VPEGGQRAVV
121 EGIHRETLEG LAPDPSASYA FELLGGFVRP AVTAAAAAVL GVPADRRADF ADLLERLRPL
181 SDSLLAPQSL RTVRAADGAL AELTALLADS DDSPGALLSA LGVTAAVQLT GNAVLALLAH
241 PEQWRELCDR PGLAAAAVEE TLRYDPPVQL DARVVRGETE LAGRRLPAGA HVVVLTAATG
301 RDPEVFTDPE RFDLARPDAA AHLALHPAGP YGPVASLVRL QAEVALRTLA GRFPGLRQAG
361 DVLRPRRAPV GRGPLSVPVS SS  (SEQ ID NO:7)
```

Amino acid sequence of desosaminyl transferase, PICCIII (des VII) (SEQ ID NO:8)

```
  1 MRVLLTSFAH HTHYYGLVPL AWALLAAGHE VRVASQPALT DTITGSGLAA VPVGTDHLIH
 61 EYRVRMAGEP RPNHPAIAFD EARPEPLDWD HALGIEAILA PYFYLLANND SMVDDLVDFA
121 RSWQPDLVLW EPTTYAGAVA AQVTGAAHAR VLWGPDVMGS ARRKFVALRD RQPPEHREDP
181 TAEWLTWTLD RYGASFEEEL LTGQFTIDPT PPSLRLDTGL PTVGMRYVPY NGTSVVPDWL
241 SEPPARPRVC LTLGVSAREV LGGDGVSQGD ILEALADLDI ELVATLDASQ RAEIRNYPKH
301 TRFTDFVPMH ALLPSCSAII HHGGAGTYAT AVINAVPQVM LAELWDAPVK ARAVAEQGAG
```

-continued

```
361 FFLPPAELTP QAVRDAVVRI LDDPSVATAA HRLREETFGD PTPAGIVPEL ERLAAQHRRP

421 PADARH (SEQ ID NO:8)
```

Partial amino acid sequence of aninotransferase-dehydrase, PICCIV (desI) (SEQ ID NO:9)

```
  1 VKSALSDLAF FGGPAAFDQP LLVGRPNRID RARLYERLDR ALDSQWLSNG GPLVREFEER

61 VAGLAGVRHA VATCNATAGL QLLAHAAGLT GEVIMPSMTF AATPHALRWI GLTPVFADID

121 PDTGNLDPDQ VAAAVTPRTS AVVGVHLWGR PCAADQLRKV ADEHGLRLYF DAAHALGCAV

181 DGRPAGSLGD AEVFSFHATK AVNAFEGGAV VTDDAFLAAR IRALHNFGFD LPGGSPAGGT

241 NAKMSEAAAA MGLTSLDAFP EVIDRNRRNH AXYREHLADL PGVLVADHDR HGLNNHQYVI

301 VEIDEATTGI HRDLVMEVLK AEGVHTRAYF S (SEQ ID NO:9)
```

Amino acid sequence of PICCV (desII) (SEQ ID NO:10)

```
  1 MTAPALSATA PAERCAHPGA DLGAAVHAVG QTLAAGGLVP PDEAGTTARH LVRLAVRYGN

61 SPFTPLEEAR HDLGVDRDAF RRLLALFGQV PELRTAVETG PAGAYWKNTL LPLEQRGVFD

121 AALARKPVFP YSVGLYPGPT CMFRCHFCVR VTGARYDPSA LDAGNAMFRS VIDEIPAGNP

181 SAMYFSGGLE PLTNPGLGSL AAHATDHGLR PTVYTNSFAL TERTLERQPG LWGLHAIRTS

241 LYGLNDEEYE QTTGKKAAFR RVRENLRRFQ QLRAERESPI NLGFAYIVLP GRASRLLDLV

301 DFIADLNDAG QGRTIDFVNI REDYSGRDDG KLPQEERAEL QEALNAFEER VRERTPGLHI

361 DYGYALNSLR TGADAELLRI KPATMRPTAH PQVAVQVDLL GDVYLYREAG FPDLDGATRY

421 IAGRVTPDTS LTEVVRDFVE RGGEVAAVDG DEYFMDGFDQ VVTARLNQLE RDAADGWEEA

481 RGFLR (SEQ ID NO:10)
```

Amino acid sequence of 3-amino dimethyl transferase, PIC-CVI (des VI) (SEQ ID NO:11)

```
  1 VYEVDHADVY DLFYLGRGKD YAAEASDIAD LVRSRTPEAS SLLDVACGTG THLEHFTKEF

61 GDTAGLELSE DMLTHARKRL PDATLHQGDM RDFRLGRKFS AVVSMFSSVG YLKTTEELGA

121 AVASFAEHLE PGGVVVVEPW WFPETFADGW VSADVVRRDG RTVARVSHSV REGNATRMEV

181 HFTVADPGKG VRHFSDVHLI TLFHQAEYEA AFTAAGLRVE YLEGGPSGRG LFVGVPA
    (SEQ ID NO:11)
```

Partial amino acid sequence of beta-glucosidase, ORF11 (desR) (SEQ ID NO:12)

```
  1 MTLDEKISFV HWALDPDRQN VGYLPGVPRL GIPELRAADG PNGIRLVGQT ATALPAPVAL

61 ASTFDDTMAD SYGKVMGRDG RALNQDMVLG PMMNNIRVPH GGRNYETFSE DPLVSSRTAV

121 AQIKGIQGAG LMTTAKHFAA NNQENNRFSV NANVDEQTLR EIEFPAFEAS SKAGAGSFMC

181 AYNGLNGKPS CGNDELLNNV LRTQWGFQGW VMSDWALTPG TDAITKGLDQ EMGVELPGDV
```

-continued

```
241 PKGEPSPPAK FFGEALKTAV LNGTVPEAAV TRSAERIVGQ MEKFGLLLAT PAPRPERDKA

301 GAQAVSRKVA ENGAVLLRNE GQALPLAGDA GKSIAVIGPT AVDPKVTGLG SAHVVPDSAA

361 APLDTIKARA GAGATVTYET GEETFGTQIP AGNLSPAFNQ GHQLEPGKAG ALYDGTLTVP

421 ADGEYRIAVR ATGGYATVQL GSHTIEAGQV YGKVSSPLLK LTKGTHKLTI SGFAMSATPL

481 SLELGWVTPA AADATIAKAV ESARKARTAV VFAYDDGTEG VDRONLSLPG TQDKLISAVA

541 DANPNTIVVL NTGSSVLMPW LSKTRAVLDM WYPGQAGAEA TAALLYGDVN PSGKLTQSFP

601 AAENQHAVAG DPTSYPGVDN QQTYREGIHV GYRWFDKENV KPLEPFGHGL SYTSFTQSAP

661 TVVRTSTGGL KVTVTVRNSG KRAGQEVVQA YLGASPNVTA PQAKKKLVGY TKVSLAAGEA8

721 KTVTVNVDRR QLQFWDAATD NWKTGTGNRL LQTGSSSADL RGSATVNVW  (SEQ ID NO:12)
```

Amino acid sequence of transcriptional activator, ORF12 (regulatory) (SEQ ID NO:13)

```
  1 MNLVERDGEI AHLRAVLDAS AAGDGTLLLV SGPAGSGKTE LLRSLRRLAA ERETPVWSVR

61 ALPGDRDIPL GVLCQLLRSA EQHGADTSAV RDLLDAASRR AGTSPPPPTR RSASTRHTAC

121 TTGCSPSPAG TPFLVAVDDL THADTASLRF LLYCAAHHDQ GGIGFVMTER ASQRAGYRVF

181 RAELLRQPHC RNMWLSGLPP SGVRQLLAHY YGPEAAERRA PAYHATTGGN PLLLRALTQD

241 RQASHTTLGA AGGDEPVHGD AFAQAVLDCL HRSAEGTLET ARWLAVLEQS DPLLVERLTG

301 TTAAAVERHI QELAAIGLLD EDGTLGQPAI REAALQDLPA GERTELHRRA AEQLHRDGAD

361 EDTVARHLLV GGAPDAPWAL PLLERGAQQA LFDDRLDDAF RILEFAVRSS TDNTQLARLA

421 PHLVAASWRM NPHMTTRALA LFDRLLSGEL PPSHPVMALI RCLVWYGRLP EAADALSRLR

481 PSSDNDALEL SLTEMWLAAL CPPLLESLPA TPEPERGPVP VRLAPRTTAL QAQAGVFQRG

541 PDNASVAQAE QILQGCRLSE ETYEALETAL LVLVHADRLD RALFWSDALL AEAVERRSLG

601 WEAVFAATRA MIAIRCGDLP TARERAELAL SHAAPESWGL AVGMPLSALL LACTEAGEYE

661 QAERVLRQPV PDAMFDSRHG MEYMHARGRY WLAXGRLHAA LGEFMLCGEI LGSWNLDQPS

721 IVPWRTSAAE VYLRLGNRQK ARALAEAQLA LVRPGRSRTR GLTLRVLAAA VDGQQAERLH

781 AEAVDMLHDS GDRLEHARAL AGMSRHQQAQ GDNYRARMTA RLAGDMAWAC GAYPLAEEIV

841 PGRGGRRAKA VSTELELPGG PDVGLLSEAE RRVAALAARG LTNRQIARRL CVTASTVEQH

901 LTRVYRKLNV TRRADLPISL AQDKSVTA  (SEQ ID NO:13)
```

Amino acid sequence of dNDP-glucose synthase (glucose-1-phosphate thymidyl transferase), ORF13 (desIII) (SEQ ID NO:14)

```
  1 MKGIVLAGGS GTRLHPATSV ISKQILPVYN KPMIYYPLSV LMLGGIREIQ IISTPQHIEL

61 FQSLLGNGRH LGIELDYAVQ KEPAGIADAL LVGAEHIGDD TCALILGDNI FHGPGLYTLL

121 RSAIARLDGC VLFGYPVKDP ERYGVAEVDA TGRLTDLVEK PVKPRSNLAV TGLYLYDNDV

181 VDIAKNIRPS PRGELEITDV NRVYLERGRA ELVNLGRGFA WLDTGTHDSL LRAAQYVQVL

241 EERQGVWIAG LEEIAFRMGF IDAEACHGLG EGLSRTEYGS YLMEIAGREG AP (SEQ ID NO:14)
```

Amino acid sequence of dNDP-glucose 4,6-dehydratase, ORF14 (desIV) (SEQ ID NO:15)

```
  1 VRLLVTGGAG FIGSHFVRQL LAGAYPDVPA DEVIVLDSLT YAGNRANLAP VDADPRLRFV
 61 HGDIRDAGLL ARELRGVDAI VHFAAESHVD RSIAGASVFT ETNVQGTQTL LQCAVDAGVG
121 RVVHVSTDEV YGSIDSGSWT ESSPLEPNSP YAASKAGSDL VARAYHRTYG LDVRITRCCN
181 NYGPYQHPEK LIPLFVTNLL DGGTLPLYGD GANVREWVHT DDHCRGIALV LAGGRAGEIY
241 HIGGGLELTN RELTGILLDS LGADWSSVRK VADRKGHDLR YSLDGGKIER ELGYRPQVSF
301 ADGLARTVRW YRENRGWWEP LKATAPQLPA TAVEVSA (SEQ ID NO:15)
```

Partial amino acid sequence of S-adenosylmethionine synthase, ORF15 (SAM synthase) (SEQ ID NO:16)

```
  1 IGYDSSKKGF DGASCGVSVS IGSQSPDIAQ GVDTAYEKRV EGASQRDEGD ELDKQGAGDQ
 61 GLMFGYASDE TPELMPLPIH LAHRLSRRLT EVRKNGTIPY LRPDGKTQVT IEYDGDRAVR
121 LDTVVVSSQH ASDIDLESLL APDVRKFVVE HVLAQLVEDG IKLDTDGYRL LVNPTGRFEI
181 GGPMGDAGLT GRKIIIDTYG GMARHGGGAF SGKDPSKVDR SAAYAMRWVA KNVVAAGLAS
241 RCEVQVAYAI GKAEPVGLFV ETFGTHKIET EKIENAIGEV FDLRPAAIIR DLDDDRPIYS
301 QTAAYGHFGR ELPDFTWERT DRVDALKKAA GL (SEQ ID NO:16)
```

Partial amino acid sequence of ORF16 (homologous to *M. tuberculosis* cbhK) (SEQ ID NO:17)

```
  1 MRIAVTGSIA TDHLMTFPGR FAEQILPDQL AHVSLSFLVD TLDIRHGGVA ANIAYGLGLL
 61 GRRPVLVGAV GKDFDGYGQL LRAAGVDTDS VRVSDRQHTA RFMCTTDEDG NQLASFYAGA
121 MAEARDIDLG ETAGRPGGID LVLVGADDPE AMVRHTRVCR ELGLRRAADP SQQLARLEGD
181 SVRELVDGAE LLFTNAYERA LLLSKTGWTE QEVLARVGTW ITTLGAKGCR (SEQ ID NO:17)
```

While not all of the insert DNA of cosmid pKOS023-26 has been sequenced, five large contigs shown of FIG. 3 have been assembled and provide sufficient sequence information to manipulate the genes therein in accordance with the methods of the invention. The sequences of each of these five contigs are shown below.

Contig 001 from cosmid pKOS023-26 contains 2401 nucleotides, the first 100 bases of which correspond to 100 bases of the insert sequence of cosmid pKOS023-27.

Nucleotides 80–2389 constitute ORF11, which encodes 1 beta glucosidase. (SEQ ID NO:20)

```
  1 CGTGGCGGCC GCCGCTCCCG GCGCCGCCGA CACGGCCAAT GTTCAGTACA CGAGCCGGGC
 61 GGCGGAGCTC GTCGCCCAGA TGACGCTCGA CGAGAAGATC AGCTTCGTCC ACTGGGCGCT
121 GGACCCCGAC CGGCAGAACG TCGGCTACCT TCCCGGCGTG CCGCGTCTGG GCATCCCGGA
181 GCTGCGTGCC GCCGACGGCC CGAACGGCAT CCGCCTGGTG GGGCAGACCG CCACCGCGCT
241 GCCCGCGCCG GTCGCCCTGG CCAGCACCTT CGACGACACC ATGGCCGACA GCTACGGCAA
301 GGTCATGGGC CGCGACGGTC GCGCGCTCAA CCAGGACATG GTCCTGGGCC CGATGATGAA
361 CAACATCCGG GTGCCGCACG GCGGCCGGAA CTACGAGACC TTCAGCGAGG ACCCCCTGGT
421 CTCCTCGCGC ACCGCGGTCG CCCAGATCAA GGGCATCCAG GGTGCGGGTC TGATGACCAC
481 GGCCAAGCAC TTCGCGGCCA ACAACCAGGA GAACAACCGC TTCTCCGTGA ACGCCAATGT
541 CGACGAGCAG ACGCTCCGCG AGATCGAGTT CCCGGCGTTC GAGGCGTCCT CCAAGGCCGG
```

```
601 CGCGGGCTCC TTCATGTGTG CCTACAACGG CCTCAACGGG AAGCCGTCCT GCGGCAACGA
661 CGAGCTCCTC AACAACGTGC TGCGCACGCA GTGGGGCTTC CAGGGCTGGG TGATGTCCGA
721 CTGGCTCGCC ACCCCGGGCA CCGACGCCAT CACCAAGGGC CTCGACCAGG AGATGGGCGT
781 CGAGCTCCCC GGCGACGTCC CGAAGGGCGA GCCCTCGCCG CCGGCCAAGT TCTTCGGCGA
841 GGCGCTGAAG ACGGCCGTCC TGAACGGCAC GGTCCCCGAG GCGGCCGTGA CGCGGTCGGC
901 GGAGCGGATC GTCGGCCAGA TGGAGAAGTT CGGTCTGCTC CTCGCCACTC CGGCGCCGCG
961 GCCCGAGCGC GACAAGGCGG GTGCCCAGGC GGTGTCCCGC AAGGTCGCCG AGAACGGCGC
1021 GGTGCTCCTG CGCAACGAGG GCCAGGCCCT GCCGCTCGCC GGTGACGCCG GCAAGAGCAT
1081 CGCGGTCATC GGCCCGACGG CCGTCGACCC CAAGGTCACC GGCCTGGGCA GCGCCCACGT
1141 CGTCCCGGAC TCGGCGGCGG CGCCACTCGA CACCATCAAG GCCCGCGCGG GTGCGGGTGC
1201 GACGGTGACG TACGAGACGG GTGAGGAGAC CTTCGGGACG CAGATCCCGG CGGGGAACCT
1261 CAGCCCGGCG TTCAACCAGG GCCACCAGCT CGAGCCGGGC AAGGCGGGGG CGCTGTACGA
1321 CGGCACGCTG ACCGTGCCCG CCGACGGCGA GTACCGCATC GCGGTCCGTG CCACCGGTGG
1381 TTACGCCACG GTGCAGCTCG GCAGCCACAC CATCGAGGCC GGTCAGGTCT ACGGCAAGGT
1441 GAGCAGCCCG CTCCTCAAGC TGACCAAGGG CACGCACAAG CTCACGATCT CGGGCTTCGC
1501 GATGAGTGCC ACCCCGCTCT CCCTGGAGCT GGGCTGGGTN ACGCCGGCGG CGGCCGACGC
1561 GACGATCGCG AAGGCCGTGG AGTCGGCGCG GAAGGCCCGT ACGGCGGTCG TCTTCGCCTA
1621 CGACGACGCG ACCGAGGGCG TCGACCGTCC GAACCTGTCG CTGCCGGGTA CGCAGGACAA
1681 GCTGATCTCG GCTGTCGCGG ACGCCAACCC GAACACGATC GTGGTCCTCA ACACCGGTTC
1741 GTCGGTGCTG ATGCCGTGGC TGTCCAAGAC CCGCGCGGTC CTGGACATGT GGTACCCGGG
1801 CCAGGCGGGC GCCGAGGCCA CCGCCGCGCT GCTCTACGGT GACGTCAACC CGAGCGGCAA
1861 GCTCACGCAG AGCTTCCCGG CCGCCGAGAA CCAGCACGCG GTCGCGGCG ACCCGACCAG
1921 CTACCCGGGC GTCGACAACC AGCAGACGTA CCGCGAGGGC ATCCACGTCG GGTACCGCTG
1981 GTTCGACAAG GAGAACGTCA AGCCGCTGTT CCCGTTCGGG CACGGCCTGT CGTACACCTC
2041 GTTCACGCAG AGCGCCCCGA CCGTCGTGCG TACGTCCACG GGTGGTCTGA AGGTCACGGT
2101 CACGGTCCGC AACAGCGGGA AGCGCGCCGG CCAGGAGGTC GTCCAGGCGT ACCTCGGTGC
2161 CAGCCCGAAC GTGACGGCTC CGCAGGCGAA GAAGAAGCTC GTGGGCTACA CGAAGGTCTC
2221 GCTCGCCGCG GGCGAGGCGA AGACGGTGAC GGTGAACGTC GACCGCCGTC AGCTGCAGTT
2281 CTGGGATGCC GCCACGGACA ACTGGAAGAC GGGAACGGGC AACCGCCTCC TGCAGACCGG
2341 TTCGTCCTCC GCCGACCTGC GGGGCAGCGC CACGGTCAAC GTCTGGTGAC GTGACGCCGT
2401 G (SEQ ID NO:20)
```

Contig 002 from cosmid pKOS023-26 contains 5970 nucleotides and the following ORFs: from nucleotide 995 to 1 is an ORF of picCIV that encodes a partial sequence of an amino transferase-dehydrase; from nucleotides 1356 to 2606 is an ORF of picK that encodes a cytochrome P450 hydroxylase; and from nucleotides 2739 to 5525 is oRF12, which encodes a transcriptional activator. (SEQ ID NO:21)

```
  1 GGCGAGAAGT AGGCGCGGGT GTGCACGCCT TCGGCCTTCA GGACCTCCAT GACGAGGTCG
 61 CGGTGGATGC CGGTGGTGGC CTCGTCGACT TCGACGATCA CGTACTGGTG GTTGTTGAGG
121 CCGTGGCGGT CGTGGTCGGC GACGAGGACG CCGGGGAGGT CCGCGAGGTG CTCGCGGTAG
181 SCGGCGTGGT TGCGCCGGTT CCGGTCGATG ACCTCGGGAA ACGCGTCGAG GGAGGTGAGG
241 CCCATGGCGG CGGCGGCCTC GCTCATCTTG GCGTTGGTCC CGCCGGCGGG GCTGCCGCCG
```

-continued

```
 301 GGCAGGTCGA AGCCGAAGTT GTGGAGGGCG CGGATCCGGG CGGCGAGGTC GGCGTCGTCG
 361 GTGACGACGG CGCCGCCCTC GAAGGCGTTG ACGGCCTTGG TGGCGTGGAA GCTGAAGACC
 421 TCGGCGTCGC CGAGGCTGCC GGCGGGCCGG CCGTCGACCG CGCAGCCGAG GGCGTGCGCG
 481 GCGTCGAAGT ACAGCCGCAG GCCGTGCTCG TCGGCGACCT TCCGCAGCTG GTCGGCGGCG
 541 CAGGGGCGGC CCCAGAGGTG GACGCCGACG ACGGCCGAGG TGCGGGGTGT GACCGCGGCG
 601 GCCACCTGGT CCGGGTCGAG GTTGCCGGTG TCCGGGTCGA TGTCGGCGAA GACCGGGGTG
 661 AGGCCGATCC AGCGCAGTGC GTGCGGGGTG GCGGCGAACG TCATCGACGG CATGATCACT
 721 TCGCCGGTGA GGCCGGCGGC GTGCGCGAGG AGCTGGAGCC CGGCCGTGGC GTTGCAGGTG
 781 GCCACGGCAT GCCGGACCCC GGCGAGCCCG GCGACGCGCT CCTCGAACTC GCGGACGAGC
 841 GGGCCGCCGT TGGACAGCCA CTGGCTGTCG AGGGCCCGGT CGAGCCGCTC GTACAGCCTG
 901 GCGCGGTCGA TGCGGTTGGG CCGCCCCACG AGGAGCGGCT GGTCGAAAGC GGCGGGGCCG
 961 CCGAAGAATG CGAGGTCGGA TAAGGCGCTT TCACGGATG TTCCCTCCGG GCCACCGTCA
1021 CGAAATGATT CGCCGATCCG GGAATCCCGA ACGAGGTCGC CGCGCTCCAC CGTGACGTAC
1081 GACGAGATGG TCGATTGTGG TGGTCGATTT CGGGGGGACT CTAATCCGCG CGGAACGGGA
1141 CCGACAAGAG CACGCTATGC GCTCTCGATG TGCTTCGGAT CACATCCGCC TCCGGGGTAT
1201 TCCATCGGCG GCCCGAATGT GATGATCCTT GACAGGATCC GGGAATCAGC CGAGCCGCCG
1261 GGAGGGCCGG GGCGCGCTCC GCGGAAGAGT ACGTGTGAGA AGTCCCGTTC CTCTTCCCGT
1321 TTCCGTTCCG CTTCCGGCCC GGTCTGGAGT TCTCCGTGCG CCGTACCCAG CAGGGAACGA
1381 CCGCTTCTCC CCCGGTACTC GACCTCGGGG CCCTGGGGCA GGATTTCGCG GCCGATCCGT
1441 ATCCGACGTA CGCGAGACTG CGTGCCGAGG GTCCGGCCCA CCGGGTGCGC ACCCCCGAGG
1501 GGGACGAGGT GTGGCTGGTC GTCGGCTACG ACCGGGCGCG GCGGTCCTC GCCGATCCCC
1561 GGTTCAGCAA GGACTGGCGC AACTCCACGA CTCCCCTGAC CGAGGCCGAG GCCGCGCTCA
1621 ACCACAAACAT GCTGGAGTCC GACCCGCCGC GGCACACCCG GCTGCGCAAG CTGGTGGCCC
1681 GTGAGTTCAC CATGCGCCGG GTCGAGTTGC TGCGGCCCCG GGTCCAGGAG ATCGTCGACG
1741 GGCTCGTGGA CGCCATGCTG GCGGCGCCCG ACGGCCGCGC CGATCTGATG GAGTCCCTGG
1801 CCTGGCCGCT GCCGATCACC GTGATCTCCG AACTCCTCGG CGTGCCCGAG CCGGACCGCG
1861 CCGCCTTCCG CGTCTGGACC GACGCCTTCG TCTTCCCGGA CGATCCCGCC CAGGCCCAGA
1921 CCGCCATGGC CGAGATGAGC GGCTATCTCT CCCGGCTCAT CGACTCCAAG CGCGGGCAGG
1981 ACGGCGAGGA CCTGCTCAGC GCGCTCGTGC GGACCAGCGA CGAGGACGGC TCCCGGCTGA
2041 CCTCCGAGGA GCTGCTCGGT ATGGCCCACA TCCTGCTCGT CGCGGGGCAC GAGACCACGG
2101 TCAATCTGAT CGCCAACGGC ATGTACGCGC TGCTCTCGCA CCCCGACCAG CTGGCCGCCC
2161 TGCGGGCCGA CATGACGCTC TTGGACGGCG CGGTGGAGGA GATGTTGCGC TACGAGGGCC
2221 CGGTGGAATC CGCGACCTAC CGCTTCCCGG TCGAGCCCGT CGACCTGGAC GGCACGGTCA
2281 TCCCGGCCGG TGACACGGTC CTCGTCGTCC TGGCCGACGC CCACCGCACC CCCGAGCGCT
2341 TCCCGGACCC GCACCGCTTC GACATCCGCC GGGACACCGC CGGCCATCTC GCCTTCGGCC
2401 ACGGCATCCA CTTCTGCATC GGCGCCCCCT TGGCCCGGTT GGAGGCCCGG ATCGCCGTCC
2461 GCGCCCTTCT CGAACGCTGC CCGGACCTCG CCCTGGACGT CTCCCCCGGC GAACTCGTGT
2521 GGTATCCGAA CCCGATGATC CGCGGGCTCA AGGCCCTGCC GATCCGCTGG CGGCGAGGAC
2581 GGGAGGCGGG CCGCCGTACC GGTTGAACCC GCACGTCACC CATTACGACT CCTTGTCACG
2641 GAAGCCCCGG ATCGGTCCCC CCTCGCCGTA ACAAGACCTG GTTAGAGTGA TGGAGGACGA
```

```
                             -continued
2701 CGAAGGGTTC GGCGCCCGGA CGAGGGGGGA CTTCCGCGAT GAATCTGGTG GAACGCGACG

2761 GGGAGATAGC CCATCTCAGG GCCGTTCTTG ACGCATCCGC CGCAGGTGAC GGGACGCTCT

2821 TACTCGTCTC CGGACCGGCC GGCAGCGGGA AGACGGAGCT GCTGCGGTCG CTCCGCCGGC

2881 TGGCCGCCGA GCGGGAGACC CCCGTCTGGT CGGTCCGGGC GCTGCCGGGT GACCGCGACA

2941 TCCCCCTGGG CGTCCTCTGC CAGTTACTCC GCAGCGCCGA CAACACGGT GCCGACACCT

3001 CCGCCGTCCG CGACCTGCTG GACGCCGCCT CGCGGCGGGC CGGAACCTCA CCTCCCCCGC

3061 CGACGCGCCG CTCCGCGTCG ACGAGACACA CCGCCTGCAC GACTGGCTGC TCTCCGTCTC

3121 CCGCCGGCAC CCCGTTCCTC GTCGCCGTCG ACGACCTGAC CCACGCCGAC ACCGCGTCCC

3181 TGAGGTTCCT CCTGTACTGC GCCGCCCACC ACGACCAGGG CGGCATCGGC TTCGTCATGA

3241 CCGAGCGGGC CTCGCAGCGC GCCGGATACC GGGTGTTCCG CGCCGAGCTG CTCCGCCAGC

3301 CGCACTGCCG CAACATGTGG CTCTCCGGGC TTCCCCCCAG CGGGGTACGC CAGTTACTCG

3361 CCCACTACTA CGGCCCCGAG GCCGCCGAGC GGCGGGCCCC CGCGTACCAC GCGACGACCG

3421 GCGGGAACCC GCTGCTCCTG CGGGCGCTGA CCCAGGACCG GCAGGCCTCC CACACCACCC

3481 TCGGCGCGGC CGGCGGCGAC GAGCCCGTCC ACGGCGACGC CTTCGCCCAG GCCGTCCTCG

3541 ACTGCCTGCA CCGCAGCGCC GAGGGCACAC TGGAGACCGC CCGCTGGCTC GCGGTCCTCG

3601 AACAGTCCGA CCCGCTCCTG GTGGAGCGGC TCACGGGAAC GACCGCCGCC GCCGTCGAGC

3661 GCCACATCCA GGAGCTCGCC GCCATCGGCC TCCTGGACGA GGACGGCACC CTGGGACAGC

3721 CCGCGATCCG CGAGGCCGCC CTCCAGGACC TGCCGGCCGG CGAGCGCACC GAACTGCACC

3781 GGCGCGCCGC GGAGCAGCTG CACCGGGACG GCGCCGACGA GGACACCGTG GCCCGCCACC

3841 TGCTGGTCGG CGGCGCCCCC GACGCTCCCT GGGCGCTGCC CCTGCTCGAA CGGGGCGCGC

3901 AGCAGGCCCT GTTCGACGAC CGACTCGACG ACGCCTTCCG GATCCTCGAG TTCGCCGTGC

3961 GGTCGAGCAC CGACAACACC CAGCTGGCCC GCCTCGCCCC ACACCTGGTC GCGGCCTCCT

4021 GGCGGATGAA CCCGCACATG ACGACCCGGG CCCTCGCACT CTTCGACCGG CTCCTGAGCG

4081 GAGAACTGCC GCCCAGCCAC CCGGTCATGG CCCTGATCCG CTGCCTCGTC TGGTACGGNC

4141 GGCTGCCCGA GGCCGCCGAC GCGCTGTCCC GGCTGCGGCC CAGCTCCGAC AACGATGCCT

4201 TGGAGCTGTC GCTCACCCGG ATGTGGCTCG CGGCGCTGTG CCCGCCGCTC CTGGAGTCCC

4261 TGCCGGCCAC GCCGGAGCCG GAGCGGGGTC CCGTCCCCGT ACGGCTCGCG CCGCGGACGA

4321 CCGCGCTCCA GGCCCAGGCC GGCGTCTTCC AGCGGGGCCC GGACAACGCC TCGGTCGCGC

4381 AGGCCGAACA GATCCTGCAG GGCTGCCGGC TGTCGGAGGA GACGTACGAG GCCCTGGAGA

4441 CGGCCCTCTT GGTCCTCGTC CACGCCGACC GGCTCGACCG GGCGCTGTTC TGGTCGGACG

4501 CCCTGCTCGC CGAGGCCGTG GAGCGGCGGT CGCTCGGCTG GGAGGCGGTC TTCGCCGCGA

4561 CCCGGGCGAT GATCGCGATC CGCTGCGGCG ACCTCCCGAC GGCGCGGGAG CGGGCCGAGC

4621 TGGCGCTCTC CCACGCGGCG CCGGAGAGCT GGGGCCTCGC CGTGGGCATG CCCCTCTCCG

4681 CGCTGCTGCT CGCCTGCACG GAGGCCGGCG AGTACGAACA GGCGGAGCGG GTCCTGCGGC

4741 AGCCGGTGCC GGACGCGATG TTCGACTCGC GGCACGGCAT GGAGTACATG CACGCCCGGG

4801 GCCGCTACTG GCTGGCGANC GGCCGGCTGC ACGCGGCGCT GGGCGAGTTC ATGCTCTGCG

4861 GGGAGATCCT GGGCAGCTGG AACCTCGACC AGCCCTCGAT CGTGCCCTGG CGGACCTCCG

4921 CCGCCGAGGT GTACCTGCGG CTCGGCAACC GCCAGAAGGC CAGGGCGCTG GCCGAGGCCC

4981 AGCTCGCCCT GGTGCGGCCC GGGCGCTCCC GCACCCGGGG TCTCACCCTG CGGGTCCTGG

5041 CGGCGGCGGT GGACGGCCAG CAGGCGGAGC GGCTGCACGC CGAGGCGGTC GACATGCTGC
```

-continued

```
5101 ACGACAGCGG CGACCGGCTC GAACACGCCC GCGCGCTCGC CGGGATGAGC CGCCACCAGC

5161 AGGCCCAGGG GGACAACTAC CGGGCGAGGA TGACGGCGCG GCTCGCCGGC GACATGGCGT

5221 GGGCCTGCGG CGCGTACCCG CTGGCCGAGG AGATCGTGCC GGGCCGCGGC GGCCGCCGGG

5281 CGAAGGCGGT GAGCACGGAG CTGGAACTGC CGGGCGGCCC GGACGTCGGC CTGCTCTCGG

5341 AGGCCGAACG CCGGGTGGCG GCCCTGGCAG CCCGAGGATT GACGAACCGC CAGATAGCGC

5401 GCCGGCTCTG CGTCACCGCG AGCACGGTCG AACAGCACCT GACGCGCGTC TACCGCAAAC

5461 TGAACGTGAC CCGCCGAGCA GACCTCCCGA TCAGCCTCGC CCAGGACAAG TCCGTCACGG

5521 CCTGAGCCAC CCCCGGTGTC CCCGTGCGAC GACCCGCCGC ACGGGCCACC GGGCCCGCCG

5581 GGACACGCCG GTGCGACACG GGGGCGCGCC AGGTGCCATG GGGACCTCCG TGACCGCCCG

5641 AGGCGCCCGA GGCGCCCGGT GCGGCACCCG GAGACGCCAG GACCGCCGGG ACCACCGGAG

5701 ACGCCAGGGA CCGCTGGGGA CACCGGGACC TCAGGGACCG CCGGGACCGC CCGAGTTGCA

5761 CCCGGTGCGC CCGGGGACAC CAGACCGCCG GGACCACCCG AGGGTGCCCG GTGTGGCCCC

5821 GGCGGCCGGG GTGTCCTTCA TCGGTGGGCC TTCATCGGCA GGAGGAAGCG ACCGTGAGAC

5881 CCGTCGTGCC GTCGGCGATC AGCCGCCTGT ACGGGCGTCG GACTCCCTGG CGGTCCCGGA

5941 CCCGTCGTAC GGGCTCGCGG GACCCGGTGC (SEQ ID NO:21)
```

Contig 003 from cosmid pKOS023-26 contains 3292 nucleotides and the following ORFs: from nucleotide 104 to 982 is ORF13, which encodes dNDP glucose synthase (glucose-1-phosphate thymidyl transferase); from nucleotide 1114 to 2127 is ORF14, which encodes dNDP-glucose 4,6dehydratase; and from nucleotide 2124 to 3263 is the picCI ORF. (SEQ ID NO:22)

```
   1 ACCCCCCAAA GGGGTGGTGA CACTCCCCCT GCGCAGCCCC TAGCGCCCCC CTAACTCGCC

61 ACGCCGACCG TTATCACCGG CGCCCTGCTG CTAGTTTCCG AGAATGAAGG GAATAGTCCT

121 GGCCGGCGGG AGCGGAACTC GGCTGCATCC GGCGACCTCG GTCATTTCGA AGCAGATTCT

181 TCCGGTCTAC AACAAACCGA TGATCTACTA TCCGCTGTCG GTTCTCATGC TCGGCGGTAT

241 TCGCGAGATT CAAATCATCT CGACCCCCCA GCACATCGAA CTCTTCCAGT CGCTTCTCGG

301 AAACGGCAGG CACCTGGGAA TAGAACTCGA CTATGCGGTC CAGAAAGAGC CCGCAGGAAT

361 CGCGGACGCA CTTCTCGTCG GAGCCGAGCA CATCGGCGAC GACACCTGCG CCCTGATCCT

421 GGGCGACAAC ATCTTCCACG GGCCCGGCCT CTACACGCTC CTGCGGGACA GCATCGCGCG

481 CCTCGACGGC TGCGTGCTCT TCGGCTACCC GGTCAAGGAC CCCGAGCGGT ACGGCGTCGC

541 CGAGGTGGAC GCGACGGGCC GGCTGACCGA CCTCGTCGAG AAGCCCGTCA AGCCGCGCTC

601 CAACCTCGCC GTCACCGGCC TCTACCTCTA CGACAACGAC GTCGTCGACA TCGCCAAGAA

661 CATCCGGCCC TCGCCGCGCG GCGAGCTGGA GATCACCGAC GTCAACCGCG TCTACCTGGA

721 GCGGGGCCGG GCCGAACTCG TCAACCTGGG CCGCGGCTTC GCCTGGCTGG ACACCGGCAC

781 CCACGACTCG CTCCTGCGGG CCGCCCAGTA CGTCCAGGTC CTGGAGGAGC GGCAGGGCGT

841 CTGGATCGCG GGCCTTGAGG AGATCGCCTT CCGCATGGGC TTCATCGACG CCGAGGCCTG

901 TCACGGCCTG GGAGAAGGCC TCTCCCGCAC CGAGTACGGC AGCTATCTGA TGGAGATCGC

961 CGGCCGCGAG GGAGCCCCGT GAGGGCACCT CGCGGCCGAC GCGTTCCCAC GACCGACAGC

1021 GCCACCGACA GTGCGACCCA CACCGCGACC CGCACCGCCA CCGACAGTGC GACCCACACC

1081 GCGACCTACA GCGCGACCGA AAGGAAGACG GCAGTGCGGC TTCTGGTGAC CGGAGGTGCG

1141 GGCTTCATCG GCTCGCACTT CGTGCGGCAG CTCCTCGCCG GGGCGTACCC CGACGTGCCC

1201 GCCGATGAGG TGATCGTCCT GGACAGCCTC ACCTACGCGG GCAACCGCGC CAACCTCGCC
```

-continued

```
1261 CCGGTGGACG CGGACCCGCG ACTGCGCTTC GTCCACGGCG ACATCCGCGA CGCCGGCCTC

1321 CTCGCCCGGG AACTGCGCGG CGTGGACGCC ATCGTCCACT TCGCGGCCGA GAGCCACGTG

1381 GACCGCTCCA TCGCGGGCGC GTCCGTGTTC ACCGAGACCA ACGTGCAGGG CACGCAGACG

1441 CTGCTCCAGT GCGCCGTCGA CGCCGGCGTC GGCCGGGTCG TGCACGTCTC CACCGACGAG

1501 GTGTACGGGT CGATCGACTC CGGCTCCTGG ACCGAGAGCA GCCCGCTGGA GCCCAACTCG

1561 CCCTACGCGG CGTCCAAGGC CGGCTCCGAC CTCGTTGCCC GCGCCTACCA CCGGACGTAC

1621 GGCCTCGACG TACGGATCAC CCGCTGCTGC AACAACTACG GCCGTACCA GCACCCCGAG

1681 AAGCTCATCC CCCTCTTCGT GACGAACCTC CTCGACGGCG GGACGCTCCC GCTGTACGGC

1741 GACGGCGCGA ACGTCCGCGA GTGGGTGCAC ACCGACGACC CATGCCGGGG CATCGCGCTC

1801 GTCCTCGCGG GCGGCCGGGC CGGCGAGATC TACCACATCG GCGGCGGCCT GGAGCTGACC

1861 AACCGCGAAC TCACCGGCAT CCTCCTGGAC TCGCTCGGCG CCGACTGGTC CTCGGTCCGG

1921 AAGGTCGCCG ACCGCAAGGG CCACGACCTG CGCTACTCCC TCGACGGCGG CAAGATCGAG

1981 CGCGAGCTCG GCTACCGCCC GCAGGTCTCC TTCGCGGACG GCCTCGCGCG GACCGTCCGC

2041 TGGTACCGGG AGAACCGCGG CTGGTGGGAG CCGCTCAAGG CGACCGCCCC GCAGCTGCCC

2101 GCCACCGCCG TGGAGGTGTC CGCGTGAGCA GCCGCGCCGA GACCCCCCGC GTCCCCTTCC

2161 TCGACCTCAA GGCCGCCTAC GAGGAGCTCC GCGCGGAGAC CGACGCCGCG ATCGCCCGCG

2221 TCCTCGACTC GGGGCGCTAC CTCCTCGGAC CCGAACTCGA AGGATTCGAG GCGGAGTTCG

2281 CCGCGTACTG CGAGACGGAC CACGCCGTCG GCGTGAACAG CGGGATGGAC GCCCTCCAGC

2341 TCGCCCTCCG CGGCCTCGGC ATCGGACCCG GGGACGAGGT GATCGTCCCC TCGCACACGT

2401 ACATCGCCAG CTGGCTCGCG GTGTCCGCCA CCGGCGCGAC CCCCGTGCCC GTCGAGCCGC

2461 ACGAGGACCA CCCCACCCTG GACCCGCTGC TCGTCGAGAA GGCGATCACC CCCCGCACCC

2521 GGGCGCTCCT CCCCGTCCAC CTCTACGGGC ACCCCGCCGA CATGGACGCC CTCCGCGAGC

2581 TCGCGGACCG GCACGGCCTG CACATCGTCG AGGACGCCGC GCAGGCCCAC GGCGCCCGCT

2641 ACCGGGGCCG GCGGATCGGC GCCGGGTCGT CGGTGGCCGC GTTCAGCTTC TACCCGGGCA

2701 AGAACCTCGG CTGCTTCGGC GACGGCGGCG CCGTCGTCAC CGGCGACCCC GAGCTCGCCG

2761 AACGGCTCCG GATGCTCCGC AACTACGGCT CGCGGCAGAA GTACAGCCAC GAGACGAAGG

2821 GCACCAACTC CCGCCTGGAC GAGATGCAGG CCGCCGTGCT GCGGATCCGG CTCGNCCACC

2881 TGGACAGCTG GAACGGCCGC AGGTCGGCGC TGGCCGCGGA GTACCTCTCC GGGCTCGCCG

2941 GACTGCCCGG CATCGGCCTG CCGGTGACCG CGCCCGACAC CGACCCGGTC TGGCACCTCT

3001 TCACCGTGCG CACCGAGCGC CGCGACGAGC TGCGCAGCCA CCTCGACGCC CGCGGCATCG

3061 ACACCCTCAC GCACTACCCG GTACCCGTGC ACCTCTCGCC CGCCTACGCG GGCGAGGCAC

3121 CGCCGGAAGG CTCGCTCCCG CGGGCCGAGA GCTTCGCGCG GCAGGTCCTC AGCCTGCCGA

3181 TCGGCCCGCA CCTGGAGCGC CCGCAGGCGC TGCGGGTGAT CGACGCCGTG CGCGAATGGG

3241 CCGAGCGGGT CGACCAGGCC TAGTCAGGTG GTCCGGTAGA CCCAGCAGGC CG
(SEQ ID NO:22)
```

Contig 004 from cosmid pKOS023-26 contains 1693 nucleotides and the following ORFs: from nucleotide 1692 to 694 is ORF1 5, which encodes a part of S-adenosylmethionine synthetase; and from nucleotide 692 to 1 is ORF16, which encodes a part of a protein homologous to the M. tuberculosis cbhK gene. (SEQ ID NO:23)

```
  1 ATGCGGCACC CCTTGGCGCC GAGCGTGGTG ATCCAGGTGC CGACCCGGGC GAGCACCTCC

61 TGCTCGGTCC AGCCCGTCTT GCTGAGCAGC AGCGCCCGCT CGTAGGCGTT CGTGAACAGC
```

-continued

```
 121 AGCTCGGCTC CGTCGACGAG CTCCCGGACG CTGACGCCCT CCAGCCGGGC GAGCTGCTGC

181 GAGGGGTCCG CGGCCCGGCG GAGGCCCAGC TCGCGGCAGA CCCGCGTGTG CCGCACCATC

241 GCCTCGGGGT CGTCCGCGCC GACGAGGACG AGGTCGATCC CGCCGGGCCG GCCGGCCGTC

301 TCGCCCAGGT CGATGTCGCG CGCCTCGGCC ATCGCGCCCG CGTAGAACGA GGCGAGCTGA

361 TTGCCGTCCT CGTCGGTGGT GCACATGAAG CGGGCGGTGT GCTGACGGTC CGACACCCGC

421 ACGGAGTCGG TGTCGACGCC CGCGGCGCGG AGCAGCTGCC CGTACCCGTC GAAGTCCTTG

481 CCGACGGCGC CGACGAGGAC GGGGCGGCGA CCGAGCAGGC CGAGGCCGTA CGCGATGTTG

541 GCGGCGACGC CGCCGTGCCG GATGTCCAGG GTGTCGACGA GGAACGACAG GGACACGTGG

601 GCGAGCTGGT CCGGCAGGAT CTGCTCGGCG AAGCGGCCCG GGAAGGTCAT CAGGTGGTCG

661 GTGGCGATCG ACCCGGTGAC GGCTATACGC ATGTCAGAGC CCCGCGGCCT TCTTCAGGGC

721 GTCCACGCGG TCGGTGCGCT CCCAGGTGAA GTCCGGCAGC TCGCGGCCGA AGTGGCCGTA

781 GGCGGCGGTC TGGGAGTAGA TCGGGCGGAG CAGGTCGAGG TCGCGGATGA TCGCGGCCGG

841 GCGGAGGTCG AAGACCTCGC CGATGGCGTT CTCGATCTTC TCGGTCTCGA TCTTGTGGGT

901 GCCGAAGGTC TCGACGAAGA GGCCGACGGG CTCGGCCTTG CCGATCGCGT ACGCGACCTG

961 GACCTCGCAG CGCGAGGCGA GACCGGCGGC GACGACGTTC TTCGCCACCC AGCGCATCGC

1021 GTACGCGGCG GAGCGGTCGA CCTTCGACGG GTCCTTGCCG GAGAAGGCGC CGCCACCGTG

1081 GCGGGCCATG CCGCCGTAGG TGTCGATGAT GATCTTGCGG CCGGTGAGGC CGGCGTCGCC

1141 CATCGGGCCG CCGATCTCGA AGCGACCGGT CGGGTTCACG AGCAGGCGGT AGCCGTCGGT

1201 GTCGAGCTTG ATGCCGTCCT CGACGAGCTG CGCAAGCACG TGCTCGACGA CGAACTTCCG

1261 CACGTCGGGG GCGAGCAGCG ACTCCAGGTC GATGTCCGAG GCGTGCTGCG AGGAGACGAC

1321 GACCGTGTCG AGACGGACCG CCCTGTCGCC GTCGTACTCG ATGGTGACCT GGGTCTTGCC

1381 GTCGGGACGC AGGTACGGGA TGGTCCCGTT CTTGCGGACC TCGGTCAGGC GGCGCGAGAG

1441 ACGGTGCGCG AGGTGGATCG GCAGCGGCAT CAGCTCGGGC GTCTCGTCCG AGGCATAGCC

1501 GAACATCAGG CCCTGGTCAC CGGCGCCCTG CTTGTCGAGC TCGTCCCCCT CGTCCCGCTG

1561 GGAGGCACCC TCGACCCGCT TCTCGTACGC GGTGTCGACA CCCTGGGCGA TGTCCGGGGA

1621 CTGCGACCCG ATGGACACCG ACACGCCGCA GGAGGCGCCG TCGAAGCCCT TCTTCGAGGA

1681 GTCGTACCCG ATC (SEQ ID NO:23)
```

Contig 005 from cosmid pKOS023-26 contains 1565 nucleotides and contains the ORF of the picCV gene that encodes PICCV, involved in desosamine biosynthesis. (SEQ ID NO:24)

```
   1 CCCCGCTCGC GGCCCCCCAG ACATCCACGC CCACGATTGG ACGCTCCCGA TGACCGCCCC

61 CGCCCTCTCC GCCACCGCCC CGGCCGAACG CTGCGCGCAC CCCGGAGCCG ATCTGGGGGC

121 GGCGGTCCAC GCCGTCGGCC AGACCCTCGC CGCCGGCGGC CTCGTGCCGC CGACGAGGC

181 CGGAACGACC GCCCGCCACC TCGTCCGGCT CGCCGTGCGC TACGGCAACA GCCCCTTCAC

241 CCCGCTGGAG GAGGCCCGCC ACGACCTGGG CGTCGACCGG GACGCCTTCC GGCGCCTCCT

301 CGCCCTGTTC GGGCAGGTCC CGGAGCTCCG CACCGCGGTC GAGACCGGCC CGCCGGGGC

361 GTACTGGAAG AACACCCTGC TCCCGCTCGA ACAGCGCGGC GTCTTCGACG CGGCGCTCGC

421 CAGGAAGCCC GTCTTCCCGT ACAGCGTCGG CCTCTACCCC GGCCCGACCT GCATGTTCCG
```

```
-continued
 481 CTGCCACTTC TGCGTCCGTG TGACCGGCGC CCGCTACGAC CCGTCCGCCC TCGACGCCGG

541 CAACGCCATG TTCCGGTCGG TCATCGACGA GATACCCGCG GGCAACCCCT CGGCGATGTA

601 CTTCTCCGGC GGCCTGGAGC CGCTCACCAA CCCCGGCCTC GGGAGCCTGG CCGCGCACGC

661 CACCGACCAC GGCCTGCGGC CCACCGTCTA CACGAACTCC TTCGCGCTCA CCGAGCGCAC

721 CCTGGAGCGC CAGCCCGGCC TCTGGGGCCT GCACGCCATC CGCACCTCGC TCTACGGCCT

781 CAACGACGAG GAGTACGAGC AGACCACCGG CAAGAAGGCC GCCTTCCGCC GCGTCCGCGA

841 GAACCTGCGC CGCTTCCAGC AGCTGCGCGC CGAGCGCGAG TCGCCGATCA ACCTCGGCTT

901 CGCCTACATC GTGCTCCCGG GCCGTGCCTC CCGCCTGCTC GACCTGGTCG ACTTCATCGC

961 CGACCTCAAC GACGCCGGGC AGGGCAGGAC GATCGACTTC GTCAACATTC GCGAGGACTA

1021 CAGCGGCCGT GACGACGGCA AGCTGCCGCA GGAGGAGCGG GCCGAGCTCC AGGAGGCCCT

1081 CAACGCCTTC GAGGAGCGGG TCCGCGAGCG CACCCCCGGA CTCCACATCG ACTACGGCTA

1141 CGCCCTGAAC AGCCTGCGCA CCGGGGCCGA CGCCGAACTG CTGCGGATCA AGCCCGCCAC

1201 CATGCGGCCC ACCGCGCACC CGCAGGTCGC GGTGCAGGTC GATCTCCTCG GCGACGTGTA

1261 CCTGTACCGC GAGGCCGGCT TCCCCGACCT GGACGGCGCG ACCCGCTACA TCGCGGGCCG

1321 CGTGACCCCC GACACCTCCC TCACCGAGGT CGTCAGGGAC TTCGTCGAGC GCGGCGGCGA

1381 GGTGGCGGCC GTCGACGGCG ACGAGTACTT CATGGACGGC TTCGATCAGG TCGTCACCGC

1441 CCGCCTGAAC CAGCTGGAGC GCGACGCCGC GGACGGCTGG GAGGAGGCCC GCGGCTTCCT

1501 GCGCTGACCC GCACCCGCCC CGATCCCCCC GATCCCCCCC CCACGATCCC CCCACCTGAG

1561 GGCCC (SEQ ID NO:24)
```

The recombinant desosamine biosynthesis and transfer and beta-glucosidase genes and proteins provided by the invention are useful in the production of glycosylated polyketides in a variety of host cells, as described in Section IV below.

Section III. The Genes for Macrolide Ring Modification: the picK Hydroxylase Gene The present invention provides the picK gene in recombinant form as well as recombinant PicK protein. The availability of the hydroxylase encoded by the picK gene in recombinant form is of significant benefit in that the enzyme can convert narbomycin into picromycin and accepts in addition a variety of polyketide substrates, particularly those related to narbomycin in structure. The present invention also provides methods of hydroxylating polyketides, which method comprises contacting the polyketide with the recombinant PicK enzyme under conditions such that hydroxylation occurs. This methodology is applicable to large numbers of polyketides.

DNA encoding the picK gene can be isolated from cosmid pKOS023-26 of the invention. The DNA sequence of the picK gene is shown in the preceding section. This DNA sequence encodes one of the recombinant forms of the enzyme provided by the invention. The amino acid sequence of this form of the picK gene is shown below. The present invention also provides a recombinant picK gene that encodes a picK gene product in which the PicK protein is fused to a number of consecutive histidine residues, which facilitates purification from recombinant host cells.

Amino acid sequence of picromycin/methymycin cytochrome P450 hydroxylase, PicK

```
  1 VRRTQQGTTA SPPVLDLGAL GQDFAADPYP TYARLRAEGP AHRVRTPEGD EVWLVVGYDR

61 ARAVLADPRF SKDWRNSTTP LTEAEAALNH NMLESDPPRH TRLRKLVARE FTMRRVELLR

121 PRVQEIVDGL VDAMLAAPDG RADLMESLAW PLPITVISEL LGVPEPDRAA FRVWTDAFVF

181 PDDPAQAQTA MAEMSGYLSR LIDSKRGQDG EDLLSALVRT SDEDGSRLTS EELLGMAHIL

241 LVAGHETTVN LIANGMYALL SHPDQLAALR ADMTLLDGAV EEMLRYEGPV ESATYRFPVE

301 PVDLDGTVIP AGDTVLVVLA DAHRTPERFP DPHRFDIRRD TAGHLAFGHG IHFCIGAPLA

361 RLEARIAVRA LLERCPDLAL DVSPGELVWY PNPMIRGLKA LPIRWRRGRE AGRRTG
```

(SEQ ID NO:18)

The recombinant PicK enzyme of the invention hydroxylates narbomycin at the C12 position and YC-17 at either the C10 or C12 position. Hydroxylation of these compounds at the respective positions increases the antibiotic activity of the compound relative to the unhydroxylated compound. Hydroxylation can be achieved by a number of methods. First, the hydroxylation may be performed in vitro using purified hydroxylase, or the relevant hydroxylase can be produced recombinantly and utilized directly in the cell that produces it. Thus, hydroxylation may be effected by supplying the nonhydroxylated precursor to a cell that expresses the hydroxylase. These and other details of this embodiment of the invention are described in additional detail below in Section IV and the examples.

Section IV: Heterologous Expression of the Narbonolide PKS; the Desosamine Biosynthetic and Transferase Genes; the Beta-Glucosidase Gene; and the picK Hydroxylase Gene In one important embodiment, the invention provides methods for the heterologous expression of one or more of the genes involved in picromycin biosynthesis and recombinant DNA expression vectors useful in the method. Thus, included within the scope of the invention in addition to isolated nucleic acids encoding domains, modules, or proteins of the narbonolide PKS, glycosylation, and/or hydroxylation enzymes, are recombinant expression systems. These systems contain the coding sequences operably linked to promoters, enhancers, and/or termination sequences that operate to effect expression of the coding sequence in compatible host cells. The host cells are modified by transformation with the recombinant DNA expression vectors of the invention to contain these sequences either as extrachromosomal elements or integrated into the chromosome. The invention also provides methods to produce PKS and post-PKS tailoring enzymes as well as polyketides and antibiotics using these modified host cells.

As used herein, the term expression vector refers to a nucleic acid that can be introduced into a host cell or cell-free transcription and translation medium. An expression vector can be maintained stably or transiently in a cell, whether as part of the chromosomal or other DNA in the cell or in any cellular compartment, such as a replicating vector in the cytoplasm. An expression vector also comprises a gene that serves to produce RNA, which typically is translated into a polypeptide in the cell or cell extract. To drive production of the RNA, the expression vector typically comprises one or more promoter elements. Furthermore, expression vectors typically contain additional functional elements, such as, for example, a resistance-conferring gene that acts as a selectable marker.

The various components of an expression vector can vary widely, depending on the intended use of the vector. In particular, the components depend on the host cell(s) in which the vector will be introduced or in which it is intended to function. Components for expression and maintenance of vectors in $E.$ $coli$ are widely known and commercially available, as are components for other commonly used organisms, such as yeast cells and Streptomyces cells.

One important component is the promoter, which can be referred to as, or can be included within, a control sequence or control element, which drives expression of the desired gene product in the heterologous host cell. Suitable promoters include those that function in eucaryotic or procaryotic host cells. In addition to a promoter, a control element can include, optionally, operator sequences, and other elements, such as ribosome binding sites, depending on the nature of the host. Regulatory sequences that allow for regulation of expression of the heterologous gene relative to the growth of the host cell may also be included. Examples of such regulatory sequences known to those of skill in the art are those that cause the expression of a gene to be turned on or off in response to a chemical or physical stimulus.

Preferred host cells for purposes of selecting vector components include fungal host cells such as yeast and procaryotic, especially $E.$ $coli$ and Streptomyces, host cells, but single cell cultures of, for example, mammalian cells can also be used. In hosts such as yeasts, plants, or mammalian cells that ordinarily do not produce polyketides, it may be necessary to provide, also typically by recombinant means, suitable holo-ACP synthases to convert the recombinantly produced PKS to functionality. Provision of such enzymes is described, for example, in PCT publication Nos. WO 97/13845 and WO 98/27203, each of which is incorporated herein by reference. Control systems for expression in yeast, including controls that effect secretion are widely available and can be routinely used. For $E.$ $coli$ or other bacterial host cells, promoters such as those derived from sugar metabolizing enzymes, such as galactose, lactose (lac), and maltose, can be used. Additional examples include promoters derived from genes encoding biosynthetic enzymes, and the tryptophan (trp), the beta-lactamase (bla), bacteriophage lambda PL, and T5 promoters. In addition, synthetic promoters, such as the tac promoter (U.S. Pat. No. 4,551,433), can also be used.

Particularly preferred are control sequences compatible with Streptomyces spp. Particularly useful promoters for Streptomyces host cells include those from PKS gene clusters that result in the production of polyketides as secondary metabolites, including promoters from aromatic (Type II) PKS gene clusters. Examples of Type II PKS gene cluster promoters are act gene promoters and tcm gene promoters; an example of a Type I PKS gene cluster promoter is the spiramycin PKS gene promoter.

If a Streptomyces or other host ordinarily produces polyketides, it may be desirable to modify the host so as to prevent the production of endogenous polyketides prior to its use to express a recombinant PKS of the invention. Such hosts have been described, for example, in U.S. Pat. No. 5,672,491, incorporated herein by reference. In such hosts, it may not be necessary to provide enzymatic activities for all of the desired post-transactional modifications of the enzymes that make up the recombinantly produced PKS, because the host naturally expresses such enzymes. In particular, these hosts generally contain holo-ACP synthases that provide the pantotheinyl residue needed for functionality of the PKS. Thus, in one important embodiment, the vectors of the invention are used to transform Streptomyces host cells to provide the recombinant Streptomyces host cells of the invention. Streptomyces is a convenient host for expressing narbonolide or 10-deoxymethynolide or derivatives of those compounds, because narbonolide and 10-deoxymethynolide are naturally produced in certain Streptomyces species, and Streptomyces generally produce the precursors needed to form the desired polyketide. The present invention also provides the narbonolide PKS gene promoter in recombinant form, located upstream of the picAI gene on cosmid pKOS023-27. This promoter can be used to drive expression of the narbonolide PKS or any other coding sequence of interest in host cells in which the promoter functions, particularly $S.$ $venezuelae$ and generally any Streptomyces species. As described below, however, promoters other than the promoter of the narbonolide PKS genes will typically be used for heterologous expression.

For purposes of the invention, any host cell other than *Streptomyces venezuelae* is a heterologous host cell. Thus, *S. narbonensis*, which produces narbomycin but not picromycin is a heterologous host cell of the invention, although other host cells are generally preferred for purposes of heterologous expression. Those of skill in the art will recognize that, if a Streptomyces host that produces a picromycin or methymycin precursor is used as the host cell, the recombinant vector need drive expression of only a portion of the genes constituting the picromycin gene cluster. As used herein, the picromycin gene cluster includes the narbonolide PKS, the desosamine biosynthetic and transferase genes, the beta-glucosidase gene, and the picK hydroxylase gene. Thus, such a vector may comprise only a single ORF, with the desired remainder of the polypeptides encoded by the picromycin gene cluster provided by the genes on the host cell chromosomal DNA.

The present invention also provides compounds and recombinant DNA vectors useful for disrupting any gene in the picromycin gene cluster (as described above and illustrated in the examples below). Thus, the invention provides a variety of modified host cells (particularly, *S. narbonensis* and *S. venezuelae*) in which one or more of the genes in the picromycin gene cluster have been disrupted. These cells are especially useful when it is desired to replace the disrupted function with a gene product expressed by a recombinant DNA vector. Thus, the invention provides such Streptomyces host cells, which are preferred host cells for expressing narbonolide derivatives of the invention. Particularly preferred host cells of this type include those in which the coding sequence for the loading module has been disrupted, those in which one or more of any of the PKS gene ORFs has been disrupted, and/or those in which the picK gene has been disrupted.

In a preferred embodiment, the expression vectors of the invention are used to construct a heterologous recombinant Streptomyces host cell that expresses a recombinant PKS of the invention. As noted above, a heterologous host cell for purposes of the present invention is any host cell other than *S. venezuelae*, and in most cases other than *S. narbonensis* as well. Particularly preferred heterologous host cells are those which lack endogenous functional PKS genes. Illustrative host cells of this type include the modified *Streptomyces coelicolor* CH999 and similarly modified *S. lividans* described in PCT publication No. WO 96/40968.

The invention provides a wide variety of expression vectors for use in Streptomyces. For replicating vectors, the origin of replication can be, for example and without limitation, a low copy number vector, such as SCP2* (see Hopwood et al., *Genetic Manipulation of Streptomyces: A Laboratory manual* (The John Innes Foundation, Norwich, U.K., 1985); Lydiate et al., 1985, *Gene* 35: 223–235; and Kieser and Melton, 1988, *Gene* 65: 83–91, each of which is incorporated herein by reference), SLP1.2 (Thompson et al., 1982, *Gene* 20: 51–62, incorporated herein by reference), and pSG5(ts) (Muth et al., 1989, *Mol. Gen. Genet.* 219: 341–348, and Bierman et al., 1992, *Gene* 116: 4349, each of which is incorporated herein by reference), or a high copy number vector, such as pIJ101 and pJV1 (see Katz et al., 1983, *J. Gen. Microbiol.* 129: 2703–2714; Vara et al., 1989, *J. Bacteriol.* 171: 5782–5781; and Servin-Gonzalez, 1993, *Plasmid* 30: 131–140, each of which is incorporated herein by reference). High copy number vectors are generally, however, not preferred for expression of large genes or multiple genes. For non-replicating and integrating vectors and generally for any vector, it is useful to include at least an *E. coli* origin of replication, such as from pUC, p1P, p1I, and pBR. For phage based vectors, the phage phiC31 and its derivative KC515 can be employed (see Hopwood et al., supra). Also, plasmid pSET152, plasmid pSAM, plasmids pSE101 and pSE211, all of which integrate site-specifically in the chromosomal DNA of *S. lividans*, can be employed.

Preferred Streptomyces host cell/vector combinations of the invention include *S. coelicolor* CH999 and *S. lividans* K4-114 host cells, which do not produce actinorhodin, and expression vectors derived from the pRM1 and pRM5 vectors, as described in U.S. Pat. No. 5,830,750 and U.S. patent application Ser. Nos. 08/828,898, filed Mar. 31, 1997, and 09/181,833, filed Oct. 28, 1998, each of which is incorporated herein by reference.

As described above, particularly useful control sequences are those that alone or together with suitable regulatory systems activate expression during transition from growth to stationary phase in the vegetative mycelium. The system contained in the illustrative plasmid pRM5, i.e., the actI/actIII promoter pair and the actII-ORF4 activator gene, is particularly preferred. Other useful Streptomyces promoters include without limitation those from the ermE gene and the melC1 gene, which act constitutively, and the tipA gene and the merA gene, which can be induced at any growth stage. In addition, the T7 RNA polymerase system has been transferred to Streptomyces and can be employed in the vectors and host cells of the invention. In this system, the coding sequence for the T7 RNA polymerase is inserted into a neutral site of the chromosome or in a vector under the control of the inducible merA promoter, and the gene of interest is placed under the control of the T7 promoter. As noted above, one or more activator genes can also be employed to enhance the activity of a promoter. Activator genes in addition to the actII-ORF4 gene described above include dnrI, redD, and ptpA genes (see U.S. patent application Ser. No. 09/181,833, supra).

Typically, the expression vector will comprise one or more marker genes by which host cells containing the vector can be identified and/or selected. Selectable markers are often preferred for recombinant expression vectors. A variety of markers are known that are useful in selecting for transformed cell lines and generally comprise a gene that confers a selectable phenotype on transformed cells when the cells are grown in an appropriate selective medium. Such markers include, for example, genes that confer antibiotic resistance or sensitivity to the plasmid. Alternatively, several polyketides are naturally colored, and this characteristic can provide a built-in marker for identifying cells. Preferred selectable markers include antibiotic resistance conferring genes. Preferred for use in Streptomyces host cells are the ermE (confers resistance to erythromycin and lincomycin), tsr (confers resistance to thiostrepton), aada (confers resistance to spectinomycin and streptomycin), aacC4 (confers resistance to apramycin, kanamycin, gentamicin, geneticin (G418), and neomycin), hyg (confers resistance to hygromycin), and vph (confers resistance to viomycin) resistance conferring genes.

To provide a preferred host cell and vector for purposes of the invention, the narbonolide PKS genes were placed on a recombinant expression vector that was transferred to the non-macrolide producing host *Streptomyces lividans* K4-114, as described in Example 3. Transformation of *S. lividans* K4-114 with this expression vector resulted in a strain which produced two compounds in similar yield (~5–10 mg/L each). Analysis of extracts by LC/MS followed by 1H-NMR spectroscopy of the purified compounds established their identity as narbonolide (FIG. 5, compound 4) and 10-deoxymethynolide (FIG. 5, compound 5), the respective 14 and 12-membered polyketide precursors of narbomycin and YC17.

To provide a host cell of the invention that produces the narbonolide PKS as well as an additional narbonolide biosynthetic gene and to investigate the possible role of the PIC TEII in picromycin biosynthesis, the picB gene was integrated into the chromosome to provide the host cell of the invention *Streptomyces lividans* K39-18. The picB gene was cloned into the Streptomyces genome integrating vector pSET152 (see Bierman et al., 1992, *Gene* 116: 43, incorporated herein by reference) under control of the same promoter (PactI) as the PKS on plasmid pKOS039-86.

A comparison of strains *Streptomyces lividans* K39-18/pKOS039-86 and K4-114/pKOS039-86 grown under identical conditions indicated that the strain containing TEII produced 4–7 times more total polyketide. This increased production indicates that the enzyme is functional in this strain and is consistent with the observation that yields fall to below 5% for both picromycin and methymycin when picB is disrupted in *S. venezuelae*. Because the production levels of compound 4 and 5 from K39-18/pKOS03986 increased by the same relative amounts, TEII does not appear to influence the ratio of 12 and 14-membered lactone ring formation. Thus, the invention provides methods of coexpressing the picB gene product or any other type II thioesterase with the narbonolide PKS or any other PKS in heterologous host cells to increase polyketide production. However, transformation of a 6-dEB-producing *Streptomyces lividans*/pCK7 strain with an expression vector of the invention that produces PIC TEII resulted in little or no increase in 6dEB levels, indicating that TEII enzymes may have some specificity for their cognate PKS complexes and that use of homologous TEII enzymes will provide optimal activity.

In accordance with the methods of the invention, picromycin biosynthetic genes in addition to the genes encoding the PKS and PIC TEII can be introduced into heterologous host cells. In particular, the picK gene, desosamine biosynthetic genes, and the desosaminyl transferase gene can be expressed in the recombinant host cells of the invention to produce any and all of the polyketides in the picromycin biosynthetic pathway (or derivatives thereof). Those of skill will recognize that the present invention enables one to select whether only the 12-membered polyketides, or only the 14-membered polyketides, or both 12- and 14-membered polyketides will be produced. To produce only the 12-membered polyketides, the invention provides expression vectors in which the last module is deleted or the KS domain of that module is deleted or rendered inactive. If module 6 is deleted, then one preferably deletes only the non-TE domain portion of that module or one inserts a heterologous TE domain, as the TE domain facilitates cleavage of the polyketide from the PKS and cyclization and thus generally increases yields of the desired polyketide. To produce only the 14-membered polyketides, the invention provides expression vectors in which the coding sequences of extender modules 5 and 6 are fused to provide only a single polypeptide.

In one important embodiment, the invention provides methods for desosaminylating polyketides or other compounds. In this method, a host cell other than *Streptomyces venezuelae* is transformed with one or more recombinant vectors of the invention comprising the desosamine biosynthetic and desosaminyl transferase genes and control sequences positioned to express those genes. The host cells so transformed can either produce the polyketide to be desosaminylated naturally or can be transformed with expression vectors encoding the PKS that produces the desired polyketide. Alternatively, the polyketide can be supplied to the host cell containing those genes. Upon production of the polyketide and expression of the desosamine biosynthetic and desosaminyl transferase genes, the desired desosaminylated polyketide is produced. This method is especially useful in the production of polyketides to be used as antibiotics, because the presence of the desosamine residue is known to increase, relative to their undesosaminylated counterparts, the antibiotic activity of many polyketides significantly. The present invention also provides a method for desosaminylating a polyketide by transforming an *S. venezuelae* or *S. narbonensis* host cell with a recombinant vector that encodes a PKS that produces the polyketide and culturing the transformed cell under conditions such that said polyketide is produced and desosaminylated. In this method, use of an *S. venezuelae* or *S. narbonensis* host cell of the invention that does not produce a functional endogenous narbonolide PKS is preferred.

In a related aspect, the invention provides a method for improving the yield of a desired desosaminylated polyketide in a host cell, which method comprises transforming the host cell with a beta-glucosidase gene. This method is not limited to host cells that have been transformed with expression vectors of the invention encoding the desosamine biosynthetic and desosaminyl transferase genes of the invention but instead can be applied to any host cell that desosaminylates polyketides or other compounds. Moreover, while the beta-glucosidase gene from *Streptomyces venezuelae* provided by the invention is preferred for use in the method, any beta-glucosidase gene may be employed. In another embodiment, the beta-glucosidase treatment is conducted in a cell free extract.

Thus, the invention provides methods not only for producing narbonolide and 10-deoxymethynolide in heterologous host cells but also for producing narbomycin and YC-17 in heterologous host cells. In addition, the invention provides methods for expressing the picK gene product in heterologous host cells, thus providing a means to produce picromycin, methymycin, and neomethymycin in heterologous host cells. Moreover, because the recombinant expression vectors provided by the invention enable the artisan to provide for desosamine biosynthesis and transfer and/or C10 or C12 hydroxylation in any host cell, the invention provides methods and reagents for producing a very wide variety of glycosylated and/or hydroxylated polyketides. This variety of polyketides provided by the invention can be better appreciated upon consideration of the following section relating to the production of polyketides from heterologous or hybrid PKS enzymes provided by the invention.

Section V: Hybrid PKS Genes

The present invention provides recombinant DNA compounds encoding each of the domains of each of the modules of the narbonolide PKS, the proteins involved in desosamine biosynthesis and transfer to narbonolide, and the PicK protein. The availability of these compounds permits their use in recombinant procedures for production of desired portions of the narbonolide PKS fused to or expressed in conjunction with all or a portion of a heterologous PKS. The resulting hybrid PKS can then be expressed in a host cell, optionally with the desosamine biosynthesis and transfer genes and/or the picK hydroxylase gene to produce a desired polyketide.

Thus, in accordance with the methods of the invention, a portion of the narbonolide PKS coding sequence that encodes a particular activity can be isolated and manipulated, for example, to replace the corresponding region in a different modular PKS. In addition, coding sequences for individual modules of the PKS can be ligated into suitable expression systems and used to produce the portion of the protein encoded. The resulting protein can be isolated and purified or can may be employed in situ to effect polyketide synthesis. Depending on the host for the recombinant production of the domain, module, protein, or combination of proteins, suitable control sequences such as promoters, termination sequences, enhancers, and the like are ligated to the nucleotide sequence encoding the desired protein in the construction of the expression vector.

In one important embodiment, the invention thus provides a hybrid PKS and the corresponding recombinant DNA compounds that encode those hybrid PKS enzymes. For purposes of the invention, a hybrid PKS is a recombinant PKS that comprises all or part of one or more extender modules, loading module, and/or thioesterase/cyclase domain of a first PKS and all or part of one or more extender modules, loading module, and/or thioesterase/cyclase domain of a second PKS. In one preferred embodiment, the first PKS is most but not all of the narbonolide PKS, and the second PKS is only a portion or all of a non-narbonolide PKS. An illustrative example of such a hybrid PKS includes a narbonolide PKS in which the natural loading module has been replaced with a loading module of another PKS. Another example of such a hybrid PKS is a narbonolide PKS in which the AT domain of extender module 3 is replaced with an AT domain that binds only malonyl CoA.

In another preferred embodiment, the first PKS is most but not all of a non-narbonolide PKS, and the second PKS is only a portion or all of the narbonolide PKS. An illustrative example of such a hybrid PKS includes a DEBS PKS in which an AT specific for methylmalonyl CoA is replaced with the AT from the narbonolide PKS specific for malonyl CoA.

Those of skill in the art will recognize that all or part of either the first or second PKS in a hybrid PKS of the invention need not be isolated from a naturally occurring source. For example, only a small portion of an AT domain determines its specificity. See U.S. provisional patent application Serial No. 60/091,526, and Lau et al., infra, incorporated herein by reference. The state of the art in DNA synthesis allows the artisan to construct de novo DNA compounds of size sufficient to construct a useful portion of a PKS module or domain. Thus, the desired derivative coding sequences can be synthesized using standard solid phase synthesis methods such as those described by Jaye et al., 1984, *J. Biol. Chem.* 259: 6331, and instruments for automated synthesis are available commercially from, for example, Applied Biosystems, Inc. For purposes of the invention, such synthetic DNA compounds are deemed to be a portion of a PKS.

With this general background regarding hybrid PKSs of the invention, one can better appreciate the benefit provided by the DNA compounds of the invention that encode the individual domains, modules, and proteins that comprise the narbonolide PKS. As described above, the narbonolide PKS is comprised of a loading module, six extender modules composed of a KS, AT, ACP, and optional KR, DH, and ER domains, and a thioesterase domain. The DNA compounds of the invention that encode these domains individually or in combination are useful in the construction of the hybrid PKS encoding DNA compounds of the invention.

The recombinant DNA compounds of the invention that encode the loading module of the narbonolide PKS and the corresponding polypeptides encoded thereby are useful for a variety of applications. In one embodiment, a DNA compound comprising a sequence that encodes the narbonolide PKS loading module is inserted into a DNA compound that comprises the coding sequence for a heterologous PKS. The resulting construct, in which the coding sequence for the loading module of the heterologous PKS is replaced by that for the coding sequence of the narbonolide PKS loading module provides a novel PKS. Examples include the 6-deoxyerythronolide B, rapamycin, FK506, FK520, rifamycin, and avernectin PKS coding sequences. In another embodiment, a DNA compound comprising a sequence that encodes the narbonolide PKS loading module is inserted into a DNA compound that comprises the coding sequence for the narbonolide PKS or a recombinant narbonolide PKS that produces a narbonolide derivative in a different location in the modular system.

In another embodiment, a portion of the loading module coding sequence is utilized in conjunction with a heterologous coding sequence. In this embodiment, the invention provides, for example, replacing the propionyl CoA specific AT with an acetyl CoA, butyryl CoA, or other CoA specific AT. In addition, the $KS^Q$ and/or ACP can be replaced by another inactivated KS and/or another ACP. Alternatively, the $KS^Q$, AT, and ACP of the loading module can be replaced by an AT and ACP of a loading module such as that of DEBS. The resulting heterologous loading module coding sequence can be utilized in conjunction with a coding sequence for a PKS that synthesizes narbonolide, a narbonolide derivative, or another polyketide.

The recombinant DNA compounds of the invention that encode the first extender module of the narbonolide PKS and the corresponding polypeptides encoded thereby are useful for a variety of applications. In one embodiment, a DNA compound comprising a sequence that encodes the narbonolide PKS first extender module is inserted into a DNA compound that comprises the coding sequence for a heterologous PKS. The resulting construct, in which the coding sequence for a module of the heterologous PKS is either replaced by that for the first extender module of the narbonolide PKS or the latter is merely added to coding sequences for modules of the heterologous PKS, provides a novel PKS coding sequence. In another embodiment, a DNA compound comprising a sequence that encodes the first extender module of the narbonolide PKS is inserted into a DNA compound that comprises coding sequences for the narbonolide PKS or a recombinant narbonolide PKS that produces a narbonolide derivative or into a different location in the modular system.

In another embodiment, a portion or all of the first extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or carboxyglycolyl CoA specific AT; deleting (which includes inactivating) the KR; inserting a DH or a DH and ER; and/or replacing the KR with another KR, a DH and KR, or a DH, KR, and ER. In addition, the KS and/or ACP can be replaced with another KS and/or ACP. In each of these replacements or insertions, the heterologous KS, AT, DH, KR, ER, or ACP coding sequence can originate from a coding sequence for another module of the narbonolide PKS, from a gene for a PKS that produces a polyketide other than narbonolide, or from chemical synthesis. The resulting heterologous first extender module coding sequence can be utilized in conjunction with a coding sequence for a PKS that synthesizes narbonolide, a narbonolide derivative, or another polyketide.

In an illustrative embodiment of this aspect of the invention, the invention provides recombinant PKSs and recombinant DNA compounds and vectors that encode such PKSs in which the KS domain of the first extender module has been inactivated. Such constructs are especially useful when placed in translational reading frame with the, remaining modules and domains of a narbonolide PKS or narbonolide derivative PKS. The utility of these constructs is that host cells expressing, or cell free extracts containing, the PKS encoded thereby can be fed or supplied with N-acetylcysteamine thioesters of novel precursor molecules to prepare narbonolide derivatives. See U.S. patent application Ser. No. 60/117,384, filed Jan. 27, 1999, and PCT publication Nos. WO 99/03986 and WO 97/02358, each of which is incorporated herein by reference.

The recombinant DNA compounds of the invention that encode the second extender module of the narbonolide PKS and the corresponding polypeptides encoded thereby are useful for a variety of applications. In one embodiment, a DNA compound comprising a sequence that encodes the narbonolide PKS second extender module is inserted into a DNA compound that comprises the coding sequence for a heterologous PKS. The resulting construct, in which the coding sequence for a module of the heterologous PKS is either replaced by that for the second extender module of the narbonolide PKS or the latter is merely added to coding sequences for the modules of the heterologous PKS, provides a novel PKS. In another embodiment, a DNA compound comprising a sequence that encodes the second extender module of the narbonolide PKS is inserted into a DNA compound that comprises the coding sequences for the narbonolide PKS or a recombinant narbonolide PKS that produces a narbonolide derivative.

In another embodiment, a portion or all of the second extender module coding sequence is utilized in conjunction with other PKS coding sequences to create a hybrid module. In this embodiment, the invention provides, for example, replacing the malonyl CoA specific AT with a methylmalonyl CoA, ethyimalonyl CoA, or carboxyglycolyl CoA specific AT; deleting (or inactivating) the KR, the DH, or both the DH and KR; replacing the KR or the KR and DH with a KR, a KR and a DH, or a KR, DH, and ER; and/or inserting an ER. In addition, the KS and/or ACP can be replaced with another KS and/or ACP. In each of these replacements or insertions, the heterologous KS, AT, DH, KR, ER, or ACP coding sequence can originate from a coding sequence for another module of the narbonolide PKS, from a coding sequence for a PKS that produces a polyketide other than narbonolide, or from chemical synthesis. The resulting heterologous second extender module coding sequence can be utilized in conjunction with a coding sequence from a PKS that synthesizes narbonolide, a narbonolide derivative, or another polyketide.

The recombinant DNA compounds of the invention that encode the third extender module of thenarbonolide PKS and the corresponding polypeptides encoded thereby are useful for a variety of applications. In one embodiment, a DNA compound comprising a sequence that encodes the narbonolide PKS third extender module is inserted into a DNA compound that comprises the coding sequence for a heterologous PKS. The resulting construct, in which the coding sequence for a module of the heterologous PKS is either replaced by that for the third extender module of the narbonolide PKS or the latter is merely added to coding sequences for the modules of the heterologous PKS, provides a novel PKS. In another embodiment, a DNA compound comprising a sequence that encodes the third extender module of the narbonolide PKS is inserted into a DNA compound that comprises coding sequences for the narbonolide PKS or a recombinant narbonolide PKS that produces a narbonolide derivative.

In another embodiment, a portion or all of the third extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or carboxyglycolyl CoA specific AT; deleting the inactive KR; and/or inserting a KR, or a KR and DH, or a KR, DH, and ER. In addition, the KS and/or ACP can be replaced with another KS and/or ACP. In each of these replacements or insertions, the heterologous KS, AT, DH, KR, ER, or ACP coding sequence can originate from a coding sequence for another module of the narbonolide PKS, from a gene for a PKS that produces a polyketide other than narbonolide, or from chemical synthesis. The resulting heterologous third extender module coding sequence can be utilized in conjunction with a coding sequence for a PKS that synthesizes narbonolide, a narbonolide derivative, or another polyketide.

The recombinant DNA compounds of the invention that encode the fourth extender module of the narbonolide PKS and the corresponding polypeptides encoded thereby are useful for a variety of applications. In one embodiment, a DNA compound comprising a sequence that encodes the narbonolide PKS fourth extender module is inserted into a DNA compound that comprises the coding sequence for a heterologous PKS. The resulting construct, in which the coding sequence for a module of the heterologous PKS is either replaced by that for the fourth extender module of the narbonolide PKS or the latter is merely added to coding sequences for the modules of the heterologous PKS, provides a novel PKS. In another embodiment, a DNA compound comprising a sequence that encodes the fourth extender module of the narbonolide PKS is inserted into a DNA compound that comprises coding sequences for the narbonolide PKS or a recombinant narbonolide PKS that produces a narbonolide derivative.

In another embodiment, a portion of the fourth extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or carboxyglycolyl CoA specific AT; deleting any one, two, or all three of the ER, DH, and KR; and/or replacing any one. two, or all three of the ER, DH, and KR with either a KR, a DH and KR, or a KR, DH, and ER. In addition, the KS and/or ACP can be replaced with another KS and/or ACP. In each of these replacements or insertions, the heterologous KS, AT, DH, KR, ER, or ACP coding sequence can originate from a coding sequence for another module of the narbonolide PKS, from a coding sequence for a PKS that produces a polyketide other than narbonolide, or from chemical synthesis. The resulting heterologous fourth extender module coding sequence can be utilized in conjunction with a coding sequence for a PKS that synthesizes narbonolide, a narbonolide derivative, or another polyketide.

The recombinant DNA compounds of the invention that encode the fifth extender module of the narbonolide PKS and the corresponding polypeptides encoded thereby are useful for a variety of applications. In one embodiment, a DNA compound comprising a sequence that encodes the narbonolide PKS fifth extender module is inserted into a DNA compound that comprises the coding sequence for a heterologous PKS. The resulting construct, in which the coding sequence for a module of the heterologous PKS is either replaced by that for the fifth extender module of the narbonolide PKS or the latter is merely added to coding sequences for the modules of the heterologous PKS, provides a novel PKS. In another embodiment, a DNA compound comprising a sequence that encodes the fifth extender module of the narbonolide PKS is inserted into a DNA compound that comprises the coding sequence for the narbonolide PKS or a recombinant narbonolide PKS that produces a narbonolide derivative.

In another embodiment, a portion or all of the fifth extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or carboxyglycolyl CoA specific AT; deleting (or inactivating) the KR; inserting a DH or a DH and ER; and/or replacing the KR with another KR, a DH and KR, or a DH, KR, and ER. In addition, the KS and/or ACP can be replaced with another KS and/or ACP. In each of these replacements or insertions, the heterologous KS, AT, DH, KR, ER, or ACP coding sequence can originate from a coding sequence for another module of the narbonolide PKS, from a coding sequence for a PKS that produces a polyketide other than narbonolide, or from chemical synthesis. The resulting heterologous fifth extender module coding sequence can be utilized in conjunction with a coding sequence for a PKS that synthesizes narbonolide, a narbonolide derivative, or another polyketide.

The recombinant DNA compounds of the invention that encode the sixth extender module of the narbonolide PKS and the corresponding polypeptides encoded thereby are useful for a variety of applications. In one embodiment, a DNA compound comprising a sequence that encodes the narbonolide PKS sixth extender module is inserted into a DNA compound that comprises the coding sequence for a heterologous PKS. The resulting construct, in which the coding sequence for a module of the heterologous PKS is either replaced by that for the sixth extender module of the narbonolide PKS or the latter is merely added to coding sequences for the modules of the heterologous PKS, provides a novel PKS. In another embodiment, a DNA compound comprising a sequence that encodes the sixth extender module of the narbonolide PKS is inserted into a DNA compound that comprises the coding sequences for the narbonolide PKS or a recombinant narbonolide PKS that produces a narbonolide derivative.

In another embodiment, a portion or all of the sixth extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or carboxyglycolyl CoA specific AT; and/or inserting a KR, a KR and DH, or a KR, DH, and an ER. In addition, the KS and/or ACP can be replaced with another KS and/or ACP. In each of these replacements or insertions, the heterologous KS, AT, DH, KR, ER, or ACP coding. sequence can originate from a coding sequence for another module of the narbonolide PKS, from a coding sequence for a PKS that produces a polyketide other than narbonolide, or from chemical synthesis. The resulting heterologous sixth extender module coding sequence can be utilized in conjunction with a coding sequence for a PKS that synthesizes narbonolide, a narbonolide derivative, or another polyketide.

The sixth extender module of the narbonolide PKS is followed by a thioesterase domain. This domain is important in the cyclization of the polyketide and its cleavage from the PKS. The present invention provides recombinant DNA compounds that encode hybrid PKS enzymes in which the narbonolide PKS is fused to a heterologous thioesterase or a heterologous PKS is fused to the narbonolide synthase thioesterase. Thus, for example, a thioesterase domain coding sequence from another PKS gene can be inserted at the end of the sixth extender module coding sequence in recombinant DNA compounds of the invention. Recombinant DNA compounds encoding this thioesterase domain are therefore useful in constructing DNA compounds that encode the narbonolide PKS, a PKS that produces a narbonolide derivative, and a PKS that produces a polyketide other than narbonolide or a narbonolide derivative.

The following Table lists references describing illustrative PKS genes and corresponding enzymes that can be utilized in the construction of the recombinant hybrid PKSs and the corresponding DNA compounds that encode them of the invention. Also presented are various references describing tailoring enzymes and corresponding genes that can be employed in accordance with the methods of the invention.

Avermectin

U.S. Pat. No. 5,252,474 to Merck.

MacNeil et al., 1993, *Industrial Microorganisms: Basic and Applied Molecular Genetics*, Baltz, Hegeman, & Skatrud, eds. (ASM), pp. 245–256, A Comparison of the Genes Encoding the Polyketide Synthases for Avermectin, Erythromycin, and Nemadectin.

MacNeil et al., 1992, *Gene* 115: 119–125, Complex Organization of the *Streptomyces avermitilis* genes encoding the avermectin polyketide synthase.

Candicidin (FR008)

Hu et al., 1994, *Mol. Microbiol.* 14: 163–172.

Epothilone

U.S. patent application Ser. No. 60/130,560, filed Apr. 22, 1999, and Ser. No. 60/122,620, filed Mar. 3, 1999.

Erythromycin

PCT Pub. No. WO 93/13663 to Abbott.

U.S. Pat. No. 5,824,513 to Abbott.

Donadio et al., 1991, *Science* 252:675–9.

Cortes et al., Nov. 8, 1990, *Nature* 348:176–8, An unusually large multifunctional polypeptide in the erythromycin producing polyketide synthase of *Saccharopolyspora erythraea*.

Glycosylation Enzymes

PCT Pat. App. Pub. No. WO 97/23630 to Abbott.

FK506

Motamedi et al., 1998, The biosynthetic gene cluster for the macrolactone ring of the immunosuppressant FK506, *Eur. J. Biochem.* 256: 528–534.

Motamedi et al., 1997, Structural organization of a multifunctional polyketide synthase involved in the biosynthesis of the macrolide immunosuppressant FK506, *Eur. J. Biochem.* 244: 74–80.

Methyltransferase

U.S. Pat. No. 5,264,355, issued Nov. 23, 1993, Methylating enzyme from Streptomyces MA6858. 31-O-desmethyl-FK506 methyltransferase.

Motamedi et al., 1996, Characterization of methyltransferase and hydroxylase genes involved in the biosynthesis of the immunosuppressants FK506 and FK520, *J. Bacteriol.* 178: 5243–5248.

FK520

U.S. patent application Ser. No. 60/123,800, filed Mar. 11, 1999.

Immunomycin

Nielsen et al., 1991, Biochem. 30:5789–96.

Lovastatin
U.S. Pat. No. 5,744,350 to Merck.
Nemadectin
MacNeil et al., 1993, supra.
Niddaymcin
Kakavas et al., 1997, Identification and characterization of the niddamycin polyketide synthase genes from *Streptomyces caelestis*, *J. Bacteriol.* 179: 7515–7522.
Oleandomycin
Swan et al., 1994, Characterization of a *Streptomyces antibioticus* gene encoding a type I polyketide synthase which has an unusual coding sequence, *Mol. Gen. Genet.* 242: 358–362.
Olano et al., 1998, Analysis of a Streptomyces antibioticus chromosomal region involved in oleandomycin biosynthesis, which encodes two glycosyltransferases responsible for glycosylation of the macrolactone ring, Mol. Gen. Genet. 259(3): 299–308.
U.S. patent application Ser. No. 60/120,254, filed Feb. 16, 1999, and Serial No. 60/106,100, filed Oct. 29, 1998.
Platenolide
EP Pat. App. Pub. No. 791,656 to Lilly.
Pradimicin
PCT Pat. Pub. No. WO 98/11230 to Bristol-Myers Squibb.
Rapamycin
Schwecke et al., August 1995, The biosynthetic gene cluster for the polyketide rapamycin, *Proc. Natl. Acad. Sci. USA* 92:7839–7843.
Aparicio et al., 1996, Organization of the biosynthetic gene cluster for rapamycin in *Streptomyces hygroscopicus*: analysis of the enzymatic domains in the modular polyketide synthase, Gene 169: 9–16.
Rifamycin
August et al., Feb. 13, 1998, Biosynthesis of the ansamycin antibiotic rifamycin: deductions from the molecular analysis of the rif biosynthetic gene cluster of *Amycolatopsis mediterranei* S669, *Chemistry & Biology*, 5(2): 69–79.
Soraphen
U.S. Pat. No. 5,716,849 to Novartis.
Schupp et al., 1995, *J. Bacteriology* 177: 3673–3679. A *Sorangium cellulosum* (Myxobacterium) Gene Cluster for the Biosynthesis of the Macrolide Antibiotic Soraphen A: Cloning, Characterization, and Homology to Polyketide Synthase Genes from Actinomycetes.
Spiramycin
U.S. Pat. No. 5,098,837 to Lilly.
Activator Gene
U.S. Pat. No. 5,514,544 to Lilly.
Tylosin
EP Pub. No. 791,655 to Lilly.
Kuhstoss et al., 1996, *Gene* 183:231–6., Production of a novel polyketide through the construction of a hybrid polyketide synthase.
U.S. Pat. No. 5,876,991 to Lilly.
Tailoring enzymes
Merson-Davies and Cundliffe, 1994, *Mol. Microbiol.* 13: 349–355. Analysis of five tylosin biosynthetic genes from the tylBA region of the *Streptomyces fradiae* genome.

As the above Table illustrates, there is a wide variety of PKS genes that serve as readily available sources of DNA and sequence information for use in constructing the hybrid PKS-encoding DNA compounds of the invention. Methods for constructing hybrid PKS-encoding DNA compounds are described without reference to the narbonolide PKS in U.S. Pat. Nos. 5,672,491 and 5,712,146 and PCT publication No. WO 98/49315, each of which is incorporated herein by reference.

In constructing hybrid PKSs of the invention, certain general methods may be helpful. For example, it is often beneficial to retain the framework of the module to be altered to make the hybrid PKS. Thus, if one desires to add DH and ER functionalities to a module, it is often preferred to replace the KR domain of the original module with a KR, DH, and ER domain-containing segment from another module, instead of merely inserting DH and ER domains. One can alter the stereochemical specificity of a module by replacement of the KS domain with a KS domain from a module that specifies a different stereochemistry. See Lau et al., 1999, "Dissecting the role of acyltransferase domains of modular polyketide synthases in the choice and stereochemical fate of extender units" *Biochemistry* 38(5):1643–1651, incorporated herein by reference. One can alter the specificity of an AT domain by changing only a small segment of the domain. See Lau et al., supra. One can also take advantage of known linker regions in PKS proteins to link modules from two different PKSs to create a hybrid PKS. See Gokhale et al., Apr. 16, 1999, Dissecting and Exploiting Intermodular Communication' in Polyketide Synthases", *Science* 284: 482–485, incorporated herein by reference.

The hybrid PKS-encoding DNA compounds of the invention can be and often are hybrids of more than two PKS genes. Even where only two genes are used, there are often two or more modules in the hybrid gene in which all or part of the module is derived from a second (or third) PKS gene. Thus, as one illustrative example, the invention provides a hybrid narbonolide PKS that contains the naturally occurring loading module and thioesterase domain as well as extender modules one, two, four, and six of the narbonolide PKS and further contains hybrid or heterologous extender modules three and five. Hybrid or heterologous extender modules three and five contain AT domains specific for malonyl CoA and derived from, for example, the rapamycin PKS genes.

To construct a hybrid PKS or narbonolide derivative PKS of the invention, one can employ a technique, describedin PCT Pub. No. WO 98/27203, which is incorporated herein by reference, in which the large PKS gene cluster is divided into two or more, typically three, segments, and each segment is placed on a separate expression vector. In this manner, each of the segments of the gene can be altered, and various altered segments can be combined in a single host cell to provide a recombinant PKS gene of the invention. This technique makes more efficient the construction of large libraries of recombinant PKS genes, vectors for expressing those genes, and host cells comprising those vectors.

Included in the definition of "hybrid" are PKS where alterations (including deletions, insertions and substitutions) are made directly using the narbonolide PKS as a substrate.

The invention also provides libraries of PKS genes, PKS proteins, and ultimately, of polyketides, that are constructed by generating modifications in the narbonolide PKS so that the protein complexes produced have altered activities in one or more respects and thus produce polyketides other than the natural product of the PKS. Novel polyketides may thus be prepared, or polyketides in general prepared more readily, using this method. By providing a large number of different genes or gene clusters derived from a naturally occurring PKS gene cluster, each of which has been modified in a different way from the native cluster, an effectively combinatorial library of polyketides can be produced as a result of the multiple variations in these activities. As will be further described below, the metes and bounds of this embodiment of the invention can be described on both the protein level and the encoding nucleotide sequence level.

As described above, a modular PKS "derived from" the narbonolide or other naturally occurring PKS is a subset of the "hybrid" PKS family and includes a modular PKS (or its corresponding encoding gene(s)) that retains the scaffolding of the utilized portion of the naturally occurring gene. Not all modules need be included in the constructs. On the constant scaffold, at least one enzymatic activity is mutated, deleted, replaced, or inserted so as to alter the activity of the resulting PKS relative to the original PKS. Alteration results when these activities are deleted or are replaced by a different version of the activity, or simply mutated in such a way that a polyketide other than the natural product results from these collective activities. This occurs because there has been a resulting alteration of the starter unit and/or extender unit, and/or stereochemistry, and/or chain length or cyclization, and/or reductive or dehydration cycle outcome at a corresponding position in the product polyketide. Where a deleted activity is replaced, the origin of the replacement activity may come from a corresponding activity in a different naturally occurring PKS or from a different region of the narbonolide PKS. Any or all of the narbonolide PKS genes may be included in the derivative or portions of any of these may be included, but the scaffolding of the PKS protein is retained in whatever derivative is constructed. The derivative preferably contains a thioesterase activity from the narbonolide or another PKS.

In summary, a PKS "derived from" the narbonolide PKS includes a PKS that contains the scaffolding of all or a portion of the narbonolide PKS. The derived PKS also contains at least two extender modules that are functional, preferably three extender modules, and more preferably four or more extender modules, and most preferably six extender modules. The derived PKS also contains mutations, deletions, insertions, or replacements of one or more of the activities of the functional modules of the narbonolide PKS so that the nature of the resulting polyketide is altered. This definition applies both at the protein and DNA sequence levels. Particular preferred embodiments include those wherein a KS, AT, KR, DH, or ER has been deleted or replaced by a version of the activity from a different PKS or from another location within the same PKS. Also preferred are derivatives where at least one non-condensation cycle enzymatic activity (KR, DH, or ER) has been deleted or added or wherein any of these activities has been mutated so as to change the structure of the polyketide synthesized by the PKS.

Conversely, also included within the definition of a PKS derived from the narbonolide PKS are functional PKS modules or their encoding genes wherein at least one portion, preferably two portions, of the narbonolide PKS activities have been inserted. Exemplary is the use of the narbonolide AT for extender module 2 which accepts a malonyl CoA extender unit rather than methylmalonyl CoA to replace a methylmalonyl specific AT in a PKS. Other examples include insertion of portions of nonondensation cycle enzymatic activities or other regions of narbonolide synthase activity into a heterologous PKS. Again, the derived from definition applies to the PKS at both the genetic and protein levels.

Thus, there are at least five degrees of freedom for constructing a hybrid PKS in terms of the polyketide that will be produced. First, the polyketide chain length is determined by the number of modules in the PKS. Second, the nature of the carbon skeleton of the PKS is determined by the specificities of the acyl transferases that determine the nature of the extender units at each position, e.g., malonyl, methylmalonyl, ethylmalonyl, or other substituted malonyl.

Third, the loading module specificity also has an effect on the resulting carbon skeleton of the polyketide. The loading module may use a different starter unit, such as acetyl, butyryl, and the like. As noted above and in the examples below, another method for varying loading module specificity involves inactivating the KS activity in extender module 1 (KS 1) and providing alternative substrates, called diketides that are chemically synthesized analogs of extender module 1 diketide products, for extender module 2. This approach was illustrated in PCT publication Nos. WO 97/02358 and WO 99/03986, incorporated herein by reference, wherein the KS1 activity was inactivated through mutation. Fourth, the oxidation state at various positions of the polyketide will be determined by the dehydratase and reductase portions of the modules. This will determine the presence and location of ketone and alcohol moieties and C—C double bonds or C—C single bonds in the polyketide. Finally, the stereochemistry of the resulting polyketide is a function of three aspects of the synthase. The first aspect is related to the AT/KS specificity associated with substituted malonyls as extender units, which affects stereochemistry only when the reductive cycle is missing or when it contains only a ketoreductase, as the dehydratase would abolish chirality. Second, the specificity of the ketoreductase may determine the chirality of any beta-OH. Finally, the enoyl-reductase specificity for substituted malonyls as extender units may influence the result when there is a complete KR/DH/ER available.

Thus, the modular PKS systems, and in particular, the narbonolide PKS system, permit a wide range of polyketides to be synthesized. As compared to the aromatic PKS systems, a wider range of starter units including aliphatic monomers (acetyl, propionyl, butyryl, isovaleryl, etc.), aromatics (aminohydroxybenzoyl), alicyclics (cyclohexanoyl), and heterocyclics (thiazolyl) are found in various macrocyclic polyketides. Recent studies have shown that modular PKSs have relaxed specificity for their starter units (Kao et al., 1994, Science, supra). Modular PKSs also exhibit considerable variety with regard to the choice of extender units in each condensation cycle. The degree of beta-ketoreduction following a condensation reaction has also been shown to be altered by genetic manipulation (Donadio et al., 1991, Science, supra; Donadio et al., 1993, Proc. Natl. Acad. Sci. USA 90: 7119–7123). Likewise, the size of the polyketide product can be varied by designing mutants with the appropriate number of modules (Kao et al., 1994, J. Am. Chem. Soc. 116:11612–11613). Lastly, these enzymes are particularly well known for generating an impressive range of asymmetric centers in their products in a highly controlled manner. The polyketides and antibiotics produced by the methods of the invention are typically single stereoisomeric forms. Although the compounds of the invention can occur as mixtures of stereoisomers, it may be beneficial in some instances to generate individual stereoisomers. Thus, the combinatorial potential within modular PKS pathways based on any naturally occurring modular, such as the narbonolide, PKS scaffold is virtually unlimited.

The combinatorial potential is increased even further when one considers that mutations in DNA encoding a polypeptide can be used to introduce, alter, or delete an activity in the encoded polypeptide. Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion. See, e.g., Kunkel, 1985, *Proc. Natl. Acad. Sci. USA* 82: 448; Geisselsoder et al., 1987, *BioTechniques* 5:786. Alternatively, the mutations can be effected using a mismatched primer (generally 10–20 nucleotides in length) that hybridizes to the native nucleotide sequence, at a temperature below the melting temperature of the mismatched duplex. The primer can be made specific by keeping primer length and base composition within relatively narrow limits and by keeping the mutant base centrally located. See Zoller and Smith, 1983, *Methods Enzymol.* 100:468. Primer extension is effected using DNA polymerase, the product cloned, and clones containing the mutated DNA, derived by segregation of the primer extended strand, selected. Identification can be accomplished using the mutant primer as a hybridization probe. The technique is also applicable for generating multiple point mutations. See, e.g., Dalbie-McFarland et al., 1982, *Proc. Natl. Acad. Sci. USA* 79: 6409. PCR mutagenesis can also be used to effect the desired mutations.

Random mutagenesis of selected portions of the nucleotide sequences encoding enzymatic activities can also be accomplished by several different techniques known in the art, e.g., by inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants, or by damaging plasmid DNA in vitro with chemicals. Chemical mutagens include, for example, sodium bisulfite, nitrous acid, nitrosoguanidine, hydroxylamine, agents which damage or remove bases thereby preventing normal base-pairing such as hydrazine or formic acid, analogues of nucleotide precursors such as 5-bromouracil, 2-aminopurine, or acridine intercalating agents such as proflavine, acriflavine, quinacrine, and the like. Generally, plasmid DNA or DNA fragments are treated with chemicals, transformed into *E. coli* and propagated as a pool or library of mutant plasmids.

In constructing a hybrid PKS of the invention, regions encoding enzymatic activity, i.e., regions encoding corresponding activities from different PKS synthases or from different locations in the same PKS, can be recovered, for example, using PCR techniques with appropriate primers. By "corresponding" activity encoding regions is meant those regions encoding the same general type of activity. For example, a KR activity encoded at one location of a gene cluster "corresponds" to a KR encoding activity in another location in the gene cluster or in a different gene cluster. Similarly, a complete reductase cycle could be considered corresponding. For example, KR/DH/ER corresponds to KR alone.

If replacement of a particular target region in a host PKS is to be made, this replacement can be conducted in vitro using suitable restriction enzymes. The replacement can also be effected in vivo using recombinant techniques involving homologous sequences framing the replacement gene in a donor plasmid and a receptor region in a recipient plasmid. Such systems, advantageously involving plasmids of differing temperature sensitivities are described, for example, in PCT publication No. WO 96/40968, incorporated herein by reference. The vectors used to perform the various operations to replace the enzymatic activity in the host PKS genes or to support mutations in these regions of the host PKS genes can be chosen to contain control sequences operably linked to the resulting coding sequences in a manner such that expression of the coding sequences can be effected in an appropriate host.

However, simple cloning vectors may be used as well. If the cloning vectors employed to obtain PKS genes encoding derived PKS lack control sequences for expression operably linked to the encoding nucleotide sequences, the nucleotide sequences are inserted into appropriate expression vectors. This need not be done individually, but a pool of isolated encoding nucleotide sequences can be inserted into expression vectors, the resulting vectors transformed or transfected into host cells, and the resulting cells plated out into individual colonies.

The various PKS nucleotide sequences can be cloned into one or more recombinant vectors as individual cassettes, with separate control elements, or under the control of, e.g., a single promoter. The PKS subunit encoding regions can include flanking restriction sites to allow for the easy deletion and insertion of other PKS subunit encoding sequences so that hybrid PKSs can be generated. The design of such unique restriction sites is known to those of skill in the art and can be accomplished using the techniques described above, such as site-directed mutagenesis and PCR.

The expression vectors containing nucleotide sequences encoding a variety of PKS enzymes for the production of different polyketides are then transformed into the appropriate host cells to construct the library. In one straightforward approach, a mixture of such vectors is transformed into the selected host cells and the resulting cells plated into individual colonies and selected to identify successful transformants. Each individual colony has the ability to produce a particular PKS synthase and ultimately a particular polyketide. Typically, there will be duplications in some, most, or all of the colonies; the subset of the transformed colonies that contains a different PKS in each member colony can be considered the library. Alternatively, the expression vectors can be used individually to transform hosts, which transformed hosts are then assembled into a library. A variety of strategies are available to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, and more preferably at least 50, reflecting similar numbers of different altered PKS gene clusters and PKS gene products. The number of members in the library is arbitrarily chosen; however, the degrees of freedom outlined above with respect to the variation of starter, extender units, stereochemistry, oxidation state, and chain length is quite large.

Methods for introducing the recombinant vectors of the invention into suitable hosts are known to those of skill in the art and typically include the use of CaC12 or agents such as other divalent cations, lipofection, DMSO, protoplast transformation, infection, transfection, and electroporation. The polyketide producing colonies can be identified and isolated using known techniques and the produced polyketides further characterized. The polyketides produced by these colonies can be used collectively in a panel to represent a library or may be assessed individually for activity.

The libraries of the invention can thus be considered at four levels: (1) a multiplicity of colonies each with a different PKS encoding sequence; (2) colonies that contain the proteins that are members of the PKS library produced by the coding sequences; (3) the polyketides produced; and (4) antibiotics or compounds with other desired activities derived from the polyketides. Of course, combination libraries can also be constructed wherein members of a library derived, for example, from the narbonolide PKS can be considered as a part of the same library as those derived from, for example, the rapamycin PKS or DEBS.

Colonies in the library are induced to produce the relevant synthases and thus to produce the relevant polyketides to obtain a library of polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand. Binding can be detected either directly or through a competition assay. Means to screen such libraries for binding are well known in the art. Alternatively, individual polyketide members of the library can be tested against a desired target. In this event, screens wherein the biological response of the target is measured can more readily be included. Antibiotic activity can be verified using typical screening assays such as those set forth in Lehrer et al., 1991, *J. Immunol. Meth.* 137:167–173, incorporated herein by reference, and in the examples below.

The invention provides methods for the preparation of a large number of polyketides. These polyketides are useful intermediates in formation of compounds with antibiotic or other activity through hydroxylation and glycosylation reactions as described above. In general, the polyketide products of the PKS must be further modified, typically by hydroxylation and glycosylation, to exhibit antibiotic activity. Hydroxylation results in the novel polyketides of the invention that contain hydroxyl groups at C6, which can be accomplished using the hydroxylase encoded by the eryF gene, and/or C12, which can be accomplished using the hydroxylase encoded by the picK or eryK gene. The presence of hydroxyl groups at these positions can enhance the antibiotic activity of the resulting compound relative to its unhydroxylated counterpart.

Gycosylation is important in conferring antibiotic activity to a polyketide as well. Methods for glycosylating the polyketides are generally known in the art; the glycosylation may be effected intracellularly by providing the appropriate glycosylation enzymes or may be effected in vitro using chemical synthetic means as described herein and in PCT publication No. WO 98/49315, incorporated herein by reference. Preferably, glycosylation with desosamine is effected in accordance with the methods of the invention in recombinant host cells provided by the invention. In general, the approaches to effecting glycosylation mirror those described above with respect to hydroxylation. The purified enzymes, isolated from native sources or recombinantly produced may be used in vitro. Alternatively and as noted, glycosylation may be effected intracellularly using endogenous or recombinantly produced intracellular glycosylases. In addition, synthetic chemical methods may be employed.

The antibiotic modular polyketides may contain any of a number of different sugars, although D-desosamine, or a close analog thereof, is most common. Erythromycin, picromycin, narbomycin and methymycin contain desosamine. Erythromycin also contains L-cladinose (3-O-methyl mycarose). Tylosin contains mycaminose (4-hydroxy desosamine), mycarose and 6-deoxy-D-allose. 2-acetyl-1-bromodesosamine has been used as a donor to glycosylate polyketides by Masamune et al., 1975, *J. Am. Chem. Soc.* 97: 3512–3513. Other, apparently more stable donors include glycosyl fluorides, thioglycosides, and trichloroacetimidates; see Woodward et al., 1981, *J. Am. Chem. Soc.* 103: 3215; Martin et al., 1997, *J. Am. Chem. Soc.* 119: 3193; Toshima et al., 1995, *J. Am. Chem. Soc.* 117: 3717; Matsumoto et al., 1988, *Tetrahedron Lett.* 29: 3575. Glycosylation can also be effected using the polyketide aglycones as starting materials and using *Saccharopolyspora erythraea* or *Streptomyces venezuelae* to make the conversion, preferably using mutants unable to synthesize macrolides.

To provide an illustrative hybrid PKS of the invention as well as an expression vector for that hybrid PKS and host cells comprising the vector and producing the hybrid polyketide, a portion of the narbonolide PKS gene was fused to the DEBS genes. This construct also allowed the examination of whether the TE domain of the narbonolide PKS (pikTE) could promote formation of 12-membered lactones in the context of a different PKS. A construct was generated, plasmid pKOS039-18, in which the pikTE ORF was fused with the DEBS genes in place of the DEBS TE ORF (see FIG. 5). To allow the TE to distinguish between substrates most closely resembling those generated by the narbonolide PKS, the fusion junction was chosen between the AT and ACP to eliminate ketoreductase activity in DEBS extender module 6 ($KR^6$). This results in a hybrid PKS that presents the TE with a β-ketone heptaketide intermediate and a β-(S)-hydroxy hexaketide intermediate to cyclize, as in narbonolide and 10-deoxymethynolide biosynthesis.

Figure 5:
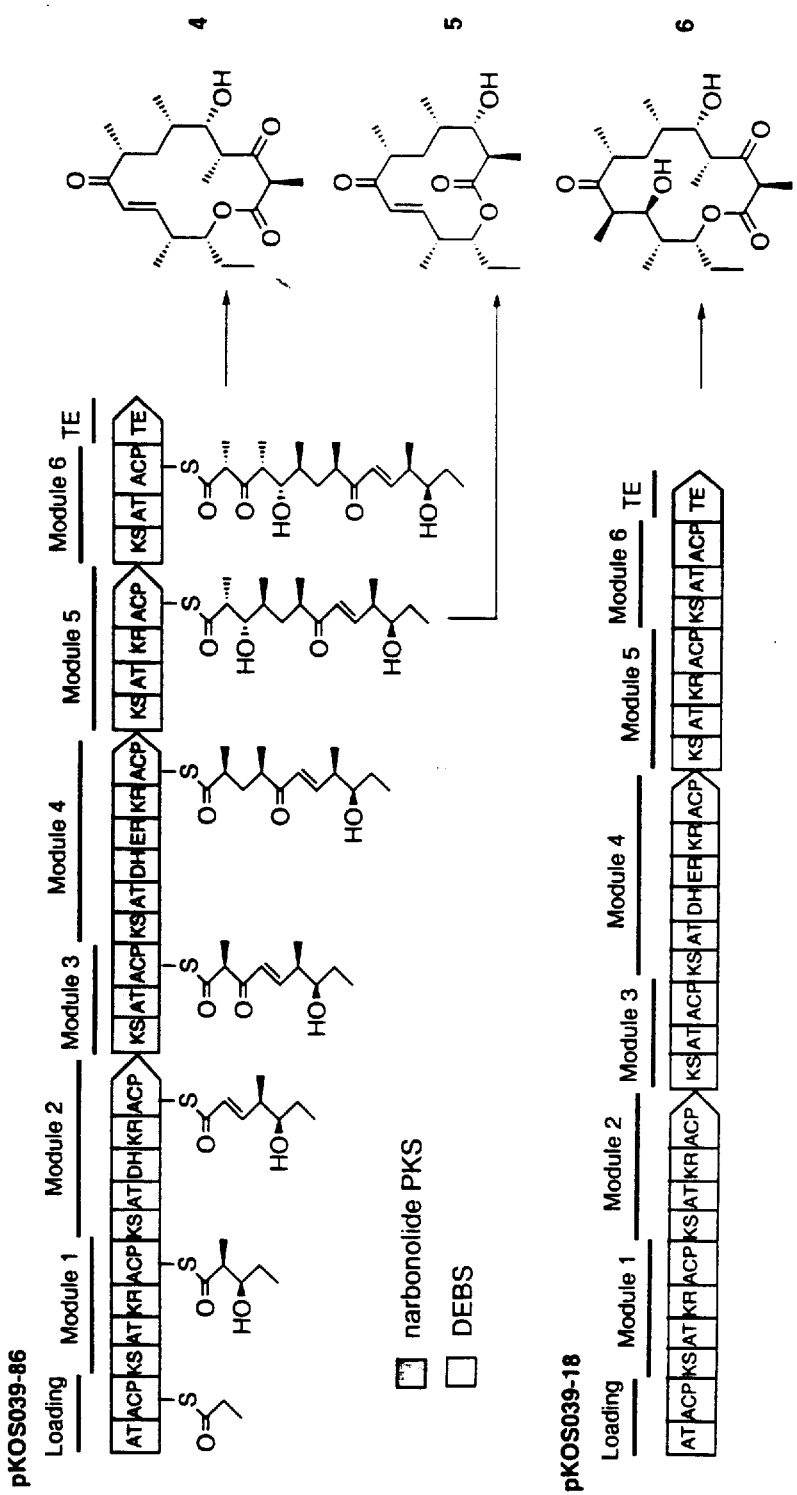
FIG. 5 shows the narbonolide PKS genes encoded by plasmid pKOS039-86, the compounds synthesized by each module of that PKS and the narbonolide (compound 4) and 10-deoxymethynolide (compound 5) products produced in heterologous host cells transformed with the plasmid. The Figure also shows a hybrid PKS of the invention produced by plasmid pKOS038-18, which encodes a hybrid of DEBS and the narbonolide PKS. The Figure also shows the compound, 3,6-dideoxy-3-oxo-erythronolide B (compound 6), produced in heterologous host cells comprising the plasmid.

Analysis of this construct indicated the production of the 14-membered ketolide 3,6-dideoxy-3-oxo-erythronolide B (FIG. 5, compound 6). Extracts were analyzed by LC/MS. The identity of compound 6 was verified by comparison to a previously authenticated sample (see PCT publication No. WO 98/49315, incorporated herein by reference). The predicted 12-membered macrolactone, (8R,9S)-8,9-dihydro-8-methyl-9-hydroxy-10-deoxymethynolide (see Kao et al. *J. Am. Chem. Soc.* (1995) 117:9105–9106 incorporated herein by reference) was not detected. Because the 12-membered intermediate can be formed by other recombinant PKS enzymes, see Kao et al., 1995, supra, the PIC TE domain appears incapable of forcing premature cyclization of the hexaketide intermediate generated by DEBS. This result, along with others reported herein, suggests that protein interactions between the narbonolide PKS modules play a role in formation of the 12 and 14-membered macrolides.

The above example illustrates also how engineered PKSs can be improved for production of novel compounds. Compound 6 was originally produced by deletion of the $KR^6$ domain in DEBS to create a 3-ketolide producing PKS (see U.S. patent application Ser. No. 09/073,538, filed May 6, 1998, and PCT publication No. WO 98/49315, each of which is incorporated herein by reference). Although the desired molecule was made, purification of compound 6 from this strain was hampered by the presence of 2-desmethyl ketolides that could not be easily separated. Extracts from *Streptomyces lividans* K4-114/pKOS039-18, however, do not contain the 2-desmethyl compounds, greatly simplifying purification. Thus, the invention provides a useful method of producing such compounds. The ability to combine the narbonolide PKS with DEBS and other modular PKSs provides a significant advantage in the production of macrolide antibiotics.

Two other hybrid PKSs of the invention were constructed that yield this same compound. These constructs also illustrate the method of the invention in which hybrid PKSs are constructed at the protein, as opposed to the module, level. Thus, the invention provides a method for constructing a hybrid PKS which comprises the coexpression of at least one gene from a first modular PKS gene cluster in a host cell that also expresses at least one gene from a second PKS gene cluster. The invention also provides novel hybrid PKS enzymes prepared in accordance with the method. This method is not limited to hybrid PKS enzymes composed of at least one narbonolide PKS gene, although such constructs are illustrative and preferred. Moreover, the hybrid PKS enzymes are not limited to hybrids composed of unmodified proteins; as illustrated below, at least one of the genes can optionally be a hybrid PKS gene.

In the first construct, the eryAI and eryAII genes were coexpressed with picAIV and a gene encoding a hybrid extender module 5 composed of the KS and AT domains of extender module 5 of DEBS3 and the KR and ACP domains of extender module 5 of the narbonolide PKS. In the second construct, the picIV coding sequence was fused to the hybrid extender module 5 coding sequence used in the first construct to yield a single protein. Each of these constructs produced 3-deoxy-3-oxo-6deoxyerythronolide B. In a third construct, the coding sequence for extender module 5 of DEBS3 was fused to the picIV coding sequence, but the levels of product produced were below the detection limits of the assay.

A variant of the first construct hybrid PKS was constructed that contained an inactivated DEBS1 extender module 1 KS domain. When host cells containing the resultant hybrid PKS were supplied the appropriate diketide precursor, the desired 13-desethyl-13-propyl compounds were obtained, as described in the examples below.

Other illustrative hybrid PKSs of the invention were made by coexpressing the picAI and picAII genes with genes encoding DEBS3 or DEBS3 variants. These constructs illustrate the method of the invention in which a hybrid PKS is produced from coexpression of PKS genes unmodified at the modular or domain level. In the first construct, the eryAIII gene was coexpressed with the picAI and picAII genes, and the hybrid PKS produced 10-desmethyl-10,11-anhydro-6-deoxyerythronolide B in *Streptomyces lividans*. Such a hybrid PKS could also be constructed in accordance with the method of the invention by transformation of *S. venezuelae* with an expression vector that produces the eryAIII gene product, DEBS3. In a preferred embodiment, the *S. venezuelae* host cell has been modified to inactivate the picAIII gene.

In the second construct, the DEBS3 gene was a variant that had an inactive KR in extender module 5. The hybrid PKS produced 5,6-dideoxy-5-oxo-10-desmethyl-10,11-anhydroerythronolide B in *Streptomyces lividans*.

In the third construct, the DEBS3 gene was a variant in which the KR domain of extender module 5 was replaced by the DH and KR domains of extender module 4 of the rapamycin PKS. This construct produced 5,6-dideoxy-5-oxo-10-desmethyl-10,11-anhydroerythronolide B and 5,6-dideoxy4,5-anhydro-10-desmethyl-10,11-anhydroerythronolide B in *Streptomyces lividans*, indicating that the rapamycin DH and KR domains functioned only inefficiently in this construct.

In the fourth construct, the DEBS3 gene was a variant in which the KR domain of extender module 5 was replaced by the DH, KR, and ER domains of extender module 1 of the rapamycin PKS. This construct produced 5,6-dideoxy-5oxo-10-desmethyl-10,11-anhydroerythronolide B as well as 5,6-dideoxy-10-desmethyl-10,11-anhydroerythronolide B in *Streptomyces lividans*, indicating that the rapamycin DH, KR, and ER domains functioned only inefficiently in this construct.

In the fifth construct, the DEBS3 gene was a variant in which the KR domain of extender module 6 was replaced by the DH and KR domains of extender module 4 of the rapamycin PKS. This construct produced 3,6-dideoxy-2,3-anhydro-10-desmethyl-10,11-anhydroerythronolide B in *Streptomyces lividans*.

In the sixth construct, the DEBS3 gene was a variant in which the AT domain of extender module 6 was replaced by the AT domain of extender module 2 of the rapamycin PKS. This construct produced 2,10-didesmethyl-10,11-anhydro-6-deoxyerythronolide B in *Streptomyces lividans*.

These hybrid PKSs illustrate the wide variety of polyketides that can be produced by the methods and compounds of the invention. These polyketides are useful as antibiotics and as intermediates in the synthesis of other useful compounds, as described in the following section.

Section VI: Compounds

The methods and recombinant DNA compounds of the invention are useful in the production of polyketides. In one important aspect, the invention provides methods for making ketolides, polyketide compounds with significant antibiotic activity. See Griesgraber et al., 1996, *J. Antibiot.* 49: 465477, incorporated herein by reference. Most if not all of the ketolides prepared to date are synthesized using erythromycin A, a derivative of 6-dEB, as an intermediate. While the invention provides hybrid PKSs that produce a polyketide different in structure from 6-dEB, the invention also provides methods for making intermediates useful in preparing traditional, 6-dEB-derived ketolide compounds.

Because 6-dEB in part differs from narbonolide in that it comprises a 10-methyl group, the novel hybrid PKS genes of the invention based on the narbonolide PKS provide many novel ketolides that differ from the known ketolides only in that they lack a 10-methyl group. Thus, the invention provides the 10-desmethyl analogues of the ketolides and intermediates and precursor compounds described in, for example, Griesgraber et al., supra; Agouridas et al., 1998, *J. Med Chem.* 41: 4080–4100, U.S. Pat. Nos. 5,770,579; 5,760,233; 5,750,510; 5,747,467; 5,747,466; 5,656,607; 5,635,485; 5,614,614; 5,556,118; 5,543,400; 5,527,780; 5,444,051; 5,439,890; 5,439,889; and PCT publication Nos. WO 98/09978 and WO 98/28316, each of which is incorporated herein by reference. Because the invention also provides hybrid PKS genes that include a methylmalonyl-specific AT domain in extender module 2 of the narbonolide PKS, the invention also provides hybrid PKS that can be used to produce the 10-methyl-containing ketolides known in the art.

Thus, a hybrid PKS of the invention that produces 10-methyl narbonolide is constructed by substituting the malonyl-specific AT domain of the narbonolide PKS extender module 2 with a methylmalonyl specific AT domain from a heterologous PKS. A hybrid narbonolide PKS in which the AT of extender module 2 was replaced with the AT from DEBS extender module 2 was constructed using boundaries described in PCT publication No. WO 98/49315, incorporated herein by reference. However, when the hybrid PKS expression vector was introduced into *Streptomyces venezuelae*, detectable quantities of 10-methyl picromycin were not produced. Thus, to construct such a hybrid PKS of the invention, an AT domain from a module other than DEBS extender module 2 is preferred. One could also employ DEBS extender module 2 or another methylmalonyl specific AT but utilize instead different boundaries than those used for the substitution described above. In addition, one can construct such a hybrid PKS by substituting, in addition to the AT domain, additional extender module 2 domains, including the KS, the KR, and the DH, and/or additional extender module 3 domains.

Although modification of extender module 2 of the narbonolide PKS is required, the extent of hybrid modules engineered need not be limited to module 2 to make 10-methyl narbonolide. For example, substitution of the KS domain of extender module 3 of the narbonolide PKS with a heterologous domain or module can result in more efficient processing of the intermediate generated by the hybrid extender module 2. Likewise, a heterologous TE domain may be more efficient in cyclizing 10-methyl narbonolide.

Substitution of the entire extender module 2 of the narbonolide PKS with a module encoding the correct enzymatic activities, i.e., a KS, a methylmalonyl specific AT, a KR, a DH, and an ACP, can also be used to create a hybrid PKS of the invention that produces a 10-methyl ketolide. Modules useful for such whole module replacements include extender modules 4 and 10 from the rapamycin PKS, extender modules 1 and 5 from the FK506 PKS, extender module 2 of the tylosin PKS, and extender module 4 of the rifamycin PKS. Thus, the invention provides many different hybrid PKSs that can be constructed starting from the narbonolide PKS that can be used to produce 10-methyl narbonolide. While 10-methyl narbonolide is referred to in describing these hybrid PKSs, those of skill recognize that the invention also therefore provides the corresponding derivatives produces by glycosylation and hydroxylation. For example, if the hybrid PKS is expressed in *Streptomyces narbonensis* or *S. venezuelae*, the compounds produced are 10-methyl narbomycin and picromycin, respectively. Alternatively, the PKS can be expressed in a host cell transformed with the vectors of the invention that encode the desosamine biosynthesis and desosaminyl transferase and picK hydroxylase genes.

Other important compounds provided by the invention are the 6-hydroxy ketolides. These compounds include 3-deoxy-3-oxo erythronolide B, 6-hydroxy narbonolide, and 6-hydroxy- 10-methyl narbonolide. In the examples below, the invention provides a method for utilizing EryF to hydroxylate 3-ketolides that is applicable for the production of any 6-hydroxy-3-ketolide.

Thus, the hybrid PKS genes of the invention can be expressed in a host cell that contains the desosamine biosynthetic genes and desosaminyl transferase gene as well as the required hydroxylase gene(s), which may be either picK (for the C12 position) or eryK (for the C12 position) and/or eryF (for the C6 position). The resulting compounds have antibiotic activity but can be further modified, as described in the patent publications referenced above, to yield a desired compound with improved or otherwise desired properties. Alternatively, the aglycone compounds can be produced in the recombinant host cell, and the desired glycosylation and hydroxylation steps carried out in vitro or in vivo, in the latter case by supplying the converting cell with the aglycone.

The compounds of the invention are thus optionally glycosylated forms of the polyketide set forth in formula (2) below which are hydroxylated at either the C6 or the C12 or both. The compounds of formula (2) can be prepared using the loading and the six extender modules of a modular PKS, modified or prepared in hybrid form as herein described. These polyketides have the formula:

(2)

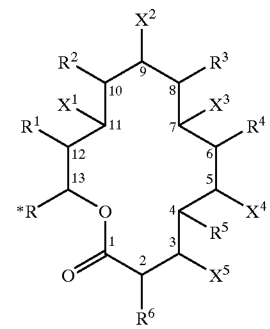

including the glycosylated and isolated stereoisomeric forms thereof;

wherein R* is a straight chain, branched or cyclic, saturated or unsaturated substituted or unsubstituted hydrocarbyl of 1–15C;

each of $R^1$–$R^6$ is independently H or alkyl (1–4C) wherein any alkyl at $R^1$ may optionally be substituted;

each of $X^1$–$X^5$ is independently two H, H and OH, or =O; or each of $X^1$–$X^5$ is independently H and the compound of formula (2) contains a double-bond in the ring adjacent to the position of said X at 2–3, 4–5, 6–7, 8–9 and/or 10–11;

with the proviso that:

at least two of $R^1$–$R^6$ are alkyl (1–4C).

Preferred compounds comprising formula 2 are those wherein at least three of $R^1$–$R^5$ are alkyl (1–4C), preferably methyl or ethyl; more preferably wherein at least four of $R^{15}$ are alkyl (1–4C), preferably methyl or ethyl. Also preferred are those wherein $X^2$ is two H, =O, or H and OH, and/or $X^3$ is H, and/or $X^1$ is OH and/or $X^4$ is OH and/or $X^5$ is OH. Also preferred are compounds with variable R* when $R^1$–$R^5$ is methyl, $X^2$ is =O, and $X^1$, $X^4$ and $X^5$ are OH. The glycosylated forms of the foregoing are also preferred.

The invention also provides the 1 2-membered macrolides corresponding to the compounds above but produced from a narbonolide-derived PKS lacking extender modules 5 and 6 of the narbonolide PKS.

The compounds of the invention can be produced by growing and fermenting the host cells of the invention under conditions known in the art for the production of other polyketides. The compounds of the invention can be isolated from the fermentation broths of these cultured cells and purified by standard procedures. The compounds can be readily formulated to provide the pharmaceutical compositions of the invention. The pharmaceutical compositions of the invention can be used in the form of a pharmaceutical preparation, for example, in solid, semisolid, or liquid form. This preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, solutions, emulsions, suspensions, and any other form suitable for use.

The carriers which can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquefied form. In addition, auxiliary stabilizing, thickening, and coloring agents and perfumes may be used. For example, the compounds of the invention may be utilized with hydroxypropyl methylcellulose essentially as described in U.S. Pat. No. 4,916,138, incorporated herein by reference, or with a surfactant essentially as described in EPO patent publication No. 428,169, incorporated herein by reference.

Oral dosage forms may be prepared essentially as described by Hondo et al., 1987, *Transplantation Proceedings XIX*, Supp. 6: 17–22, incorporated herein by reference. Dosage forms for external application may be prepared essentially as described in EPO patent publication No. 423,714, incorporated herein by reference. The active compound is included in the pharmaceutical composition in an amount sufficient to produce the desired effect upon the disease process or condition.

For the treatment of conditions and diseases caused by infection, a compound of the invention may be administered orally, topically, parenterally, by inhalation spray, or rectally in dosage unit formulations containing conventional non-toxic pharmaceutically acceptable carriers, adjuvant, and vehicles. The term parenteral, as used herein, includes subcutaneous injections, and intravenous, intramuscular, and intrasternal injection or infusion techniques.

Dosage levels of the compounds of the invention are of the order from about 0.01 mg to about 50 mg per kilogram of body weight per day, preferably from about 0.1 mg to about 10 mg per kilogram of body weight per day. The dosage levels are useful in the treatment of the above-indicated conditions (from about 0.7 mg to about 3.5 mg per patient per day, assuming a 70 kg patient). In addition, the compounds of the invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain from 0.5 mg to 5 gm of active agent compounded with an appropriate and convenient amount of carrier material, which may vary from about 5 percent to about 95 percent of the total composition. Dosage unit forms will generally contain from about 0.5 mg to about 500 mg of active ingredient For external administration, the compounds of the invention may be formulated within the range of, for example, 0.00001% to 60% by weight, preferably from 0.001% to 10% by weight, and most preferably from about 0.005% to 0.8% by weight.

It will be understood, however, that the specific dose level for any particular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

A detailed description of the invention having been provided above, the following examples are given for the purpose of illustrating the invention and shall not be construed as being a limitation on the scope of the invention or claims.

EXAMPLE 1

General Methodology

Bacterial strains, plasmids, and culture conditions. *Streptomyces coelicolor* CH999 described in WO 95/08548, published Mar. 30, 1995, or *S. lividans* K4-114, described in Ziermann and Betlach, January 99, Recombinant Polyketide Synthesis in Streptomyces: Engineering of Improved Host Strains, BioTechniques 26:106–110, incorporated herein by reference, was used as an expression host. DNA manipulations were performed in *Escherichia coli* XL1-Blue, available from Stratagene. *E. coli* MC1061 is also suitable for use as a host for plasmid manipulation. Plasmids were passaged through *E. coli* ET12567 (dam dcm hsdS Cmr) (MacNeil, 1988, *J. Bacteriol.* 170: 5607, incorporated herein by reference) to generate unmethylated DNA prior to transformation of *S. coelicolor*. *E. coli* strains were grown under standard conditions. *S. coelicolor* strains were grown on R2YE agar plates (Hopwood et al., *Genetic manipulation of Streptomyces. A laboratory manual*. The John Innes Foundation: Norwich, 1985, incorporated herein by reference).

Many of the expression vectors of the invention illustrated in the examples are derived from plasmid pRM5, described in WO 95/08548, incorporated herein by reference. This plasmid includes a colEI replicon, an appropriately truncated SCP2* Streptomyces replicon, two act-promoters to allow for bidirectional cloning, the gene encoding the actII-ORF4 activator which induces transcription from act promoters during the transition from growth phase to stationary phase, and appropriate marker genes. Engineered restriction sites in the plasmid facilitate the combinatorial construction of PKS gene clusters starting from cassettes encoding individual domains of naturally occurring PKSs. When plasmid pRM5 is used for expression of a PKS, all relevant biosynthetic genes can be plasmid-bome and therefore amenable to facile manipulation and mutagenesis in *E. coli*. This plasmid is also suitable for use in Streptomyces host cells. Streptomyces is genetically and physiologically well-characterized and expresses the ancillary activities required for in vivo production of most polyketides. Plasmid pRM5 utilizes the act promoter for PKS gene expression, so polyketides are produced in a secondary metabolite-like manner, thereby alleviating the toxic effects of synthesizing potentially bioactive compounds in vivo.

Manipulation of DNA and organisms. Polymerase chain reaction (PCR) was performed using Pfu polymerase (Stratagene; Taq polymerase from Perkin Elmer Cetus can also be used) under conditions recommended by the enzyme manufacturer. Standard in vitro techniques were used for DNA manipulations (Sambrook et al. Molecular Cloning: A Laboratory Manual (Current Edition)). *E. coli* was transformed using standard calcium chloride-based methods; a Bio-Rad *E. coli* pulsing apparatus and protocols provided by Bio-Rad could also be used. *S. coelicolor* was transformed by standard procedures (Hopwood et al. *Genetic manipulation of Streptomyces. A laboratory manual*. The John Innes Foundation: Norwich, 1985), and depending on what selectable marker was employed, transformants were selected using 1 mL of a 1.5 mg/mL thiostrepton overlay, 1 mL of a 2 mg/mL apramycin overlay, or both.

EXAMPLE 2

Cloning of the Picromycin Biosynthetic Gene Cluster from *Streptomyces venezuelae*

Genomic DNA (100 $\mu$g) isolated from Streptomyces venezuelae ATCC15439 using standard procedures was partially digested with Sau3AI endonuclease to generate fragments ~40 kbp in length. SuperCosI (Stratagene) DNA cosmid arms were prepared as directed by the manufacturer. A cosmid library was prepared by ligating 2.5 $\mu$g of the digested genomic DNA with 1.5 $\mu$g of cosmid arms in a 20

μL reaction. One microliter of the ligation mixture was propagated in *E. coli* XL1-Blue MR (Stratagene) using a GigapackIII XL packaging extract kit (Stratagene). The resulting library of ~3000 colonies was plated on a 10×150 mm agar plate and replicated to a nylon membrane.

The library was initially screened by direct colony hybridization with a DNA probe specific for ketosynthase domain coding sequences of PKS genes. Colonies were alkaline lysed, and the DNA was crosslinked to the membrane using UV irradiation. After overnight incubation with the probe at 42° C., the membrane was washed twice at 25° C. in 2×SSC buffer+0.1% SDS for 15 minutes, followed by two 15 minute washes with 2×SSC buffer at 55° C. Approximately 30 colonies gave positive hybridization signals with the degenerate probe. Several cosmids were selected and divided into two classes based on restriction digestion patterns. A representative cosmid was selected from each class for further analysis. The representative cosmids were designated pKOS023-26 and pKOS023-27. These cosmids were determined by DNA sequencing to comprise the narbonolide PKS genes, the desosamine biosynthesis and transferase genes, the beta-glucosidase gene, and the picK hydroxylase gene.

These cosmids were deposited with the American Type Culture Collection in accordance with the terms of the Budapest Treaty. Cosmid pKOS023-26 was assigned accession number ATCC 203141, and cosmid pKOS023-27 was assigned accession number ATCC 203142.

To demonstrate that the narbonolide PKS genes had been cloned and to illustrate how the invention provides methods and reagents for constructing deletion variants of narbonolide PKS genes, a narbonolide PKS gene was deleted from the chromosome of *Streptomyces venezuelae*. This deletion is shown schematically in FIG. 4, parts B and C. A ~2.4 kb EcoRI—KpnI fragment and a ~2.1 kb KpnI—XhoI fragment, which together comprise both ends of the picAI gene (but lack a large portion of the coding sequence), were isolated from cosmid pKOS023-27 and ligated together into the commercially available vector pLitmus 28 (digested with restriction enzymes EcoRI and XhoI) to give plasmid pKOS039-07. The -4.5 kb HindIII-SpeI fragment from plasmid pKOS039-07 was ligated with the 2.5 kb HindIII-NheI fragment of integrating vector pSET152, available from the NRRL, which contains an *E. coli* origin of replication and an apramycin resistance-conferring gene to create plasmid pKOS039-16. This vector was used to transform *S. venezuelae*, and apramycin-resistant transformants were selected.

Then, to select for double-crossover mutants, the selected transformants were grown in TSB liquid medium without antibiotics for three transfers and then plated onto non-selective media to provide single colony isolates. The isolated colonies were tested for sensitivity to apramycin, and the apramycin-sensitive colonies were then tested to determine if they produced picromycin. The tests performed included a bioassay and LC/MS analysis of the fermentation media Colonies determined not to produce picromycin (or methymycin or neomethymycin) were then analyzed using PCR to detect an amplification product diagnostic of the deletion. A colony designated K39-03 was identified, providing confirmation that the narbonolide PKS genes had been cloned. Transformation of strain K39-03 with plasmid pKOS039-27 comprising an intact picA gene under the control of the ermE* promoter from plasmid pW3 (see Vara et al., *J Bact.* (1989) 171: 5872–5881, incorporated herein by reference) was able to restore picromycin production.

To determine that the cosmids also contained the picK hydroxylase gene, each cosmid was probed by Southern hybridization using a labeled DNA fragment amplified by PCR from the *Saccharopolyspora erythraea* C12-hydroxylase gene, eryK. The cosmids were digested with BamHI endonuclease and electrophoresed on a 1% agarose gel, and the resulting fragments were transferred to a nylon membrane. The membrane was incubated with the eryK probe overnight at 42° C., washed twice at 25° C. in 2×SSC buffer with 0.1% SDS for 15 minutes, followed by two 15 minute washes with 2×SSC buffer at 50° C. Cosmid pKOS023-26 produced an ~3 kb fragment that hybridized with the probe under these conditions. This fragment was subcloned into the PCRscript™ (Stratagene) cloning vector to yield plasmid pKOS023-28 and sequenced. The ~1.2 kb gene designated picK above was thus identified. The picK gene product is homologous to eryK and other known macrolide cytochrome P450 hydroxylases.

By such methodology, the complete set of picromycin biosynthetic genes were isolated and identified. DNA sequencing of the cloned DNA provided further confirmation that the correct genes had been cloned. In addition, and as described in the following example, the identity of the genes was confirmed by expression of narbomycin in heterologous host cells.

EXAMPLE 3

Heterologous Expression of the Narbonolide PKS and the Picromycin Biosynthetic Gene Cluster To provide a preferred host cell and vector for purposes of the invention, the narbonolide PKS was transferred to the non-macrolide producing host *Streptomyces lividans* K4-114 (see Ziermann and Betlach, 1999, *Biotechniques* 26, 106–110, and U.S. patent application Ser. No. 09/181,833, filed Oct. 28, 1998, each of which is incorporated herein by reference). This was accomplished by replacing the three DEBS ORFs on a modified version of pCK7 (see Kao et al., 1994, *Science* 265, 509–512, and U.S. Pat. No. 5,672,491, each of which is incorporated herein by reference) with all four narbonolide PKS ORFs to generate plasmid pKOS039-86 (see FIG. 5). The pCK7 derivative employed, designated pCK7'Kan', differs from pCK7 only in that it contains a kanamycin resistance conferring gene inserted at its HindIII restriction enzyme recognition site. Because the plasmid contains two selectable markers, one can select for both markers and so minimize contamination with cells containing rearranged, undesired vectors.

Protoplasts were transformed using standard procedures and transformants selected using overlays containing antibiotics. The strains were grown in liquid R5 medium for growth/seed and production cultures at 30° C. A 2 L shake flask culture of *S. lividans* K4-114/pKOS039-86 was grown for 7 days at 30° C. The mycelia was filtered, and the aqueous layer was extracted with 2×2 L ethyl acetate. The organic layers were combined, dried over MgSO4, filtered, and evaporated to dryness. Polyketides were separated from the crude extract by silica gel chromatography (1:4 to 1:2 ethyl acetate:hexane gradient) to give an ~10 mg mixture of narbonolide and 10-deoxymethynolide, as indicated by LC/MS and 1H NMR. Purification of these two compounds was achieved by HPLC on a C-18 reverse phase column (20–80% acetonitrile in water over 45 minutes). This procedure yielded 5 mg each of narbonolide and 10-deoxymethynolide. Polyketides produced in the host cells were analyzed by bioassay against *Bacillus subtilis* and by LC/MS analysis. Analysis of extracts by LC/MS followed by 1H-NMR spectroscopy of the purified compounds established their identity as narbonolide (FIG. 5, compound 4; see Kaiho et al., 1982, *J. Org. Chem.* 47: 1612–1614, incorporated herein by reference) and 10-deoxymethynolide (FIG. 5, compound 5; see Lambalot et al., 1992, *J. Antibiotics* 45, 1981–1982, incorporated herein by reference), the respective 14 and 12-membered polyketide aglycones of YC17, narbomycin, picromycin, and methymycin.

The production of narbonolide in *Streptomyces lividans* represents the expression of an entire modular polyketide pathway in a heterologous host. The combined yields of compounds 4 and 5 are similar to those obtained with expression of DEBS from pCK7 (see Kao et al., 1994, *Science* 265: 509–512, incorporated herein by reference). Furthermore, based on the relative ratios (~1:1) of compounds 4 and 5 produced, it is apparent that the narbonolide PKS itself possesses an inherent ability to produce both 12 and 14-membered macrolactones without the requirement of additional activities unique to *S. venezuelae*. Although the existence of a complementary enzyme present in *S. lividans* that provides this function is possible, it would be unusual to find such a specific enzyme in an organism that does not produce any known macrolide.

To provide a heterologous host cell of the invention that produces the narbonolide PKS and the picB gene, the picB gene was integrated into the chromosome of *Streptomyces lividans* harboring plasmid pKOS039-86 to yield *S. lividans* K39-18/pKOS039-86. To provide the integrating vector utilized, the picB gene was cloned into the Streptomyces genome integrating vector pSET152 (see Bierman et al., 1992, *Gene* 116, 43, incorporated herein by reference) under control of the same promoter (PactI) as the PKS on plasmid pKOS039-86.

A comparison of strains K39-18/pKOS039-86 and K4-114/pKOS039-86 grown under identical conditions indicated that the strain containing TEII produced 4–7 times more total polyketide. Each strain was grown in 30 mL of RS (see Hopwood et al., *Genetic Manipulation of Streptomyces: A Laboratory Manual*; John Innes Foundation: Norwich, UK, 1985, incorporated herein by reference) liquid (with 20 μg/mL thiostrepton) at 30° C. for 9 days. The fermentation broth was analyzed directly by reverse phase HPLC. Absorbance at 235 nm was used to monitor compounds and measure relative abundance. This increased production indicates that the enzyme is functional in this strain. As noted above, because the production levels of compound 4 and 5 from K39-18/pKOS03986 increased by the same relative amounts, TEII does not appear to influence the ratio of 12 and 14-membered lactone ring formation.

To express the glycosylated counterparts of narbonolide (narbomycin) and 10-deoxymethynolide (YC17) in heterologous host cells, the desosamine biosynthetic genes and desosaminyl transferase gene were transformed into the host cells harboring plasmid pKOS039-86 (and, optionally, the picB gene, which can be integrated into the chromosome as described above).

Figure 6:
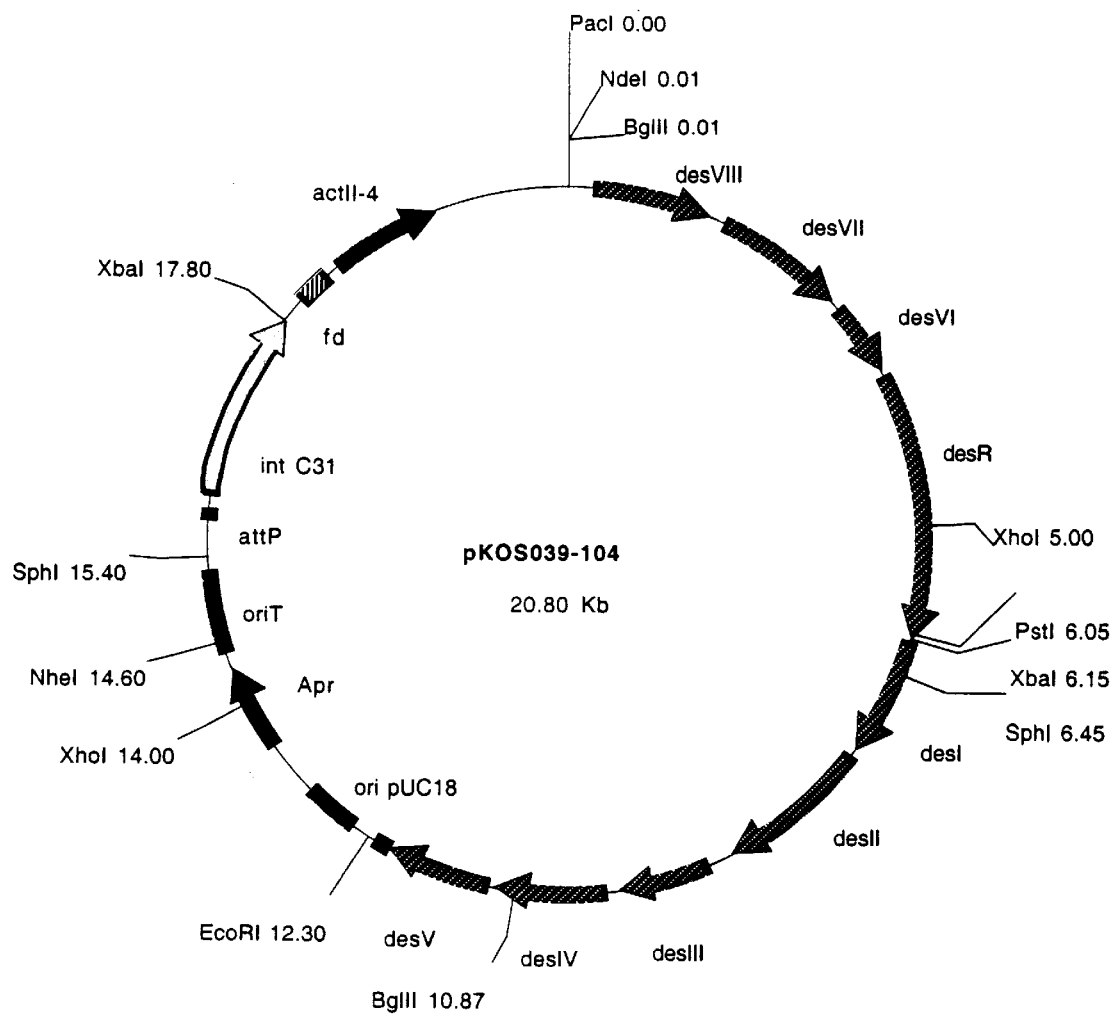
FIG. 6 shows a restriction site and function map of plasmid pKOS039-104, which contains the desosamine biosynthetic, beta-glucosidase, and desosaminyl transferase genes under transcriptional control of actII-4.

Plasmid pKOS039-104, see FIG. 6, comprises the desosamine biosynthetic genes, the beta-glucosidase gene, and the desosaminyl transferase gene. This plasmid was constructed by first inserting a polylinker oligonucleotide, containing a restriction enzyme recognition site for PacI, a Shine-Dalgarno sequence, and restriction enzyme recognition sites for NdeI, BglII, and HindIII, into a pUC 19 derivative, called pKOS24-47, to yield plasmid pKOS039-98.

An ~0.3 kb PCR fragment comprising the coding sequence for the N-terminus of the desI gene product and an ~0.12 kb PCR fragment comprising the coding sequence for the C-terminus of the desR gene product were amplified from cosmid pKOS23-26 (ATCC 203141) and inserted together into pLitmus28 treated with restriction enzymes NsiI and EcoRI to produce plasmid pKOS039-101. The ~6 kb SphI-PstI restriction fragment of pKOS23-26 containing the desI, desII, desIII, desIV, and desV genes was inserted into plasmid pUC19 (Stratagene) to yield plasmid pKOS039-102. The ~6 kb SphI-EcoRI restriction fragment from plasmid pKOS039-102 was inserted into pKOS039-101 to produce plasmid pKOS039-103. The ~6 kb BglII-PstI fragment from pKOS23-26 that contains the desR, des VI, des VII, and des VIII genes was inserted into pKOS39-98 to yield pKOS39-100. The ~6 kb PacI-PstI restriction fragment of pKOS39-100 and the ~6.4 kb NsiI-EcoRI fragment of pKOS039-103 were cloned into pKOS039-44 to yield pKOS039-104.

When introduced into *Streptomyces lividans* host cells comprising the recombinant narbonolide PKS of the invention, plasmid pKOS039-104 drives expression of the desosamine biosynthetic genes, the beta-glucosidase gene, and the desosaminyl transferase gene. The glycosylated antibiotic narbomycin was produced in these host cells, and it is believed that YC17 was produced as well. When these host cells are transformed with vectors that drive expression of the picK gene, the antibiotics methymycin, neomethymycin, and picromycin are produced.

In similar fashion, when plasmid pKOS039-18, which encodes a hybrid PKS of the invention that produces 3-deoxy-3-oxo-6-deoxyerythronolide B was expressed in *Streptomyces lividans* host cells transformed with plasmid pKOS039-104, the 5-desosaminylated analog was produced. Likewise, when plasmid pCK7, which encodes DEBS, which produces 6-deoxyerythronolide B, was expressed in Streptomyces lividans host cells transformed with plasmid pKOS039-104, the 5-desosaminylated analog was produced. These compounds have antibiotic activity and are useful as intermediates in the synthesis of other antibiotics.

EXAMPLE 4

Expression Vector for Desosaminyl Transferase

While the invention provides expression vectors comprising all of the genes required for desosamine biosynthesis and transfer to a polyketide, the invention also provides expression vectors that encode any subset of those genes or any single gene. As one illustrative example, the invention provides an expression vector for desosaminyl transferase. This vector is useful to desosaminylate polyketides in host cells that produce NDP-desosamine but lack a desosaminyl transferase gene or express a desosaminyl i transferase that does not function as efficiently on the polyketide of interest as does the desosaminyl transferase of *Streptomyces venezuelae*. This expression vector was constructed by first amplifying the desosaminyl transferase coding sequence from pKOS023-27 using the primers:

N3917: 5'-CCCTGCAGCGGCAAGGAAGGACACG ACGCCA-3' (SEQ ID NO:25); and

N3918: 5'-AGGTCTAGAGCTCAGTGCCGGGCGTC GGCCGG-3' (SEQ ID NO:26), to give a 1.5 kb product. This product was then treated with restriction enzymes PstI and XbaI and ligated with HindIII and XbaI digested plasmid pKOS039-06 together with the 7.6 kb PstI-HindIII restriction fragment of plasmid pWHM1104 to provide plasmid pKOS039-14. Plasmid pWHM1104, described in Tang et al., 1996, *Molec. Microbiol.* 22(5): 801–813, incorporated herein by reference, encodes the ermE* promoter. Plasmid pKOS039-14 is constructed so that the desosaminyl transferase gene is placed under the control of the ermE* promoter and is suitable for expression of the desosaminyl transferase in Streptomyces, *Saccharopolyspora erythraea*, and other host cells in which the ermE* promoter functions.

EXAMPLE 5

Heterologous Expression of the picK Gene Product in *E. coli*

The picK gene was PCR amplified from plasmid pKOS023-28 using the oligonucleotide primers:

N024-36B (forward):
5'-TTGCATGCATATGCGCCGTACCCAGCAGGG AACGACC (SEQ ID NO:27); and N024-37B (reverse):
5'-TTGAATTCTCAACTAGTACGGCGGCCCGCC TCCCGTCC (SEQ ID NO:28).

These primers alter the Streptomyces GTG start codon to ATG and introduce a SpeI site at the C-terminal end of the gene, resulting in the substitution of a serine for the terminal glycine amino acid residue. The blunt-ended PCR product was subcloned into the commercially available vector pCR-script at the SrfI site to yield plasmid pKOS023-60. An ~1.3 kb NdeI-XhoI fragment was then inserted into the NdeIIX-hoI sites of the T7 expression vector pET22b (Novagen, Madison, Wis.) to generate pKOS023-61. Plasmid pKOS023-61 was digested with restriction enzymes SpeI and EcoRI, and a short linker fragment encoding 6 histidine residues and a stop codon (composed of oligonucleotides 30–85a: 5'-CTAGTATGCATCATCATCATCATCATTAA-3' (SEQ ID NO:29); and 30–85b: 5'-AATTTTAAT GATGATGATGATGATGCATA-3' (SEQ ID NO:30) was inserted to obtain plasmid pKOS023-68. Both plasmid pKOS023-61 and pKOS023-68 produced active PicK enzyme in recombinant *E. coli* host cells.

Plasmid pKOS023-61 was transformed into *E. coli* BL21-DE3. Successful transformants were grown in LB-containing carbenicillin (100 $\mu$g/ml) at 37° C. to an OD600 of 0.6. Isopropyl-beta-D-thiogalactopyranoside (IPTG) was added to a final concentration of 1 mM, and the cells were grown for an additional 3 hours before harvesting. The cells were collected by centriflugation and frozen at −80° C. A control culture of BL21-DE3 containing the vector plasmid pET21c (Invitrogen) was prepared in parallel.

The frozen BL21-DE3/pKOS023-61 cells were thawed, suspended in 2 $\mu$L of cold cell disruption buffer (5 mM imidazole, 500 mM NaCl, 20 mM Tris/HCl, pH 8.0) and sonicated to facilitate lysis. Cellular debris and supernatant were separated by centrifugation and subjected to SDS-PAGE on 10–15% gradient gels, with Coomassie Blue staining, using a Pharmacia Phast Gel Electrophoresis system. The soluble crude extract from BL21-DE3/pKOS023-61 contained a Coomassie stained band of Mr~46 kDa, which was absent in the control strain BL21-DE3/pET21c.

The hydroxylase activity of the picK protein was assayed as follows. The crude supernatant (20 $\mu$L) was added to a reaction mixture (100 $\mu$L total volume) containing 50 mM Tris/HCl (pH 7.5), 20 $\mu$M spinach ferredoxin, 0.025 Unit of spinach ferredoxin:NADP+oxidoreductase, 0.8 Unit of glucose-6-phosphate dehydrogenase, 1.4 mM NADP+, 7.6 mM glucose-6phosphate, and 20 nmol of narbomycin. The narbomycin was purified from a culture of *Streptomyces narbonensis*, and upon LC/MS analysis gave a single peak of [M+H]+=510. The reaction was allowed to proceed for 105 minutes at 30° C. Half of the reaction mixture was loaded onto an HPLC, and the effluent was analyzed by evaporative light scattering (ELSD) and mass spectrometry. The control extract (BL21-DE3/pET21c) was processed identically. The BL21-DE3/pKOS023-61 reaction contained a compound not present in the control having the same retention time, molecular weight and mass fragmentation pattern as picromycin ([M+H]+=526). The conversion of narbomycin to picromycin under these conditions was estimated to be greater than 90% by ELSD peak area.

The poly-histidine-linked PicK hydroxylase was prepared from pKOS023-68 transformed into *E. coli* BL21 (DE3) and cultured as described above. The cells were harvested and the PicK protein purified as follows. All purification steps were performed at 4° C. *E. coli* cell pellets were suspended in 32 $\mu$L of cold binding buffer (20 mM Tris/HCl, pH 8.0, 5 mM imidazole, 500 mM NaCl) per mL of culture and lysed by sonication. For analysis of *E. coli* cell-free extracts, the cellular debris was removed by low-speed centrifugation, and the supernatant was used directly in assays. For purification of PicK/6-His, the supernatant was loaded (0.5 mL/min.) onto a 5 mL HiTrap Chelating column (Pharmacia, Piscataway, N.J.), equilibrated with binding buffer. The column was washed with 25 $\mu$L of binding buffer and the protein was eluted with a 35 $\mu$L linear gradient (5–500 mM imidazole in binding buffer). Column effluent was monitored at 280 nm and 416 nm. Fractions corresponding to the 416 nm absorbance peak were pooled and dialyzed against storage buffer (45 mM Tris/HCl, pH 7.5, 0.1 mM EDTA, 0.2 mM DTT, 10% glycerol). The purified 46 kDa protein was analyzed by SDS-PAGE using Coomassie blue staining, and enzyme concentration and yield were determined.

Narbomycin was purified as described above from a culture of Streptomyces narbonensis ATCC 19790. Reactions for kinetic assays (100 $\mu$L) consisted of 50 mM Tris/HCl (pH 7.5), 100 $\mu$M spinach ferredoxin, 0.025 Unit of spinach ferredoxin:NADP+oxidoreductase, 0.8 U glucose-6-phosphate dehydrogenase, 1.4 mM NADP+, 7.6 mM glucose-6-phosphate, 20–500 $\mu$M narbomycin substrate, and 50–500 nM of PicK enzyme. The reaction proceeded at 30° C., and samples were withdrawn for analysis at 5, 10, 15, and 90 minutes. Reactions were stopped by heating to 100° C. for 1 minute, and denatured protein was removed by centrifugation. Depletion of narbomycin and formation of picromycin were determined by high performance liquid chromatography (HPLC, Beckman C-18 0.46×15 cm column) coupled to atmospheric pressure chemical ionization (APCI) mass spectroscopic detection (Perkin Elmer/Sciex API 100) and evaporative light scattering detection (Alltech 500 ELSD).

EXAMPLE 6

Expression of the picK Gene Encoding the Hydroxylase in *Streptomyces narbonensis*

To produce picromycin in Streptomyces narbonensis, a host that produces narbomycin but not picromycin, the methods and vectors of the invention were used to express the picK gene in this host.

The picK gene was amplified from cosmid pKOS023-26 using the primers:

N3903: 5'-TCCTCTAGACGTTTCCGT-3' (SEQ ID NO:31); and

N3904: 5'-TGAAGCTTGAATTCAACCGGT-3' (SEQ ID NO:32) to obtain an -1.3 kb product. The product was treated with restriction enzymes XbaI and HindIII and ligated with the 7.6 kb XbaI-HindIII restriction fragment of plasmid pWHM1104 to provide plasmid pKOS039-01, placing the picK gene under the control of the ermE* promoter. The resulting plasmid was transformed into purified stocks of *S. narbonensis* by protoplast fusion and electroporation. The transformants were grown in suitable media and shown to convert narbomycin to picromycin at a yield of over 95%.

EXAMPLE 7

Construction of a Hybrid DEBS/Narbonolide PKS

This example describes the construction of illustrative hybrid PKS expression vectors of the invention. The hybrid PKS contains portions of the narbonolide PKS and portions of rapamycin and/or DEBS PKS. In the first constructs, pKOS039-18 and pKOS039-19, the hybrid PKS comprises the narbonolide PKS extender module 6 ACP and thioesterase domains and the DEBS loading module and extender modules 1–5 as well as the KS and AT domains of DEBS extender module 6 (but not the KR domain of extender module 6). In pKOS039-19, the hybrid PKS is identical except that the KS1 domain is inactivated, i.e., the ketosynthase in extender module 1 is disabled. The inactive DEBS KS1 domain and its construction are described in detail in PCT publication Nos. WO 97/02358 and WO 99/03986, each of which is incorporated herein by reference. To construct pKOS039-18, the 2.33 kb BamHI-EcoRI fragment of pKOS023-27, which contains the desired sequence, was amplified by PCR and subcloned into plasmid pUC19. The primers used in the PCR were:

N3905: 5'-TTTATGCATCCCGCGGGTCCCGGCGAG-3' (SEQ ID NO:33); and

N3906: 5'-TCAGAATCTGTCGGTCACTTGCCCGC-3' (SEQ ID NO:34).

The 1.6 kb PCR product was digested with PstI and EcoRI and cloned into the corresponding sites of plasmid pKOS015-52 (this plasmid contains the relevant portions of the coding sequence for the DEBS extender module 6) and commercially available plasmid pLitmus 28 to provide plasmids pKOS039-12 and pKOS039-13, respectively. The BglII—EcoRI fragment of plasmid pKOS039-12 was cloned into plasmid pKOS011-77, which contains the functional DEBS gene cluster and into plasmid pJRJ2, which contains the mutated DEBS gene that produces a DEBS PKS in which the KS domain of extender module I has been rendered inactive. Plasmid pJRJ2 is described in PCT publication Nos. WO 99/03986 and WO 97/02358, incorporated herein by reference.

Plasmids pKOS039-18 and pKOS039-19, respectively, were obtained. These two plasmids were transformed into *Streptomyces coelicolor* CH999 by protoplast fusion. The resulting cells were cultured under conditions such that expression of the PKS occurred. Cells transformed with plasmid pKOS039-18 produced the expected product 3-deoxy-3-oxo-6-deoxyerythronolide B. When cells transformed with plasmid pKOS039-19 were provided (2S,3R)-2-methyl-3-hydroxyhexanoate NACS, 13-desethyl-13-propyl-3-deoxy-3-oxo-6-deoxyerythronolide B was produced.

EXAMPLE 8

6-Hydroxylation of 3,6-dideoxy-3-oxoerythronolide B using the eryF Hydroxylase

Certain compounds of the invention can be hydroxylated at the C6 position in a host cell that expresses the eryF gene. These compounds can also be hydroxylated in vitro, as illustrated by this example.

The 6-hydroxylase encoded by eryF was expressed in *E. coli*, and partially purified. The hydroxylase (100 pmol in 10 μL) was added to a reaction mixture (100 μl total volume) containing 50 mM Tris/HCl (pH 7.5), 20 μM spinach ferredoxin, 0.025 Unit of spinach ferredoxin:NADP+ oxidoreductase, 0.8 Unit of glucose6-phosphate dehydrogenase, 1.4 mM NADP+, 7.6 mM glucose-6-phosphate, and 10 mnol 6-deoxyerythronolide B. The reaction was allowed to proceed for 90 minutes at 30° C. Half of the reaction mixture was loaded onto an HPLC, and the effluent was analyzed by mass spectrometry. The production of erythronolide B as evidenced by a new peak eluting earlier in the gradient and showing [M+H]+=401. Conversion was estimated at 50% based on relative total ion counts.

Those of skill in the art will recognize the potential for hemiketal formation in the above compound and compounds of similar structure. To reduce the amount of hemiketal formed, one can use more basic (as opposed to acidic) conditions or employ sterically hindered derivative compounds, such as 5-desosaminylated compounds.

EXAMPLE 9

Measurement of Antibacterial Activity

Antibacterial activity was determined using either disk diffusion assays with *Bacillus cereus* as the test organism or by measurement of minimum inhibitory concentrations (MIC) in liquid culture against sensitive and resistant strains of *Staphylococcus pneumoniae*.

The invention having now been described by way of written description and example, those of skill in the art will recognize that the invention can be practiced in a variety of embodiments and that the foregoing description and examples are for purposes of illustration and not limitation of the following claims.

---

What is claimed is:

1. A recombinant DNA compound that comprises a coding sequence for a desosamine transferase gene of *Streptomyces venezuelae* wherein said coding sequence encodes the desosamine transferase having an amino acid sequence of SEQ ID NO:8.

2. A recombinant DNA compound that comprises a coding sequence for a desosamine transferase gene of *Streptomyces venezuelae* comprising the sequence of nucleotides 36159–37439 of SEQ ID NO:19.

* * * * *